United States Patent
Weaver et al.

(10) Patent No.: US 10,676,423 B2
(45) Date of Patent: Jun. 9, 2020

(54) STRUCTURE AND SYNTHESIS OF HIGHLY FLUORINATED AMINO ACID DERIVATIVES

(71) Applicant: The Board of Regents for Oklahoma State University, Stillwater, OK (US)

(72) Inventors: Jimmie Dean Weaver, Stillwater, OK (US); Kip Allen Teegardin, Glencoe, OK (US); Amandeep Arora, Stillwater, OK (US)

(73) Assignee: The Board of Regents for Oklahoma State University, Stillwater, OK (US)

(*) Notice: Subject to any disclaimer, the term of this patent is extended or adjusted under 35 U.S.C. 154(b) by 0 days.

(21) Appl. No.: 16/483,636

(22) PCT Filed: Feb. 20, 2018

(86) PCT No.: PCT/US2018/018766
§ 371 (c)(1),
(2) Date: Aug. 5, 2019

(87) PCT Pub. No.: WO2018/156500
PCT Pub. Date: Aug. 30, 2018

(65) Prior Publication Data
US 2020/0123099 A1  Apr. 23, 2020

Related U.S. Application Data

(60) Provisional application No. 62/461,257, filed on Feb. 21, 2017.

(51) Int. Cl.
| | | |
|---|---|---|
| *C07C 227/18* | (2006.01) | |
| *C07C 319/12* | (2006.01) | |
| *C07D 209/20* | (2006.01) | |
| *C07D 207/16* | (2006.01) | |
| *C07D 233/64* | (2006.01) | |
| *C07C 277/08* | (2006.01) | |

(52) U.S. Cl.
CPC .......... *C07C 227/18* (2013.01); *C07C 277/08* (2013.01); *C07C 319/12* (2013.01); *C07D 207/16* (2013.01); *C07D 209/20* (2013.01); *C07D 233/64* (2013.01)

(58) Field of Classification Search
None
See application file for complete search history.

(56) References Cited

U.S. PATENT DOCUMENTS

2005/0153357 A1   7/2005   Eichler et al.

FOREIGN PATENT DOCUMENTS

WO   2016090305 A1   6/2016

OTHER PUBLICATIONS

Liu, et al.; "Palladium-Catalyzed Alpha-Arylation of Azlactones to Form Quaternary Amino Acid Derivatives," Organic Letters (2003), vol. 5, No. 11; retrieved from the Internet: <URL:https://pubs.acs.org/doi/abs/10.1021/01034570q>.

Teegardin, et al.; "Polyfluoroarylation of Oxazolones: Access to Non-Natural Fluorinated Amino Acids," Chemical Communications (Mar. 30, 2017), vol. 53, No. 35; retrieved from the Internet <URL:http://pubs.rsc.org/en/content/articlelanding/2017/cc/c7cc01606a#!divAbstract>.

Pubchem, Compound Summary for SID 77224539, Available date: Jun. 12, 2009; retrieved from the Internet <URL: https://pubchem.ncbi.nlm.nih.gov/substance/77224539>.

International Search Report, dated Apr. 25, 2018, in PCT/US2018/018766, filed Feb. 20, 2018.

Written Opinion of the International Searching Authority, dated Apr. 25, 2018, in PCT/US2018/018766, filed Feb. 20, 2018.

*Primary Examiner* — Kamal A Saeed
(74) *Attorney, Agent, or Firm* — Dunlap Codding, P.C.

(57) ABSTRACT

Methods of synthesizing polyfluorinated amino acid derivatives are disclosed, along with polyfluorinated amino acid derivatives produced from said methods, as well as compositions containing same. The synthesis methods utilize an oxazolone and a perfluoroarene to produce the polyfluorinated amino acid derivatives.

26 Claims, 92 Drawing Sheets

FIG. 1
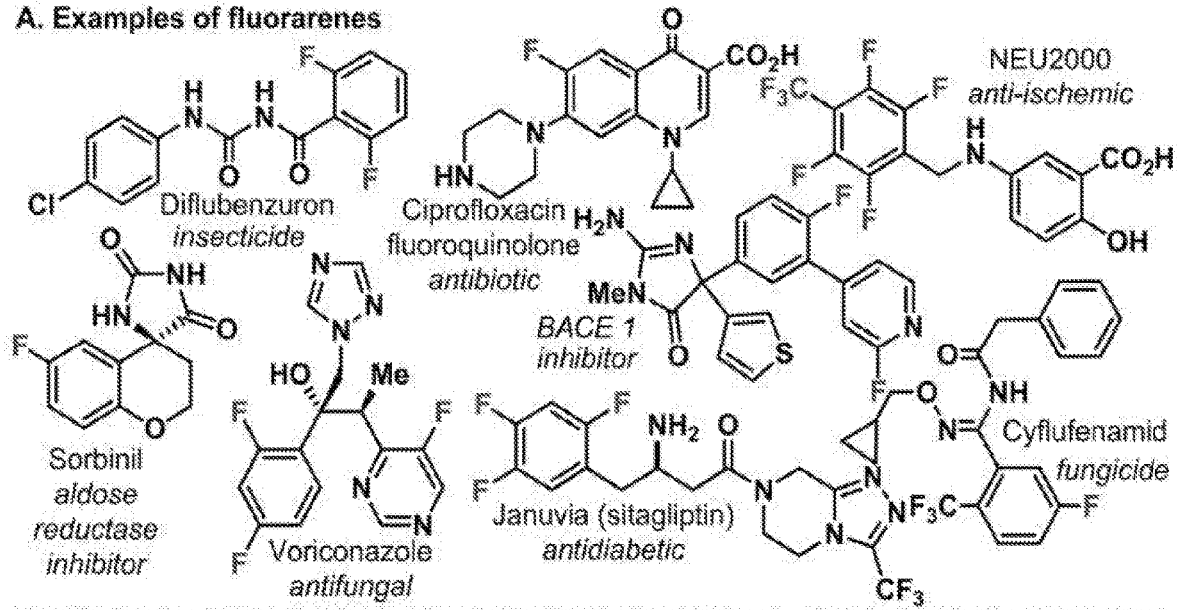
A. Examples of fluorarenes
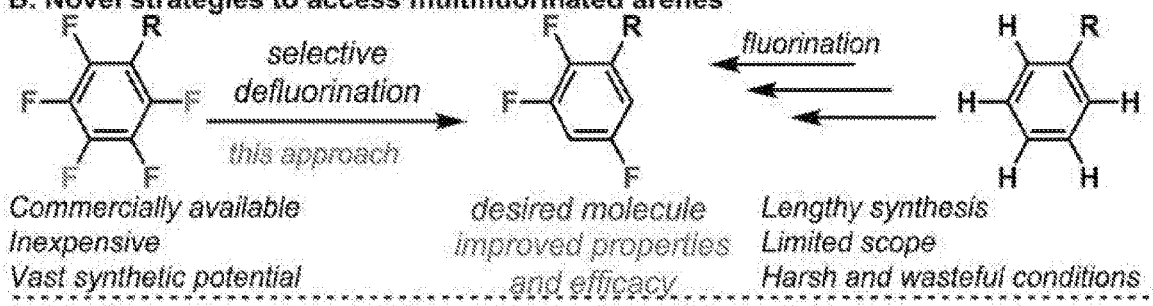
B. Novel strategies to access multifluorinated arenes
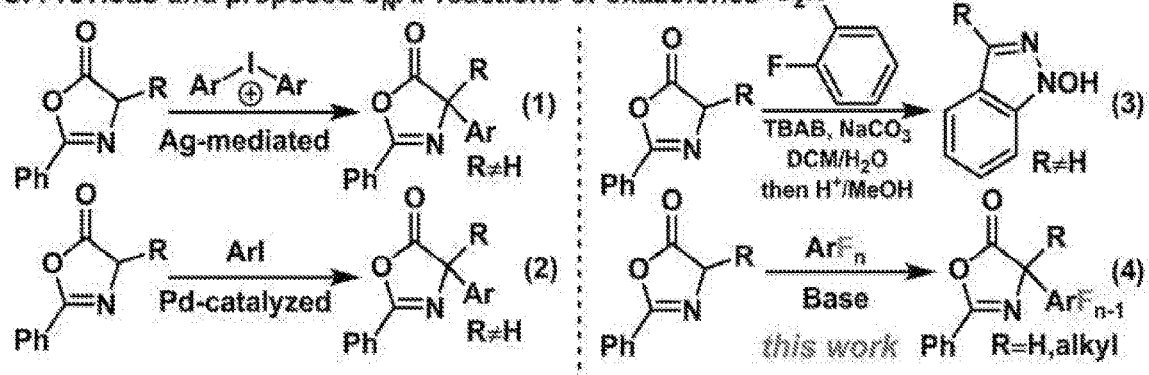
C. Previous and proposed S$_N$Ar reactions of oxazolones Next, we evaluated the perfluoroarylations of substituted FIG. 8
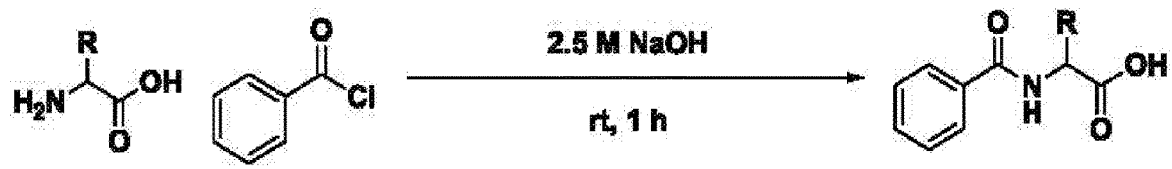
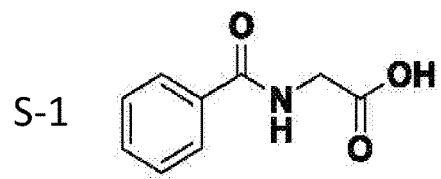
S-1
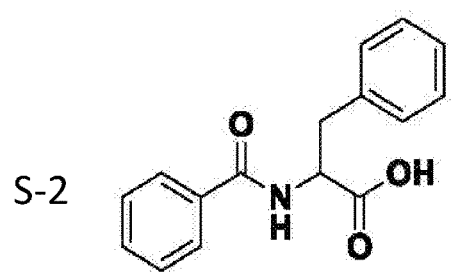
S-2
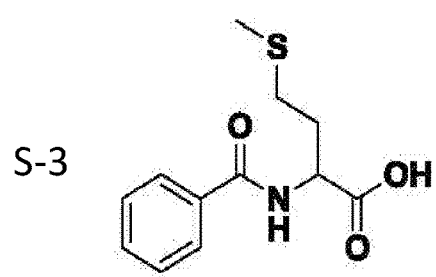
S-3
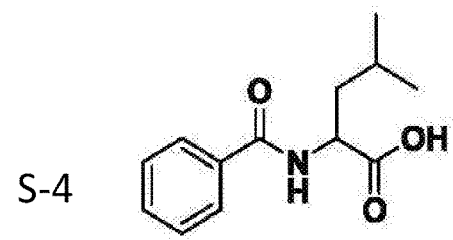
S-4

NMR spectra $^{19}$F NMR (376 MHz, Chloroform-$d$) 2a $^{13}$C NMR (101 MHz, Chloroform-$d$) 2a $^1$H NMR (400 MHz, Chloroform-$d$) 2b $^{13}$C NMR (101 MHz, Chloroform-$d$) 2b

$^{19}$F NMR (376 MHz, Chloroform-*d*) 2c

13C NMR (101 MHz, Chloroform-d) 2c

¹H NMR (400 MHz, Acetonitrile-$d_3$) 2d

19F NMR (376 MHz, Acetonitrile-$d_3$) 2d

¹H NMR (400 MHz, Chloroform-d) 2e

19F NMR (376 MHz, Chloroform-d) 2e

13C NMR (101 MHz, Chloroform-d) 2e

19F NMR (376 MHz, Chloroform-*d*) 2f

13C NMR (101 MHz, Chloroform-*d*) 2f

¹H NMR (400 MHz, Chloroform-*d*) 2g

¹⁹F NMR (376 MHz, Chloroform-d) 2g

13C NMR (101 MHz, Chloroform-d) 2g

¹H NMR (400 MHz, Chloroform-*d*) 2h

19F NMR (376 MHz, Chloroform-d) 2h

13C NMR (101 MHz, Chloroform-d) 2h $^1$H NMR (400 MHz, Chloroform-$d$) 2i

19F NMR (376 MHz, Chloroform-d) 2i $^{13}$C NMR (101 MHz, Chloroform-d) 2i

19F NMR (376 MHz, Acetonitrile-$d_3$) 3a

13C NMR (101 MHz, Acetonitrile-$d_3$) 3a

19F NMR (376 MHz, Acetonitrile-$d_3$) 3b

13C NMR (101 MHz, Acetonitrile-$d_3$) 3b

¹H NMR (400 MHz, Acetonitrile-$d_3$) 3c

19F NMR (376 MHz, Acetonitrile-$d_3$) 3c $^{13}$C NMR (101 MHz, Acetonitrile-$d_3$) 3c ¹H NMR (400 MHz, Acetonitrile-$d_3$) 3d 19F NMR (376 MHz, Acetonitrile-$d_3$) 3d 13C NMR (101 MHz, Acetonitrile-$d_3$) 3d ¹H NMR (400 MHz, Acetonitrile-$d_3$) 3e 19F NMR (376 MHz, Acetonitrile-$d_3$) 3e $^{13}$C NMR (101 MHz, Acetonitrile-$d_3$) 3e 1H NMR (400 MHz, D2O) 4a ¹³C NMR (101 MHz, D₂O) 4a 1H NMR (400 MHz, D2O) 4b 19F NMR (376 MHz, D2O) 4b 13C NMR (101 MHz, D2O) 4b ¹H NMR (400 MHz, D₂O) 4c $^{13}$C NMR (101 MHz, Acetonitrile-$d_3$) 4c ¹H NMR (400 MHz, D₂O) 5a 19F NMR (376 MHz, D2O) 5a ¹³C NMR (101 MHz, D₂O) 5a ¹H NMR (400 MHz, D₂O) 5b 13C NMR (101 MHz, D2O) 5b $^1$H NMR (400 MHz, DMSO-$d_6$) 5c 19F NMR (376 MHz, DMSO-$d_6$) 5c 13C NMR (101 MHz, DMSO-$d_6$) 5c 19F NMR (376 MHz, Chloroform-*d*) 6a 13C NMR (101 MHz, Chloroform-d) 6a $^1$H NMR (400 MHz, Chloroform-$d$) 6b 19F NMR (376 MHz, Chloroform-*d*) 6b ¹H NMR (400 MHz, Chloroform-*d*) 6c 19F NMR (376 MHz, Chloroform-d) 6c 13C NMR (101 MHz, Chloroform-d) 6c ¹H NMR (400 MHz, Chloroform-d) 6d 19F NMR (376 MHz, Chloroform-d) 6d $^{13}$C NMR (101 MHz, Chloroform-d) 6d 1H NMR (400 MHz, DMSO-d6) 7a 19F NMR (376 MHz, DMSO-$d_6$) 7a 13C NMR (101 MHz, DMSO-$d_6$) 7a 1H NMR (400 MHz, DMSO-$d_6$) 7b 19F NMR (376 MHz, DMSO-$d_6$) 7b $^{13}$C NMR (101 MHz, DMSO-$d_6$) 7b $^1$H NMR (400 MHz, DMSO-$d_6$) 7c 19F NMR (376 MHz, DMSO-$d_6$) 7c 13C NMR (101 MHz, DMSO-$d_6$) 7c

STRUCTURE AND SYNTHESIS OF HIGHLY FLUORINATED AMINO ACID DERIVATIVES

CROSS REFERENCE TO RELATED APPLICATIONS/INCORPORATION BY REFERENCE STATEMENT

This application is a US National Stage Application under 35 USC § 371 of International Application No. PCT/US2018/18766, filed Feb. 20, 2018; which claims benefit under 35 U.S.C. 119(e) of U.S. Provisional Application Ser. No. 62/461,257, filed Feb. 21, 2017, the entirety of which is hereby expressly incorporated herein by reference.

STATEMENT REGARDING FEDERALLY SPONSORED RESEARCH OR DEVELOPMENT

This invention was made with U.S. Government support under NIH Grant No. 1R01GM115697-01 awarded by the Department of Health and Human Services. The Government has certain rights in this invention.

BACKGROUND

Amino acids are an essential building block of all life. Fluorinated versions are important, as they enable the study and probing of biological systems. Additionally, the inclusion of fluorine often modifies the properties in interesting ways which may confer desirable traits to a fluorinated analog. For instance, fluorination can result in resistance to oxidative cleavage within drug molecules resulting in longer circulation times of the molecules. The effect of fluorine is vast and beyond the scope here, but this is why year after year the number of FDA approved drugs that contain fluorine continue to rise; currently about 33% of new drugs contain fluorine.

Incorporation of unnatural amino acids into proteins has been an informative yet powerful approach in the study of protein structure, stability, and design. Many fluorinated phenylalanine and alanine analogs have been impactful in proteomics thus far, and finding new amino acid analogs and building blocks with unique properties has been highly desirable. Many biochemical companies and academic investigators can benefit from a broad range of fluorinated α-amino acids, and groups have studied the stability of collagen and the amino acid uptake of tumor cells by F18 [Yoder et al. *Chemical Society Reviews* (2002) 31:335; Laverman et al., *European Journal of Nuclear Medicine and Molecular Imaging* (2002) 29:681]. In addition, many peptides containing fluorine have been used as anti-microbial peptides (AMPs) to prevent microbial growth [Salwiczek, et al. *Chemical Society Reviews* (2012) 41:2135; Laverman et al., incorporated supra]. From a commercial standpoint, companies such as AP Bioscience LLC (Princeton, N.J.) offer fluorinated amino acids (see AP Bioscience Product List P #7129596).

Multifluorinated arenes and heteroarenes represent an important motif, owing to the ability of fluorine to substantially alter the performance of molecules in various applications (FIG. 1). However, in sharp contrast to their importance, there is a relative dearth of methods that rapidly yield multifluorinated arenes, and thus, there is a need for methods to access multifluorinated (hetero) arenes.

Therefore, there is a need in the art for new and improved methods of producing these desired types of molecules that overcome the disadvantages and defects of the prior art. It is to such new and improved methods, as well as products produced from said methods, that the present disclosure is directed.

BRIEF DESCRIPTION OF THE DRAWINGS

FIG. 1 illustrates multifluorinated arenes, defluorination as a strategy, and arylation of oxazolones.

FIG. 8 illustrates General procedure A for synthesis of N-benzoyl amino acids.

FIG. 16 contains a $^1$H NMR spectra (400 MHz), Chloroform-d) of species 2a.

FIG. 17 contains a $^{19}$F NMR spectra (376 MHz), Chloroform-d) of species 2a.

FIG. 18 contains a $^{13}$C NMR spectra (101 MHz), Chloroform-d) of species 2a.

FIG. 43 contains a $^{1}$H NMR spectra (400 MHz), Acetonitrile-$d_3$) of species 3a.

FIG. 44 contains a $^{19}$F NMR spectra (376 MHz), Acetonitrile-$d_3$) of species 3a.

FIG. 45 contains a $^{13}$C NMR spectra (101 MHz), Acetonitrile-$d_3$) of species 3a.

FIG. 58 contains a $^{1}$H NMR spectra (400 MHz), $D_2O$) of species 4a.

FIG. 59 contains a $^{19}$F NMR spectra (376 MHz), $D_2O$) of species 4a.

FIG. 60 contains a $^{13}$C NMR spectra (101 MHz), $D_2O$) of species 4a.

FIG. 67 contains a $^{1}$H NMR spectra (400 MHz), $D_2O$) of species 5a.

FIG. 68 contains a $^{19}$F NMR spectra (376 MHz), $D_2O$) of species 5a.

FIG. 69 contains a $^{13}$C NMR spectra (101 MHz), $D_2O$) of species 5a.

FIG. 76 contains a $^{1}$H NMR spectra (400 MHz), Chloroform-d) of species 6a.

FIG. 77 contains a $^{19}$F NMR spectra (376 MHz), Chloroform-d) of species 6a.

FIG. 78 contains a $^{13}$C NMR spectra (101 MHz), Chloroform-d) of species 6a.

FIG. 88 contains a $^{1}$H NMR spectra (400 MHz), DMSO-$d_6$) of species 7a.

FIG. 89 contains a $^{19}$F NMR spectra (376 MHz), DMSO-$d_6$) of species 7a.

FIG. 90 contains a $^{13}$C NMR spectra (101 MHz), DMSO-$d_6$) of species 7a.

DETAILED DESCRIPTION

Figure 2:
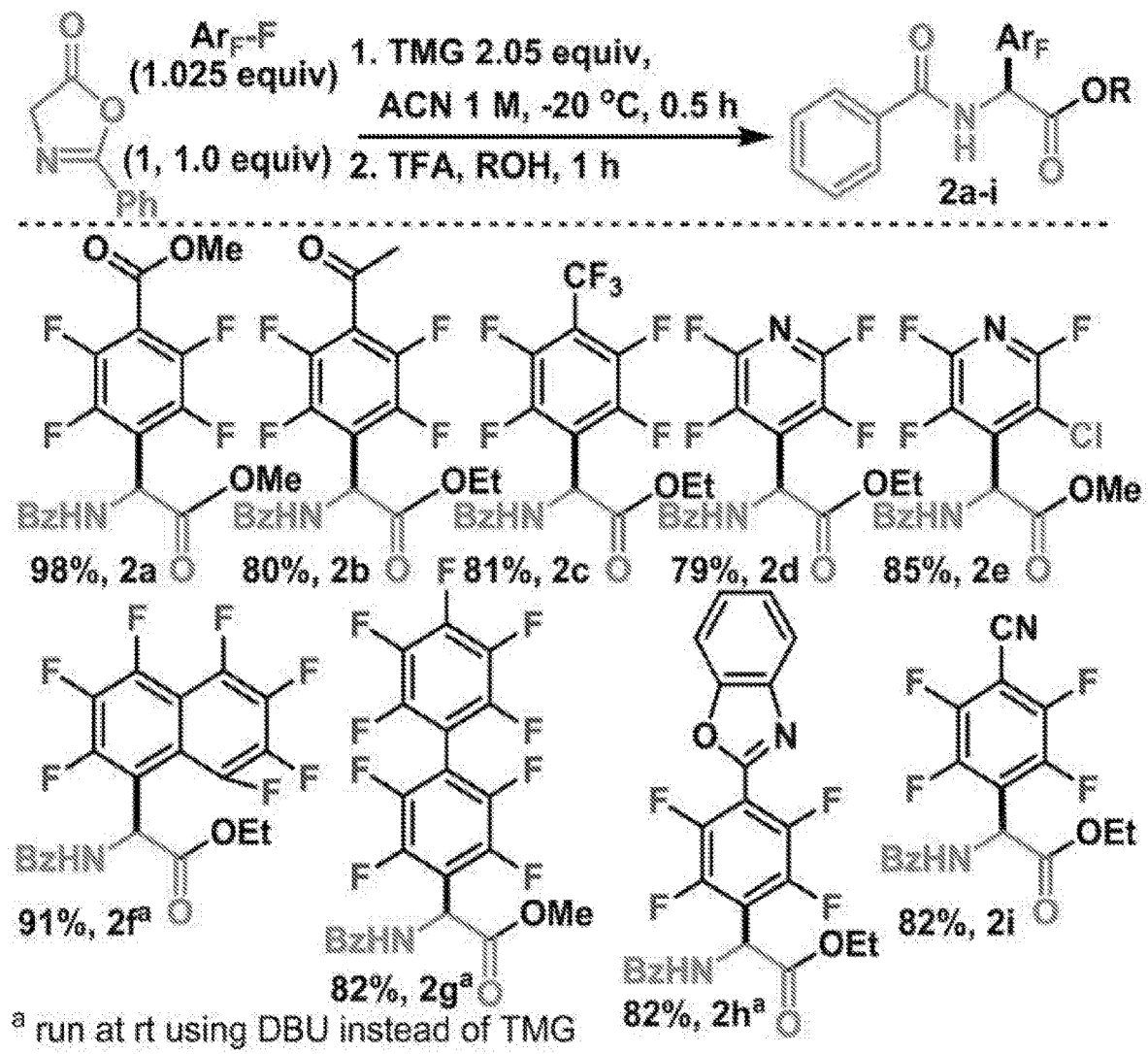
FIG. 2 illustrates arylation and esterification of oxazolone.

Before explaining at least one embodiment of the inventive concept(s) in detail by way of exemplary language and results, it is to be understood that the inventive concept(s) is not limited in its application to the details of construction and the arrangement of the components set forth in the following description. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Unless otherwise defined herein, scientific and technical terms used in connection with the presently disclosed inventive concept(s) shall have the meanings that are commonly understood by those of ordinary skill in the art. Further, unless otherwise required by context, singular terms shall include pluralities and plural terms shall include the singular. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses and chemical analyses.

All patents, published patent applications, and non-patent publications mentioned in the specification are indicative of the level of skill of those skilled in the art to which this presently disclosed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions and/or methods disclosed herein can be made and executed without undue experimentation in light of the present disclosure. While the compositions and methods of the inventive concept(s) have been described in terms of particular embodiments, it will be apparent to those of skill in the art that variations may be applied to the compositions and/or methods and in the steps or in the sequence of steps of the methods described herein without departing from the concept, spirit, and scope of the inventive concept(s). All such similar substitutions and modifications apparent to those skilled in the art are deemed to be within the spirit, scope, and concept of the inventive concept(s) as defined by the appended claims.

As utilized in accordance with the present disclosure, the following terms, unless otherwise indicated, shall be understood to have the following meanings:

The use of the term "a" or "an" when used in conjunction with the term "comprising" in the claims and/or the specification may mean "one," but it is also consistent with the meaning of "one or more," "at least one," and "one or more than one." As such, the terms "a," "an," and "the" include plural referents unless the context clearly indicates otherwise. Thus, for example, reference to "a compound" may refer to one or more compounds, two or more compounds, three or more compounds, four or more compounds, or greater numbers of compounds. The term "plurality" refers to "two or more."

The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z. The use of ordinal number terminology (i.e., "first," "second," "third," "fourth," etc.) is solely for the purpose of differentiating between two or more items and is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive. For example, a condition "A or B" is satisfied by any of the following: A is true (or present) and B is false (or not present), A is false (or not present) and B is true (or present), and both A and B are true (or present).

As used herein, any reference to "one embodiment," "an embodiment," "some embodiments," "one example," "for example," or "an example" means that a particular element, feature, structure, or characteristic described in connection with the embodiment is included in at least one embodiment. The appearance of the phrase "in some embodiments" or "one example" in various places in the specification is not necessarily all referring to the same embodiment, for example. Further, all references to one or more embodiments or examples are to be construed as non-limiting to the claims.

Throughout this application, the term "about" is used to indicate that a value includes the inherent variation of error for a composition/apparatus/device, the method being employed to determine the value, or the variation that exists among the study subjects. For example, but not by way of limitation, when the term "about" is utilized, the designated value may vary by plus or minus twenty percent, or fifteen percent, or twelve percent, or eleven percent, or ten percent, or nine percent, or eight percent, or seven percent, or six percent, or five percent, or four percent, or three percent, or two percent, or one percent from the specified value, as such variations are appropriate to perform the disclosed methods and as understood by persons having ordinary skill in the art.

As used in this specification and claim(s), the words "comprising" (and any form of comprising, such as "comprise" and "comprises"), "having" (and any form of having, such as "have" and "has"), "including" (and any form of including, such as "includes" and "include"), or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, when associated with a particular event or circumstance, the term "substantially" means that the subsequently described event or circumstance occurs at least 80% of the time, or at least 85% of the time, or at least 90% of the time, or at least 95% of the time. For example, the term "substantially adjacent" may mean that two items are 100% adjacent to one another, or that the two items are within close proximity to one another but not 100% adjacent to one another, or that a portion of one of the two items is not 100% adjacent to the other item but is within close proximity to the other item.

The term "polypeptide" as used herein will be understood to refer to a polymer of amino acids. The polymer may include d-, l-, or artificial variants of amino acids. In addition, the term "polypeptide" will be understood to include peptides, proteins, and glycoproteins.

The terms "analog," "derivative," or "variant" as used herein will be understood to refer to a variation of the normal or standard form or the wild-type form of molecules. For polypeptides, an analog may be a variant (polymorphism), a mutant, and/or a naturally or artificially chemically modified version of the wild-type polypeptide (including combinations of the above). Such analogs may have higher, full, intermediate, or lower activity than the normal form of the molecule, or no activity at all. Alternatively and/or in addition thereto, for a chemical, an analog may be any structure that has the desired functionalities (including alterations or substitutions in the core moiety), even if comprised of different atoms or isomeric arrangements.

As used herein, "substantially pure" means an object species is the predominant species present (i.e., on a molar basis it is more abundant than any other individual species in the composition), and a substantially purified fraction is a composition wherein the object species comprises at least about 50 percent (on a molar basis) of all macromolecular species present. Generally, a substantially pure composition will comprise more than about 80 percent of all macromolecular species present in the composition, such as (but not limited to) more than about 85%, 90%, 95%, and 99%. In a particular (but non-limiting) embodiment, the object species is purified to essential homogeneity (contaminant species cannot be detected in the composition by conventional detection methods), wherein the composition consists essentially of a single macromolecular species.

Turning now to the inventive concept(s), certain non-limiting embodiments of the present disclosure are directed to a method of synthesizing a polyfluorinated amino acid derivative. The method comprises the steps of: (a) deprotonating an oxazolone to yield an oxazolone enolate; (b) reacting the oxazolone enolate with a polyfluoroarene, resulting in nucleophilic aromatic substitution of the oxazolone with the polyfluoroarene to produce a polyfluoroarylated oxazolone intermediate; and (c) opening the oxazolone ring of the polyfluoroarylated oxazolone intermediate to form a polyfluoroaryl N-benzoyl protected amino acid derivative.

Any polyfluoroarenes known in the art or otherwise contemplated herein may be utilized in accordance with the present disclosure. The term "polyfluoroarene," as used herein, will be understood to refer to a composition that includes at least two fluorines; however, the term "polyfluoroarene" is not limiting of any other elements that may be present in the composition. That is, the polyfluoroarene may actually be a polyhalogenated arene and thus include one or more other halogens (i.e., chlorine, bromine, and/or iodine).

In addition, in a particular (but non-limiting) embodiment, the polyfluoroarene may be a perfluoroarene or a perhalogenated arene.

In one non-limiting example, the polyfluoroarene is a polyfluorinated heteroarene, and the product of step (c) is a polyfluoroheteroaryl N-benzoyl protected amino acid derivative. In a particular (but non-limiting) embodiment, all of the hydrogens of the arene ring have been replaced with a fluorine (i.e., a perfluoroarene) or a combination of fluorine and one or more other halogens (i.e., perhalogenated arene). In one non-limiting example, the polyfluoroarene is a perfluoroarene, and the product of step (c) is a perfluoroaryl N-benzoyl protected amino acid derivative. In another non-limiting example, the polyfluoroarene is a perfluoroheteroarene, and the product of step (c) is a perfluoroheteroaryl N-benzoyl protected amino acid derivative.

In certain non-limiting embodiments, the method further comprises the step of deprotecting the polyfluoroaryl N-benzoyl protected, amino acid derivative to produce a polyfluoroaryl amino acid derivative. Any deprotection methods known in the art or otherwise contemplated herein may be utilized in accordance with the presently disclosed methods. In one particular (but non-limiting) example, the polyfluoroaryl N-benzoyl protected, amino acid derivative is deprotected using an acid, such as (but not limited to) hydrochloric acid (HCl).

In certain non-limiting embodiments, the method further comprises the step of decarboxylating the polyfluoroaryl amino acid derivative. Any decarboxylation methods known in the art or otherwise contemplated herein may be utilized in accordance with the presently disclosed methods. In one particular (but non-limiting) example, the polyfluoroaryl amino acid derivatives are decarboxylated using acetone.

Any of the methods described herein above may further include the step of isolating the polyfluoroaryl amino acid derivatives produced therein. Methods of isolation are well known in the art, and thus no further description thereof is deemed necessary.

The products of the presently disclosed methods may be derivatives of any naturally occurring or non-naturally occurring amino acids known in the art. For example (but not by way of limitation), in certain non-limiting embodiments, the product is a derivative of alanine, glycine, methionine, phenylalanine, or valine. Alternatively (but not by way of limitation), the product is a derivative of arginine, asparagine, cysteine, glutamine, histidine, isoleucine, leucine, proline, serine, threonine, tryptophan, or tyrosine.

In certain non-limiting embodiments, step (c) of the method is further defined as opening the oxazolone ring by any methods known in the art or otherwise contemplated herein, such as (but not limited to) exposing the polyfluoroarylated oxazolone intermediate to at least one of water, an alcohol, and a nucleophile. Any alcohol or nucleophile capable of opening the oxazolone ring as described herein may be utilized in accordance with the present disclosure. Non-limiting examples of nucleophiles that can be utilized in accordance with the present disclosure include $NH_3$, primary, and secondary amines, such as (but not limited to) tetramethyl guanidine (TMG).

In certain non-limiting embodiments, the method may be further defined as a one pot synthesis method.

In one non-limiting example, the polyfluoroaryl N-benzoyl protected amino acid derivative produced by the methods disclosed herein is a polyfluoroaryl 2-aminohydantoin.

Certain non-limiting embodiments of the present disclosure are directed to a one pot synthesis method for producing a polyfluorinated amino acid derivative. In the method, the following reactants are combined, either simultaneously or wholly or partially sequentially: (i) at least one oxazolone; (ii) at least one polyfluoroarene; (iii) at least one amine; and (iv) at least one acid. Two or more of the reactants are then reacted together under one or more sets of reaction conditions to form a polyfluoroaryl N-benzoyl protected amino acid derivative.

Any polyfluoroarenes as described in detail herein above may be utilized in the one pot synthesis method. For example (but not by way of limitation), the polyfluoroarene may be a polyhalogenated arene, a perfluoroarene, a perhalogenated arene, a polyfluoro heteroarene, or a perfluoroheteroarene.

In one non-limiting example, the polyfluoroarene is a polyfluorinated heteroarene, and the product of the one pot synthesis method is a polyfluoroheteroaryl N-benzoyl protected amino acid derivative. In a particular (but non-limiting) embodiment, all of the hydrogens of the arene ring have been replaced with a fluorine (i.e., a perfluoroarene) or a combination of fluorine and one or more other halogens (i.e., a perfluoroheteroarene). In one non-limiting example, the polyfluoroarene is a perfluoroarene, and the product of the one pot synthesis method is a perfluoroaryl N-benzoyl protected amino acid derivative. In one non-limiting example, the polyfluoroarene is a perhalogenated arene, and the product of the one pot synthesis method is a perhalogenated N-benzoyl protected amino acid derivative. In another non-limiting example, the polyfluoroarene is a perfluoroheteroarene, and the product of the one pot synthesis method is a perfluoroheteroaryl N-benzoyl protected amino acid derivative.

Any amine(s) known in the art or otherwise contemplated herein that is capable of being utilized to produce the polyfluoroaryl N-benzoyl protected amino acid derivative and thus capable of functioning as described herein may be utilized in accordance with the present disclosure. Non-limiting examples of amines that can be utilized in accordance with the present disclosure include diisopropylamine (DIPEA), tetramethyl guanidine (TMG), acetonitrile (ACN), and/or 1,8-diazabicyclo[5.4.0]undec-7-ene (DBU).

Similarly, any acid(s) known in the art or otherwise contemplated herein that is capable of being utilized to produce the polyfluoroaryl N-benzoyl protected amino acid derivative and thus capable of functioning as described herein may be utilized in accordance with the present disclosure. Non-limiting examples of acids that can be utilized in accordance with the present disclosure include trifluoroacetic acid (TFA) and/or hydrochloric acid (HCl). In addition, the acid may be provided in the form of an acid/alcohol solution; non-limiting examples of alcohols that may be utilized with one or more acids as described herein include methanol and/or ethanol.

The one pot synthesis method can be utilized to produce derivatives of any naturally occurring or non-naturally occurring amino acids known in the art. For example (but not by way of limitation), in certain non-limiting embodiments, the product is a derivative of alanine, glycine, methionine, phenylalanine, or valine. Alternatively (but not by way of limitation), the product is a derivative of arginine, asparagine, cysteine, glutamine, histidine, isoleucine, leucine, proline, serine, threonine, tryptophan, or tyrosine.

In certain particular (but non-limiting) embodiments, the product of the one pot synthesis method is a polyfluorinated 2-aminohydantoin.

In certain non-limiting embodiments, the one pot synthesis method comprises at least two sets of reactions conditions, wherein: (i), (ii), and (iii) are reacted at about −20° C.
to provide a mixture, and the mixture is then allowed to warm to about room temperature prior to adding (iv). In a particular (but non-limiting) example that utilizes these reaction conditions, (iii) can be a combination of ACN and TMG; and (iv) can be HCl or a TFA/alcohol solution.

In another non-limiting embodiment, (i), (ii), and (iii) are mixed and reacted at room temperature prior to addition of (iv). In a particular (but non-limiting) example that utilizes these reaction conditions, (iii) comprises a combination of ACN and DBU or a combination of ACN and DIPEA, and (iv) is a TFA/alcohol solution.

Each of the methods described or otherwise contemplated herein may produce the polyfluoroaryl amino acid derivative with any level of yield. For example (but not by way of limitation), the polyfluoroaryl amino acid derivative can be synthesized with a yield of at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, and at least about 99%. In addition, the scope of the presently disclosure also includes the production of the polyfluoroaryl amino acid derivative at any percent yield that falls within any range formed from the combination of two values listed above (for example, a range of from about 10% to about 99%, a range of from about 30% to about 98%, a range of from about 50% to about 97%, a range of from about 60% to about 96%, a range of from about 70% to about 95%, etc.).

Certain non-limiting embodiments of the present disclosure are directed to a polyfluorinated amino acid derivative produced by any of the methods described or otherwise contemplated herein.

Certain non-limiting embodiments of the present disclosure are also directed to an isolated composition that comprises at least one polyfluoroaryl amino acid derivative, wherein the polyfluoroaryl amino acid derivative may be (in certain non-limiting embodiments) produced as described or otherwise contemplated herein.

Certain additional non-limiting embodiments of the present disclosure are directed to a peptide, polypeptide, or protein that comprises at least one polyfluoroaryl amino acid derivative, wherein the polyfluoroaryl amino acid derivative may be (in certain non-limiting embodiments) produced as described or otherwise contemplated herein. In particular (but non-limiting) embodiments, the peptide, polypeptide, or protein is isolated.

EXAMPLES

Examples are provided hereinbelow. However, the present disclosure is to be understood to not be limited in its application to the specific experimentation, results, and laboratory procedures disclosed herein. Rather, the Examples are simply provided as one of various embodiments and are meant to be exemplary, not exhaustive.

Example 1—Polyfluoroarylation of Oxazolones: Access to Non-Natural Fluorinated Amino Acids Multifluorinated arenes and heteroarenes represent an important motif, owing to the ability of fluorine to substantially alter the performance of molecules in various applications (FIG. 1). However, in sharp contrast to their importance, there is a relative dearth of methods that rapidly yield multifluorinated arenes, and thus, there is a need for methods to access multifluorinated (hetero) arenes.

Selective installation of fluorine is possible, but often is lengthy and requires a unique strategy for every fluorination pattern on every arene (FIG. 1, Panel B, right)(Lentz et al., 2013; Ahrens et al., 2015; Weaver et al., 2014; Kiplinger et al., 1994; and Amii et al., 2009), making it less than ideal for discovery chemistry, which demands the ability to rapidly synthesize analogs. Alternatively, C—F functionalization of highly fluorinated or perfluorinated (hetero) arenes is an attractive approach, since perfluorinated arenes are relatively inexpensive and already possess the difficult to install fluorines in the desired locations (FIG. 1, Panel B, left). The potential advantage of the C—F functionalization approach has been recognized by others, and inroads are being made (Lentz et al., 2013; Ahrens et al., 2015; Weaver et al., 2014; Kiplinger et al., 1994; and Amii et al., 2009). Taken in conjunction with recently developed photocatalytic C—F functionalization (Singh et al., 2016; Senaweera et al., 2016; Singh et al., 2015; Senaweera et al., 2014; Lu et al., 2016; and Xie et al., 2016), considerable access to these important motifs can be realized.

Perfluoroarenes are particularly well suited for nucleophilic aromatic substitution, since the difficult step in such a reaction is typically nucleophilic attack on the carbon by the incoming nucleophile. The small size and the electronegative nature of the fluoride facilitate the addition step, and additional ring fluorination (except para-fluorination) further accelerates the addition through inductive effects (Lentz et al., 2013; Ahrens et al., 2015; Weaver et al., 2014; Kiplinger et al., 1994; and Amii et al., 2009). However, despite the feasibility and the potential for enhancing the pool of fluorinated aryl building blocks, many of these potential reactions remain undeveloped.

Amino acids and derivatives are indispensable building blocks within mainstream organic chemistry. The addition of an oxazolone enolate to an electrophile is a common strategy to elaborate the alpha amino acid motif. α-Arylation of the oxazolone enolate has been accomplished via Ag-mediated arylation with diaryliodonium salts (FIG. 1, Panel C, eqn 1)(Chai et al., 2014), Pd-catalyzed cross-coupling of aryl-bromides (eqn 2)(Liu et al., 2003), and pyridine addition via nucleophilic addition to N-tosylated pyridines (Johnson et al., 2016). However, these methods do little to access amino acids that possess highly fluorinated arenes, because the requisite fluorinated starting materials are not available. Additionally, while these methods proved useful for accessing tertiary carbons, secondary carbons were never obtained. It was posited that the oxazolone enolate might undergo uncatalyzed substitution of the perfluoroarenes, via nucleophilic aromatic substitution ($S_NAr$), and because of the anticipated diminishment of nucleophilicity of the product, would cleanly provide the product without over arylation. Importantly, if successful, this would provide rapid and facile access to non-natural multifluoroarylated amino acids.

The oxazolone is a versatile nucleophile which can conceivably undergo addition at C2, C4, and even the C5-oxygen bond (Wang et al., 2016). The only example of $S_NAr$-type reactions with oxazolones is the addition to 2-nitroarenes, which undergoes subsequent cyclization with the nitro functional group to give indazole products (eqn 3)(D'Anello et al., 1988). Though the reaction leads to a different product, it demonstrates that oxazolone enolate might be a competent nucleophile in the addition to perfluoroarenes.

The investigation began using 2-phenyloxazol-5(4H)-one (Table 1; 1) derived from glycine with pentafluoropyridine and diisopropylamine (DIPEA) in acetonitrile which were optimal conditions in the analogous addition of Meldrum's acid enolate (Senaweera et al., 2014). Initially, the reaction was ran at 45° C. (Table 1, entry 1), but it was found that the reaction gave full conversion at room temperature, giving complete conversion to the C4-arylation product within just 20 min (Table 1, entry 2). Owing to the relatively fast addition, it was possible to lower the amount of the arene to 1.025 equiv (Table 1, entry 3) without any detectable diminishment of conversion. Previously, it was observed that DIPEA can undergo a slow N substitution/dealkylation sequence when subjected to highly electrophilic perfluoroarenes at elevated temperatures (Senaweera et al., 2014). Consequently, by keeping the amount of excess perfluoroarene low (0.025 equiv) and reactions at room temperature, the amine substituted product was not observed. A solvent screen (Table 1, entries 2-7) revealed polar aprotic solvents work best, while ethereal, hydrocarbon, and halogenated solvents gave little to no conversion (Table 1, entries 5-7). To facilitate reaction scale up, the arene loading was reduced while simultaneously concentrating the reaction to 1 M (Table 1, entry 8), which smoothly proceeded to full conversion. Next, a less activated arene, octafluorotoluene (b), instead of pentafluoropyridine (Table 1, entry 9), was evaluated, but unfortunately it gave very low conversion under these conditions.

However, upon switching to stronger base, tetramethyl guanidine (TMG-H$^+$, pKa$_{(MeCN)}$=23.3 compared to ~18.8 for DIPEA-H$^+$)(Margetic, 2009). Complete conversion was observed, even at −20° C. (Table 1, entry 10). Lower temperatures were advantageous to avoid TMG addition to the perfluoroarenes (not shown).

Thus, with the use of tetramethylguanidine (TMG) at −20° C., it was possible to achieve full conversion of 1, using just 1.025 equivalents of octafluorotoluene (Table 1; b, entry 11). When these reaction conditions were applied to pentafluoropyridine (Table 1; a, entry 12), quantitative conversion to the product was observed by $^{19}$F NMR, demonstrating that the TMG conditions would have a broader scope.

With the optimal conditions in hand (Table 1, entry 12), it was possible to explore the scope. Typically, oxazolones are not easily isolated due to their predisposition for ring opening, and instead are usually derivatized immediately to a more stable molecule (Fisk et al., 2007). This is easily accomplished under acidic conditions, since the oxazolone behaves as an activated ester. Ring opening of the oxazolone was explored with alcohols to form perfluoroaryl N-benzoyl protected esters (FIG. 2). Protonation of the oxazolone under anhydrous conditions was found to be the key to high yield, and this was best accomplished using catalytic amounts of trifluoroacetic acid in dry alcohol.

TABLE 1

Optimization of Reaction Conditions

[Reaction scheme: oxazolone (1) with Ph substituent + Ar_F—F, Base, solvent → product with positions labeled 1,2,3,4,5, Ar_F at position 4, Ph at position 2, Base-H⁺ O⁻ at position 5]

[Arenes shown: a = perfluoropyridine with site of substitution at 4-position; b = perfluorotoluene (CF_3 group) with site of substitution]

| Entry | Conditions | Arene (equiv) | Amine (equiv) | T (° C.) | % conv$^a$ |
|---|---|---|---|---|---|
| 1. | 0.3M ACN | a (2) | DIPEA (3) | 45 | 100 |
| 2. | 0.3M ACN | a (2) | DIPEA (3) | 22 | 100 |
| 3. | 0.3M DMF | a (2) | DIPEA (3) | 22 | 100 |
| 4. | 0.3M DMSO | a (2) | DIPEA (3) | 22 | 100 |
| 5. | 0.3M THF | a (2) | DIPEA (3) | 22 | 24 |
| 6. | 0.3M Tol | a (2) | DIPEA (3) | 22 | <5 |
| 7. | 0.3M DCM | a (2) | DIPEA (3) | 22 | 25 |
| 8. | 1M ACN | a (1.025) | DIPEA (3) | 22 | 100 |
| 9. | 1M ACN | b (2) | DIPEA (3) | 22 | <5 |
| 10. | 1M ACN | b (2) | TMG (2.4) | −20 | 100 |
| 11. | 1M ACN | b (1.025) | TMG (2.05) | −20 | 100 |
| 12. | 1M ACN | a (1.025) | TMG (2.05) | −20 | 100 |

$^a$Conversion determined by $^{19}$F NMR after 30 min.

The scope of the one pot perfluoroarylation and esterification of the oxazolone was explored (FIG. 2). Generally, the reaction scope was very good and worked well with many of the commercially available perfluoroarenes. No undesired reactivity was observed with esters (2a) or ketones (2b). Less activated octafluorotoluene, octafluoronapthalene, and de-cafluorobiphenyl all reacted to give the expected product in excellent yields (2c, 2f, and 2g). Both benzoxazoles (2h) and benzonitriles (2i) underwent arylation and esterification in good yield. Comparison of pyridine products 2d and 2e revealed the preference for substitution of the 4-fluoro over that of 3-chloro leaving group. This is consistent with a S$_N$Ar reaction, and is expected, as fluorine is the preferred nucleofuge, and attack of the 4-position maximizes delocalization of the charge in the Meisenheimer complex.

However, substitution of 4-chlorotetrafluoropyridine (see Example 2) leads primarily to substitution of the chloride, rather than substituting at the 2-fluoro position, to give 2d as the major product. This demonstrates, in this case, that the regioselectivity may be primarily dictated by the electronics of the arene rather than the nucleofuge.

Figure 3:
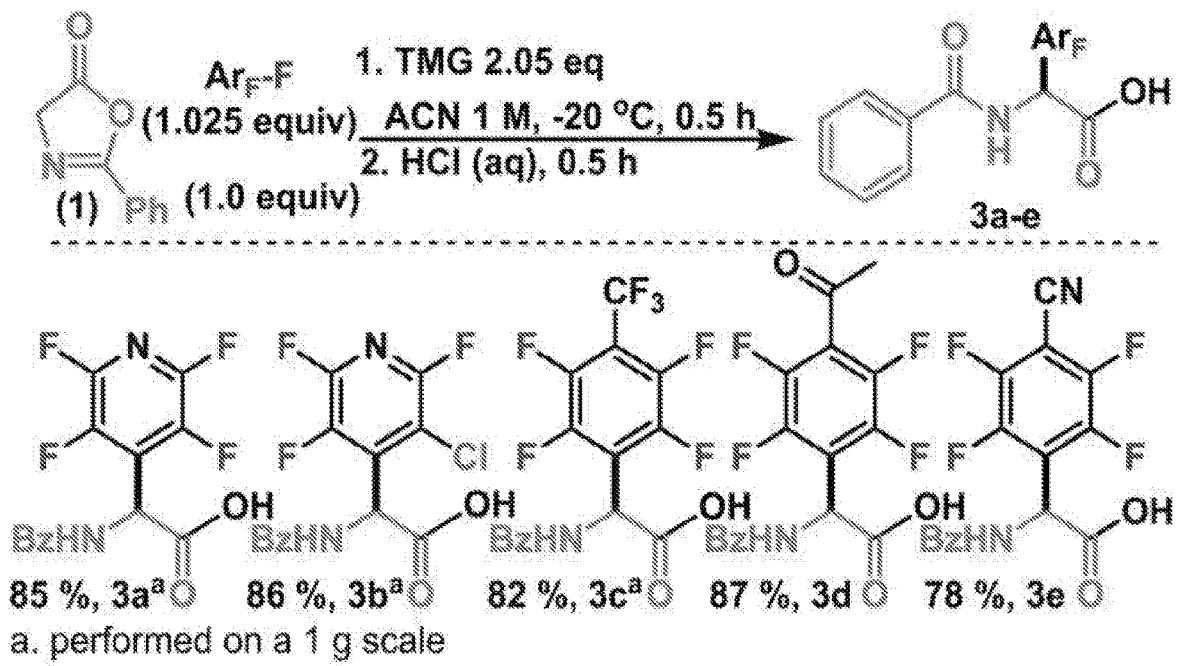
FIG. 3 illustrates multifluoroaryl amino acids.

Next, ring opening of oxazolones with water was explored, which would provide direct access to non-natural N-benzoyl protected amino acids in a rapid and facile manner (FIG. 3). The perfluoroarylated oxazolone intermediates could be efficiently hydrolyzed (3a-3e). However, since facilitating access to more elaborate fluorinated building blocks is a primary (but non-limiting) objective, chromatography-free conditions that were amenable to scaling were also developed, and allowed for synthesis of the amino acid derivatives on a gram scale with minimal effort. After initial removal of MeCN (acetonitrile), the crude acids were extracted with CHCl$_3$, washed with acidic brine, and stripped of solvent in vacuo. Next, the acid was washed with hexanes and trace dichloromethane to selectively extract the impurities and yield pure acids. This process was applied successfully on a gram scale for several substrates (3a-3c), illustrating that the method may be useful for making more sizeable quantities of the N-benzoyl protected acids.

Next, the deprotection of the N-benzoyl groups was probed in hopes of accessing the free amino acids. Unfortunately, in the case of pyridine derived 3a, standard deprotection conditions of refluxing in concentrated HCl led to the deprotected and decarboxylated ammonium salts. The amino acid derivatives apparently underwent a thermal decarboxylation; however, it was not clear whether debenzoylation occurred prior to or following decarboxylation. Fortunately, after lowering the reaction temperature to 60° C., it was found that the amino acids underwent smooth debenzoylation, but did not undergo the decarboxylation. Thus, by subjecting acids (FIG. 4; 3a-c) to aqueous HCl carefully heated to 60° C., the unprotected amino acids were acquired in quantitative yields. NMR doping experiments were performed, in which the isolated hydrochloride salts of amino acids (4a-c) were added after prolonged heating in HCl (see Example 2), and confirmed that debenzoylation occurs prior to decarboxylation.

Alternatively, upon exposure to acetone, the amino acid salts (4a-c) underwent rapid and quantitative decarboxylative protonation. Presumably, this takes place through a transiently formed Schiff base, which facilitates the decarboxylation and then undergoes hydrolysis to form (5a-c)(Al-Sayyab et al., 1968). Given the high yielding and facile nature of each step, the addition of oxazolone to perfluoroarenes is an attractive strategy to access highly fluorinated benzylic amine derivatives such as 5a-c.

Having generated a strategy to access a novel class of fluorinated amino acids and the inventors' own experience with the unexpected decarboxylation of the amino acid derivatives, the thermal stability of several derivatives was also explored. Thus, thermal gravimetric analysis was performed on several of the products that had been formed (FIG. 5). As expected, the benzoyl protected esters (2d) were thermally stable and gradually sublimed. However, the benzoyl protected acids 3a-c all underwent decarboxylation at 108° C., 132° C., and 159° C., respectively. The differences in decarboxylation temperature seem to reflect the stability of a benzylic anion; however, it may also correlate to basicity of the amide motif. Comparison of 3b and 4b shows that the HCl salts actually undergo a more facile thermal decarboxylation than the N-benzoylated substrate, and is consistent with the previous findings shown in FIG. 4. However, 4c failed to undergo decarboxylation and instead gradually sublimed. It may be possible that the 4c is sufficiently acidic that it instead sublimed through a small equilibrium of neutral (or potentially zwitterionic) amino acid.

Figure 6:
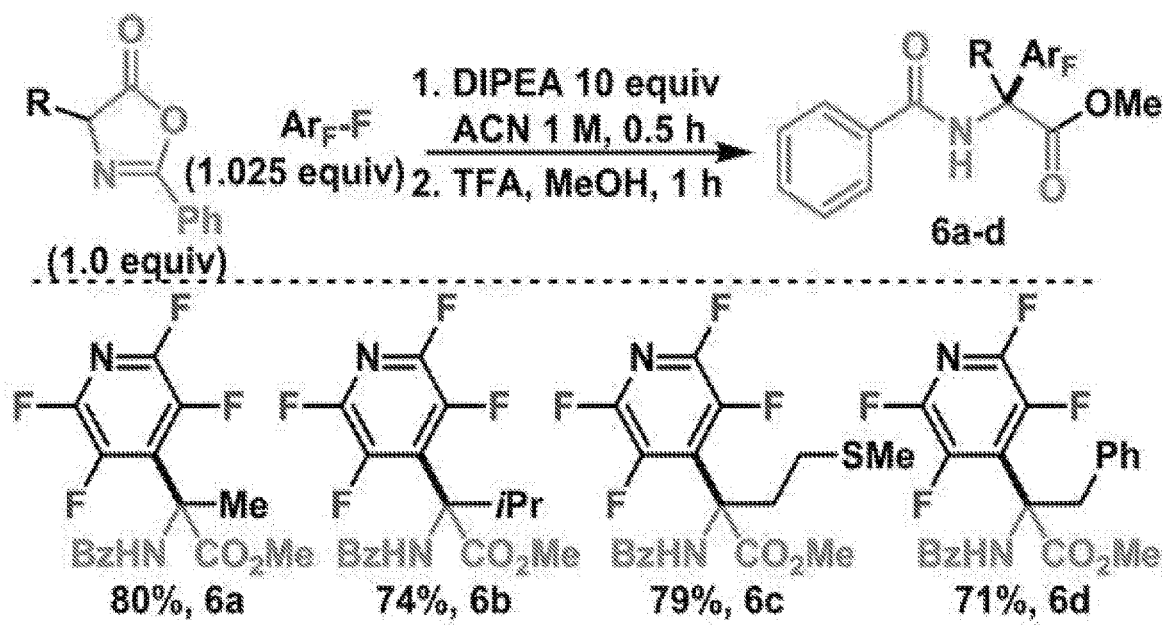
FIG. 6 illustrates fully substituted amino acid esters.

Next, the perfluoroarylations of substituted oxazolones were evaluated, which yield fully substituted, amino acid derivatives (FIG. 6). Upon additional substitution of the oxazolone, the carbonyl is permanently formed, which is prone to opening by nucleophiles, including TMG. Even the substituted oxazolone enolate underwent selective C4-addition to give the desired amino acids, rather than C2-addition, which has been observed for substituted oxazolones (Wang et al., 2016; Alemán et al., 2008). However, in order to be able to derivatize in the second step, it was advantageous to utilize DIPEA as the base. Perfluoroarylated amino acid esters were derived from alanine, valine, methionine, and phenylalanine in good yield (6a-d).

When TMG was utilized as the base, it was found that after arylation, the TMG would undergo nucleophilic ring opening to form N-acylated guanidines, which upon heating in HCl underwent debenzoylation and cyclization with extrusion of dimethyl amine. This sequence yields 2-aminohydantoins, which are currently being studied (Cruz et al., 2014; and Malamas et al., 2011) as possible inhibitors of BACE1, an enzyme believed to play a central role in the formation β-amyloid formation associated with Alzheimer's disease. Traditionally, 2-aminohydantoins have been synthesized by adding an activated carbon to the N-terminus, which then serves to bridge the N- and C-termini of the amino acid. In contrast, the guanidine serves in place of the activated carbon and is attached to the C-terminus. To the inventors' knowledge, this cyclization approach is novel and demonstrates the potential for a one-pot, three-component coupling that could be used to rapidly explore the chemical space surrounding this important motif.

In summary, it has been shown that the oxazolone enolate is capable of nucleophilic aromatic substitution and can be utilized to rapidly form fluorinated amino acid derivatives. Importantly, the reaction is highly selective both in terms of C—F and oxazolone regioselectivity. Furthermore, conditions have been provided that allow transformation of the product to valuable building blocks, namely, N-Bz esters, N-Bz acids, acid-HCl salts, and by way of Schiff-base decarboxylation, the benzylic amines. Furthermore, the behavior of these compounds towards thermal decarboxylation has also been reported, which indicate that the compounds should be stable at room temperature. Finally, the utility of the reaction and its product has been demonstrated by demonstrating its use in a 3-component reaction, which allows rapid access 2-aminohydantoins, a biologically relevant motif.

Example 2—Supporting Information for Example 1

General Experimental:

All reagents were obtained from commercial suppliers (Sigma Aldrich, St. Louis, Mo.; VWR International, Radnor, Pa.; TCI Chemicals, Portland, Oreg.; and Oakwood Chemicals, Estill, S.C.) and used without further purification unless otherwise noted. N-benzoyl alanine was purchased from Oakwood Chemicals, and all other N-benzoyl amino acids were synthesized according to literature procedures (Mesaik et al., 2004). Oxazolones were synthesized according to literature procedure (Melhado et al., 2007). Reactions were monitored by thin layer chromatography (TLC), (obtained from sorbent technology Silica XHL TLC Plates, w/UV254, glass backed, 250 μm, 20×20 cm) and were visualized with ultraviolet light, potassium permanganate stain, GC-MS (QP 2010S, Shimadzu equipped with auto sampler) and $^1$H NMR $^{19}$F NMR.

Isolations were carried out using Teledyne Isco Combiflash Rf 200i flash chromatograph with Sorbent normal phase silica (standard grade) (4 g, 12 g, 24 g, or 40 g) with product detection at 254 and 288 nm and evaporative light scattering detection. NMR spectra were obtained on a 400 MHz Bruker Avance III spectrometer and 400 MHz Varian spectrometer. $^1$H, $^{19}$F, and $^{13}$C NMR chemical shifts are reported in ppm relative to the residual protio solvent peak ($^1$H, $^{13}$C). IR spectra were recorded on Varian 800 FT-IR. Due to the C—F splitting, carbons that couple with fluorine were reported as multiplets. Melting points were determined on Stuart Digital (SMP10) melting point apparatus. High resolution mass spectrometry (HRMS) analysis was performed on LTQ-OrbitrapXL by Thermo Scientific ltd.

General procedure A for synthesis of N-benzoyl amino acids 1 (FIG. 8, upper panel):

Benzoyl chloride (1.2 equiv) was added incrementally in 4 portions over 30 minutes to a solution of the amino acid (1 equiv) and 2.5 M NaOH (3.8 equiv) in distilled water. After the addition was complete, the ice bath was removed, and the reaction was quenched by the dropwise addition of concentrated aqueous hydrochloric acid until pH 1 was reached, which resulted in precipitation of the product. The solid product was isolated by filtration and then recrystallized from water. The resulting crystals were air dried to give the desired N-benzoyl amino acid, which showed no trace of benzoic acid by $^1$H NMR.

S-1 (FIG. 8) was produced in 93% yield after isolation (10.86 g, 60.9 mmol) as a white solid. The general procedure A was followed using glycine (5.00 g, 66.6 mmol), benzoyl chloride (9.30 mL, 79.2 mmol), 2.5 M NaOH (100 mL, 251 mmol). $^1$H-NMR matched that previously reported in the literature (Mesaik et al., 2004).

S-2 (FIG. 8) was produced in 79% yield after isolation (3.20 g, 11.9 mmol) as a white solid. The general procedure A was followed using phenyl alanine (2.50 g, 15.1 mmol), benzoyl chloride (2.11 mL, 18.1 mmol), 2.5 M NaOH (23.0 mL, 57.4 mmol). $^1$H-NMR matched that previously reported in the literature (Badiola et al., 2014).

S-3 (FIG. 8) was produced in 66% yield after isolation (2.80 g, 11.1 mmol) as a white solid. The general procedure A was followed using methionine (2.50 g, 16.8 mmol), benzoyl chloride (2.34 mL, 20.1 mmol), 2.5% NaOH (25.5 mL, 63.8 mmol). $^1$H-NMR matched that previously reported in the literature (Witkowska et al., 2001).

S-4 (FIG. 8) was produced in 67% yield after isolation (2.41 g, 10.2 mmol) as a white solid. The general procedure A was followed using leucine (2.00 g, 15.2 mmol), benzoyl chloride (2.12 mL, 18.3 mmol), 2.5% NaOH (23.1 mL, 57.8 mmol). $^1$H-NMR matched that previously reported in the literature (Badiola et al., 2014).

Figure 9:
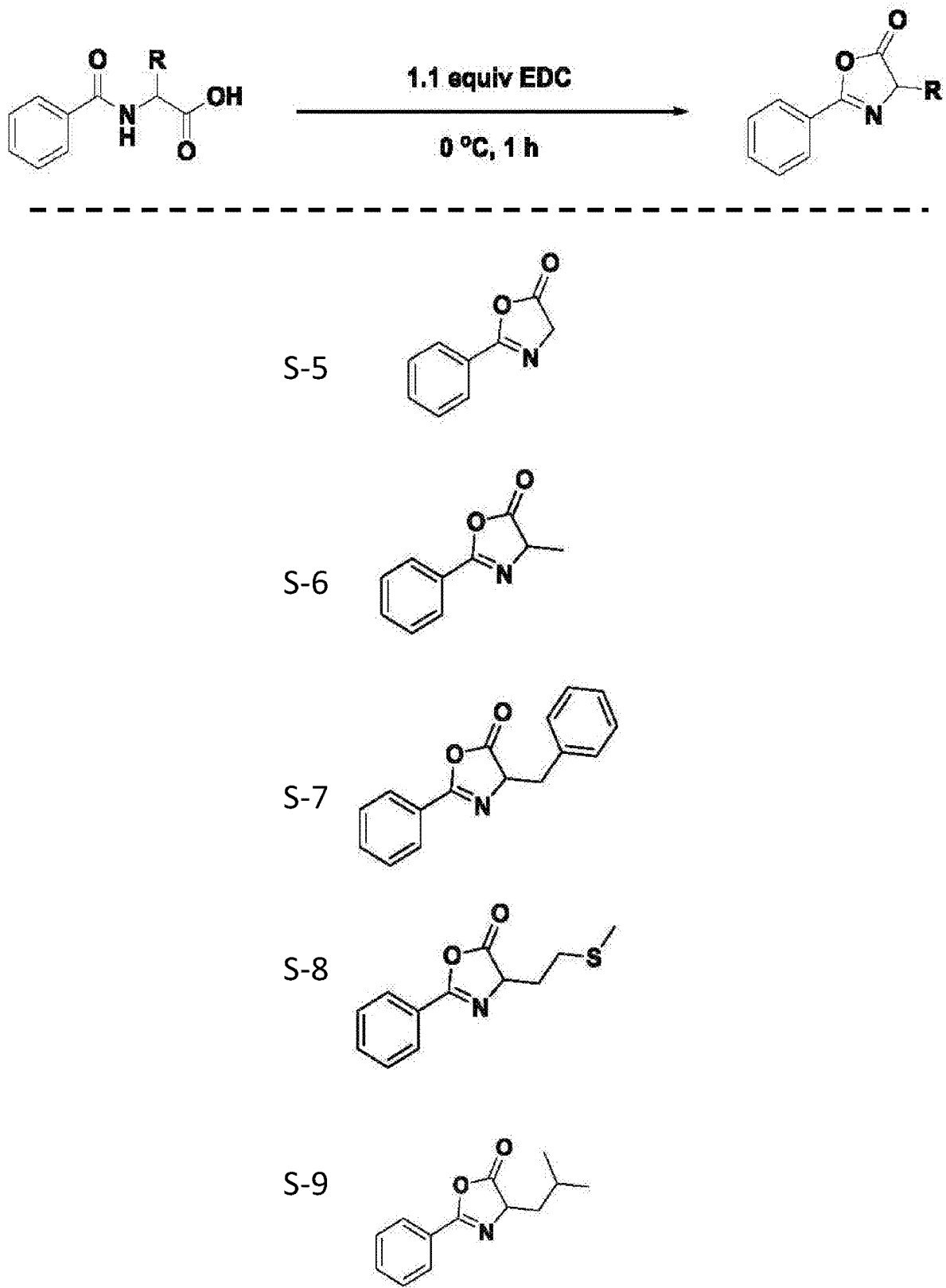
FIG. 9 illustrates General procedure B for synthesis of oxazolones.

General procedure B: for synthesis of oxazolones (FIG. 9, upper panel):

To a flame dried round bottom flask a suspension of N-benzoyl amino acid (1 equiv) in dry $CH_2Cl_2$ (0.07 M), under an argon atmosphere, at 0° C., was added EDC HCl (1.1 equiv). The materials were stirred at 0° C. for 1 hour. The reaction mixture was diluted with an equal volume of $CH_2Cl_2$, and washed successively with water, saturated aqueous $NaHCO_3$, and water (each ½ the volume of the organic phase), then dried over $MgSO_4$ and concentrated under reduced pressure. (Note: the oxazolones are moisture and thermally sensitive reagents; thus, as a precaution, the oxazolones were stored under argon at 5° C. until use).

S-5 (FIG. 9) was produced in 80% yield after isolation (1.80 g, 11.1 mmol) as a pale white solid. The general procedure B was followed using N-benzoyl glycine (2.50 g, 14.0 mmol), EDC (2.38 g, 15.3 mmol), $CH_2Cl_2$ (200 mL). $^1$H-NMR matched that previously reported in the literature (Melhado et al., 2007).

S-6 (FIG. 9) was produced in >95% yield after isolation (907 mg, 5.18 mmol) as a white solid. The general procedure B was followed using N-benzoyl alanine (1.00 g, 5.18 mmol), EDC (884 mg, 5.69 mmol), $CH_2Cl_2$ (74 mL). $^1$H-NMR matched that previously reported in the literature (Melhado et al., 2007).

S-7 (FIG. 9) was produced in 87% yield after isolation (806 mg, 3.21 mmol) as a white solid. The general procedure B was followed using N-benzoyl phenylalanine (990 mg, 3.68 mmol), EDC (628 mg, 4.04 mmol), CH$_2$Cl$_2$ (52.5 mL). $^1$H-NMR matched that previously reported in the literature (Melhado et al., 2007).

S-8 (FIG. 9) was produced in 74% yield after isolation (1.1 g, 4.68 mmol) as a pale white solid. The general procedure B was followed using N-benzoyl methionine (1.6 g, 6.32 mmol), EDC (1.08 g, 6.95 mmol), CH$_2$Cl$_2$ (90.2 mL). H-NMR matched that previously reported in the literature (Witkowska et al., 2001).

S-9 (FIG. 9) was produced in 95% yield after isolation (553 mg, 2.45 mmol) as a pale white solid. The general procedure B was followed using N-benzoyl leucine (610 mg, 2.59 mmol), EDC (443 mg, 2.85 mmol), CH$_2$Cl$_2$ (37.0 mL). $^1$H-NMR matched that previously reported in the literature (Badiola et al., 2014).

Figure 10:
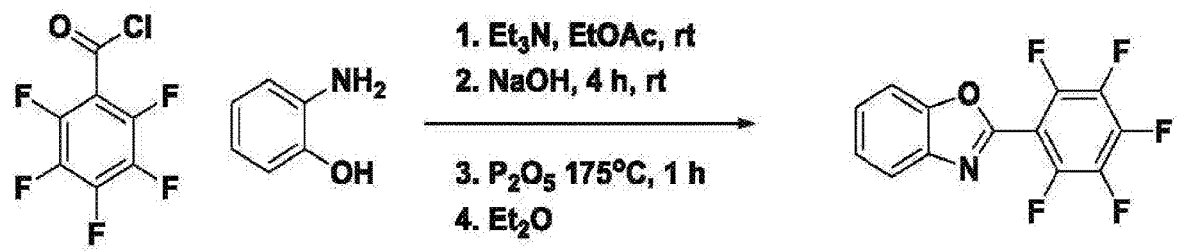
FIG. 10 illustrates synthesis of 2-(perfluorophenyl)benzo[d]oxazole.

Synthesis of 2-(perfluorophenyl)benzo[d]oxazole (FIG. 10)

2-(perfluorophenyl)benzo[d]oxazole was produced as a white solid in 33% yield. 2-(perfluorophenyl)benzo[d]oxazole was prepared by following the literature procedure (Senaweera et al., 2014). Triethylamine (1.7 g, 16.9 mmol) was added dropwise to a solution of 2-aminophenol (1.4 g, 12.7 mmol) and pentafluorobenzoyl chloride (3.2 g, 14.1 mmol) in ethyl acetate (50 mL). The mixture was refluxed overnight and then aq NaOH (1M, 30 mL) was added and stirred for 3 hours at room temperature. The resulting mixture was extracted with EtOAc (5×20 mL) and washed with H$_2$O (25 mL) and brine (25 mL). The organic layer was dried over anhydrous MgSO$_4$ to yield 4 g of intermediate. Next, P$_2$O$_5$(4.0 g, 28 mmol) was added to the intermediate and then heated at 175° C. for 1 hour. After the mixture had cooled to room temperature, ice water (50 mL) was added and mixture was extracted with EtOAc (5×20 mL). The combined organic layers were washed with aq NaOH (0.25 M, 50 mL), followed by water, brine and dried over anhydrous MgSO$_4$ and then concentrated in vacuo to afford the crude product. The resultant crude residue was purified by automated flash chromatography (hexane:EtOAc 90:10) to give the product (1.2 g, 4.2 mmol), which matches with NMR spectra of product reported in the literature (Tanaka et al., 2001).

Figure 11:
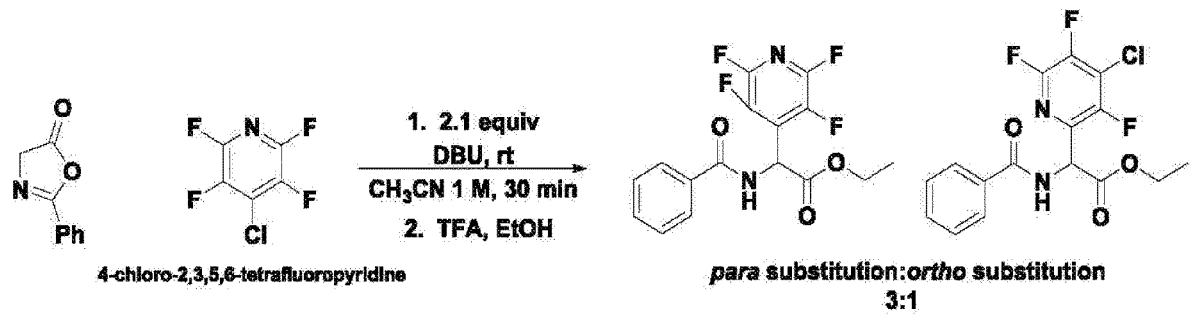
FIG. 11 illustrates a halogen selectivity experiment.

Halogen Selectivity Experiment (FIG. 11):

Under an argon atmosphere, oxazolone (50 mg, 0.310 mmol, 1 equiv), 4-chloro-2,3,5,6-tetrafluoropyridine (69 mg, 0.372 mmol, 1.2 equiv), and CH$_3$CN (0.310 mL, 1 M) were added to small test tube, which was fitted with a septum. Then a steady stream of 1,8-diazabicyclo(5.4.0) undec-7-ene (95 μL, 0.651 mmol, 2.1 equiv) was added down the side of the test tube glass. The mixture was allowed to react for 30 min. The reaction was quenched by the addition of a trifluoroacetic acid/ethanol) solution (47.4 μL, 0.620 mmol, 2 equiv/0.620 mL of ethanol). The solution was concentrated and then diluted with CHCl$_3$ (5 mL), which was then washed with 1 M HCl brine solution (2.5 mL×3). The organic layer was dried with MgSO$_4$, filtered, and concentrated to give the crude product, which was purified by column chromatography. The para/ortho product ratio was determined by integrations of peaks in the $^1$H and $^{19}$F NMR.

Figure 12:
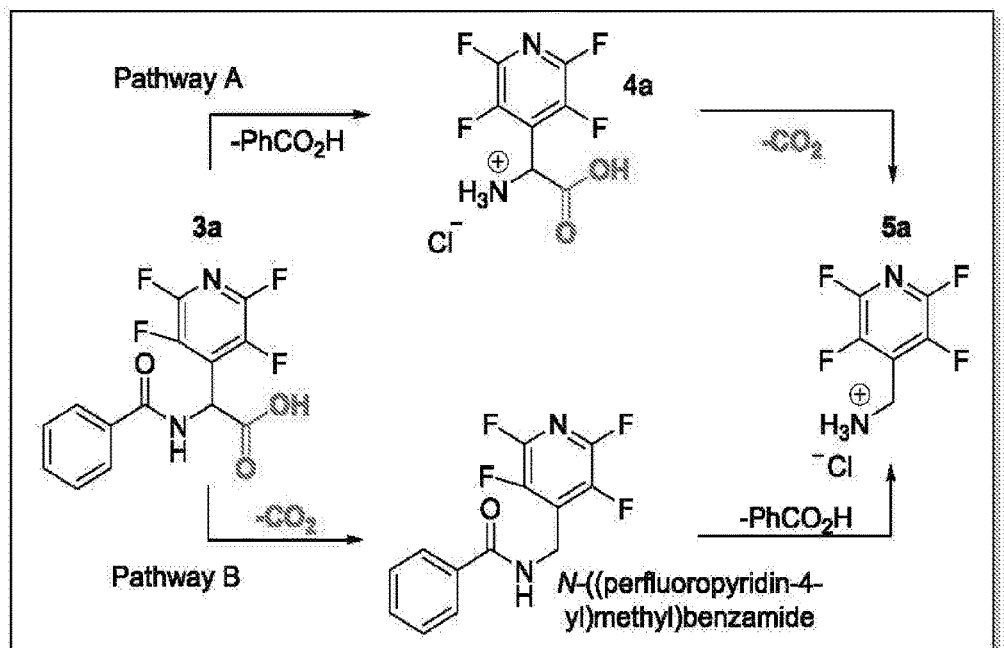
FIG. 12 illustrates a doping experiment—potential reaction sequences for producing the deprotected and decarboxylated ammonium salt (5a) from the benzoyl protected amino acid (3a).

Doping Experiment (FIGS. 12-15):

During the investigation, it was found that the standard deprotection conditions (refluxing the benzoyl protected amino acid (3a) in concentrated HCl) led to the deprotected and decarboxylated ammonium salt (5a). While the nature of the final product was apparent, the reaction sequence was not clear. In other words, did debenzoylation precede decarboxylation (FIG. 12, Pathway A) or did it proceed decarboxylation (FIG. 12, Pathway B).

Figure 13:
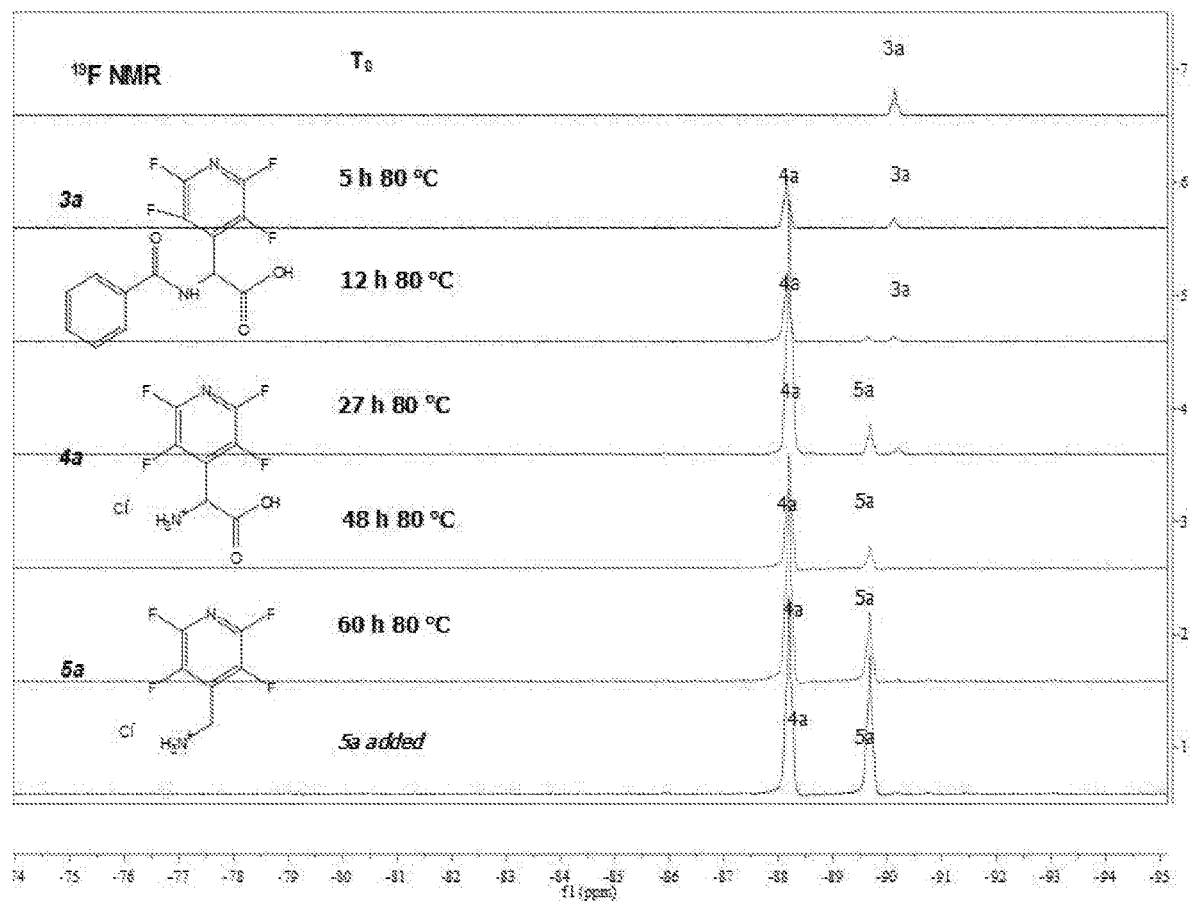
FIG. 13 illustrates a doping experiment—progression of the reaction in FIG. 12.
Figure 14:
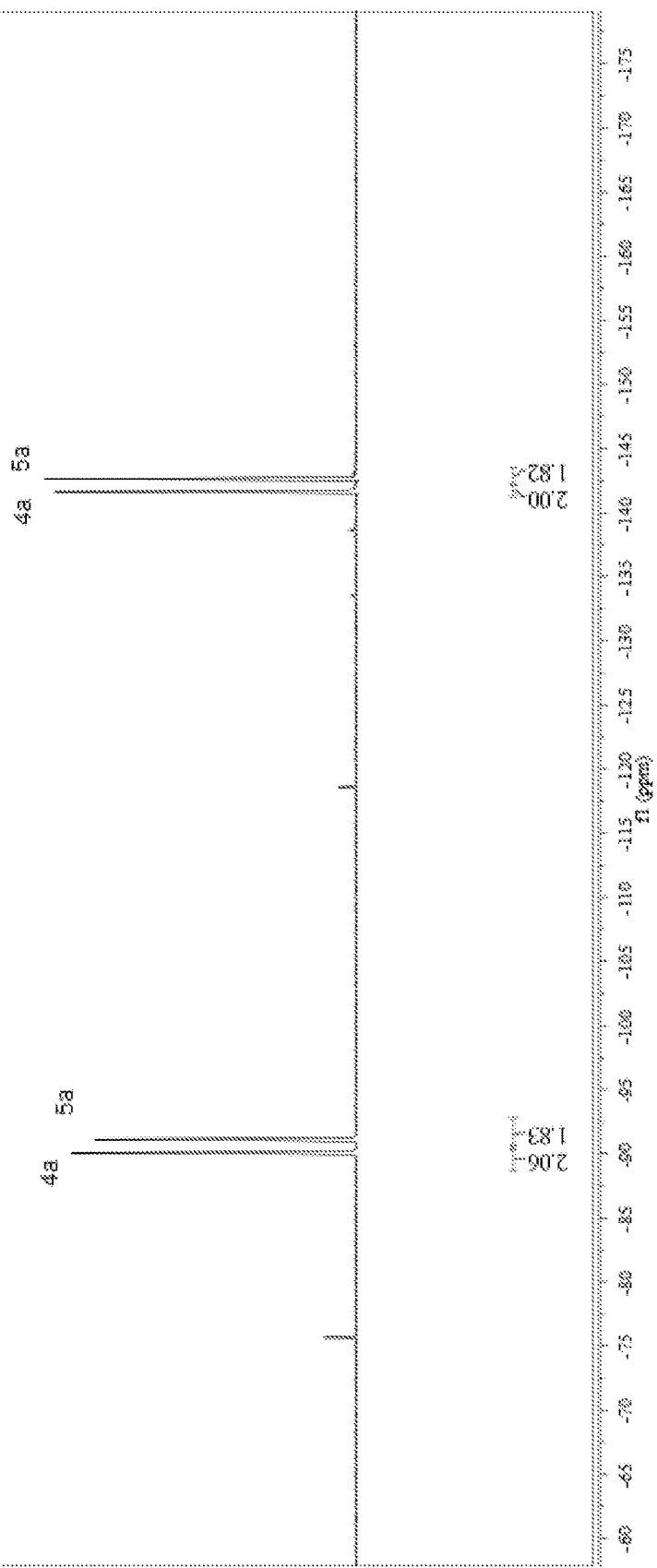
FIG. 14 illustrates a doping experiment—$^{19}$F NMR after workup 60 h+dopant.
Figure 15:
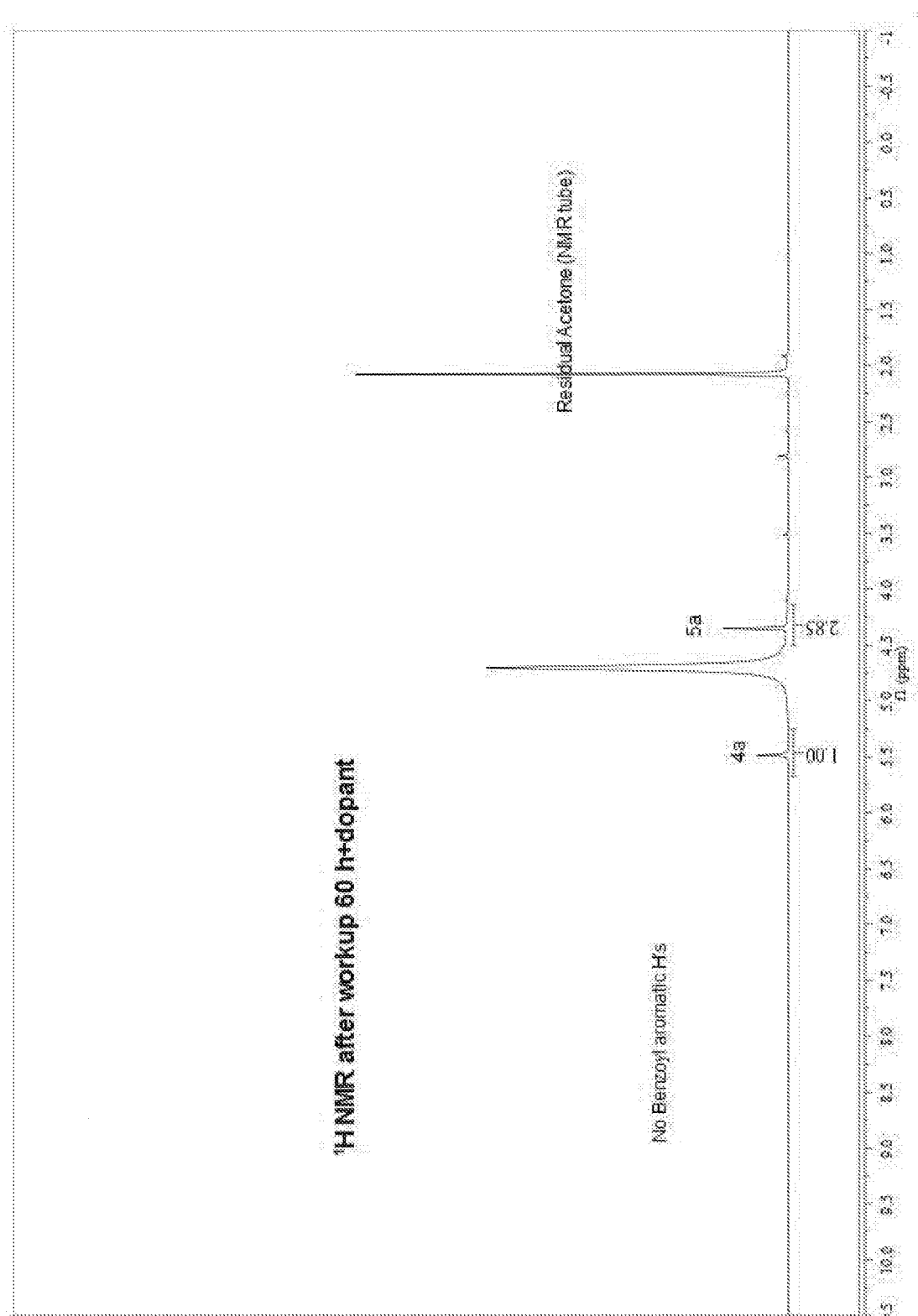
FIG. 15 illustrates a doping experiment—$^1$H NMR after workup 60 h+dopant.

To probe the reaction, 20 mg of 3a (0.061 mmol) and 0.50 mL of 12 M HCl was added to a NMR tube, and the T$_0$ $^{19}$F NMR was collected (FIG. 13, spectrum 7). The reaction was run at 80° C., and $^{19}$F NMR data was collected at 5 h, 12 h, 27 h, 48 h, and 60 h (FIG. 13, spectra 2-6, respectively). After the last time point, the NMR tube was doped with previously isolated 5a (5 mg), and the $^{19}$F NMR was taken, which confirmed the identity of the second species, and by elimination, the structure of 3a as well.

The progression of the reaction is displayed in FIG. 13, and after 5 hours, the conversion of starting material to a new intermediate is apparent, and the peak chemical shifts at −88 ppm. With prolonged heat, a second intermediate is formed, with a chemical shift of −89.5 ppm. Yet, the doping of the NMR reaction revealed 5a to be the final product shifting at −89.5 ppm. After a typical workup (see general procedure G) of the incomplete reaction (where starting material is consumed and only partial conversion of the intermediate to the 5a product), the $^{19}$F NMR (FIG. 14) and the $^1$H NMR (FIG. 15) revealed that the intermediate N-((perfluoropyridin-4-yl)methyl)benzamide was neither of the intermediates observed due to the lack of benzoyl aromatic signals. The first intermediate was found to be 4a (seen at −88 ppm) matching of what one would expect in the $^1$H NMR (s, $^1$H)$^{19}$F NMR δ −89.95--−90.40 (m), −141.50--−142.06 (m). With this evidence, the most logical route (but not by way of limitation) was concluded to be pathway A, where the benzoyl protected amino acids undergo deprotection and then thermally decarboxylate, giving the benzylic amine. This finding is consistent with TGA experiments, which show that for 3b and 4b, which differ by the deprotection of the N-benzoyl group, that the amide (3b) is less prone to thermal decarboxylation than the corresponding ammonium acid (4b).

Rationalization of the Observed Base Dependency on Fluoroarene Substrate

It is puzzling why the same acid (i.e. oxazolone) would require a stronger base as a function of electrophile (see Table 1, entries 8-10). One potential explanation for this observation is that the ammonium enolate is the minor product of an equilibrium. Due to the decreased electrophilicity of octafluorotoluene, the rate of attack by the enolate is retarded. The use of a stronger base accelerates the reaction by shifting the equilibrium in favor of the enolate. An alternative possibility is that pentafluoropyridine undergoes an aromatic π-stacking event, more specifically a donor-acceptor interaction (Lv et al., 2012; Gung et al., 2006), with the phenyl ring of the oxazolone, which could result in an acidification of the C4-H. In contrast, when octafluorotoluene is used, it is less prone to undergo this acidifying, π-stacking event, presumably due to the steric bulk of the trifluoromethyl group, and thus requires a stronger base to generate the requisite enolate.

Synthesis of Perfluoroaryl-N-Benzoyl Amino Acids/Esters

General Procedure C for Synthesis of N-Benzoyl Perfluoroaryl-Amino Esters 2a, 2b, 2c, 2d, 2e, 2i.

Under an argon atmosphere, oxazolone (1 equiv), Ar$_F$—F (1.025 equiv), and CH$_3$CN (1 M) were added to small test tube, which was fitted with a septum and cooled to −20° C. Then a steady stream of tetramethylguanidine (2.05 equiv) was added down the side of the test tube glass, which facilitated the cooling of the TMG solution prior to dissolution. The mixture was allowed to react for 30 min, then the cooling bath was removed, and the reaction was left to warm to room temperature. The reaction was quenched by the addition of a trifluoroacetic acid/alcohol (methanol or ethanol) solution (2 equiv/double volume). The solution was concentrated and then diluted with CHCl$_3$, which was then washed with 1 M HCl brine solution (half the volume of organic layer×3). The organic layer was dried with MgSO$_4$, filtered, and concentrated to give the crude product, which was purified by column chromatography.

General Procedure D for Synthesis of N-Benzoyl Perfluoroaryl-Amino Esters 2f, 2g, and 2h.

Under an argon atmosphere, oxazolone (1 equiv), Ar$_F$—F (1.025 equiv), and CH$_3$CN (1 M) were added to small test tube, which was fitted with a septum. Then a steady stream of 1,8-diazabicyclo(5.4.0)undec-7-ene (2.05 equiv) was added down the side of the test tube glass. The mixture was allowed to react for 30 min. The reaction was quenched by the addition of a trifluoroacetic acid/alcohol (methanol or ethanol) solution (2 equiv/double volume). The solution was concentrated and then diluted with CHCl$_3$, which was then washed with 1 M HCl brine solution (half the volume of organic layer×3). The organic layer was dried with MgSO$_4$, filtered, and concentrated to give the crude product, which was purified by column chromatography. ESI-9

General Procedure E for Synthesis of N-Benzoyl Perfluoroaryl-Amino Acids 3a, 3b, 3c, 3d, and 3e.

Under an argon atmosphere, oxazolone (1 equiv), Ar$_F$—F (1.025 equiv), and CH$_3$CN (1 M) were added to small test tube, which was fitted with a septum and cooled to −20° C. Then a steady stream of tetramethylguanidine (2.05 equiv) was added down the side of the test tube glass, which facilitated the cooling of the TMG solution. The reaction was left to react for 30 min, and then the cooling bath was removed, and the reaction was allowed to warm to room temperature and subsequently quenched by the addition of 6 M HCl. The solution was concentrated and extracted with CHCl$_3$, and then the organic layer was washed with half volumes of a 1 M HCl-brine solution×3. The organic layer was dried with MgSO$_4$ and concentrated, giving crude product. Purification of the crude product is accomplished without chromatography (for example, but not by way of limitation) by adding hexanes to a round bottom flask containing the crude product then carefully adding dichloromethane dropwise until the hexanes becomes yellow and a colorless solid is left behind. The solid was filtered and air dried to yield the pure acid.

General Procedure D for Synthesis of N-Benzoyl Perfluoroaryl-Amino Esters 6a, 6b, 6c, and 6d.

Under an argon atmosphere, oxazolone (1 equiv), Ar$_F$—F (1.025 equiv), and CH$_3$CN (1 M) were added to small test tube, which was fitted with a septum. Then a steady stream of DIPEA (10 equiv) was added to mixture. While stirring vigorously (note: the reaction mixture is biphasic), the reaction was left to react for 30 min. After 30 min, the bottom layer was separated and quenched by the addition of a trifluoroacetic acid/alcohol (methanol or ethanol) solution (20 equiv/20 equiv). The solution was concentrated and then diluted with CHCl$_3$, which was then washed with 1 M HCl-brine solution (half the volume of organic layer×3). The organic layer was dried with MgSO$_4$, filtered, and concentrated to give the crude product, which was purified by column chromatography.

Figure 16:
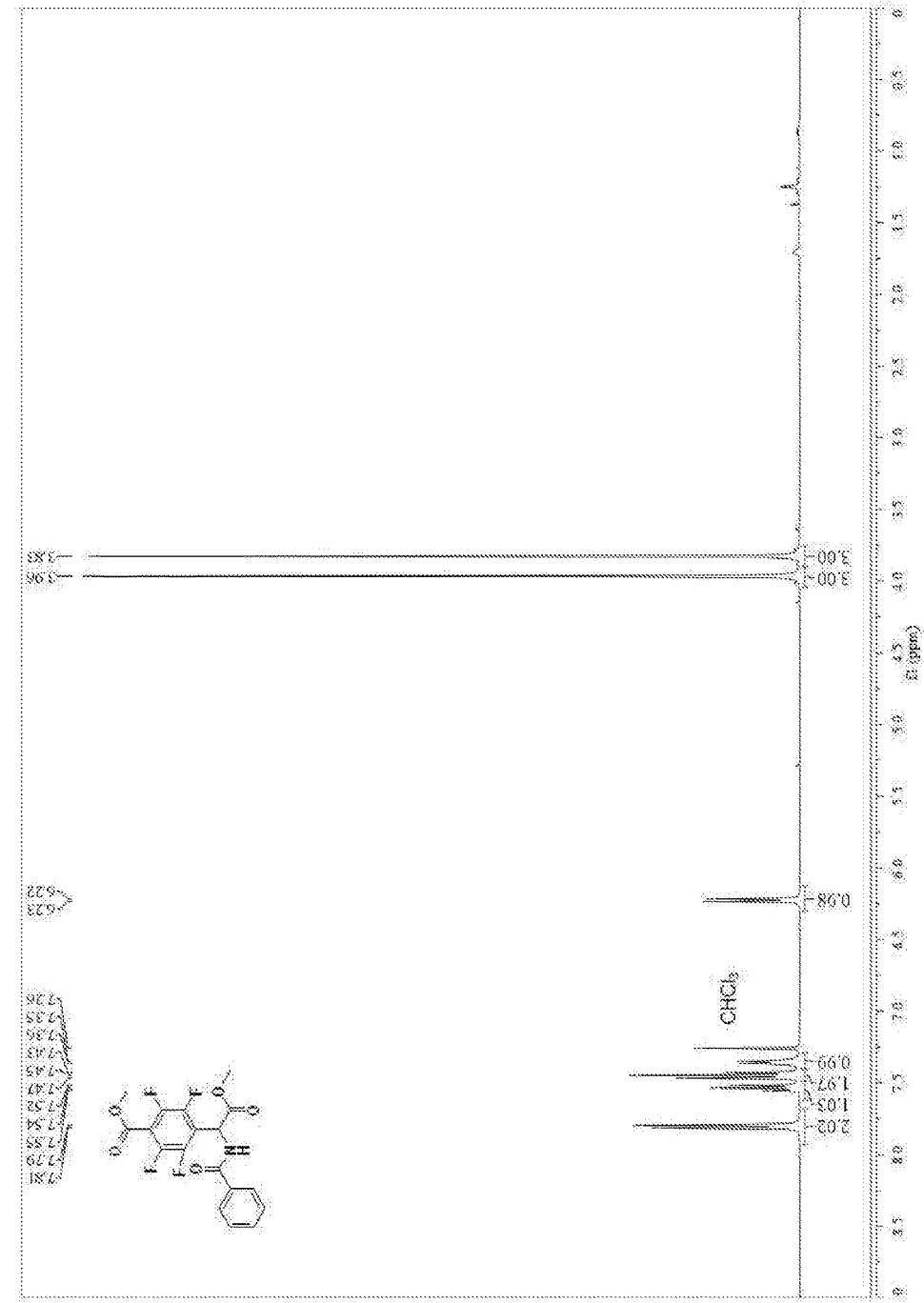
Figure 17:
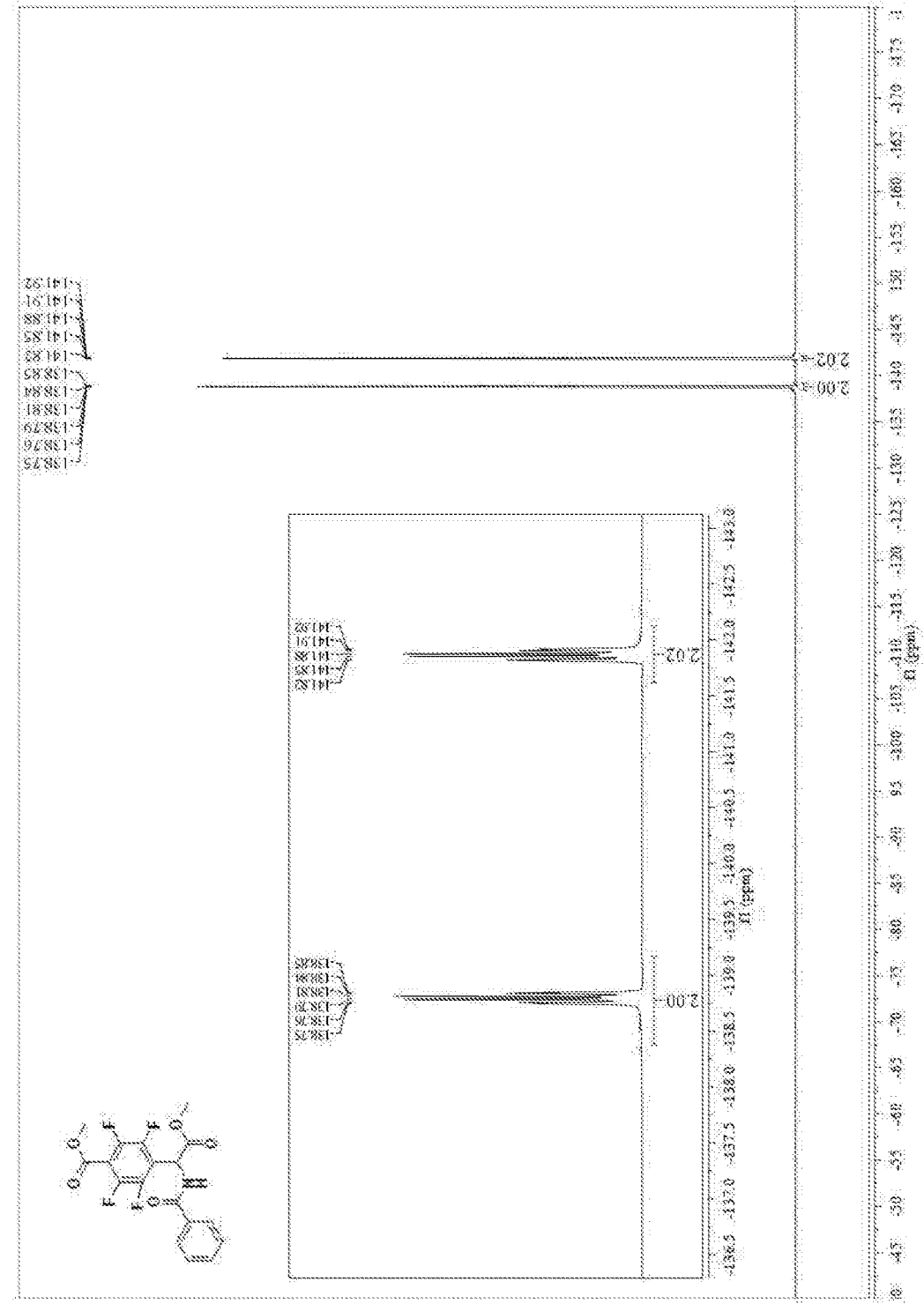
Figure 18:
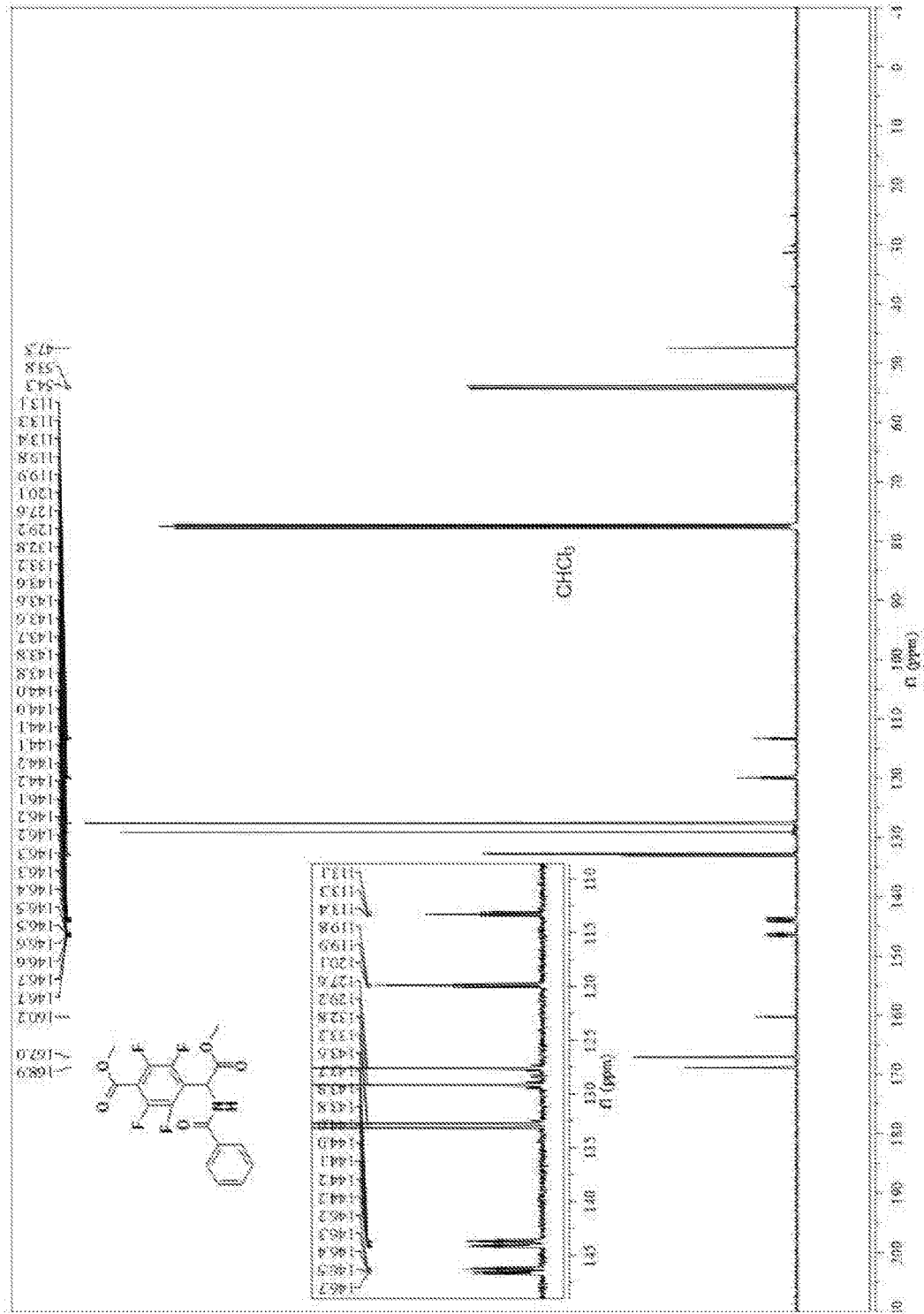

2a methyl 4-(1-benzamido-2-methoxy-2-oxoethyl)-2,3,5,6-tetrafluorobenzoate (FIGS. 2 and 16-18) was produced as a colorless oil with 98.5% yield (122 mg, 0.305 mmol). The general procedure C was followed using 2-phenyloxazol-5 (4H)-one (50.0 mg, 0.310 mmol), 2,3,4,5,6 pentafluorobenzoate (67.4 mg, 0.318 mmol), tetramethylguanidine (73.2 mg, 0.636 mmol), 0.310 mL of MeCN and trifluoroacetic acid (70.7 mg, 0.620 mmol)/methanol (0.620 mL) was used to afford 2a. FT-IR (neat) cm$^{-1}$ 1743, 1754, 1680, 1085. $^1$H NMR (400 MHz, Chloroform-d; FIG. 16) δ 7.80 (d, J=7.3 Hz, 2H), 7.54 (t, J=7.4 Hz, 1H), 7.45 (t, J=7.6 Hz, 2H), 7.36 (d, J=6.5 Hz, 1H), 6.22 (d, J=6.7 Hz, 1H), 3.96 (s, 3H), 3.83 (s, 3H). $^{19}$F NMR (376 MHz, Chloroform-d; FIG. 17) δ −138.64—139.00 (m), −141.86 (q, J=11.5 Hz). $^{13}$C NMR (101 MHz, Chloroform-d; FIG. 18) δ 168.9, 167.0, 160.3, 146.4 (ddt, J=37.7, 15.2, 4.8 Hz), 143.9 (ddt, J=44.6, 15.2, 4.9 Hz), 133.2, 132.8, 129.2, 127.6, 119.9 (t, J=15.6 Hz), 113.3 (t, J=16.1 Hz), 54.3, 53.8, 47.5. HRMS (ESI) C$_{18}$H$_{13}$F$_4$NO$_5$ calcd. [M+K]$^+$438.0361 observed 438.0337.

Figure 19:
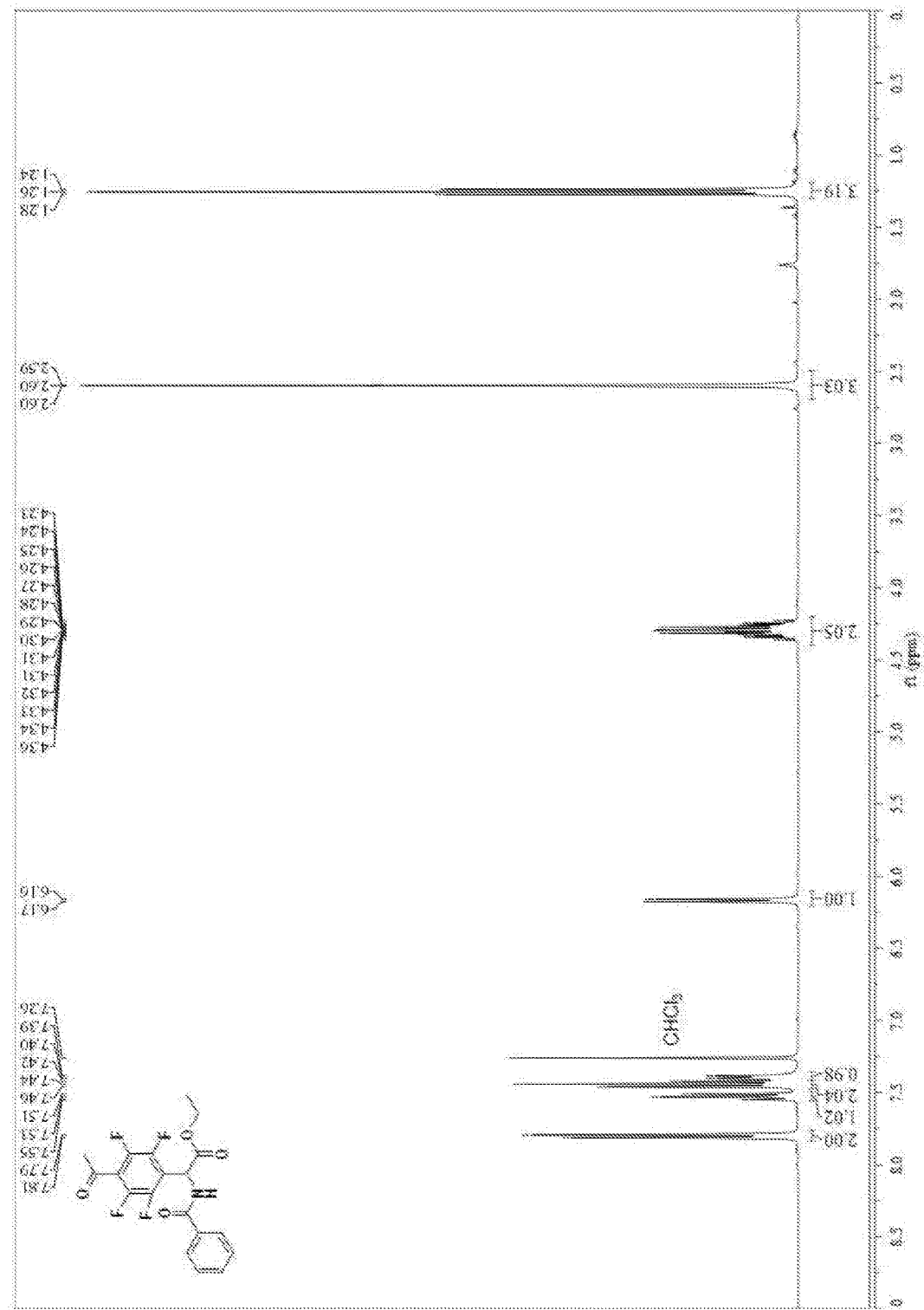
FIG. 19 contains a $^1$H NMR spectra (400 MHz), Chloroform-d) of species 2b.
Figure 20:
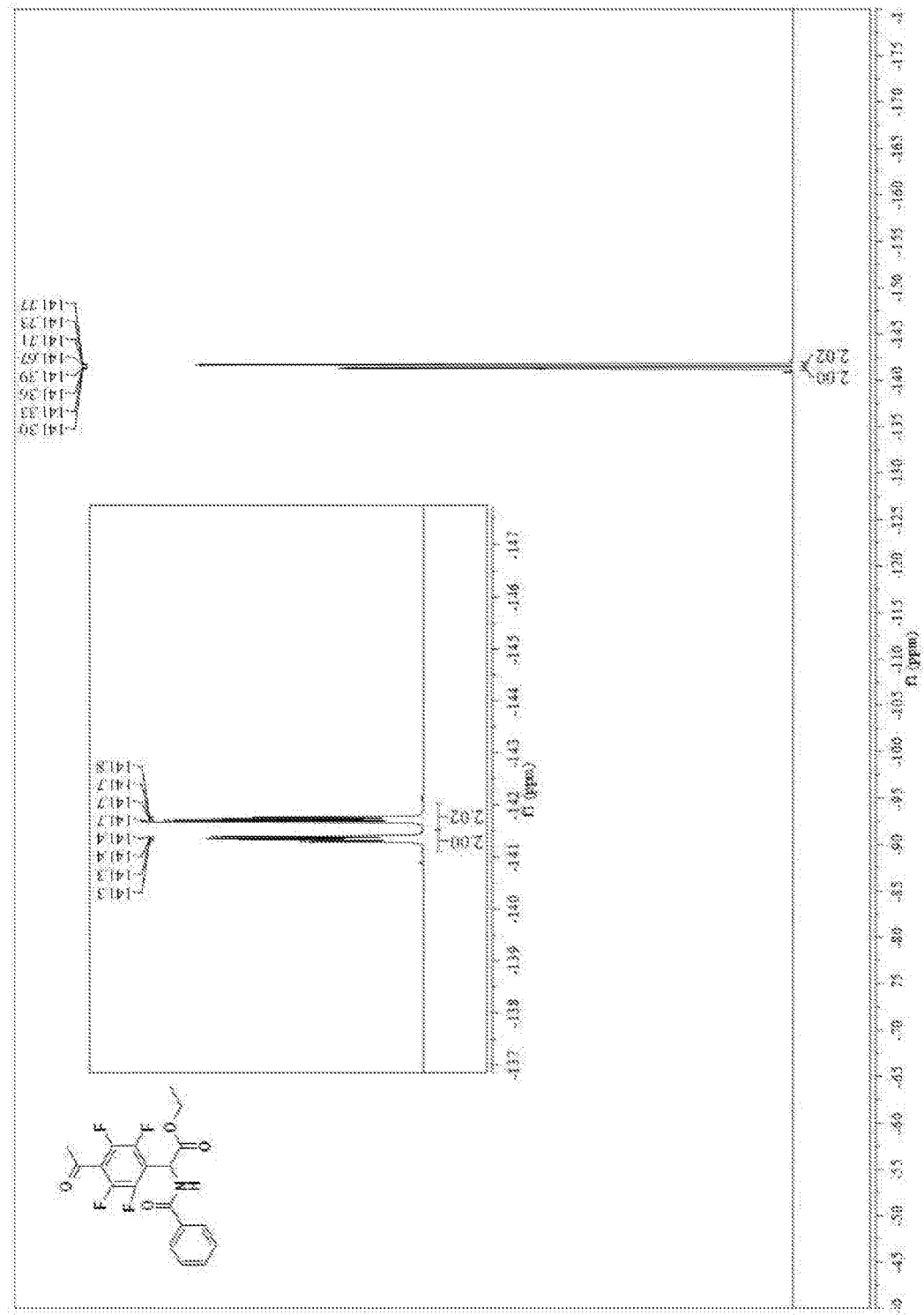
FIG. 20 contains a $^{19}$F NMR spectra (376 MHz), Chloroform-d) of species 2b.
Figure 21:
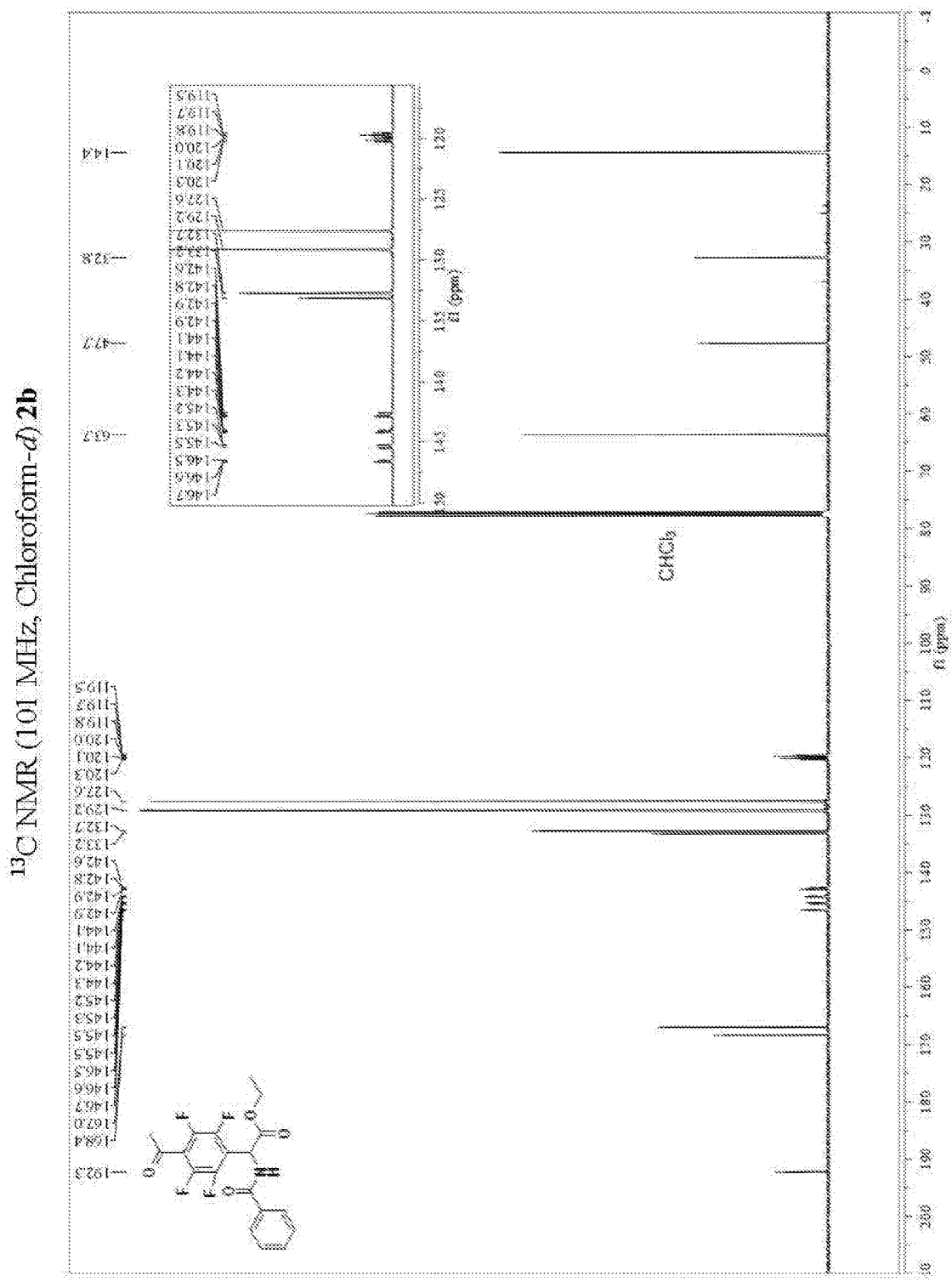
FIG. 21 contains a $^{13}$C NMR spectra (101 MHz), Chloroform-d) of species 2b.

2b ethyl 2-(4-acetyl-2,3,5,6-tetrafluorophenyl)-2-benzamidoacetate (FIGS. 2 and 19-21) was produced as a colorless oil with 80% yield (98.5 mg, 0.248 mmol). The general procedure C was followed using 2-phenyloxazol-5 (4H)-one (50 mg, 0.310 mmol), 2',3',4',5',6' pentafluoroacetophenone (66.8 mg, 0.318 mmol), tetramethylguanidine (73.2 mg, 0.636 mmol), trifluoroacetic acid (70.7 mg, 0.620 mmol)/ethanol (0.620 mL) and 0.310 mL of MeCN was used to afford 2b. FT-IR (neat) cm$^{-1}$ 1730, 1756, 1655, 1105. $^1$H NMR (400 MHz, Chloroform-d; FIG. 19) δ 7.80 (d, J=7.1 Hz, 2H), 7.53 (t, J=7.4 Hz, 1H), 7.44 (t, J=7.5 Hz, 2H), 7.39 (d, J=6.4 Hz, 1H), 6.17 (d, J=6.4 Hz, 1H), 4.32 (dq, J=10.8, 3.7 Hz, 2H), 2.60 (t, J=1.6 Hz, 3H), 1.26 (t, J=7.1 Hz, 3H). $^{19}$F NMR (376 MHz, Chloroform-d; FIG. 20) δ −141.34 (dd, J=22.3, 13.2 Hz), −141.72 (ddd, J=21.9, 13.4 Hz. $^{13}$C NMR (101 MHz, Chloroform-d; FIG. 21) δ 192.3, 168.4, 167.0, 146.1 (dd, J=116.6, 6.9 Hz), 144.4-142.5 (m), 133.2, 132.7, 129.2, 127.6, 120.1 (t, J=16.9 Hz), 119.7 (t, J=15.6 Hz), 63.7, 47.7, 32.8, 14.4. HRMS (ESI) C$_{19}$H$_{15}$F$_4$NO$_4$ calcd. [M+Na]$^+$ 420.0829 observed 420.0810.

Figure 22:
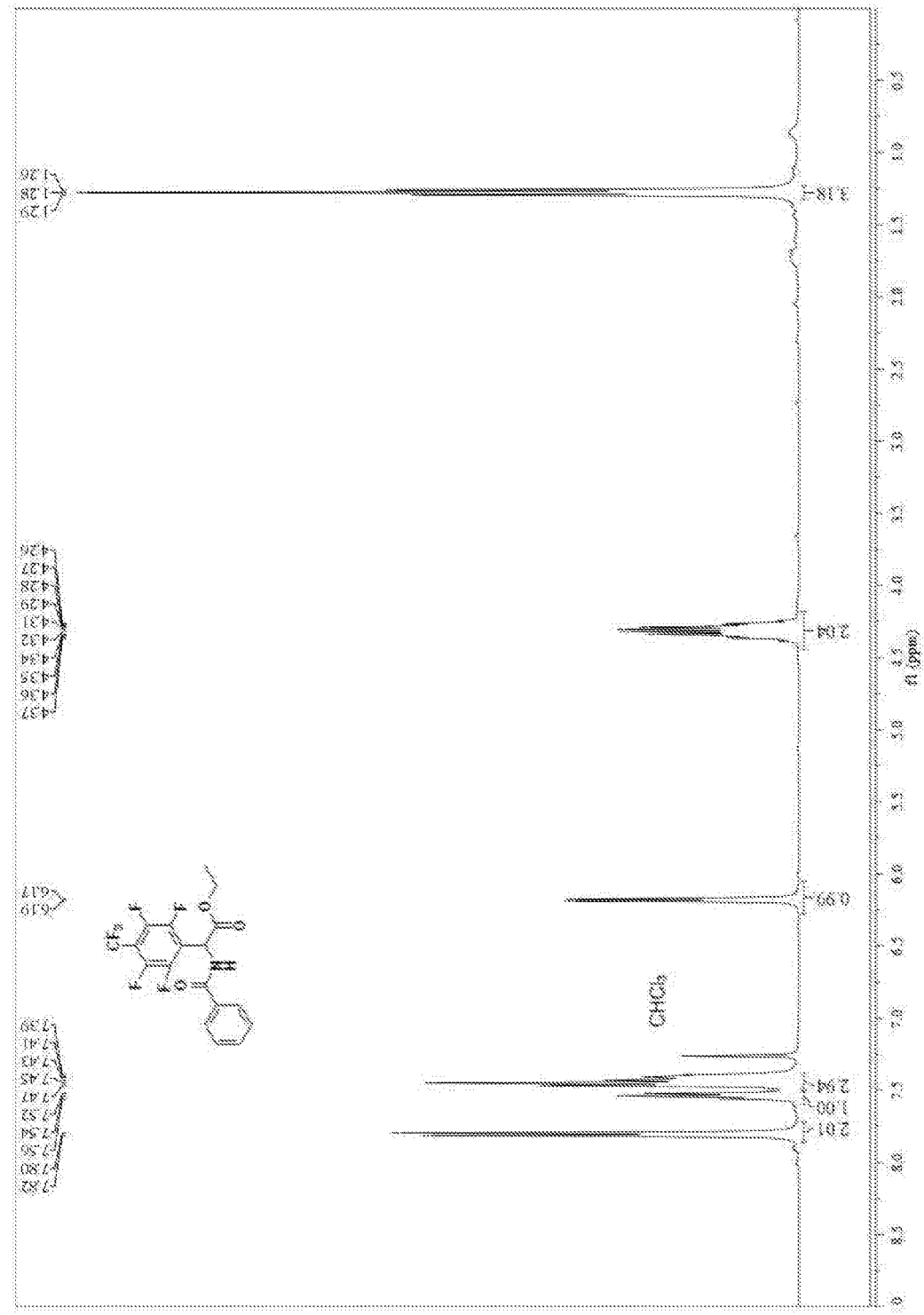
FIG. 22 contains a $^1$H NMR spectra (400 MHz), Chloroform-d) of species 2c.
Figure 23:
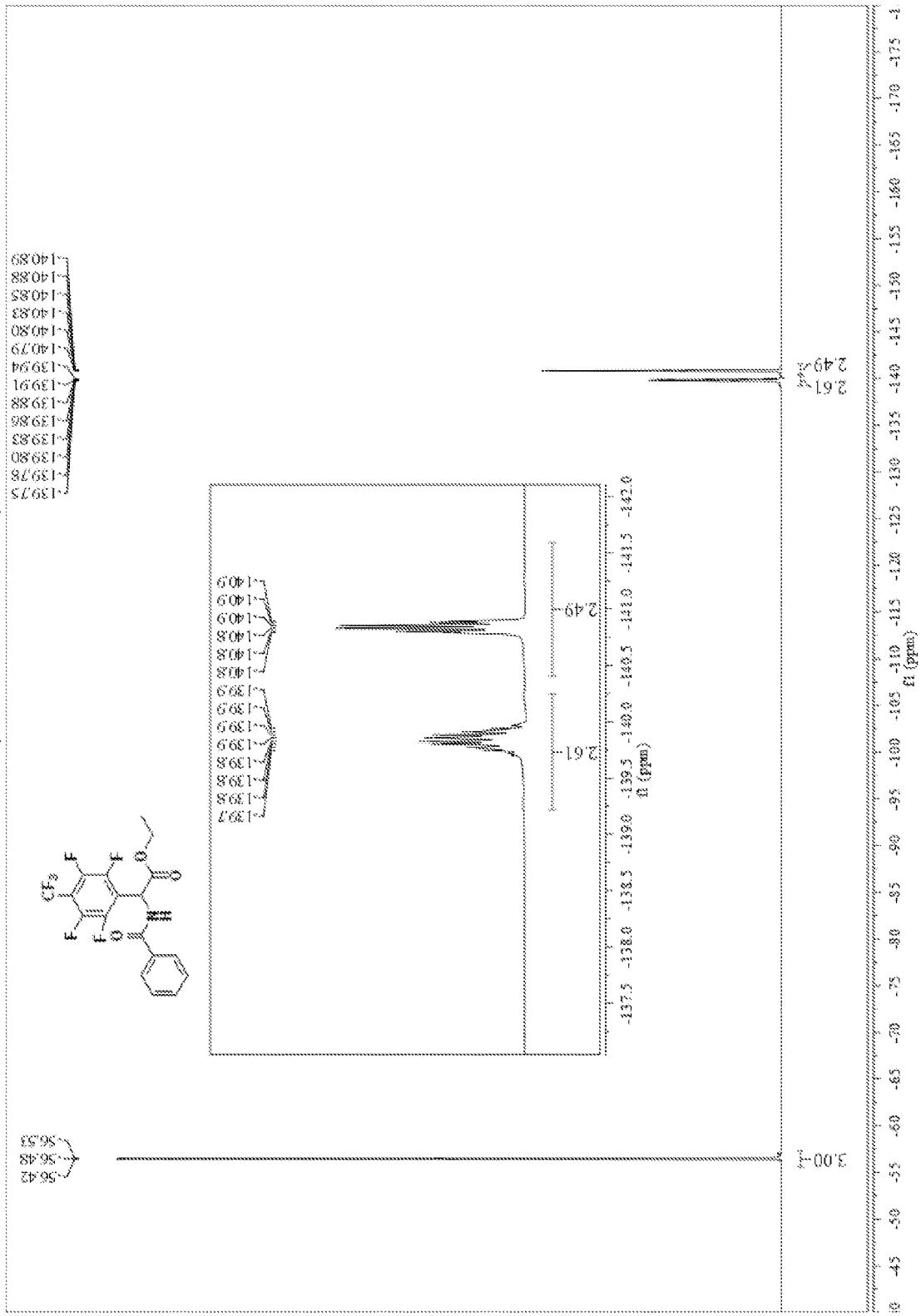
FIG. 23 contains a $^{19}$F NMR spectra (376 MHz), Chloroform-d) of species 2c.
Figure 24:
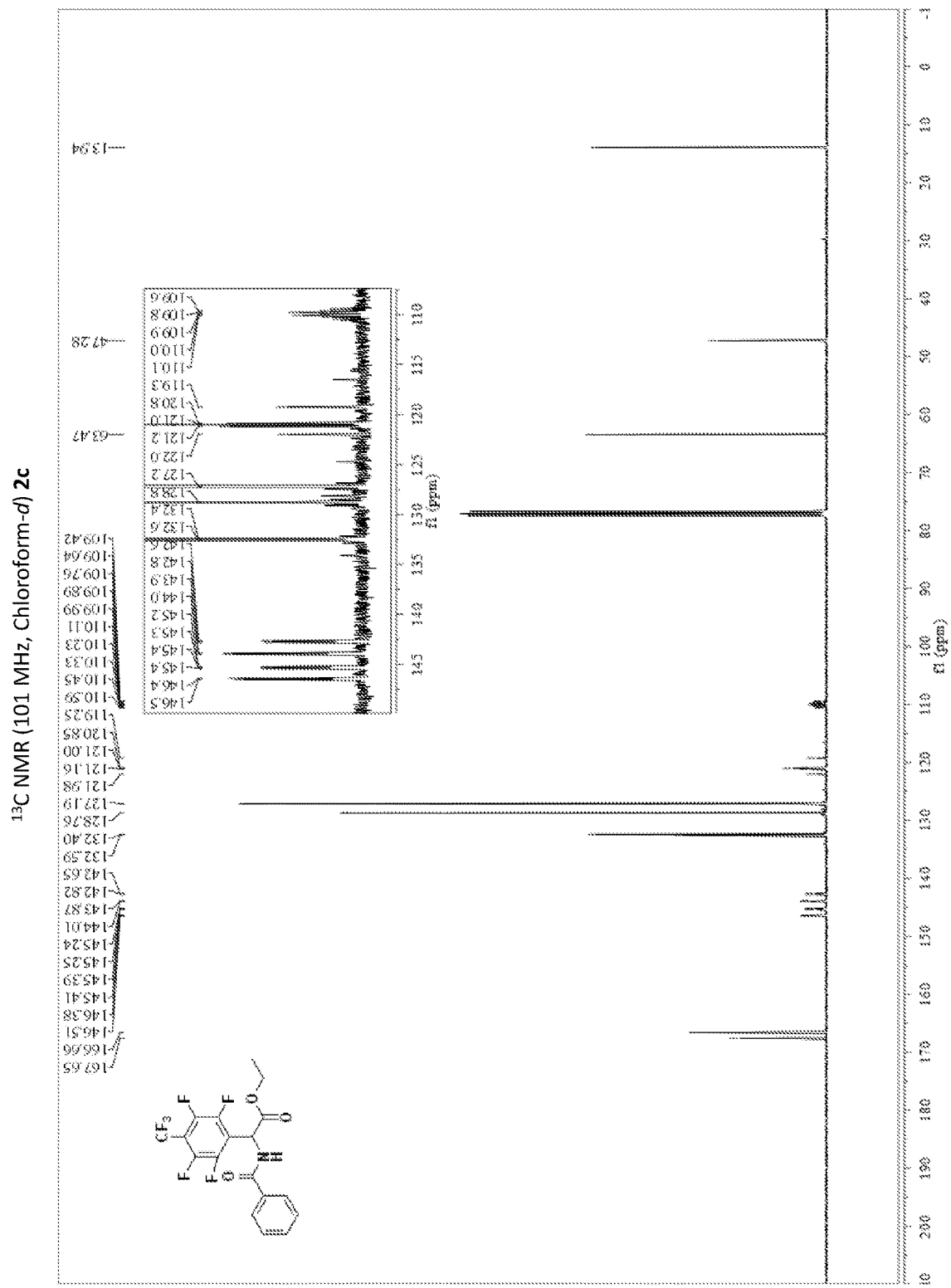
FIG. 24 contains a $^{13}$C NMR spectra (101 MHz), Chloroform-d) of species 2c.

2c ethyl 2-benzamido-2-(2,3,5,6-tetrafluoro-4-(trifluoromethyl)phenyl)acetate (FIGS. 2 and 22-24) was produced as a white solid with 81% yield (106 mg, 0.251 mmol). The general procedure C was followed using 2-phenyloxazol-5 (4H)-one (50 mg, 0.310 mmol), octafluorotoluene (38 mg, 0.318 mmol), tetramethylguanidine (73.2 mg, 0.636 mmol), trifluoroacetic acid (70.7 mg, 0.620 mmol)/ethanol (0.620 mL) and 0.310 mL of MeCN was used to afford 2c. FT-IR (neat) cm$^{-1}$ 2496, 1756, 1659, 1095. $^1$H NMR (400 MHz, Chloroform-d; FIG. 22) δ 7.81 (d, J=7.8 Hz, 2H), 7.54 (t, J=7.4 Hz, 1H), 7.49-7.35 (m, 3H), 6.18 (d, J=6.3 Hz, 1H), 4.32 (qd, J=10.8, 3.7 Hz, 2H), 1.28 (t, J=7.1 Hz, 3H). $^{19}$F NMR (376 MHz, Chloroform-d; FIG. 23) 6-56.48 (t, J=21.7 Hz), −139.84 (ddt, J=30.4, 21.7, 11.5 Hz), −140.84 (td, J=15.6, 5.6 Hz). $^{13}$C NMR (101 MHz, Chloroform-d; FIG. 24) δ 167.7, 166.7, 145.9 (dd, J=113.0, 15.4 Hz), 143.3 (dd, J=121.4, 15.4 Hz), 132.6, 132.4, 128.8, 127.2, 121.0 (t, J=15.4 Hz), 120.6 (d, J=274.7 Hz), 110.7-109.0 (m), 63.5, 47.3, 13.9. HRMS (ESI) C$_{18}$H$_{12}$F$_7$NO$_3$ calcd. [M]$^+$ 423.0700 observed 423.0698.

Figure 25:
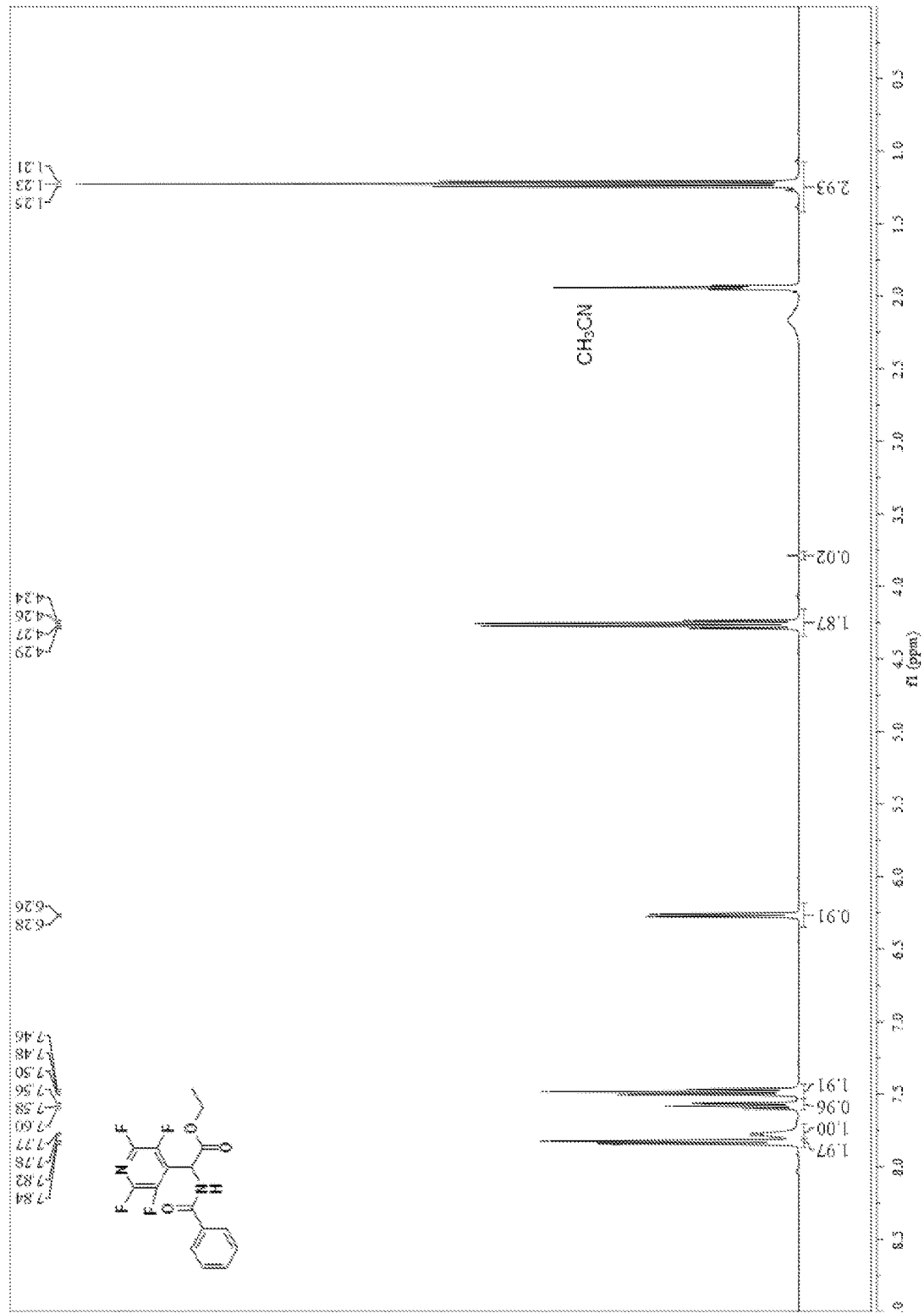
FIG. 25 contains a $^1$H NMR spectra (400 MHz), Acetonitrile-d$_3$) of species 2d.
Figure 26:
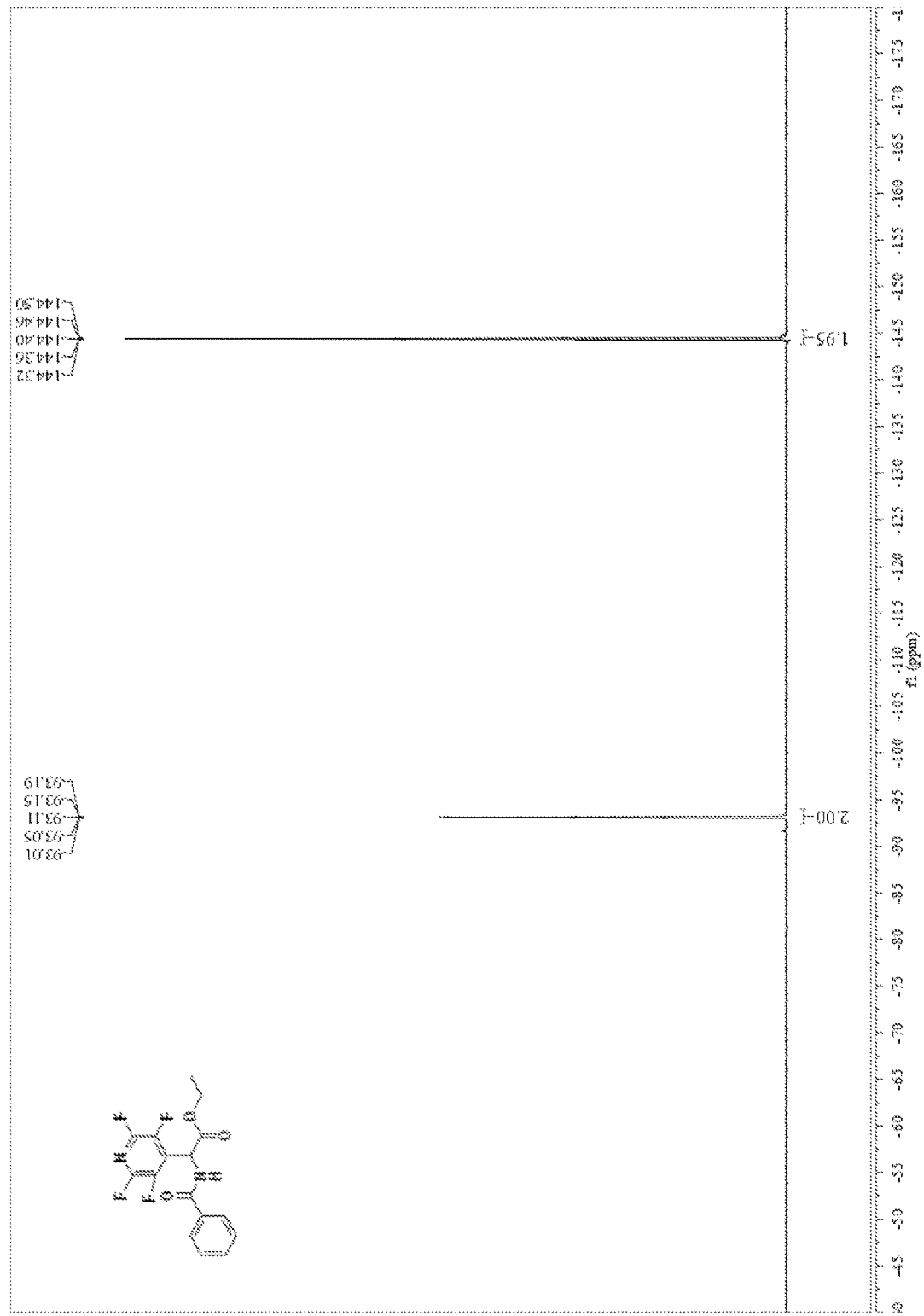
FIG. 26 contains a $^{19}$F NMR spectra (376 MHz), Acetonitrile-d$_3$) of species 2d.
Figure 27:
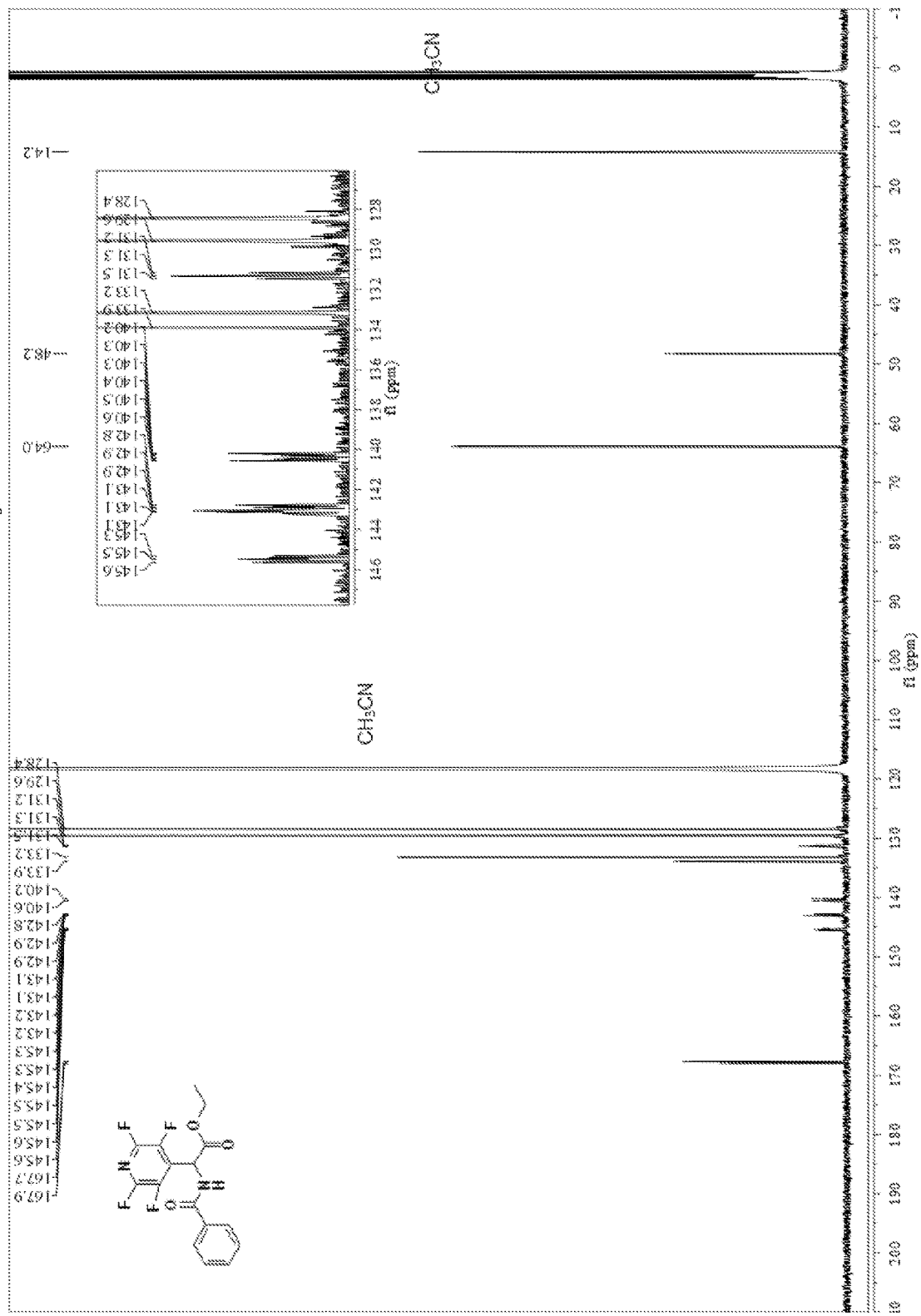
FIG. 27 contains a $^{13}$C NMR spectra (101 MHz), Acetonitrile-d$_3$) of species 2d.

2d ethyl 2-benzamido-2-(perfluoropyridin-4-yl)acetate (FIGS. 2 and 25-27) was produced as a pale white solid with 79% yield (87 mg, 0.245 mmol). The general procedure C was followed using 2-phenyloxazol-5(4H)-one (50 mg, 0.310 mmol), pentafluoropyridine (53.8 mg, 0.318 mmol), tetramethylguanidine (73.2 mg, 0.636 mmol), trifluoroacetic acid (70.7 mg, 0.620 mmol)/ethanol (0.620 mL) and 0.310 mL of MeCN was used to afford 2d. FT-IR (neat) cm$^{-1}$ 1756, 1669, 1630, 1090. $^1$H NMR (400 MHz, Acetonitrile-d$_3$; FIG. 25) δ 7.83 (d, J=8.1 Hz, 2H), 7.78 (d, J=6.0 Hz, 1H), 7.58 (t, J=7.4 Hz, 1H), 7.48 (t, J=7.6 Hz, 2H), 6.27 (d, J=7.2 Hz, 1H), 4.26 (q, J=7.1 Hz, 2H), 1.23 (t, J=7.1 Hz, 3H). $^{19}$F NMR (376 MHz, Acetonitrile-$d_3$; FIG. 26) δ −92.87−−93.35 (m), −144.21−−144.65 (m). $^{13}$C NMR (101 MHz, Acetonitrile-$d_3$; FIG. 27) δ 167.9, 167.7, 145.7-142.9 (m), 141.7 (dd, J=258.7, 35.3 Hz), 133.9, 133.2, 131.3 (t, J=14.9 Hz), 129.6, 128.4, 63.9, 48.2, 14.1. HRMS (ESI) $C_{16}H_{12}F_4N_2O_3$ calcd. [M+K]$^+$ 395.0416 observed 395.0405.

Figure 28:
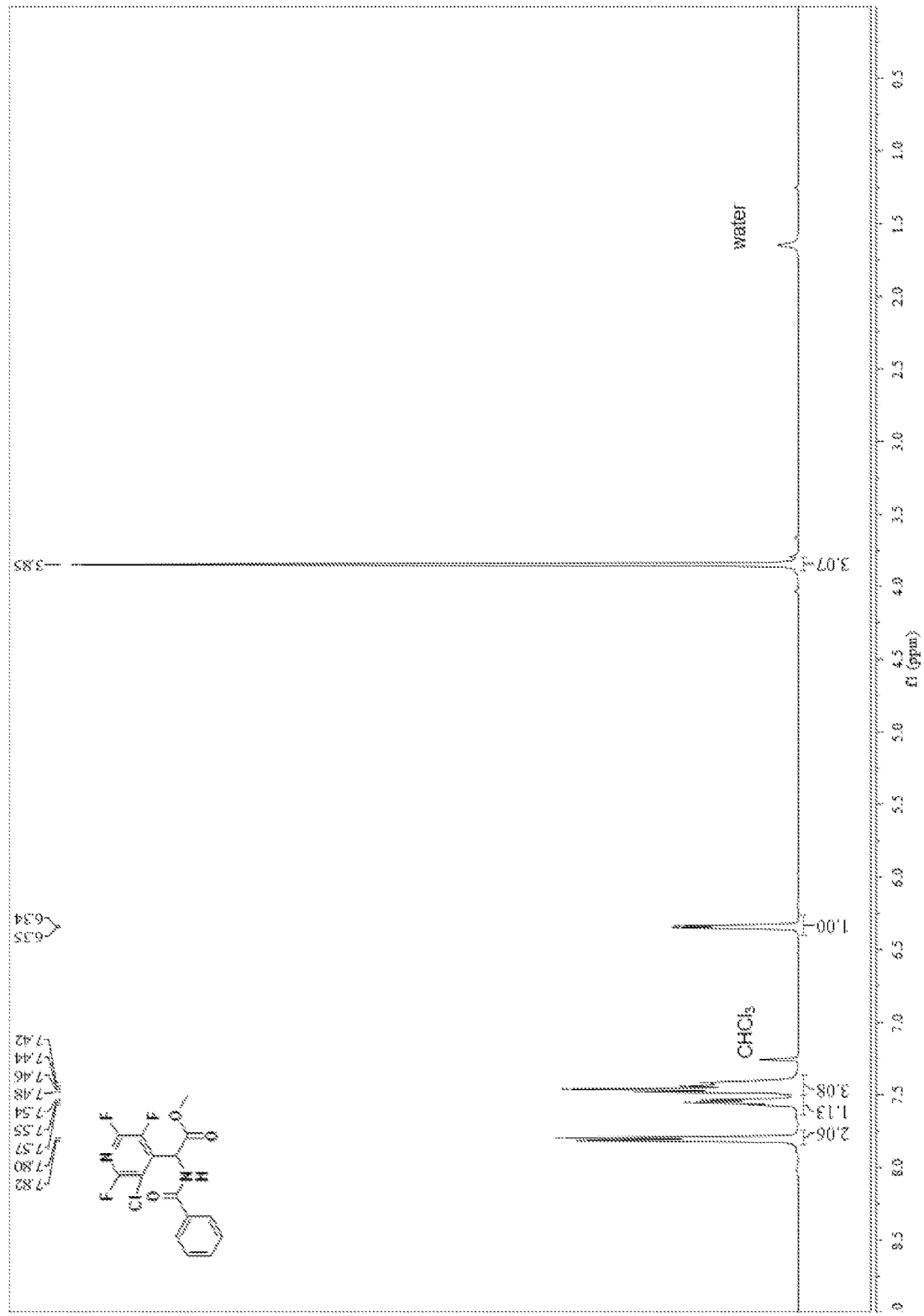
FIG. 28 contains a $^1$H NMR spectra (400 MHz), Chloroform-d) of species 2e.
Figure 29:
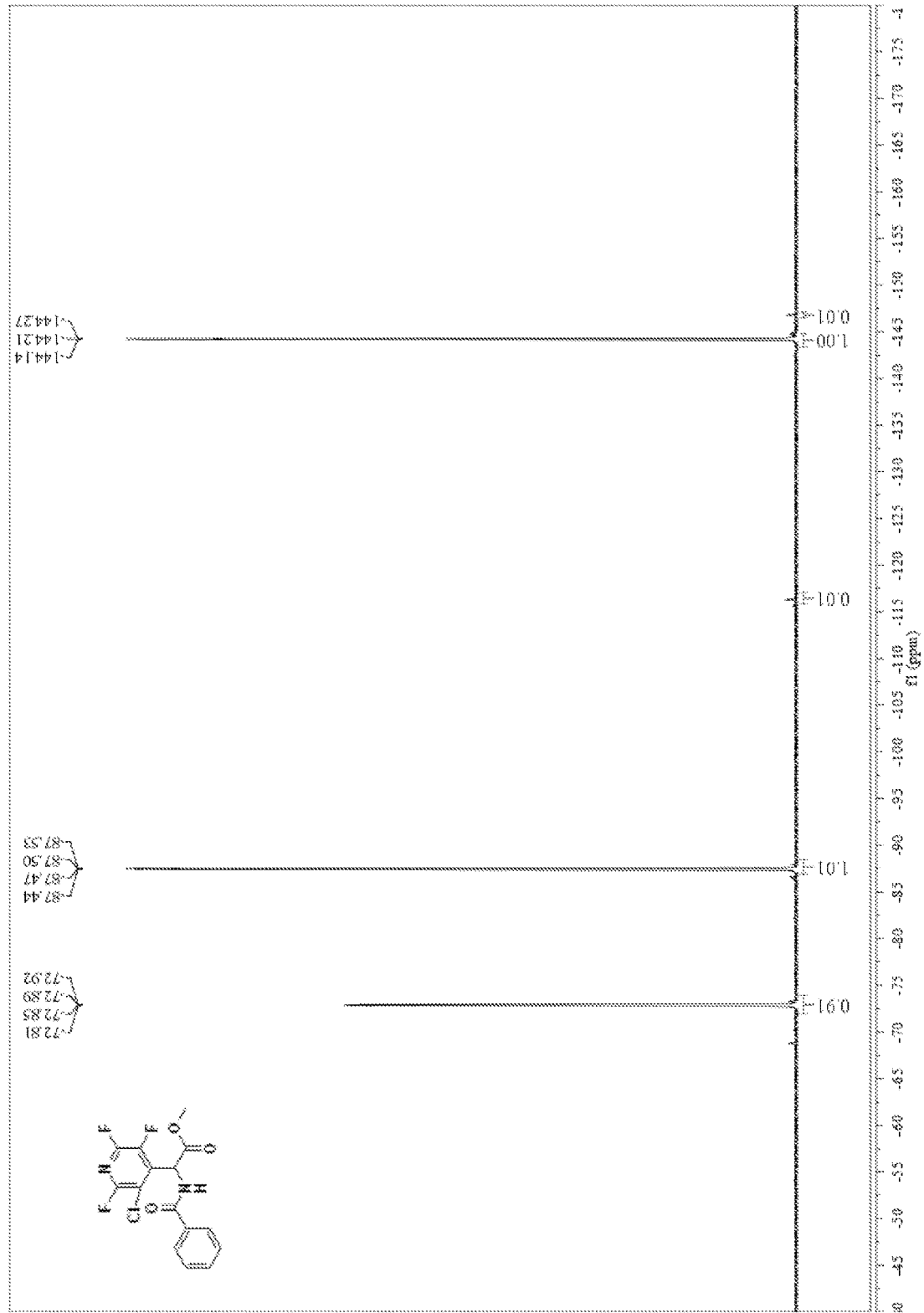
FIG. 29 contains a $^{19}$F NMR spectra (376 MHz), Chloroform-d) of species 2e.
Figure 30:
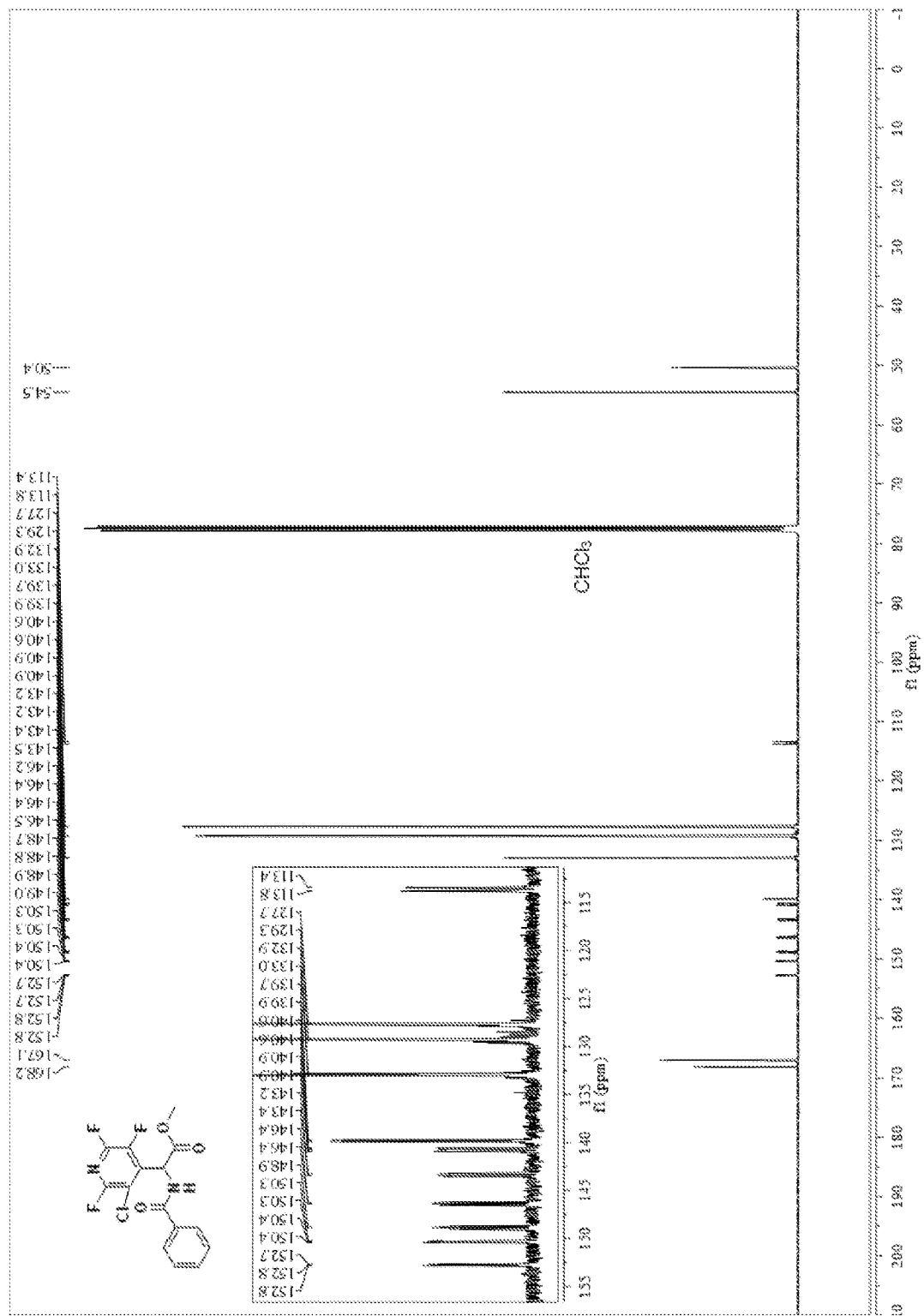
FIG. 30 contains a $^{13}$C NMR spectra (101 MHz), Chloroform-d) of species 2e.

2e methyl 2-benzamido-2-(3-chloro-2,5,6-trifluoropyridin-4-yl)acetate (FIGS. 2 and 28-30) was produced as a yellow solid with 85% yield (178 mg, 0.487 mmol). The general procedure C was followed using 2-phenyloxazol-5(4H)-one (100 mg, 0.621 mmol), 3-chloro-2,4,5,6 tetrafluoropyridine (118.0 mg, 0.636 mmol), tetramethylguanidine (145 mg, 1.27 mmol), trifluoroacetic acid (141 mg, 1.24 mmol)/methanol (1.24 mL) and 0.621 mL of MeCN was used to afford 2e. FT-IR (neat) cm$^{-1}$ 1731, 1640, 1680, 1085. $^1$H NMR (400 MHz, Chloroform-d; FIG. 28) δ 7.83 (d, J=7.6 Hz, 2H), 7.58 (t, J=7.2 Hz, $^1$H), 7.48 (m, J=17.0, 9.2 Hz, 3H), 6.37 (d, J=5.7 Hz, $^1$H), 3.88 (s, 3H). $^{19}$F NMR (376 MHz, Chloroform-d; FIG. 29) δ −72.87 (dd, J=27.8, 12.3 Hz), −87.48 (dd, J=21.4, 12.5 Hz), −143.98−−144.42 (m). $^{13}$C NMR (101 MHz, Chloroform-d; FIG. 30) δ 168.2, 167.1, 151.6 (dq, J=244.4, 12.0, 3.0 Hz), 147.6 (ddd, J=248.6, 17.4, 13.5 Hz), 142.1 (ddd, J=260.7, 27.2, 6.4 Hz), 139.8 (d, J=12.3 Hz), 132.9, 132.9, 129.3, 127.7, 113.6 (d, J=41.9 Hz), 54.5, 50.40. HRMS (ESI) $C_{15}H_{10}ClF_3N_2O_3$ calcd. [M+Na]$^+$381.0224 observed 381.0203.

Figure 31:
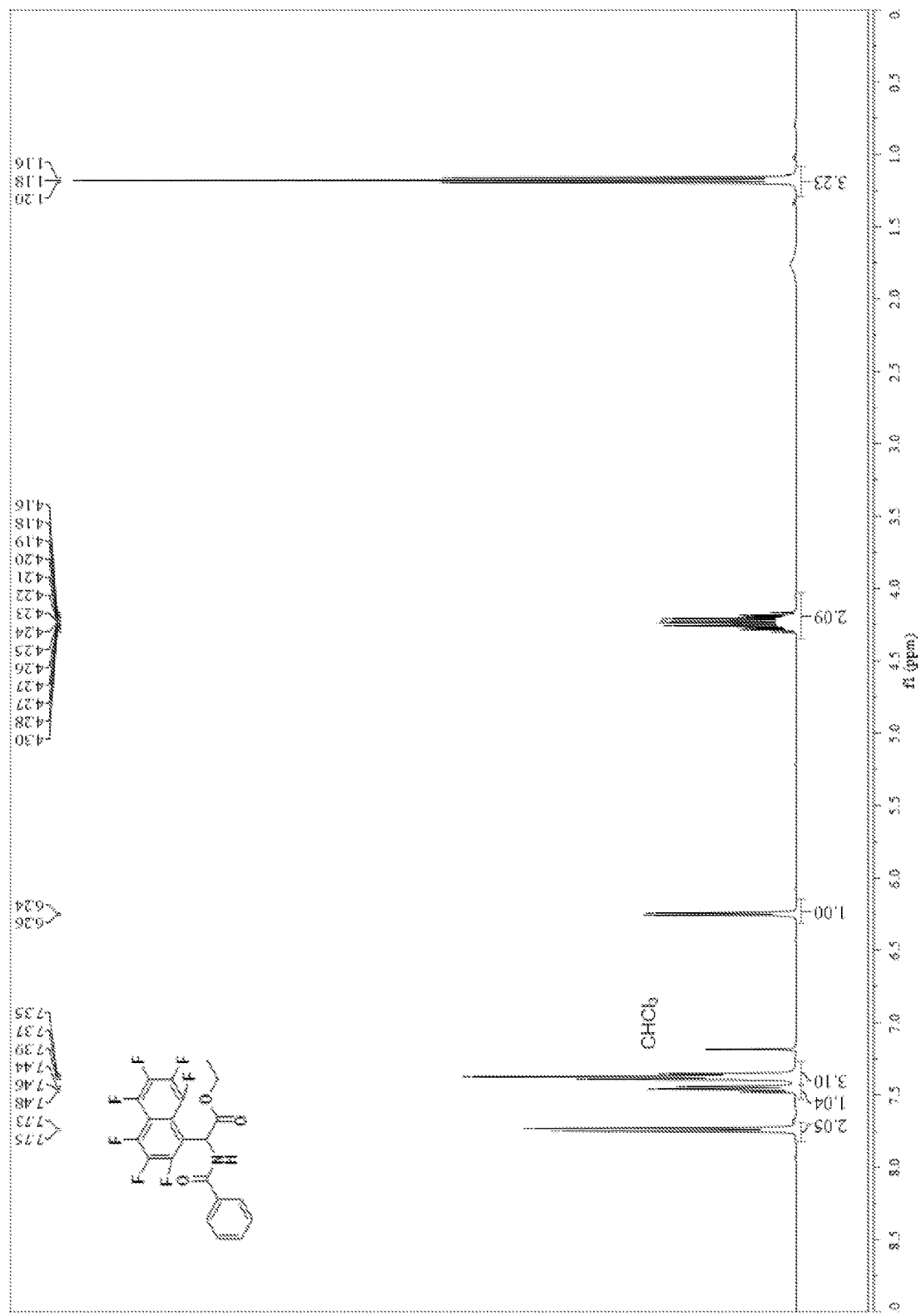
FIG. 31 contains a $^1$H NMR spectra (400 MHz), Chloroform-d) of species 2f.
Figure 32:
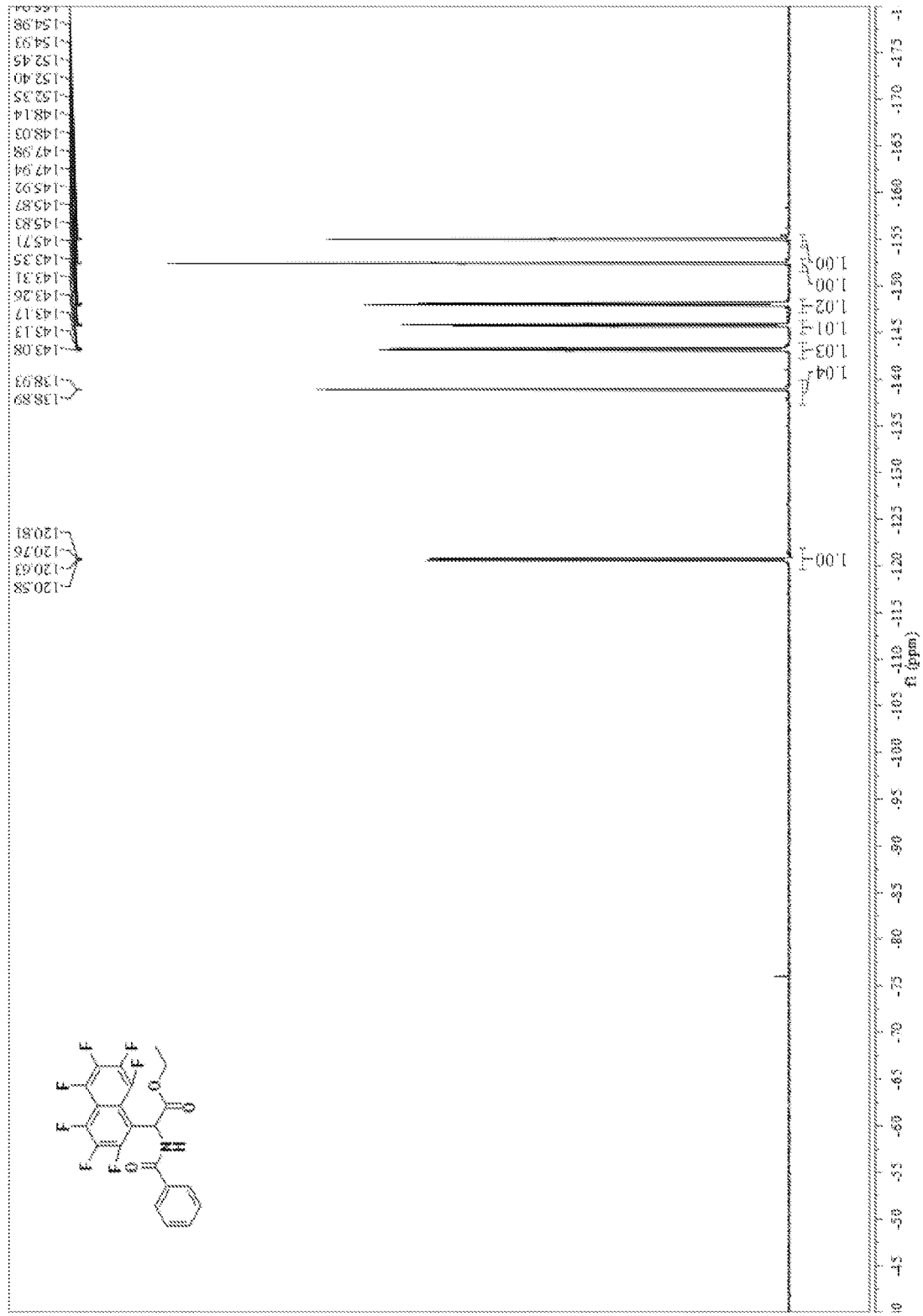
FIG. 32 contains a $^{19}$F NMR spectra (376 MHz), Chloroform-d) of species 2f.
Figure 33:
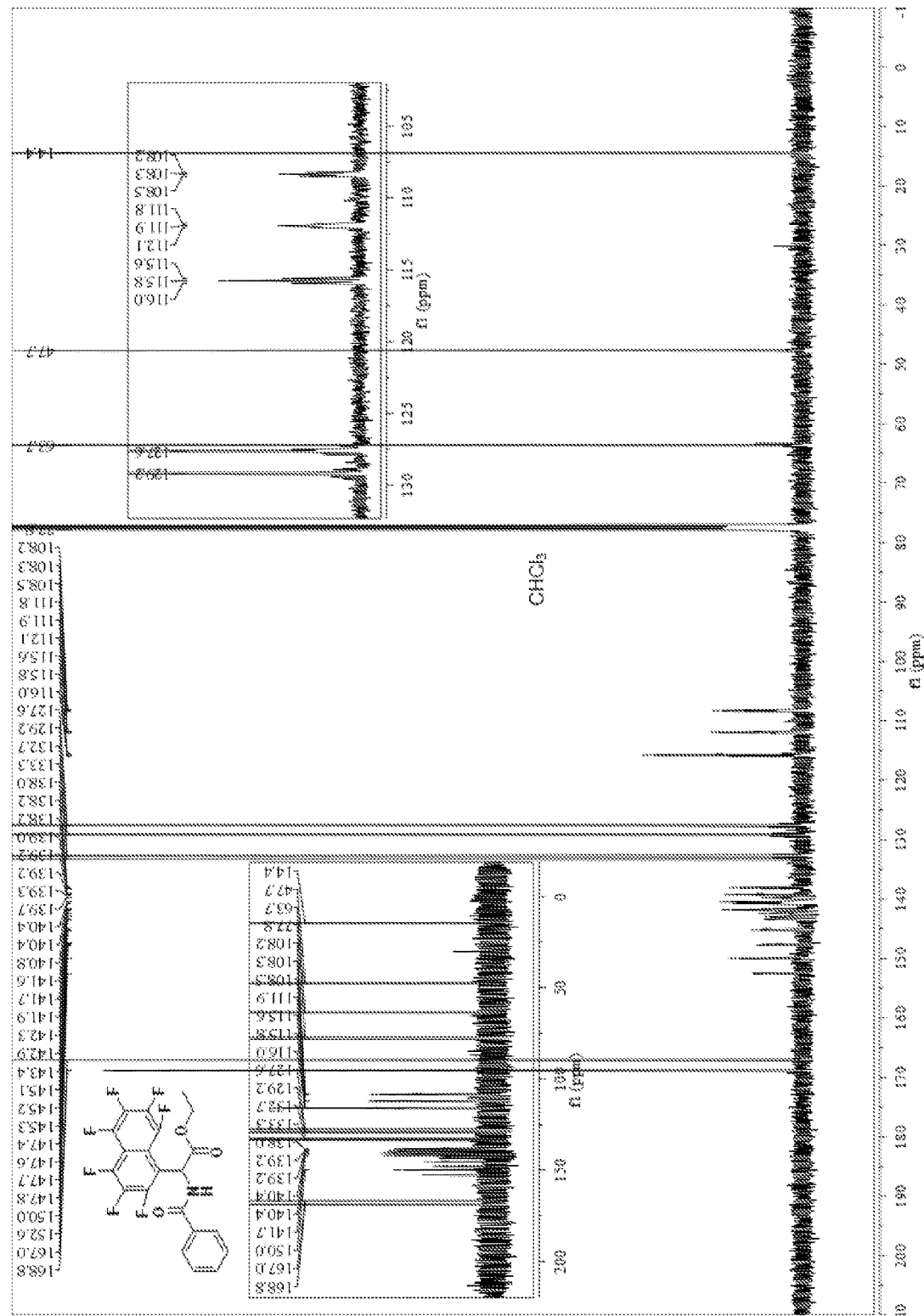
FIG. 33 contains a $^{13}$C NMR spectra (101 MHz), Chloroform-d) of species 2f.

2f ethyl 2-benzamido-2-(perfluoronaphthalen-1-yl)acetate (FIGS. 2 and 31-33) was produced as a yellow oil with 82% yield (69.2 mg, 0.254 mmol). The general procedure D was followed using 2-phenyloxazol-5(4H)-one (50 mg, 0.310 mmol), octafluoronapalene (86.5 mg, 0.318 mmol), 1,8-diazabicyclo(5.4.0)undec-7-ene (96.7 mg, 0.636 mmol), trifluoroacetic acid (141 mg, 1.24 mmol)/ethanol (0.620 mL) and 0.310 mL of MeCN was used to afford 2f. FT-IR (neat) cm$^{-1}$ 2943, 2849, 1760, 1677, 1085. $^1$H NMR (400 MHz, Chloroform-d; FIG. 31) δ 7.74 (d, J=7.2 Hz, 2H), 7.46 (t, J=7.4 Hz, $^1$H), 7.37 (m, J=7.5 Hz, 3H), 6.25 (d, J=6.5 Hz, $^1$H), 4.23 (dq, J=10.8, 7.1 Hz, 2H), 1.18 (t, J=7.1 Hz, 3H). $^{19}$F NMR (376 MHz, Chloroform-d; FIG. 32) δ −120.69 (dd, J=68.3, 18.5 Hz), −138.91 (d, J=16.6 Hz), −143.22 (dt, J=68.3, 16.8 Hz), −145.79 (dt, J=61.8, 17.5 Hz), −148.06 (dt, J=57.6, 18.0 Hz), −152.40 (t, J=18.5 Hz), −154.99 (t, J=20.3 Hz). $^{13}$C NMR (101 MHz, Chloroform-d; FIG. 33) δ 168.6, 167.1, 151.3 (d, J=266.9 Hz), 148.1-145.1 (m), 147.8-144.9 (m), 143.1 (d, J=54.7 Hz), 142.5-139.5 (m), 142.0-140.2 (m), 138.6 (dd, J=118.3 Hz), 133.3, 132.7, 129.2, 127.6, 115.8 (t, J=18.0 Hz), 111.9 (t, J=13.0 Hz), 108.7-108.1 (m), 63.7, 47.7, 14.4. HRMS (ESI) $C_{21}H_{12}F_7NO_3$ calcd. [M+K]$^+$498.0337 observed 498.0309.

Figure 34:
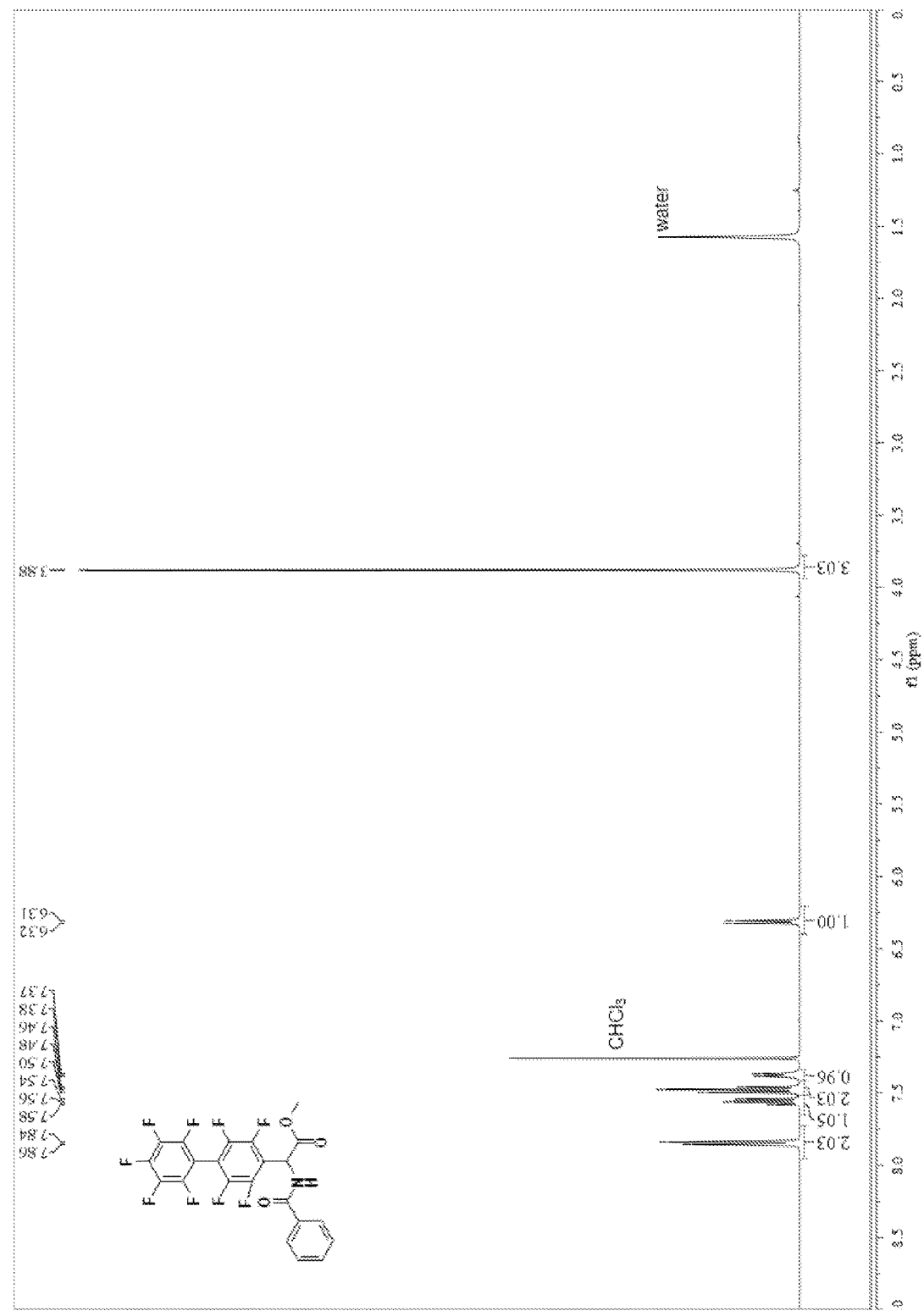
FIG. 34 contains a $^{1}$H NMR spectra (400 MHz), Chloroform-d) of species 2g.
Figure 35:
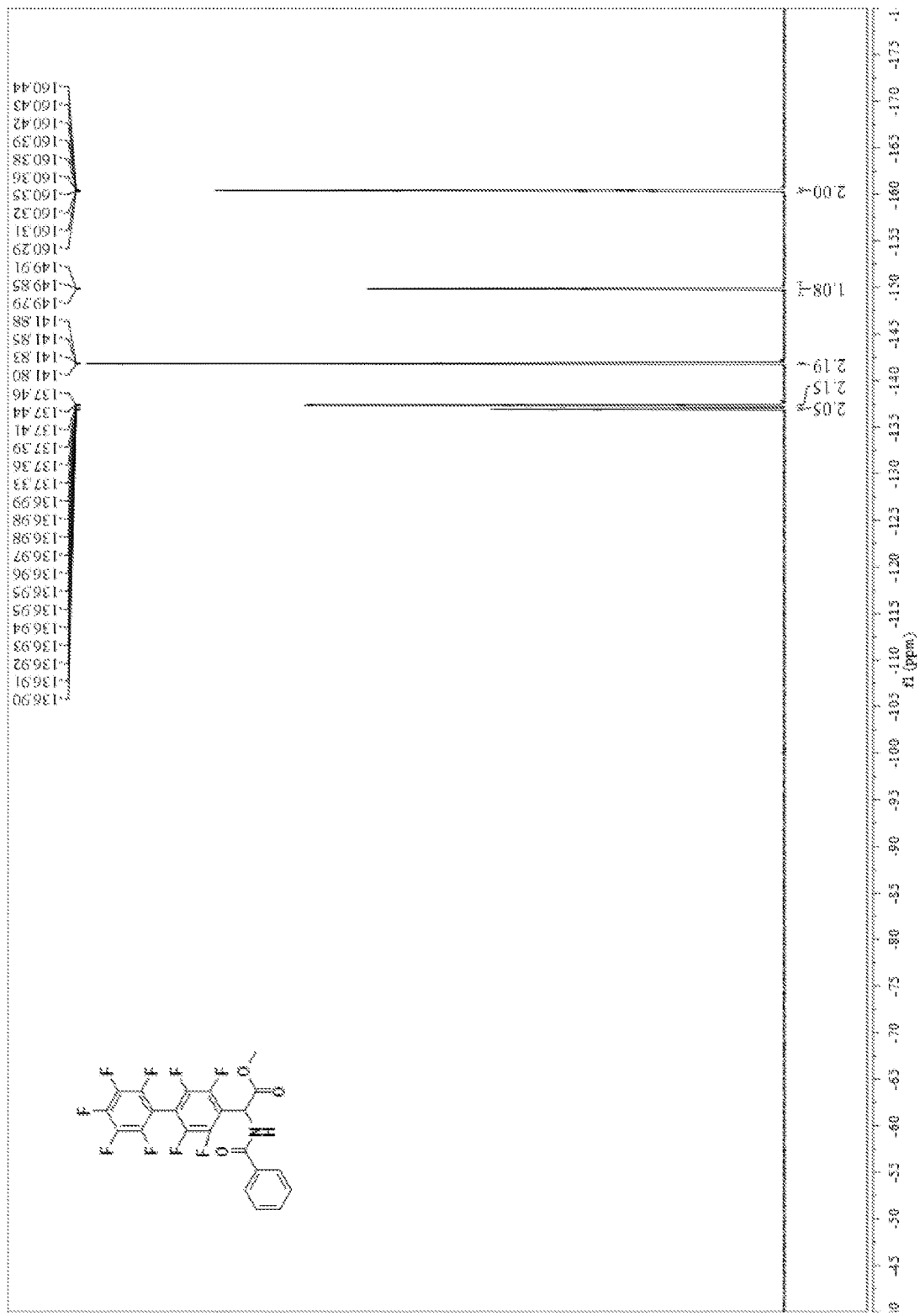
FIG. 35 contains a $^{19}$F NMR spectra (376 MHz), Chloroform-d) of species 2g.
Figure 36:
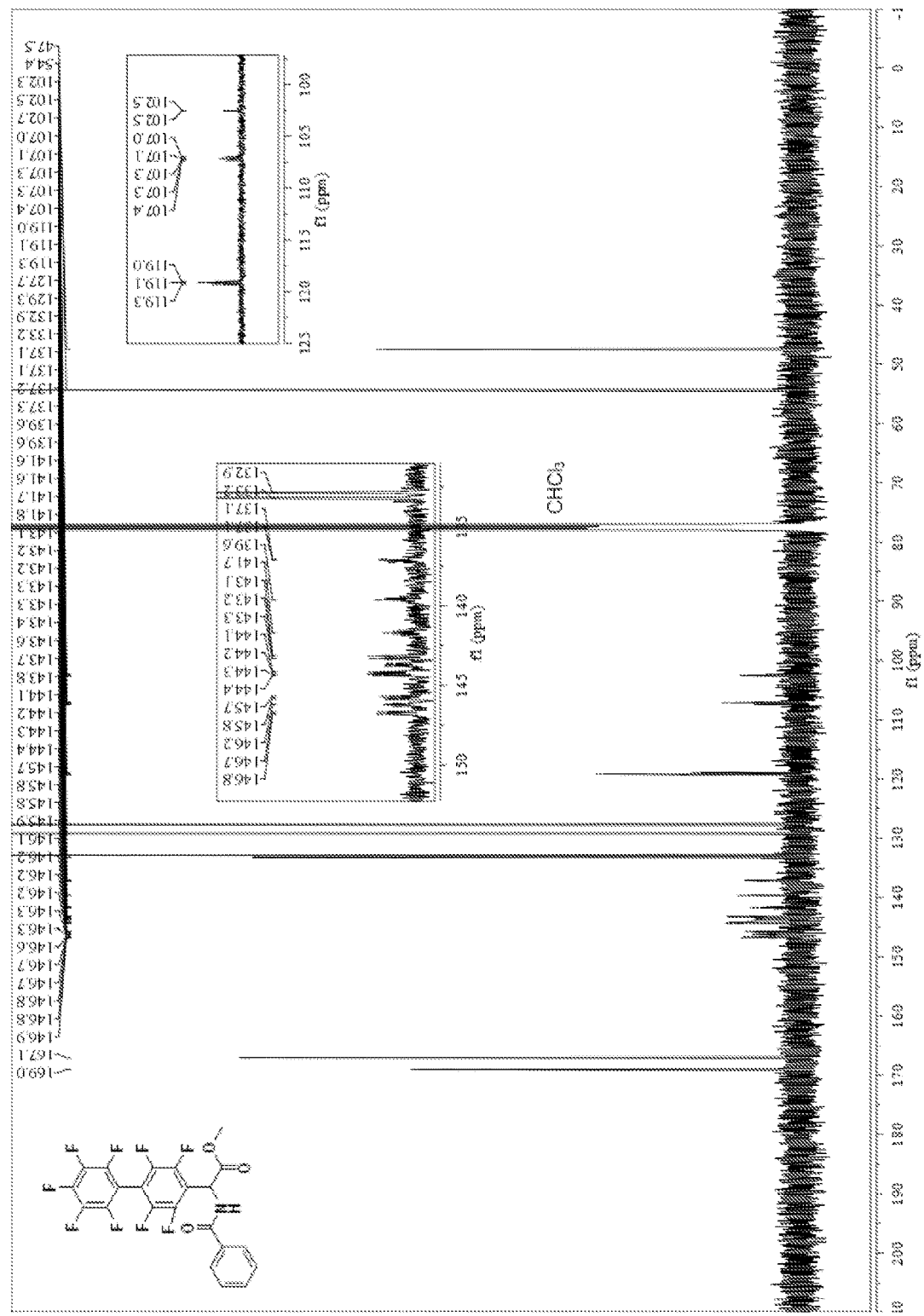
FIG. 36 contains a $^{13}$C NMR spectra (101 MHz), Chloroform-d) of species 2g.

2g methyl 2-benzamido-2-(perfluoro-[1,1'-biphenyl]-4-yl)acetate (FIGS. 2 and 34-36) was produced as a colorless oil with 82% yield (265 mg, 0.508 mmol). The general procedure D was followed using 2-phenyloxazol-5(4H)-one (100 mg, 0.621 mmol), decafluorobiphenyl (212.7 mg, 0.637 mmol), 1,8-diazabicyclo(5.4.0)undec-7-ene (193 mg, 1.27 mmol), trifluoroacetic acid (141 mg, 1.24 mmol)/methanol (1.24 mL) and 0.621 mL of MeCN was used to afford 2g. FT-IR (neat) cm$^{-1}$ 2950, 1744, 1634, 1085. $^1$H NMR (400 MHz, Chloroform-d; FIG. 34) δ 7.85 (d, J=7.1 Hz, 2H), 7.56 (t, J=7.4 Hz, $^1$H), 7.48 (t, J=7.5 Hz, 2H), 7.38 (d, J=6.8 Hz, $^1$H), 6.31 (d, J=6.8 Hz, $^1$H), 3.88 (s, 3H). $^{19}$F NMR (376 MHz, Chloroform-d; FIG. 35) δ −136.95 (dtt, J=14.0, 6.0, 2.7 Hz), −137.40 (h, J=10.4 Hz), −141.84 (q, J=11.4 Hz), −149.85 (t, J=21.0 Hz), −160.38 (tt, J=21.2, 5.4 Hz). $^{13}$C NMR (101 MHz, Chloroform-d; FIG. 36) δ 169.1, 167.1, 147.1-145.5 (m), 146.4-143.5 (m), 143.3 (dt, J=14.4, 3.9 Hz), 139.6 (d, J=8.5 Hz), 137.2 (dd, J=14.0, 5.8 Hz), 133.2, 132.9, 129.3, 127.7, 119.1 (t, J=15.6 Hz), 107.1 (t, J=16.2 Hz), 102.4 (t, J=16.8 Hz), 54.4, 47.5. HRMS (ESI) $C_{23}H_{12}F_9NO_3$ calcd. [M+H]$^+$ 508.0590 observed 508.0545.

Figure 37:
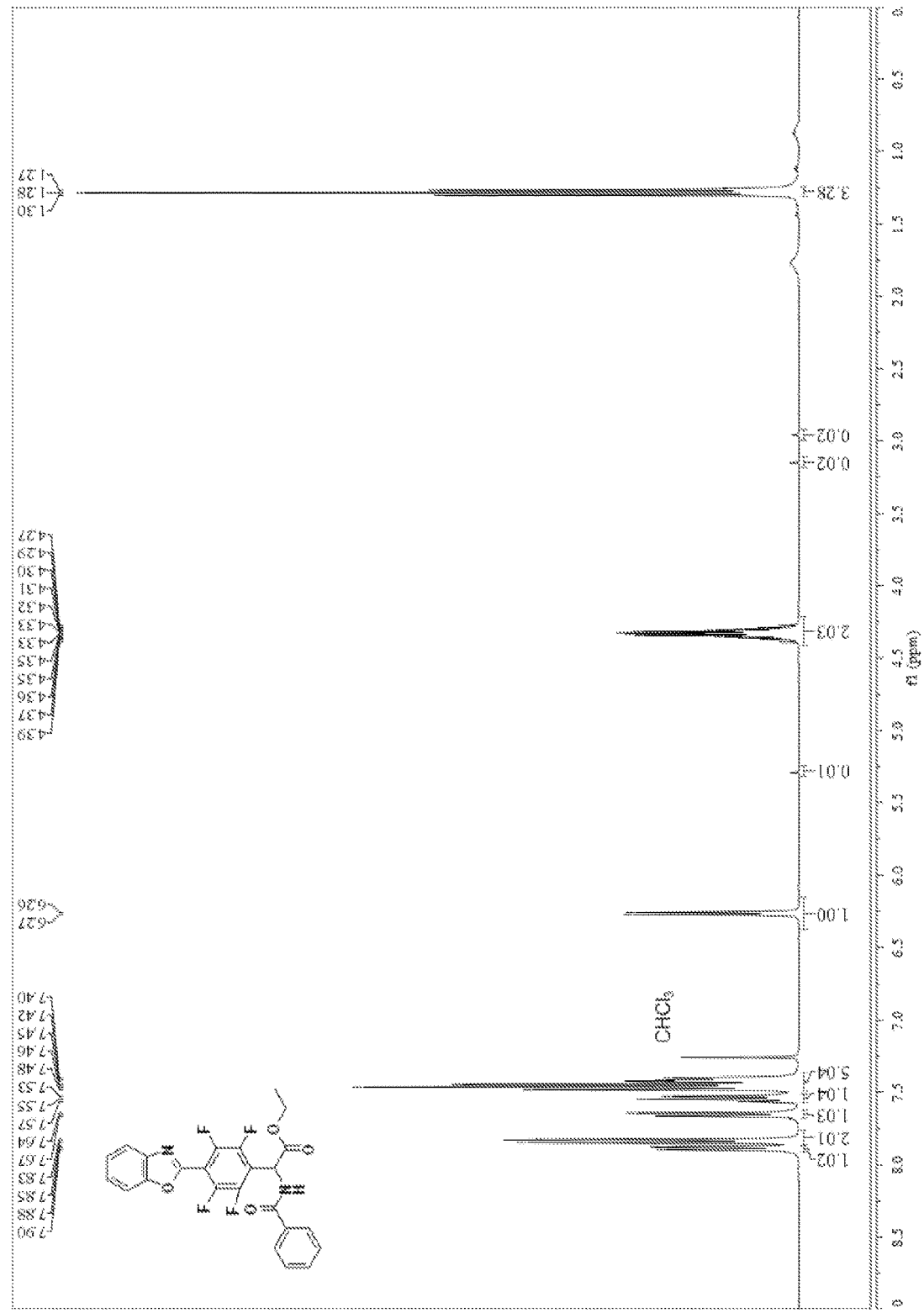
FIG. 37 contains a $^{1}$H NMR spectra (400 MHz), Chloroform-d) of species 2h.
Figure 38:
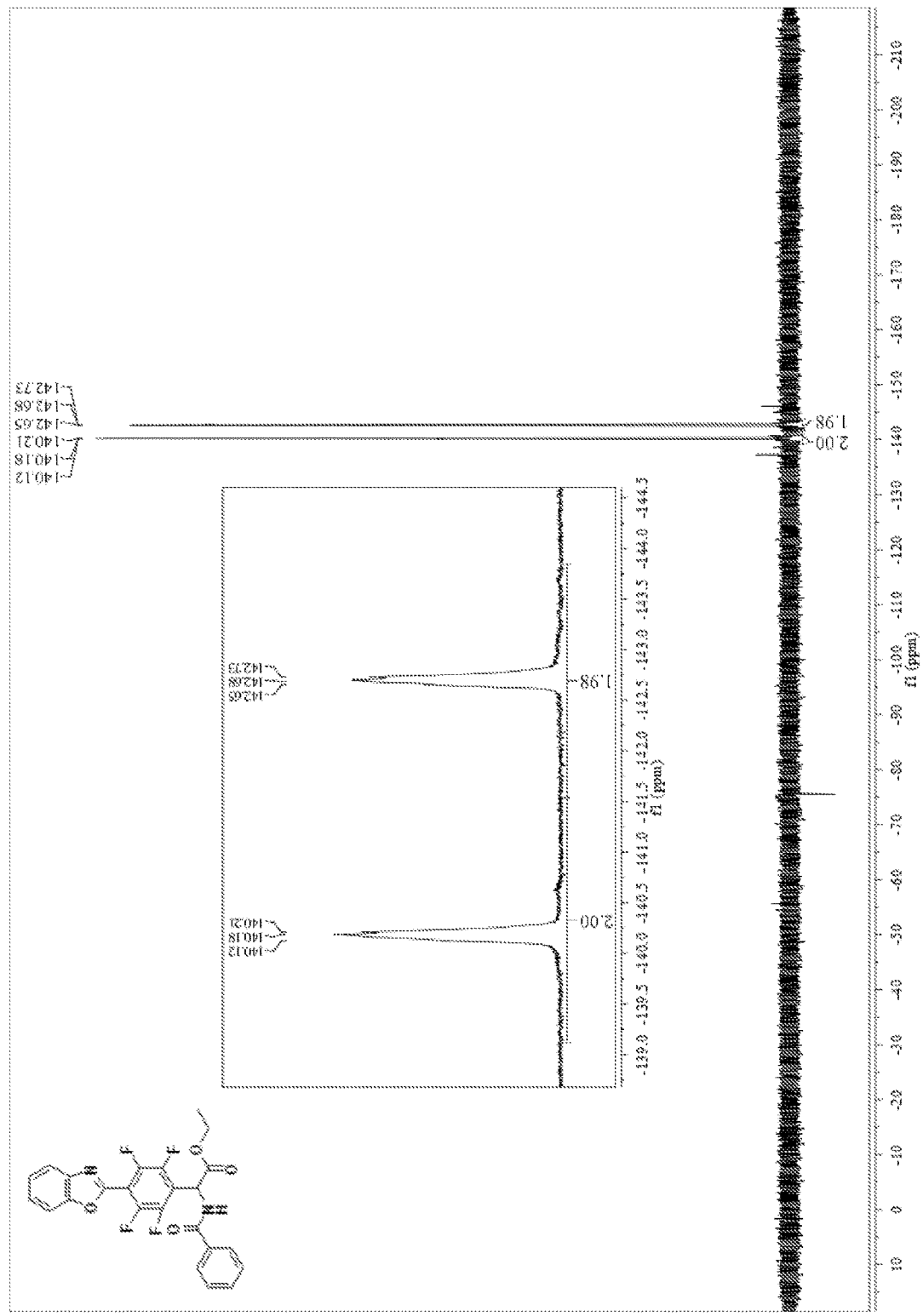
FIG. 38 contains a $^{19}$F NMR spectra (376 MHz), Chloroform-d) of species 2h.
Figure 39:
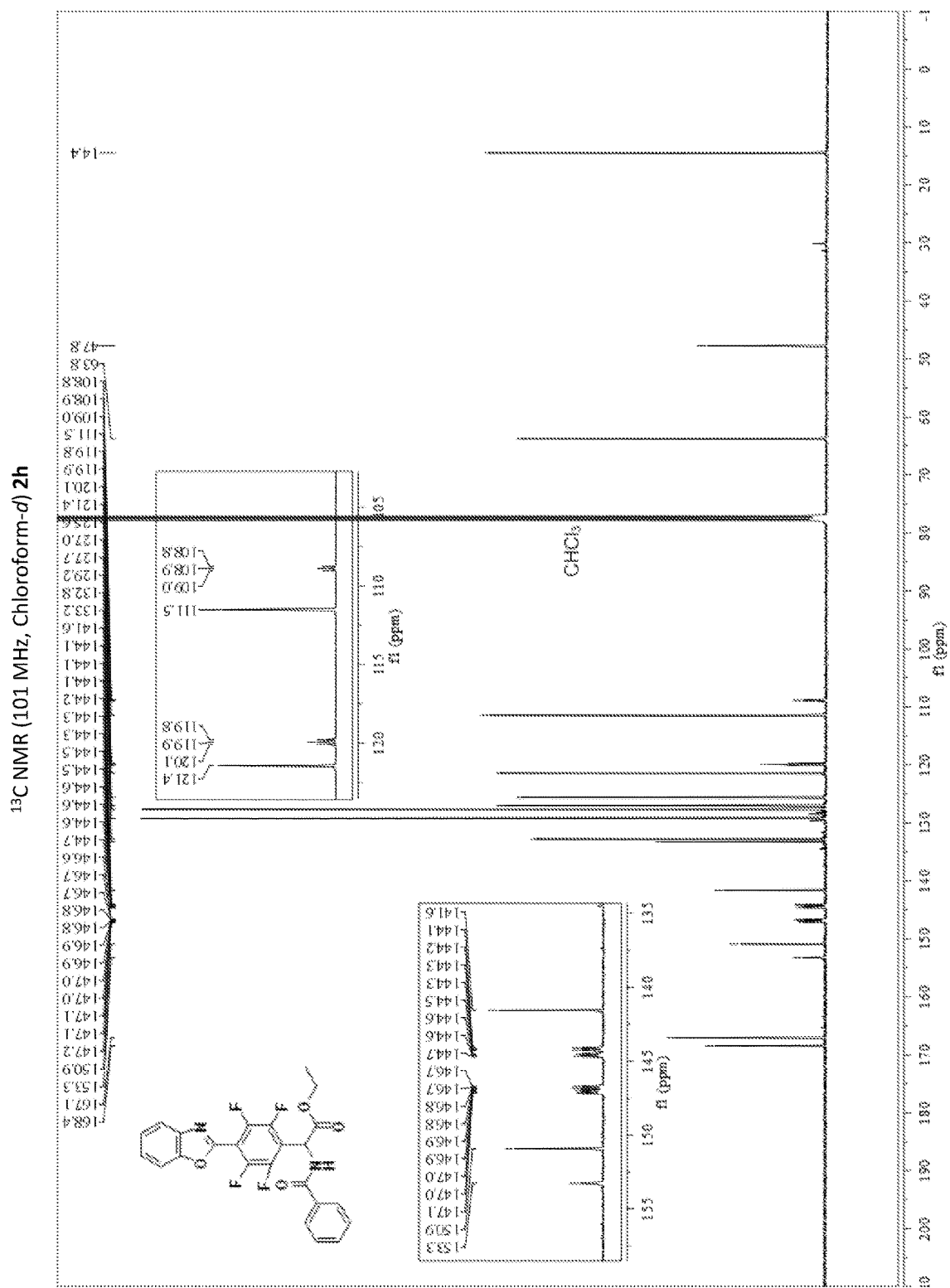
FIG. 39 contains a $^{13}$C NMR spectra (101 MHz), Chloroform-d) of species 2h.

2h ethyl 2-benzamido-2-(4-(benzo[d]oxazol-2-yl)-2,3,5,6-tetrafluorophenyl)acetate (FIGS. 2 and 37-39) was produced as a pale white solid with 82% yield (120 mg, 0.254 mmol). The general procedure D was followed using 2-phenyloxazol-5(4H)-one (50 mg, 0.310 mmol), 2-(perfluorophenyl)benzo[d]oxazole (90.6 mg, 0.318 mmol), 1,8-diazabicyclo(5.4.0)undec-7-ene (96.7 mg, 0.636 mmol), trifluoroacetic acid (70.7 mg, 0.620 mmol)/ethanol (0.620 mL) and 0.310 mL of MeCN was used to afford 2h. FT-IR (neat) cm$^{-1}$ 2950, 1749, 1634, 1140, 1085, 1052. $^1$H NMR (400 MHz, Chloroform-d; FIG. 37) δ 7.89 (d, J=8.8 Hz, $^1$H), 7.84 (d, J=8.5 Hz, 2H), 7.65 (d, J=8.4 Hz, $^1$H), 7.55 (t, J=7.4 Hz, $^1$H), 7.51-7.37 (m, 5H), 6.26 (d, J=6.6 Hz, $^1$H), 4.33 (dq, J=7.7, 3.6 Hz, 2H), 1.28 (t, J=7.1 Hz, 3H). $^{19}$F NMR (376 MHz, Chloroform-d; FIG. 38) δ −139.98−−140.48 (m), −142.52−−143.05 (m). $^{13}$C NMR (101 MHz, Chloroform-d; FIG. 39) δ 168.5, 167.1, 153.3, 150.9, 145.8 (ddt, J=250.1, 14.3, 5.3 Hz), 145.5 (ddt, J=260.3, 15.6, 4.1 Hz), 141.6, 133.3, 132.8, 129.2, 127.7, 127.0, 125.6, 121.4, 119.9 (t, J=15.8 Hz), 111.5, 108.9 (t, J=13.5 Hz), 63.8, 47.8, 14.4. HRMS (ESI) $C_{24}H_{16}F_4N_2O_4$ calcd. [M+Na]$^+$495.0938 observed 495.0911.

Figure 40:
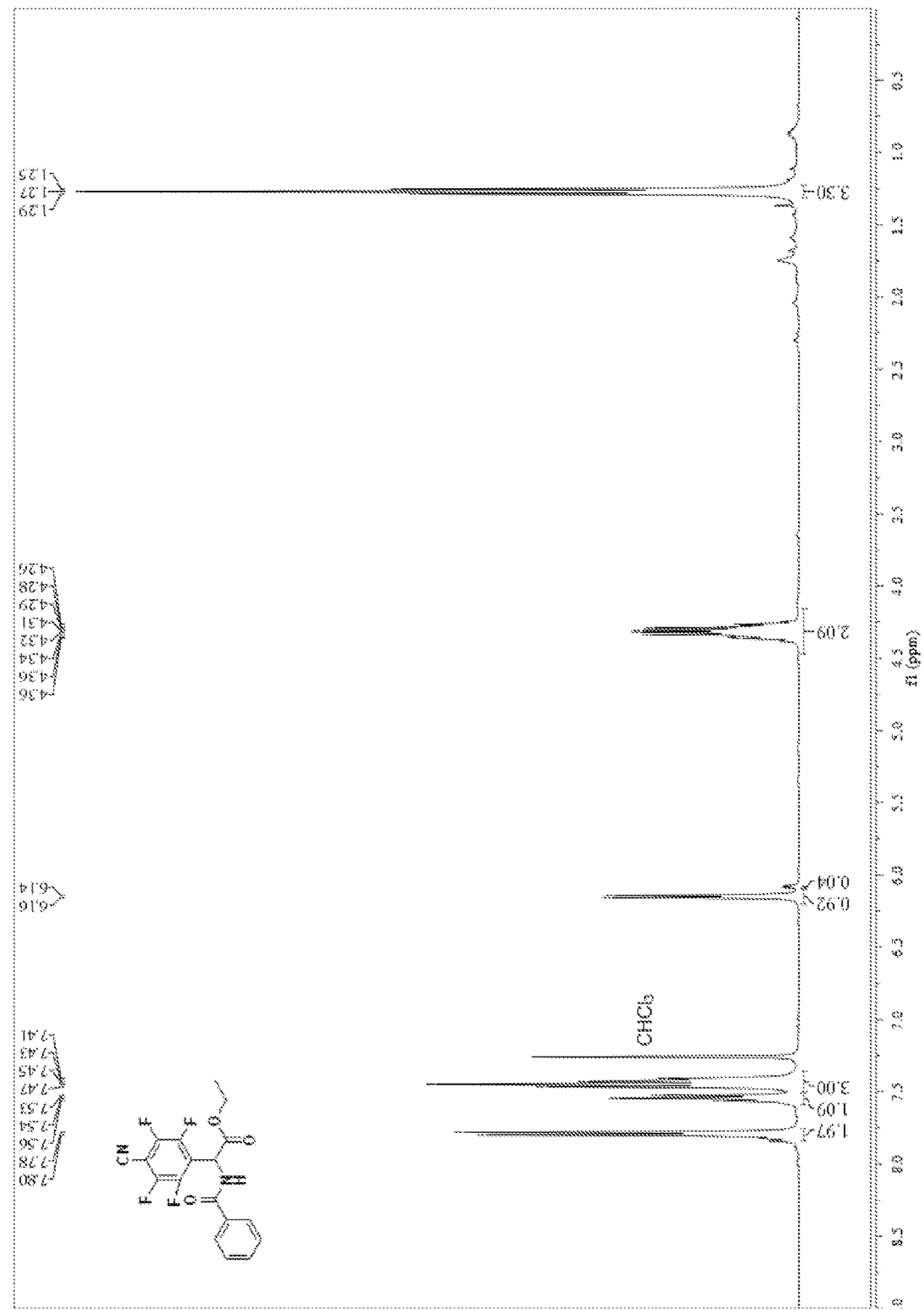
FIG. 40 contains a $^{1}$H NMR spectra (400 MHz), Chloroform-d) of species 2i.
Figure 41:
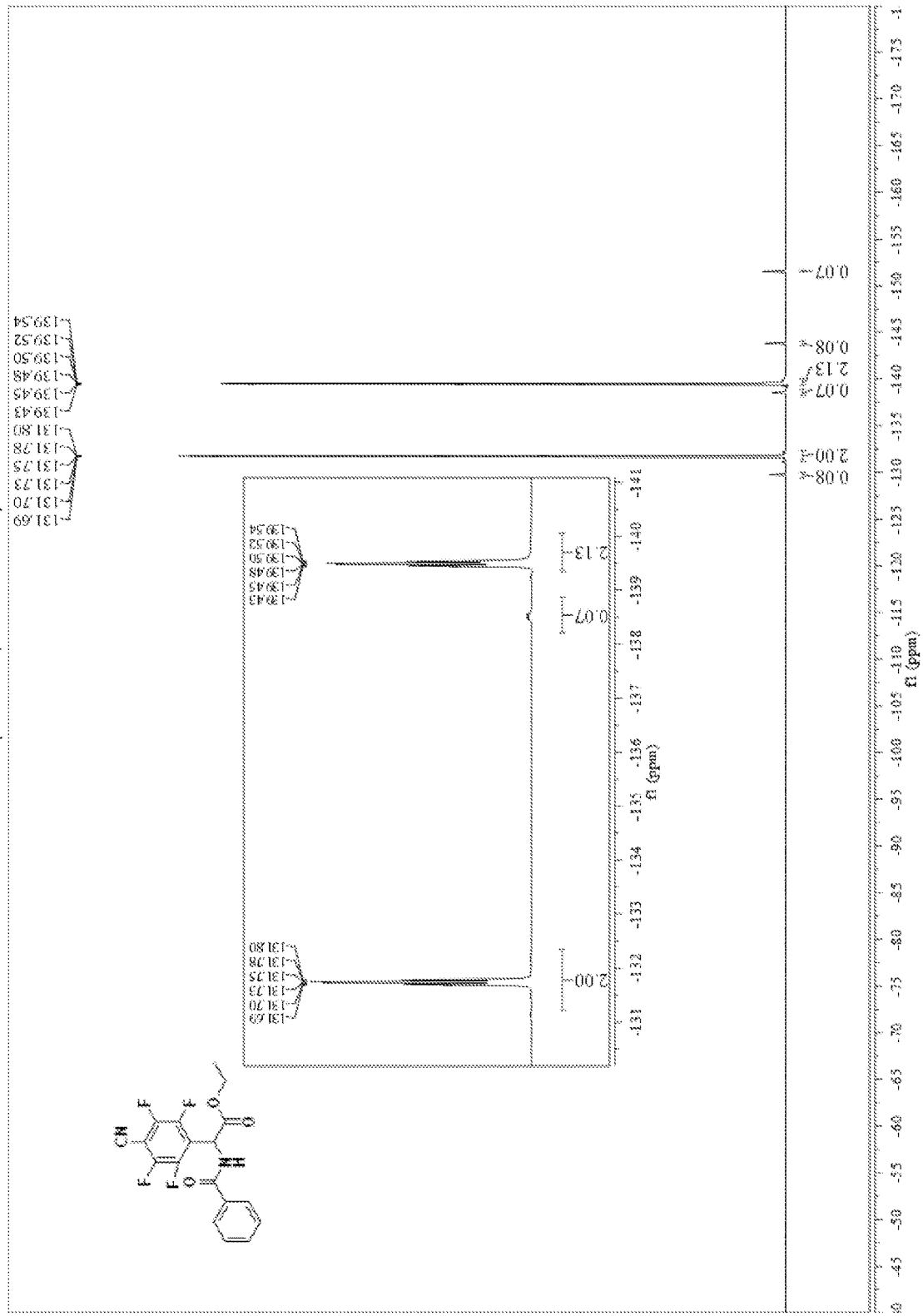
FIG. 41 contains a $^{19}$F NMR spectra (376 MHz), Chloroform-d) of species 2i.
Figure 42:
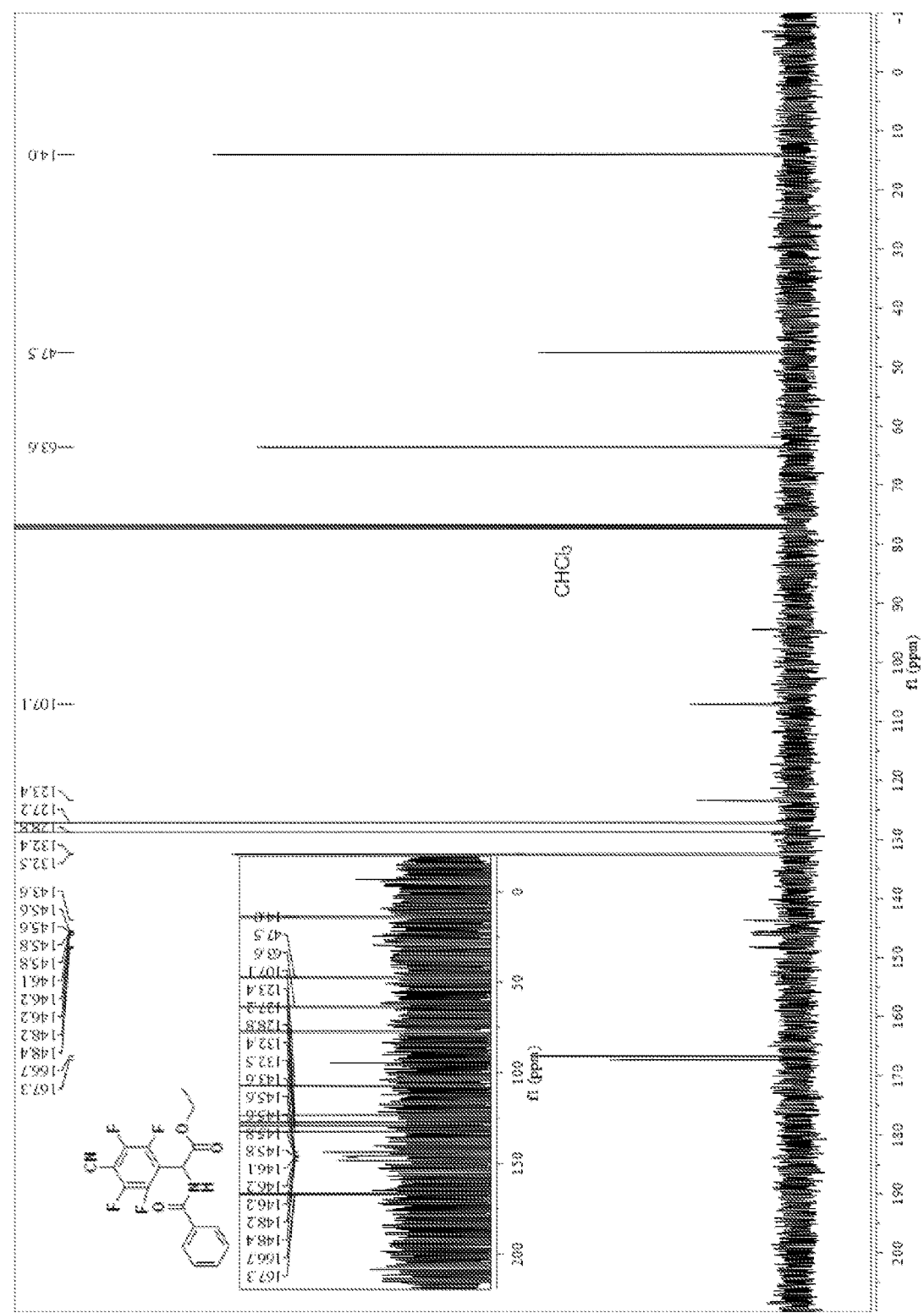
FIG. 42 contains a $^{13}$C NMR spectra (101 MHz), Chloroform-d) of species 2i.

2i ethyl 2-benzamido-2-(4-cyano-2,3,5,6-tetrafluorophenyl)acetic acid (FIGS. 2 and 40-42) was produced as a yellow oil with 79% yield (93.1 mg, 0.245 mmol). The general procedure A was followed using 2-phenyloxazol-5(4H)-one (50 mg, 0.310 mmol), 2,3,4,5,6 pentaflurobenzonitrile (61.4 mg, 0.318 mmol), tetramethylguanidine (73.2 mg, 0.636 mmol), trifluoroacetic acid (72.5 mg, 0.636 mmol)/ethanol (0.620 mL), and 0.310 mL of MeCN was used to afford 2i. FT-IR (neat) cm$^{-1}$ 2933, 2250, 1714, 1083. $^1$H NMR (400 MHz, Chloroform-d; FIG. 40) δ 7.72 (d, J=7.4 Hz, 2H), 7.47 (t, J=7.4 Hz, $^1$H), 7.43-7.29 (m, 3H), 6.08 (d, J=5.9 Hz, $^1$H), 4.24 (qd, J=10.7, 5.4 Hz, 2H), 1.20 (t, J=7.1 Hz, 3H). $^{19}$F NMR (376 MHz, Chloroform-d; FIG. 41) δ −131.74 (td, J=16.4, 6.7 Hz), −139.49 (td, J=16.3, 6.6 Hz). $^{13}$C NMR (101 MHz, Chloroform-d; FIG. 42) δ 167.3, 166.7, 148.5-146.1 (m), 148.6-145.7 (m), 145.9-143.4 (m), 132.5, 132.4, 128.8, 127.2, 123.4 (t), 107.1, 63.6, 47.5, 13.9. HRMS (ESI) $C_{18}H_{12}F_4N_2O_3$ calcd. [M+Na]$^+$ 403.0676 observed 403.0654.

Figure 43:
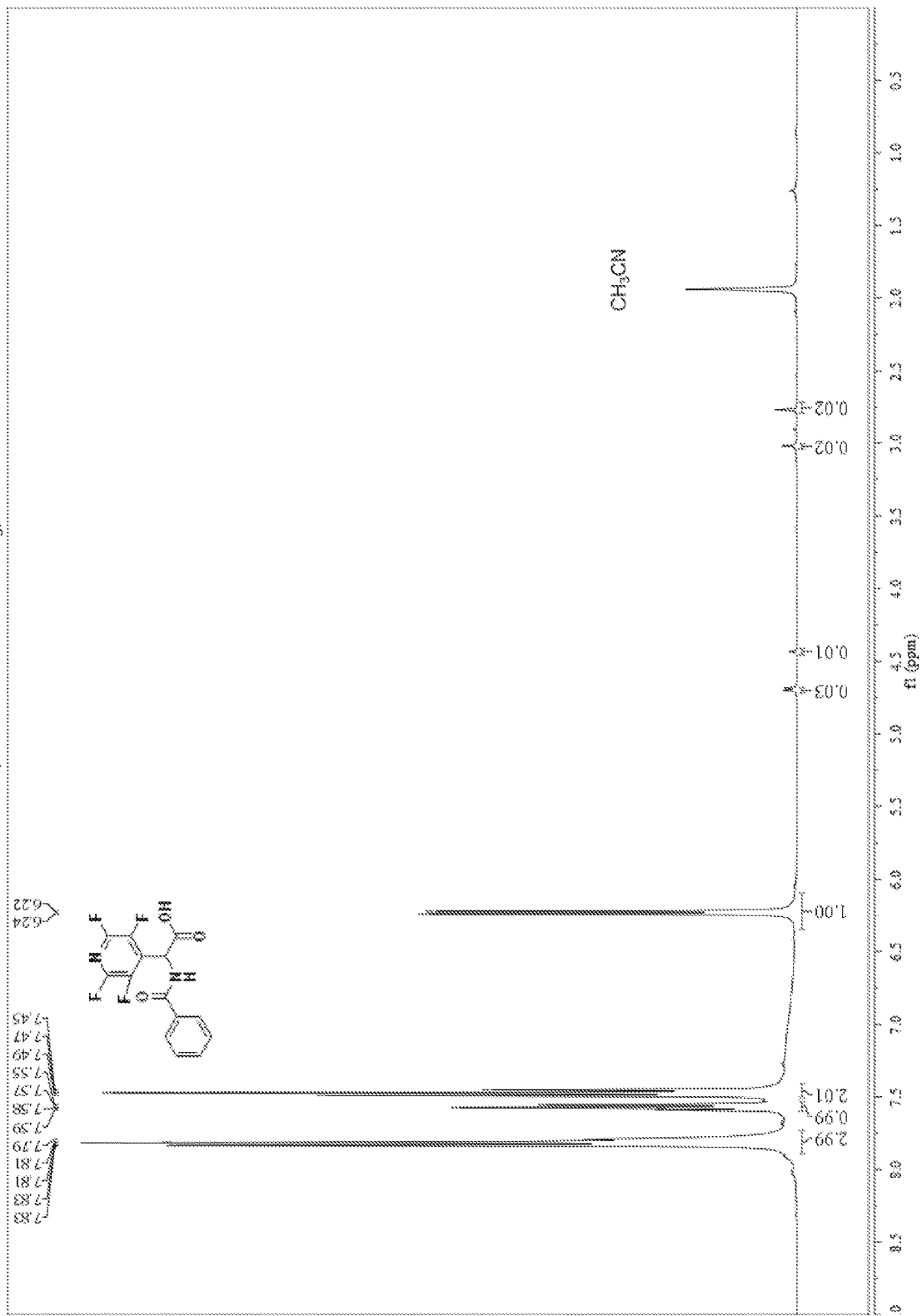
Figure 44:
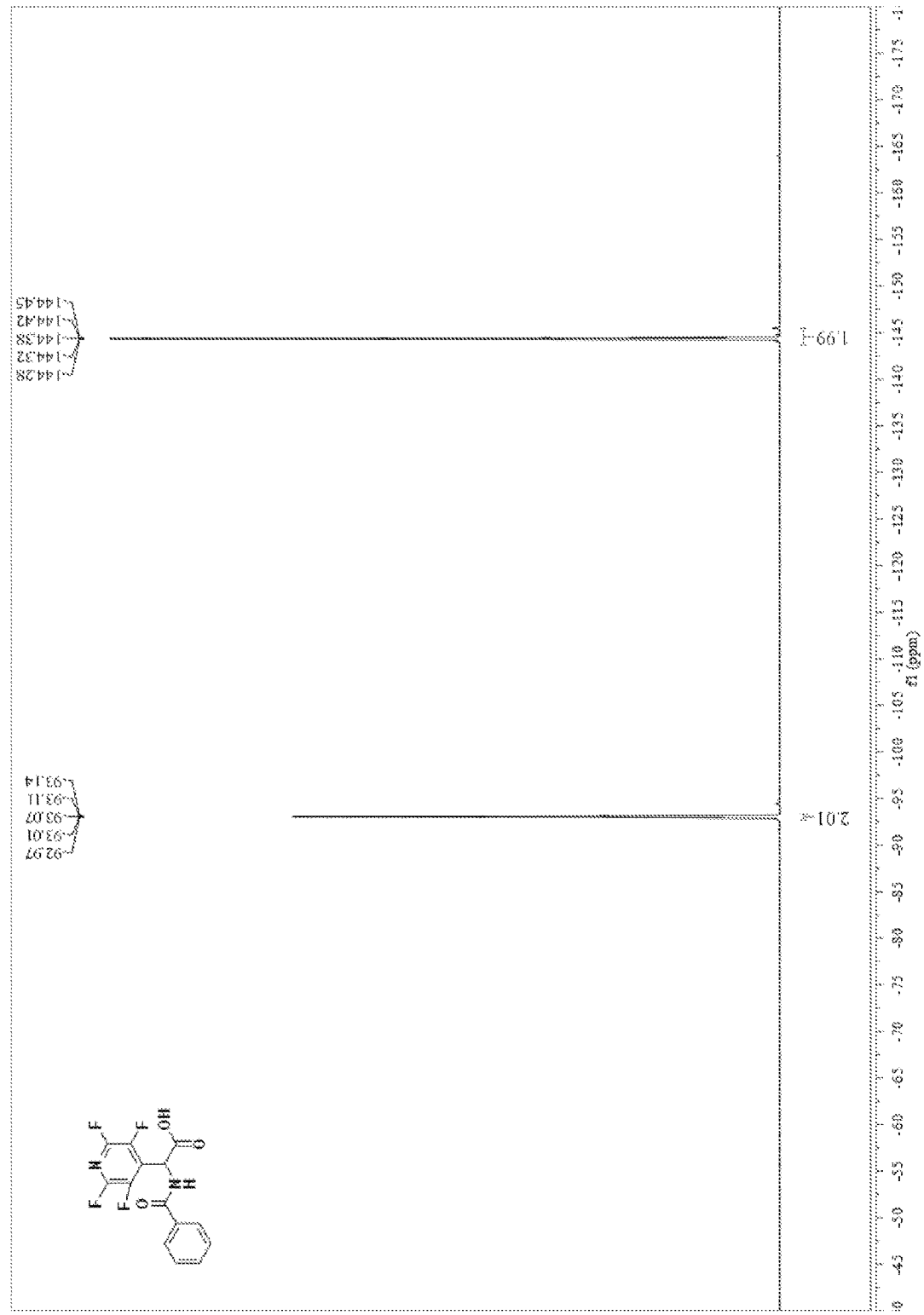
Figure 45:
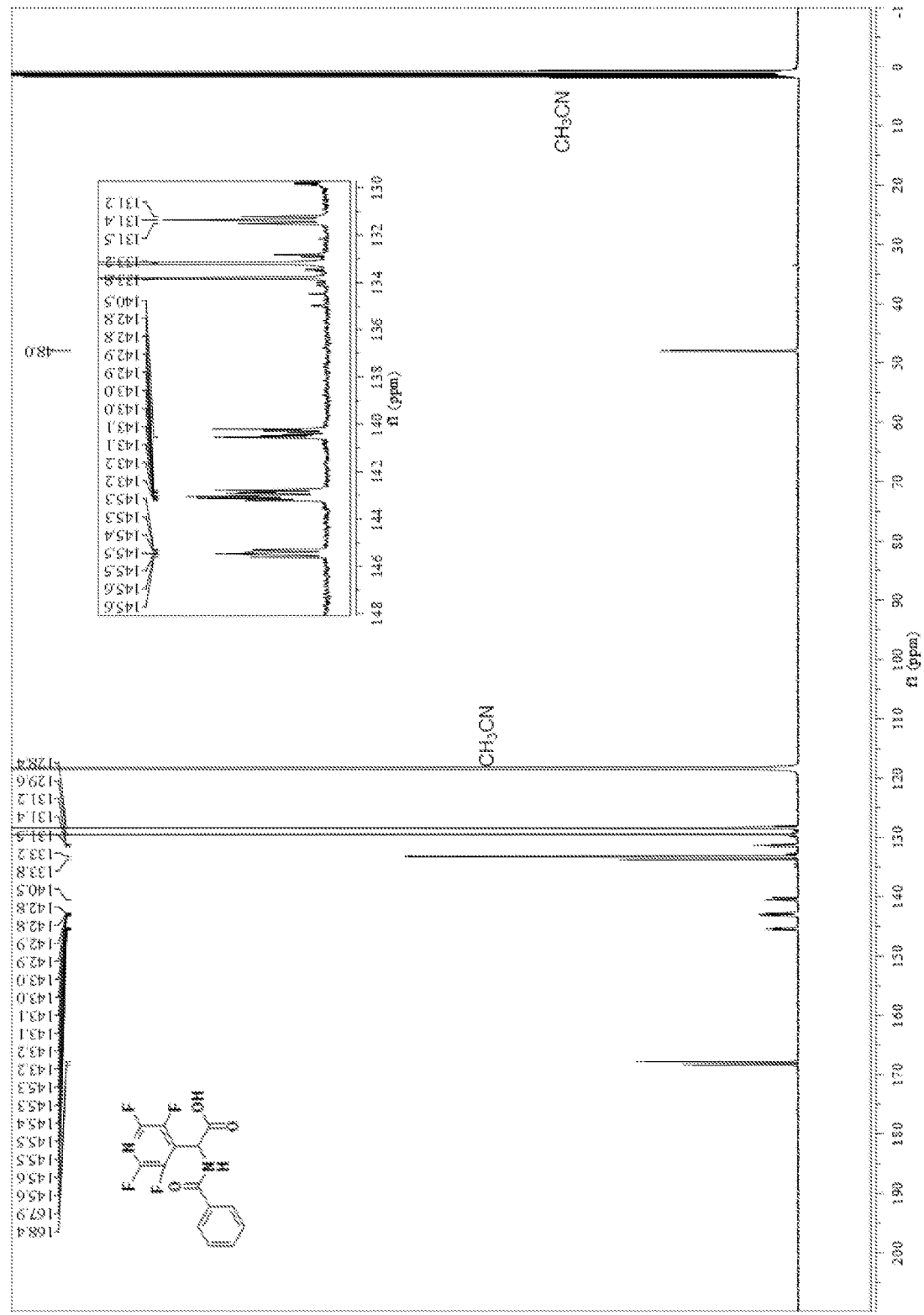

3a 2-benzamido-2-(perfluoropyridin-4-yl)acetic acid (FIGS. 3 and 43-45) was produced as a white solid with 85% yield (1.73 g, 5.27 mmol). The general procedure E was followed using 2-phenyloxazol-5(4H)-one (1.00 g, 6.20 mmol), pentafluoropyridine (1.08 g, 6.36 mmol), tetramethylguanidine (1.46 g, 12.71 mmol), and 6.20 mL of MeCN was used to afford 3a. FT-IR (neat) cm$^{-1}$ 3643, 2250, 1715, 1106. $^1$H NMR (400 MHz, Acetonitrile-$d_3$; FIG. 43) δ 7.95 -7.73 (m, 3H), 7.60 (t, J=7.4 Hz, $^1$H), 7.50 (t, J=7.6 Hz, 2H), 6.26 (d, J=6.9 Hz, $^1$H). $^{19}$F NMR (376 MHz, $CD_3CN$; FIG. 44) δ −93.07, −144.38. $^{13}$C NMR (101 MHz, Acetonitrile-$d_3$; FIG. 45) δ 168.3, 167.7, 151.9 (dd, J=240.4, 9.7 Hz), 148.1 (dq, J=244.4, 17.6, 13.9 Hz), 142.8 (ddd, J=258.2, 27.4, 6.2 Hz), 141.1 (d, J=12.7 Hz), 133.8, 133.2, 129.6, 128.4, 114.4 (dd, J=35.3, 6.5 Hz), 50.8. HRMS (ESI) $C_{14}H_8F_4N_2O_3$ calcd. [M+K]$^+$ 367.0103 observed 367.0083.

Figure 46:
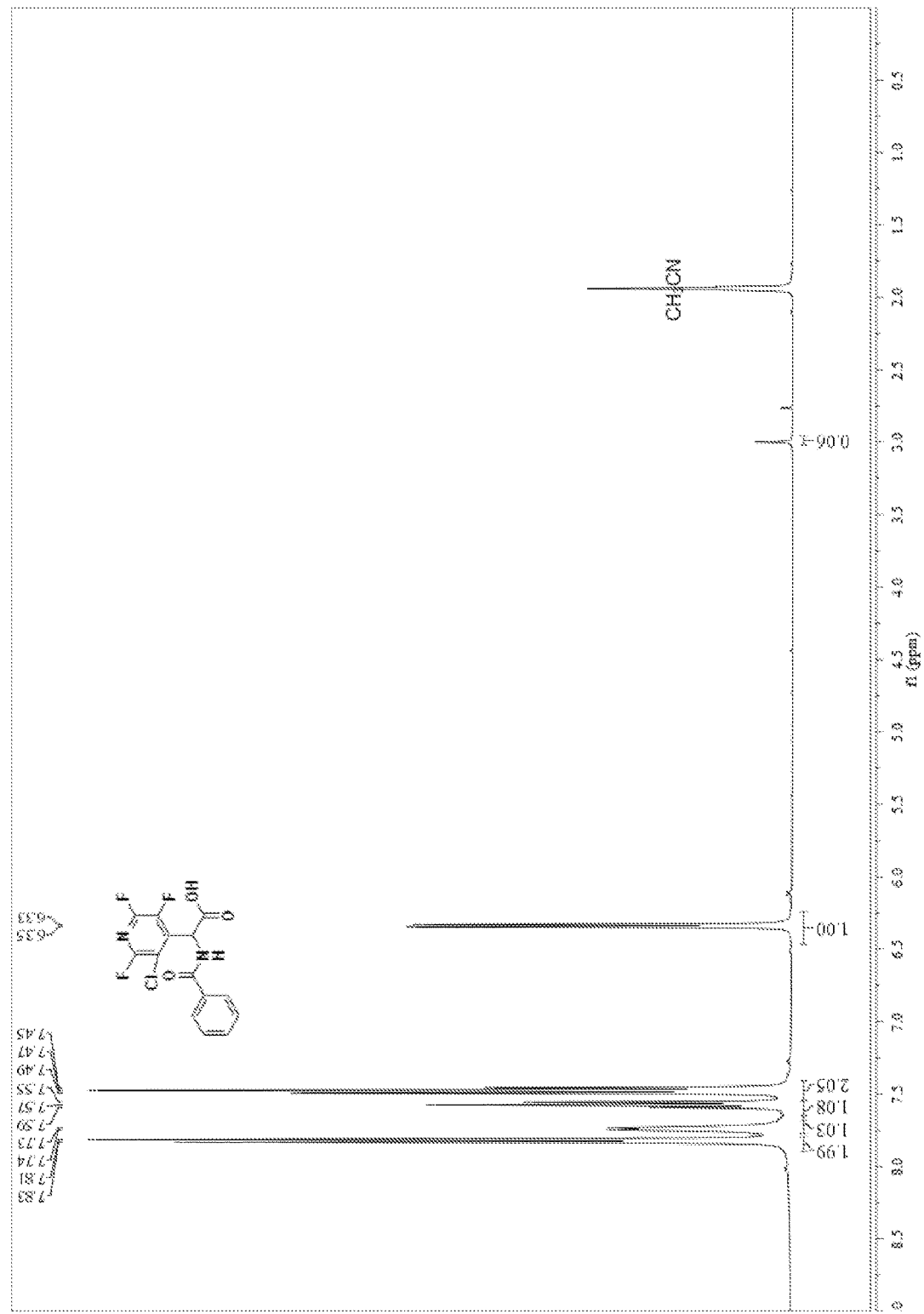
FIG. 46 contains a $^{1}$H NMR spectra (400 MHz), Acetonitrile-$d_3$) of species 3b.
Figure 47:
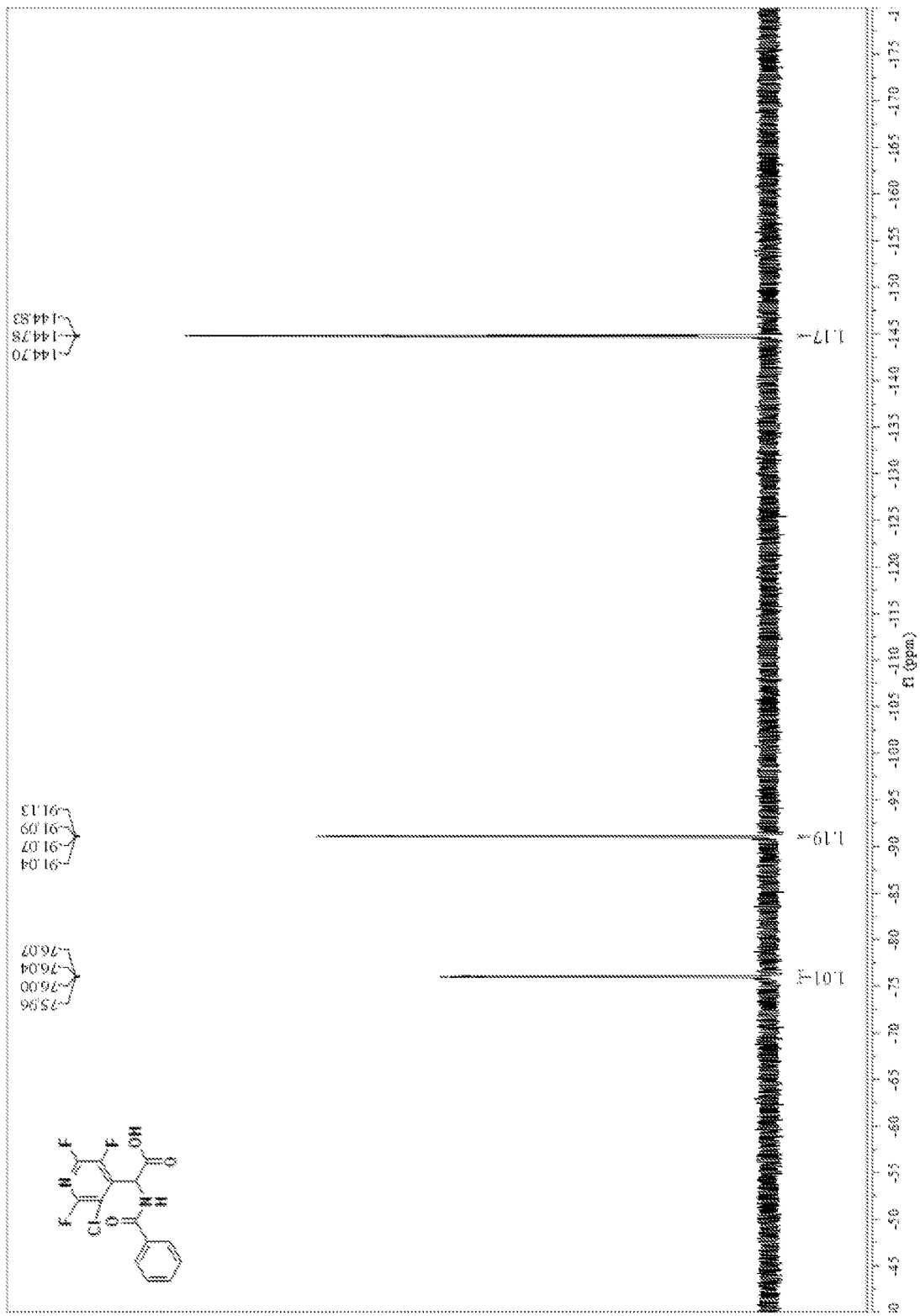
FIG. 47 contains a $^{19}$F NMR spectra (376 MHz), Acetonitrile-$d_3$) of species 3b.
Figure 48:
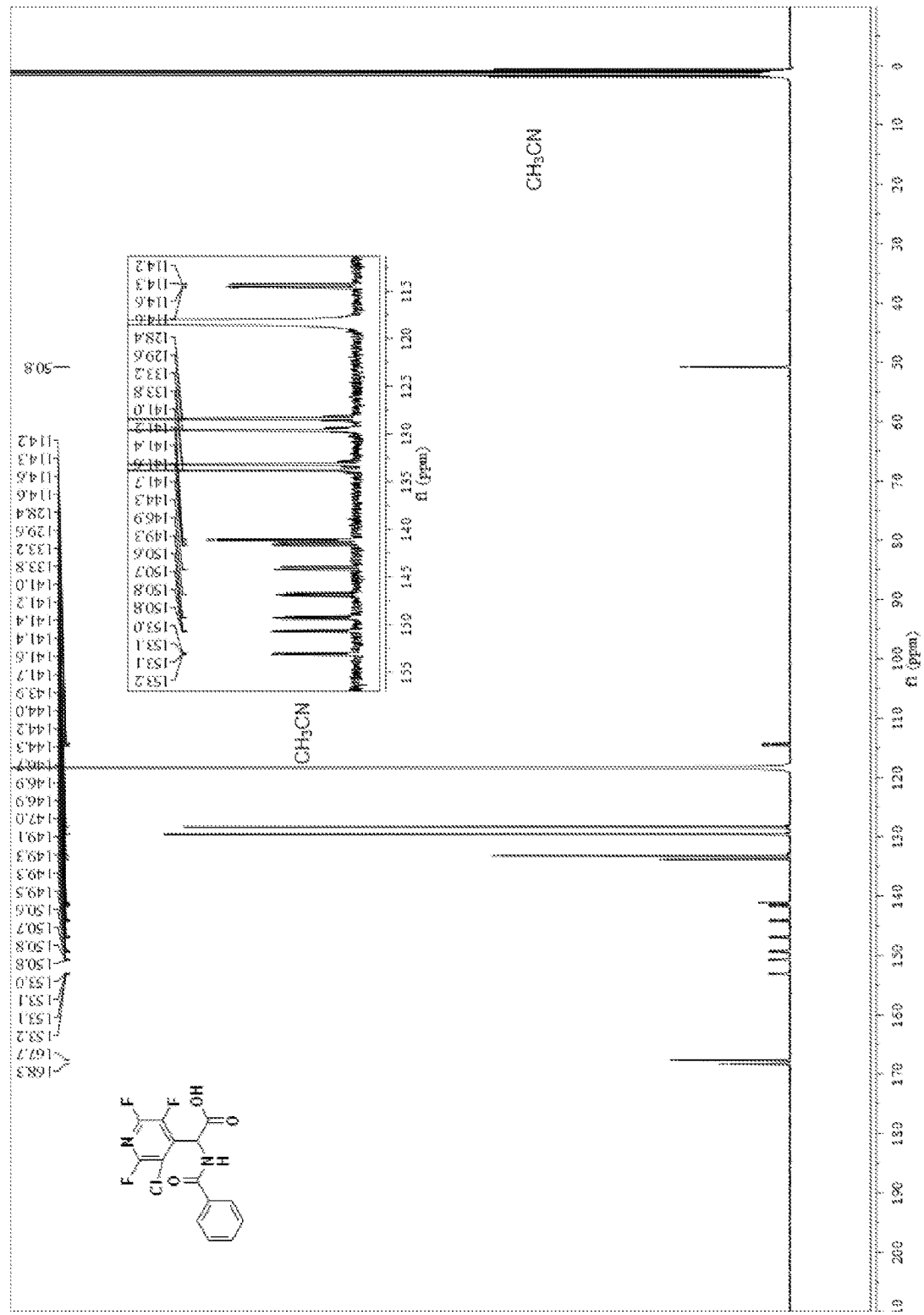
FIG. 48 contains a $^{13}$C NMR spectra (101 MHz), Acetonitrile-$d_3$) of species 3b.

3b 2-benzamido-2-(3-chloro-2,5,6-trifluoropyridin-4-yl) acetic acid (FIGS. 3 and 46-48) was produced as a pale white solid with 86% yield (1.84 g, 5.33 mmol). The general procedure E was followed using 2-phenyloxazol-5(4H)-one (1.00 g, 6.20 mmol), 3-chloro-2,4,5,6 tetrafluoropyridine (1.18 g, 6.36 mmol), tetramethylguanidine (1.46 g, 12.71 mmol), and 6.20 mL of MeCN was used to afford 3b. FT-IR (neat) cm$^{-1}$ 3604, 1722, 1664, 1085. $^1$H NMR (400 MHz, Acetonitrile-d$_3$; FIG. 46) δ 7.82 (d, J=7.4 Hz, 2H), 7.74 (d, J=5.9 Hz, $^1$H), 7.57 (t, J=7.4 Hz, $^1$H), 7.47 (t, J=7.6 Hz, 2H), 6.34 (d, J=6.6 Hz, $^1$H). $^{19}$F NMR (376 MHz, Acetonitrile-d$_3$; FIG. 47) δ −76.02 (dd, J=27.3, 12.5 Hz), −91.08 (dd, J=21.1, 13.2 Hz), −144.77 (t, J=24.3 Hz). $^{13}$C NMR (101 MHz, Acetonitrile-d$_3$; FIG. 48) δ 168.3, 167.7, 151.9 (dd, J=240.4, 9.7 Hz), 148.1 (dq, J=244.4, 17.6, 13.9 Hz), 142.8 (ddd, J=258.2, 27.4, 6.2 Hz), 141.1 (d, J=12.7 Hz), 133.8, 133.2, 129.6, 128.4, 114.4 (dd, J=35.3, 6.5 Hz), 50.8. HRMS (ESI) $C_{14}H_8ClF_3N_2O_3$ calcd. [M+Na]$^+$ 367.0068 observed 367.0047.

Figure 49:
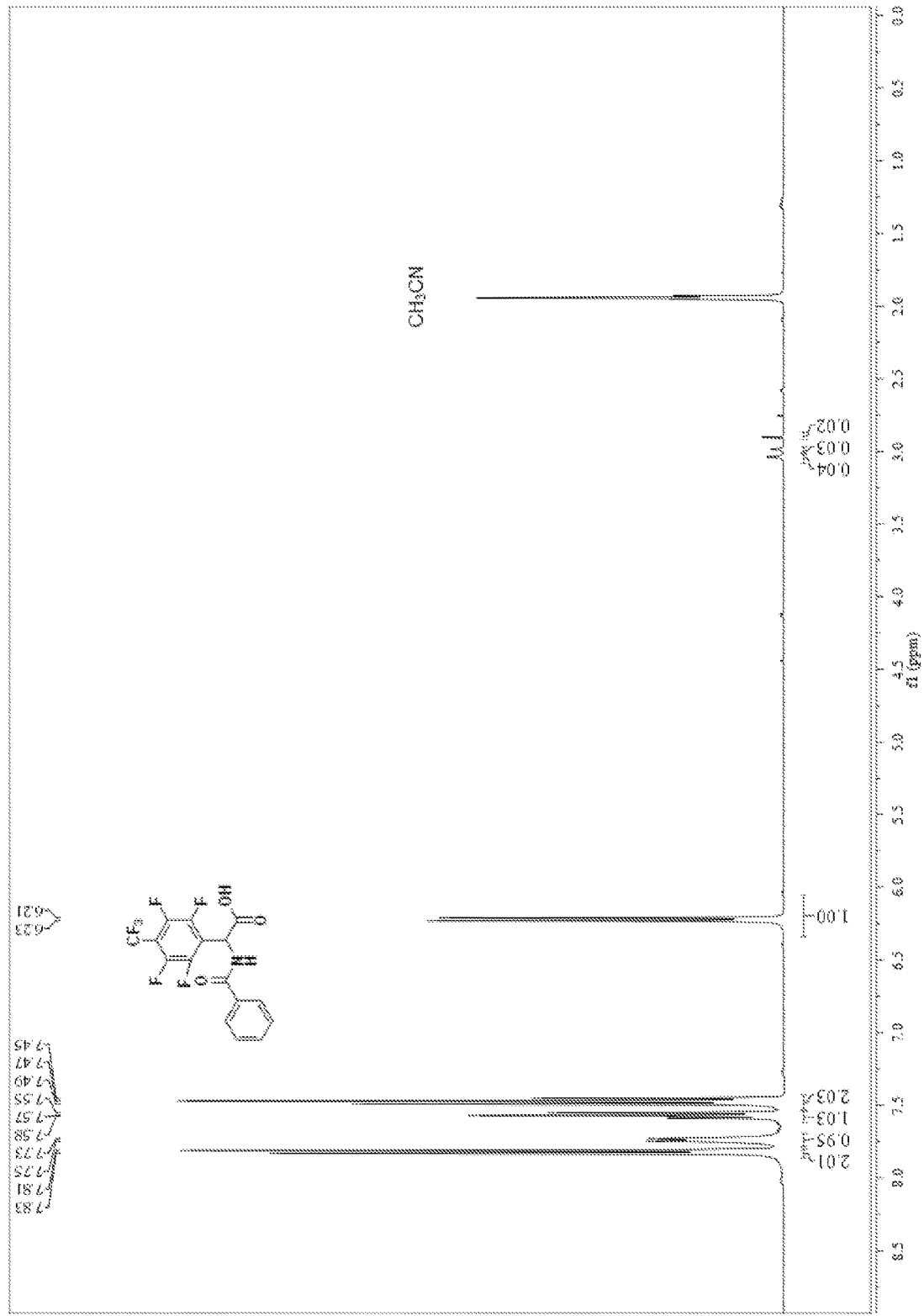
FIG. 49 contains a $^{1}$H NMR spectra (400 MHz), Acetonitrile-$d_3$) of species 3c.
Figure 50:
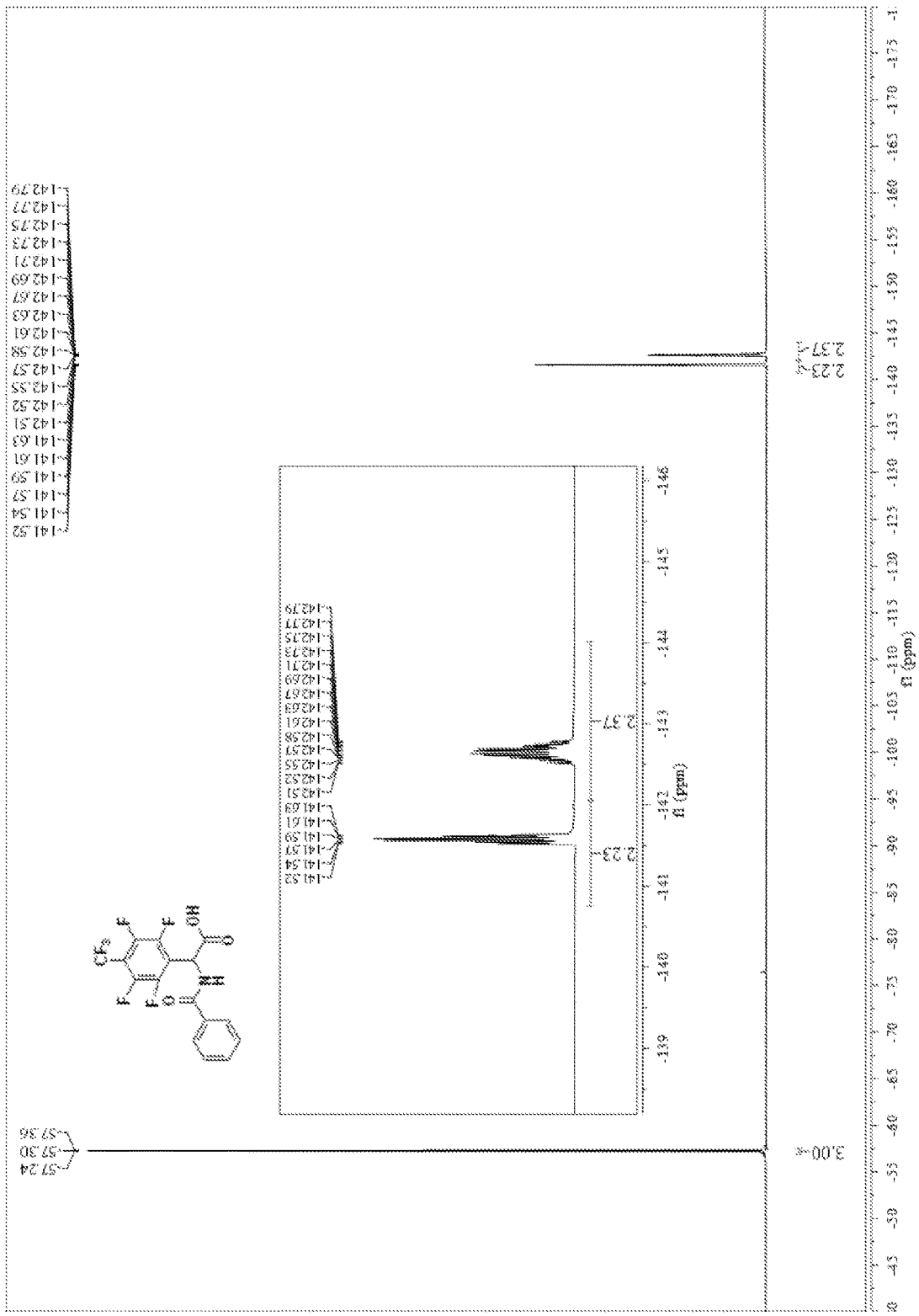
FIG. 50 contains a $^{19}$F NMR spectra (376 MHz), Acetonitrile-$d_3$) of species 3c.
Figure 51:
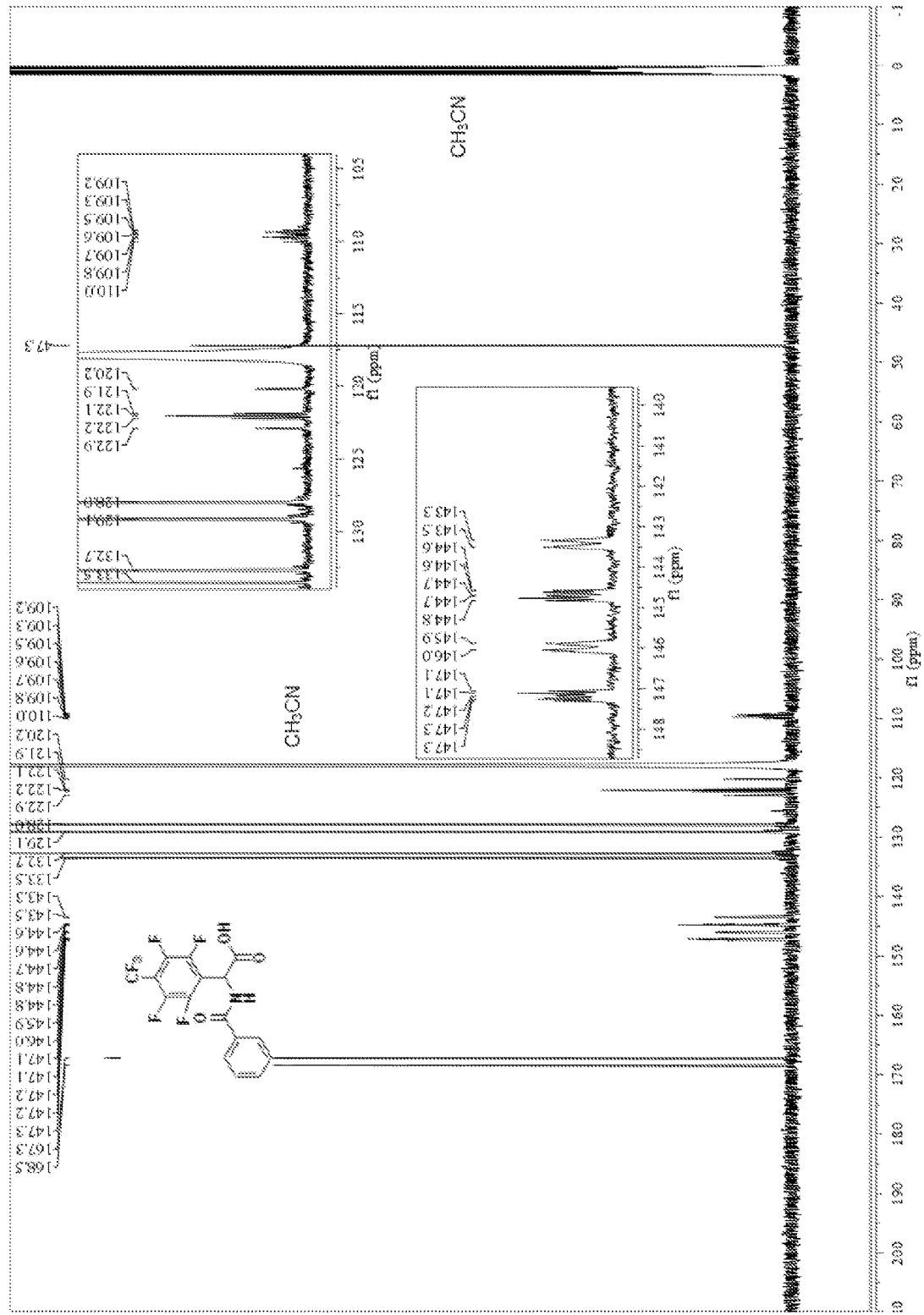
FIG. 51 contains a $^{13}$C NMR spectra (101 MHz), Acetonitrile-$d_3$) of species 3c.

3c 2-benzamido-2-(2,3,5,6-tetrafluoro-4-(trifluoromethyl)phenyl)acetic acid (FIGS. 3 and 49-51) was produced as white solid with 82% yield (2.00 g, 5.06 mmol). The general procedure E was followed using 2-phenyloxazol-5(4H)-one (1.00 g, 6.20 mmol), octafluorotoluene (1.50 g, 6.36 mmol), tetramethylguanidine (1.46 g, 12.71 mmol), and 0.620 mL of MeCN was used to afford 3c. FT-IR (neat) cm$^{-1}$ 3590, 1743, 1653, 1076. $^1$H NMR (400 MHz, Acetonitrile-d$_3$; FIG. 49) δ 7.82 (d, J=7.1 Hz, 2H), 7.74 (d, J=6.5 Hz, $^1$H), 7.62-7.53 (m, $^1$H), 7.47 (t, J=7.6 Hz, 2H), 6.22 (d, J=7.0 Hz, $^1$H). $^{19}$F NMR (376 MHz, Acetonitrile-d$_3$; FIG. 50) 6-57.30 (t, J=21.8 Hz), −141.58 (td, J=15.6, 6.2 Hz), −142.47--142.84 (m). $^{13}$C NMR (101 MHz, Acetonitrile-d$_3$; FIG. 51) δ 168.5, 133.5, 167.3, 147.5-144.4 (m), 144.7 (dd, J=256.6, 17.1 Hz), 132.7, 129.1, 127.9, 122.1 (t, J=16.2 Hz), 47.3, 121.5 (d, J=273.6 Hz), 110.5-108.3 (m). HRMS (ESI) $C_8H_{11}NOS$ calcd. [M+Na]$^+$ 418.0285 observed 418.0276.

Figure 52:
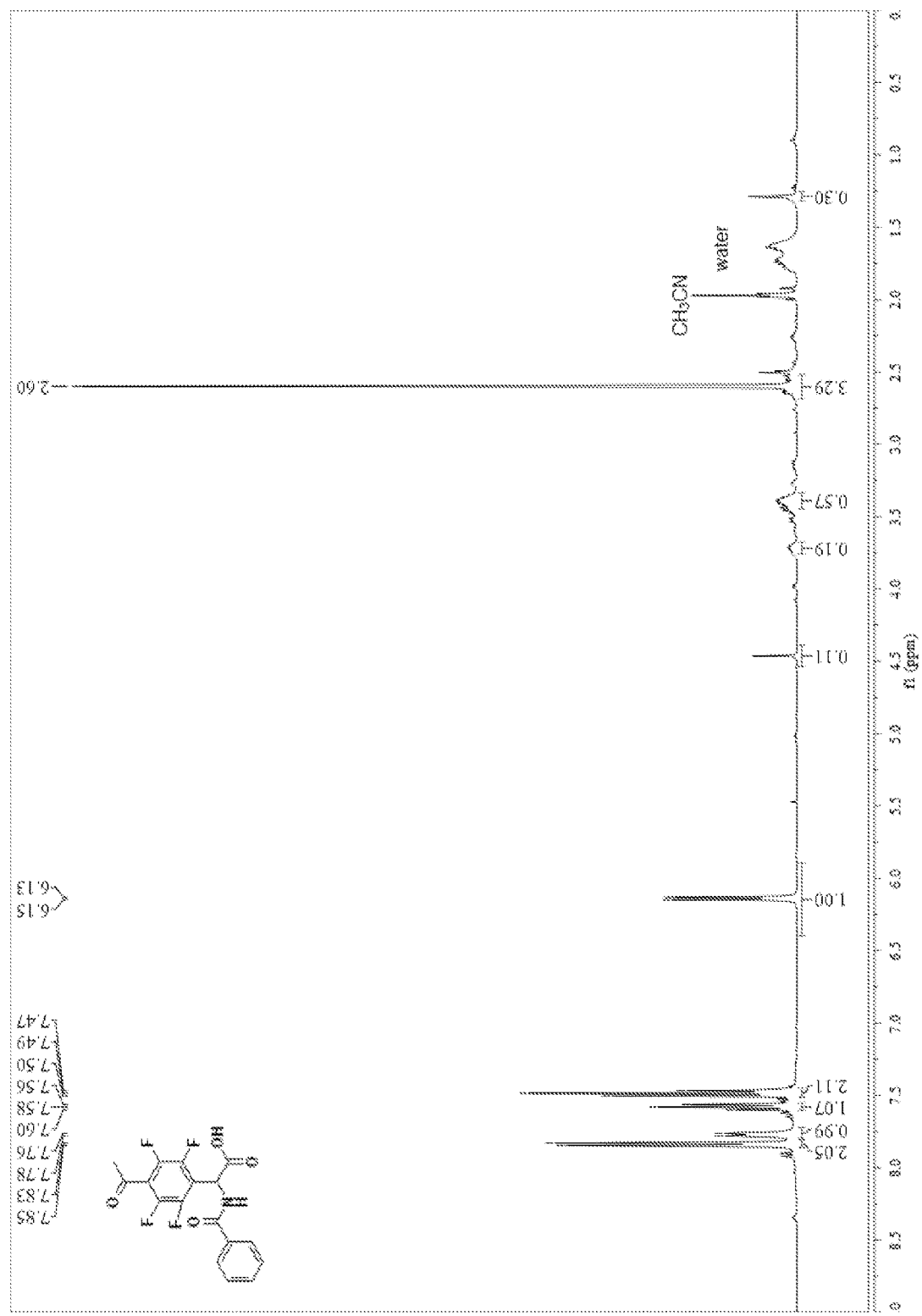
FIG. 52 contains a $^{1}$H NMR spectra (400 MHz), Acetonitrile-$d_3$) of species 3d.
Figure 53:
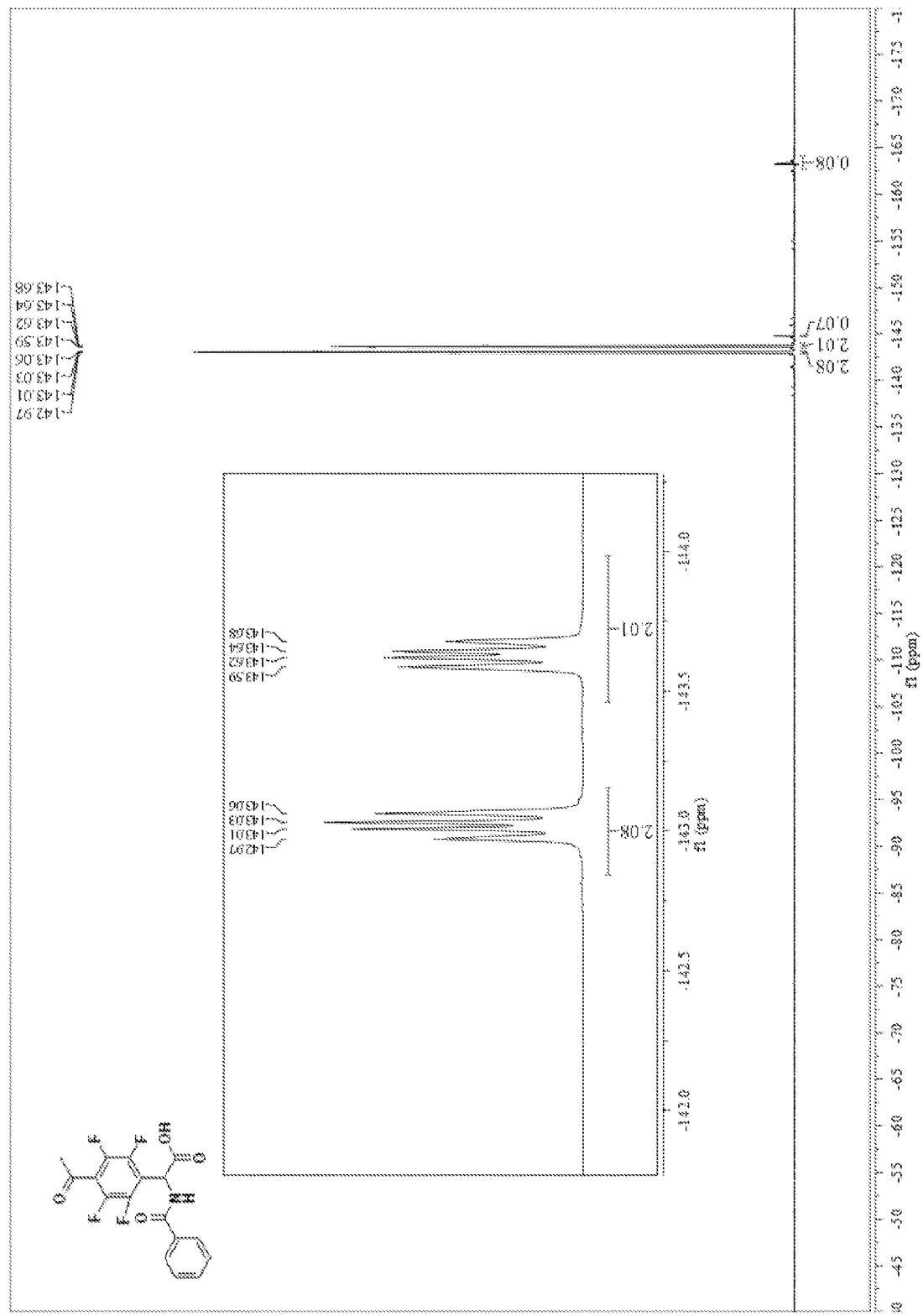
FIG. 53 contains a $^{19}$F NMR spectra (376 MHz), Acetonitrile-$d_3$) of species 3d.
Figure 54:
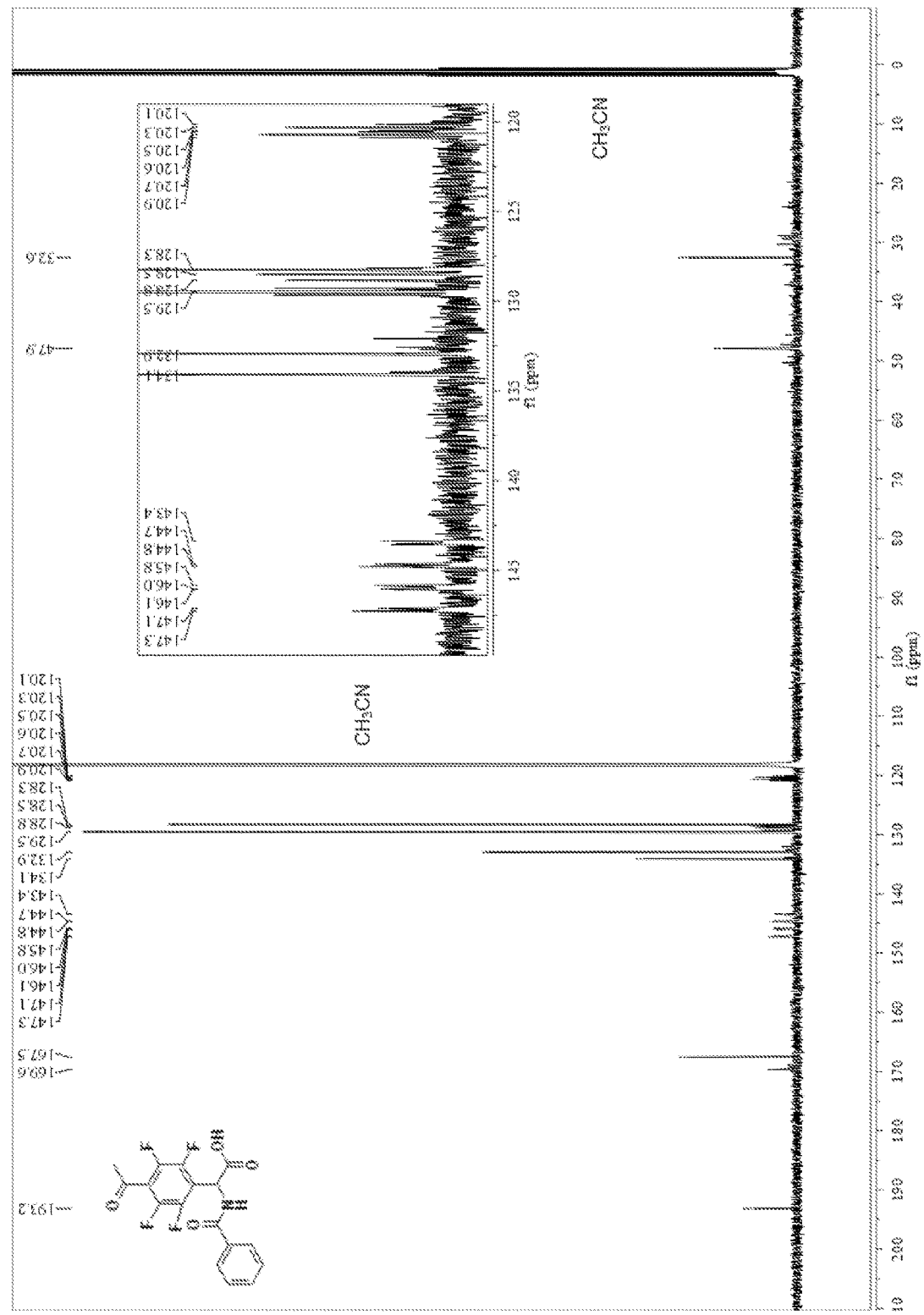
FIG. 54 contains a $^{13}$C NMR spectra (101 MHz), Acetonitrile-$d_3$) of species 3d.

3d 2-(4-acetyl-2,3,5,6-tetrafluorophenyl)-2-benzamidoacetic acid (FIGS. 3 and 52-54) was produced as a colorless oil with 87% yield (99.6 mg, 0.270 mmol). The general procedure E was followed using 2-phenyloxazol-5(4H)-one (50 mg, 0.310 mmol), 2',3',4',5',6' pentafluoroacetophenone (66.8 mg, 0.318 mmol), tetramethylguanidine (118.0 mg, 0.636 mmol), and 0.310 mL of MeCN was used to afford 3d. FT-IR (neat) cm$^{-1}$ 3640, 1721, 1630, 1006. $^1$H NMR (400 MHz, Acetonitrile-d$_3$; FIG. 52) δ 7.84 (d, J=7.3 Hz, 2H), 7.77 (d, J=6.5 Hz, $^1$H), 7.58 (t, J=7.4 Hz, $^1$H), 7.49 (t, J=7.6 Hz, 2H), 6.14 (d, J=6.7 Hz, $^1$H), 2.60 (s, 3H). $^{19}$F NMR (376 MHz, Acetonitrile-d$_3$; FIG. 52) δ −143.02 (dd, J=21.5, 12.8 Hz), −143.63 (dd, J=21.5, 12.9 Hz). $^{13}$C NMR (101 MHz, Acetonitrile-d$_3$; FIG. 54) δ 193.2, 169.6, 167.6, 147.5-144.4 (m), 143.4 (dt, J=14.8, 5.4 Hz), 134.1, 132.9, 129.5, 128.3, 120.7 (t, J=16.4 Hz), 120.3 (t, J=17.1 Hz), 47.9, 32.6. HRMS (ESI) $C_{17}H_{11}F_4NO_4$ calcd. [M+]$^+$369.0624 observed 369.0601.

Figure 55:
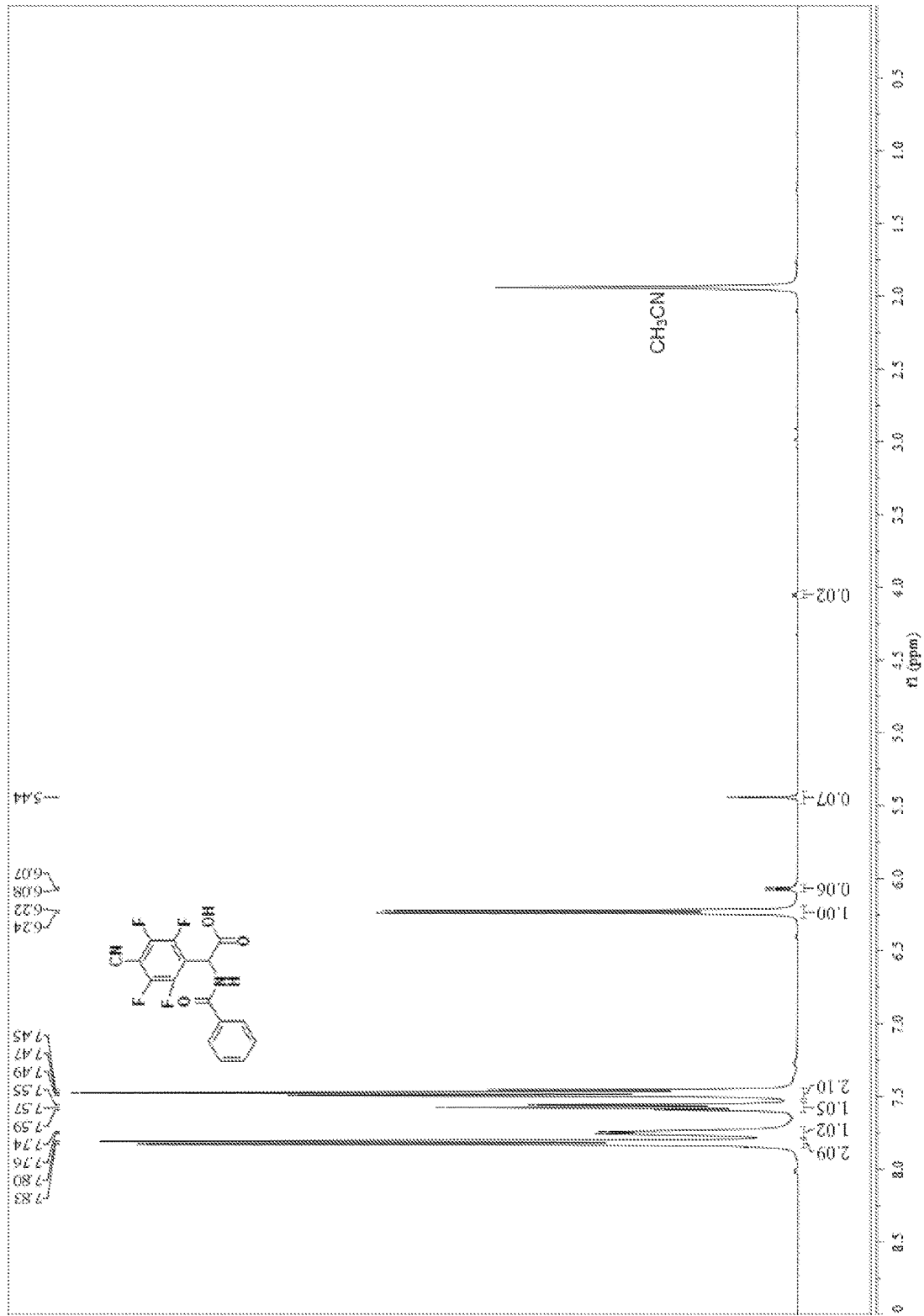
FIG. 55 contains a $^{1}$H NMR spectra (400 MHz), Acetonitrile-$d_3$) of species 3e.
Figure 56:
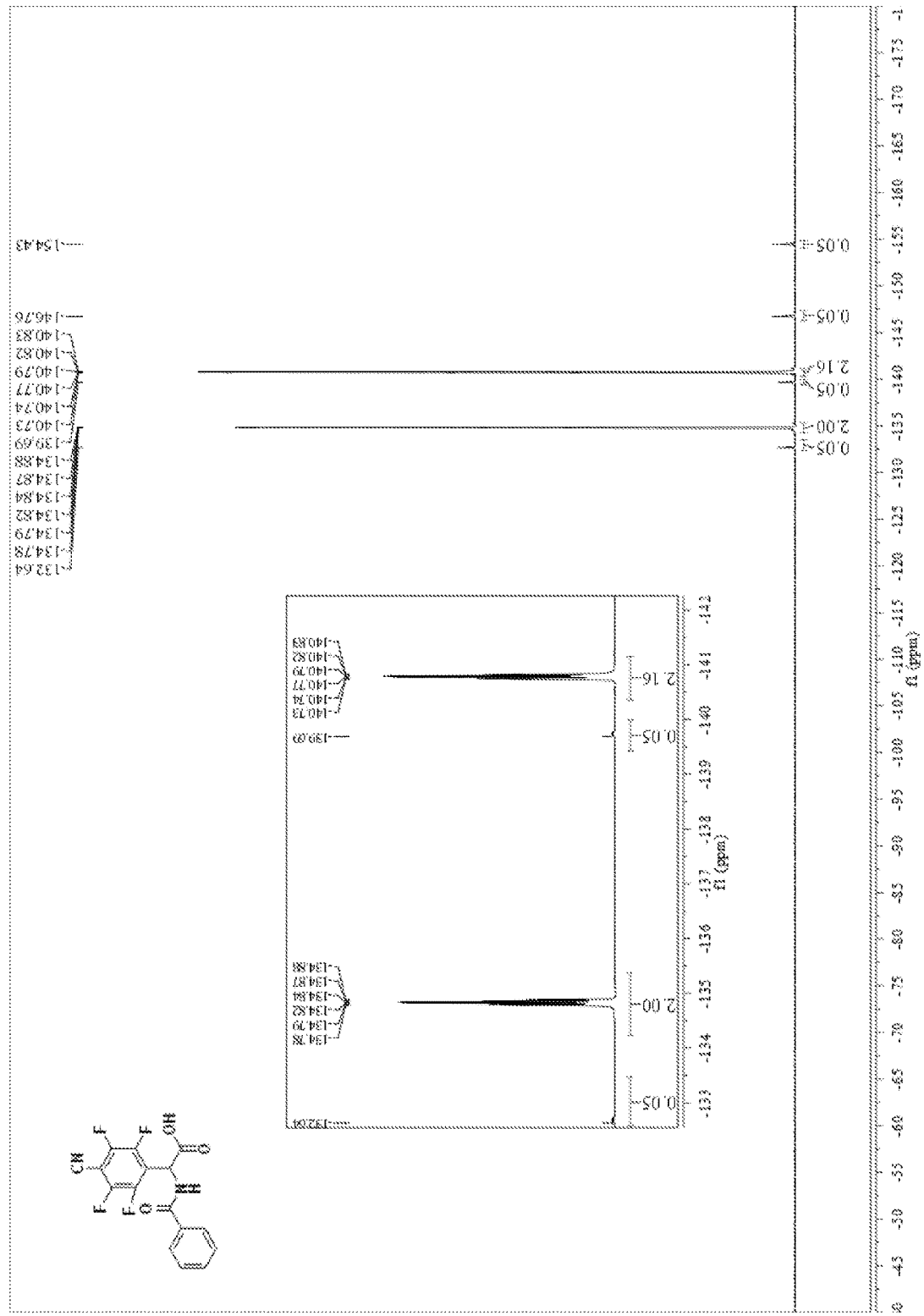
FIG. 56 contains a $^{19}$F NMR spectra (376 MHz), Acetonitrile-$d_3$) of species 3e.
Figure 57:
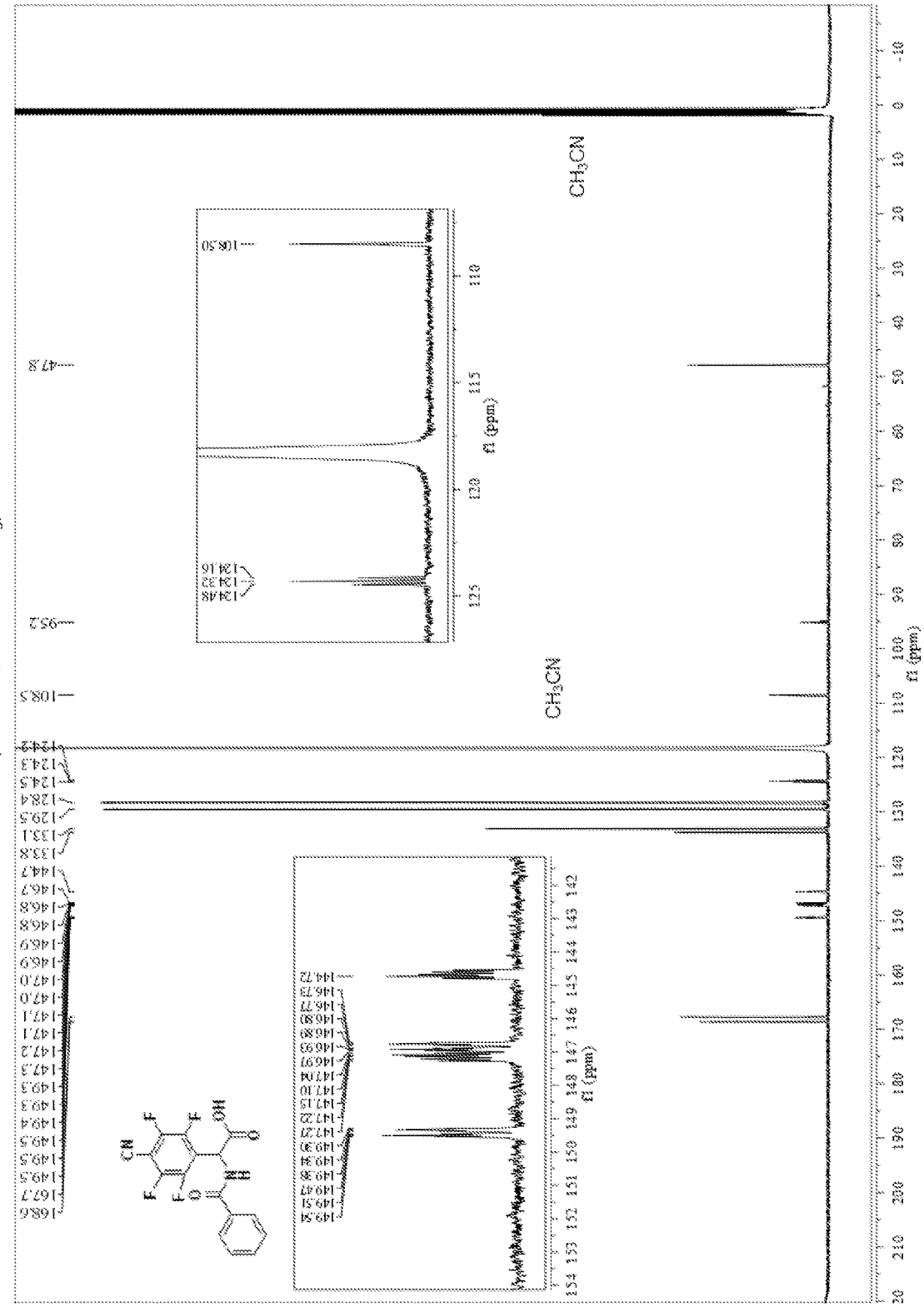
FIG. 57 contains a $^{13}$C NMR spectra (101 MHz), Acetonitrile-$d_3$) of species 3e.

3e 2-benzamido-2-(4-cyano-2,3,5,6-tetrafluorophenyl) acetic acid (FIGS. 3 and 55-57) was produced as a yellow oil with 78% yield (85.1 mg, 0.241 mmol). The general procedure E was followed using 2-phenyloxazol-5(4H)-one (50 mg, 0.310 mmol), 2,3,4,5,6 pentaflurobenzonitrile (63.4 mg, 0.318 mmol), tetramethylguanidine (118.0 mg, 0.636 mmol), and 0.310 mL of MeCN was used to afford 3e. FT-IR (neat) cm$^{-1}$ 3590, 2255, 1707, 1674. $^1$H NMR (400 MHz, Acetonitrile-d$_3$; FIG. 55) δ 7.82 (d, J=7.3 Hz, 2H), 7.75 (d, J=6.2 Hz, $^1$H), 7.57 (t, J=7.4 Hz, $^1$H), 7.47 (t, J=7.6 Hz, 2H), 6.23 (d, J=6.9 Hz, $^1$H). $^{19}$F NMR (376 MHz, Acetonitrile-d$_3$; FIG. 56) δ −134.83 (td, J=15.8, 6.5 Hz), −140.78 (td, J=15.8, 6.5 Hz). $^{13}$C NMR (101 MHz, Acetonitrile-d$_3$; FIG. 57) δ 168.6, 167.7, 148.1 (ddt, J=259.1, 16.5, 3.9 Hz), 147.5-144.4 (m), 147.4-144.2 (m), 133.8, 133.1, 129.5, 128.4, 124.3 (t, J=16.2 Hz), 108.5, 47.8. HRMS (ESI) $C_{16}H_8F_4N_2O_3$ calcd. [M+Na]$^+$403.0676 observed 403.0701.

Figure 76:
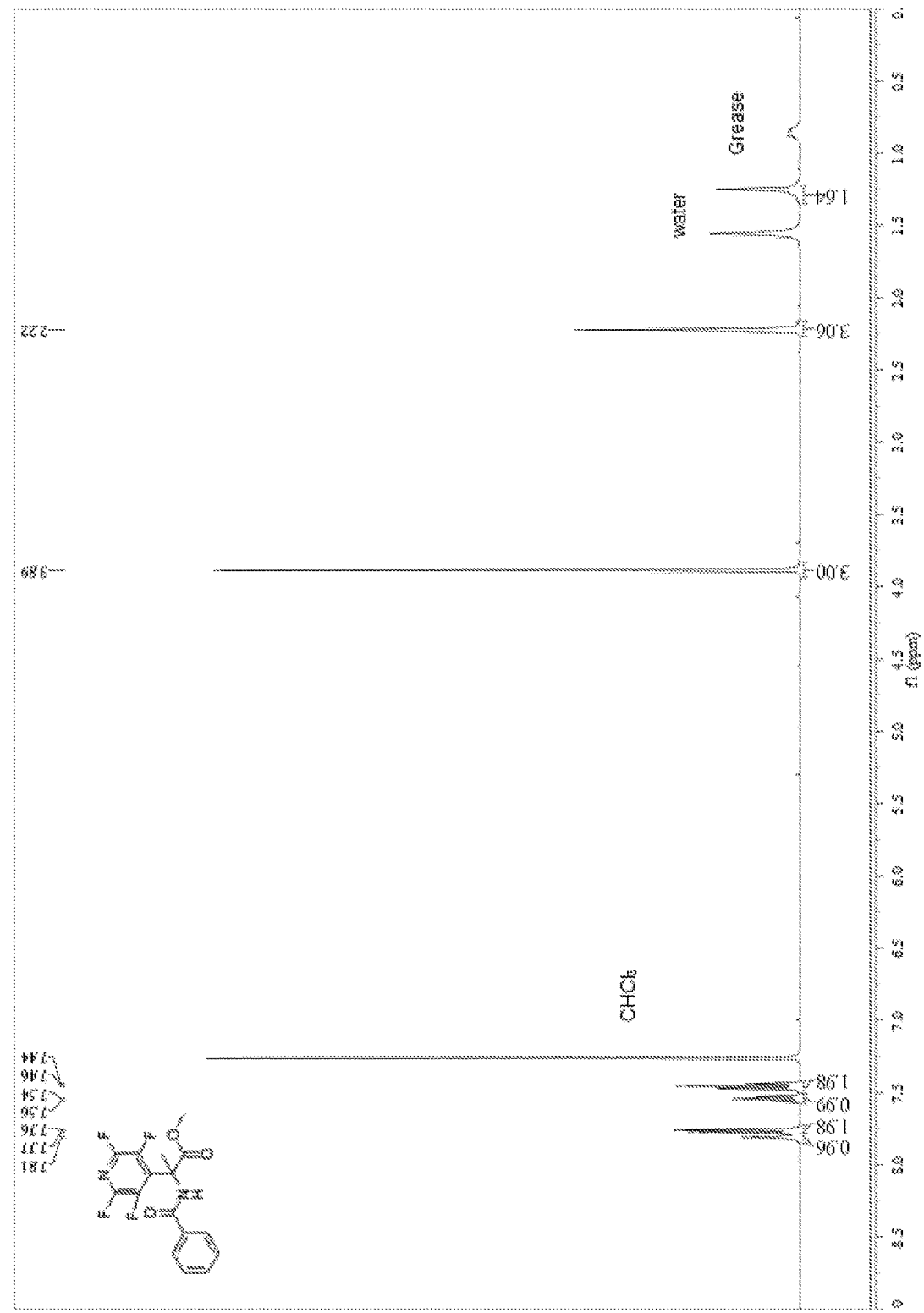
Figure 77:
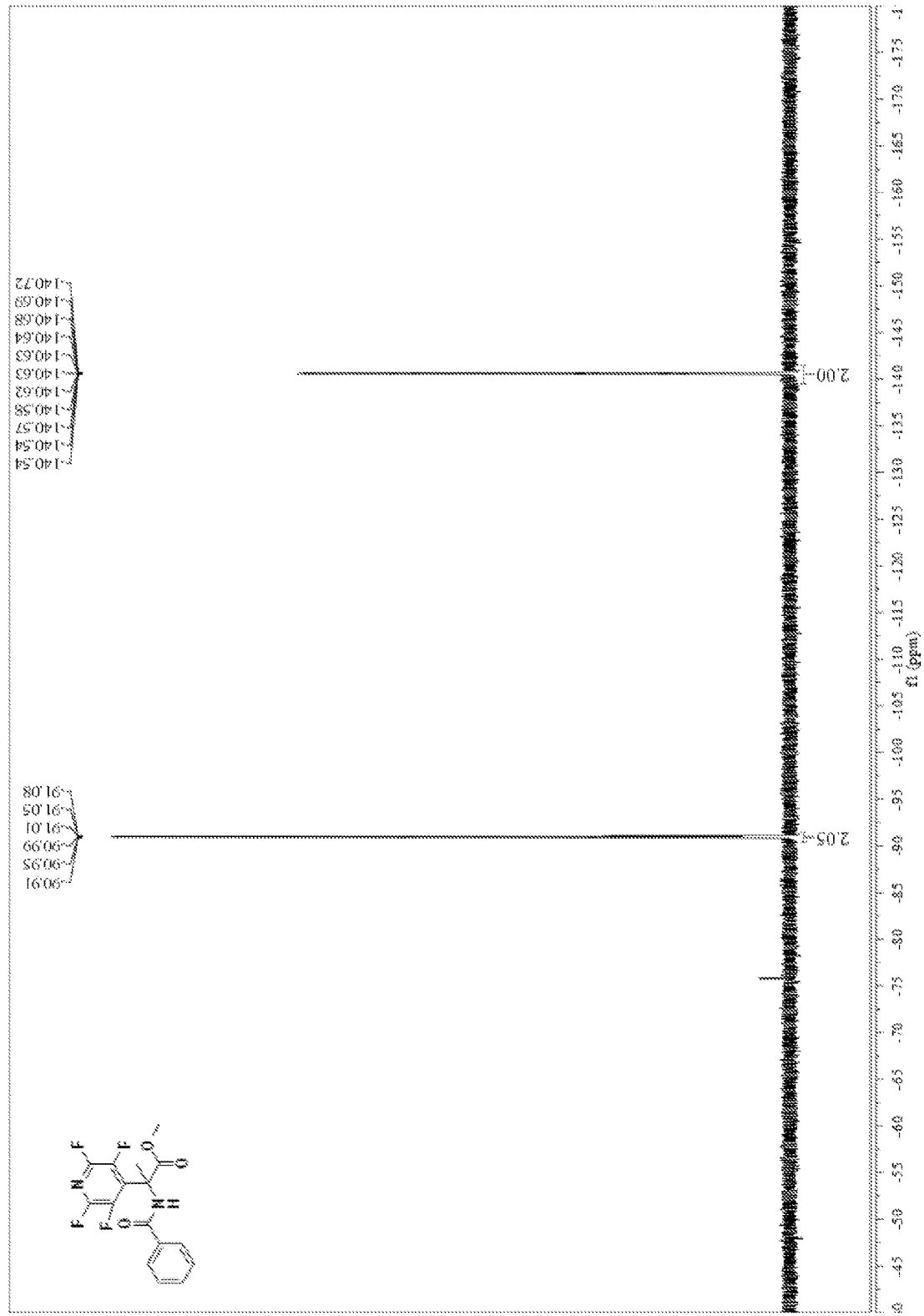
Figure 78:
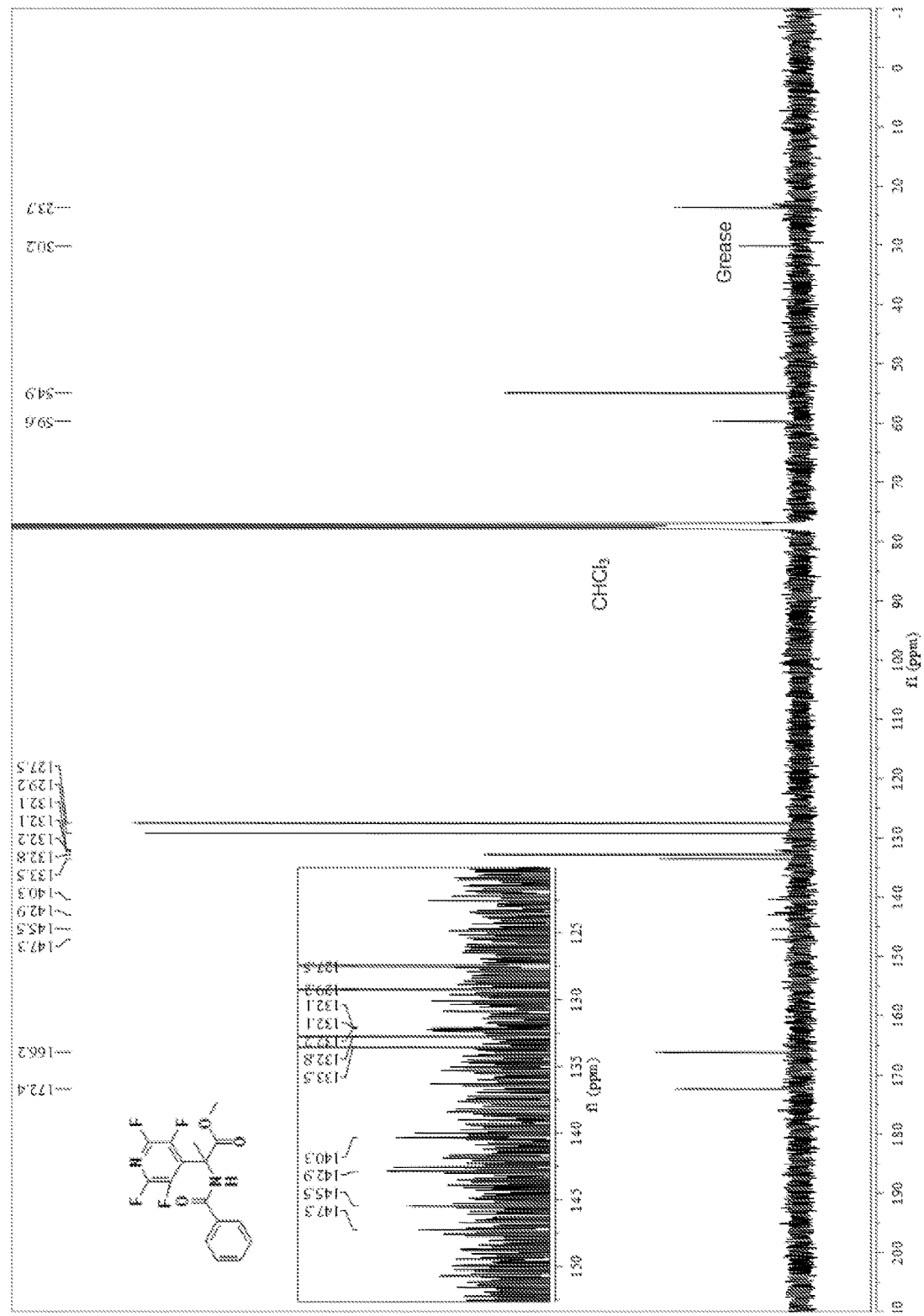

6a methyl 2-benzamido-2-(perfluoropyridin-4-yl)propanoate (FIGS. 6 and 76-78) was produced as a colorless oil with 80% yield (81.2 mg, 0.228 mmol). The general procedure F was followed using 4-methyl-2-phenyloxazol-5(4H)-one (50.0 mg, 0.285 mmol), pentafluoropyridine (49.5 mg, 0.293 mmol), N,N-diisopropylethylamine (368 mg, 2.85 mmol), trifluoroacetic acid (650 mg, 5.7 mmol)/methanol (0.230 mL) and 0.285 mL of MeCN was used to afford 6a. FT-IR (neat) cm$^{-1}$ 2833, 1740, 1634, 1095. $^1$H NMR (400 MHz, Chloroform-d; FIG. 76) δ 7.81 (s, $^1$H), 7.77 (d, J=7.2 Hz, 2H), 7.54 (t, J=7.4 Hz, $^1$H), 7.46 (t, J=7.5 Hz, 2H), 3.89 (s, 3H), 2.22 (t, J=3.3 Hz, 3H). $^{19}$F NMR (376 MHz, Chloroform-d; FIG. 77) δ −90.86--−91.11 (m), −140.47--140.85 (m). $^{13}$C NMR (101 MHz, Chloroform-d; FIG. 78) δ 172.4, 166.2, 146.4 (dt, J=180.2 Hz), 141.6 (dd, J=261.0 Hz), 133.5, 132.8, 132.1 (t, J=3.3 Hz), 129.2, 127.5, 59.7, 54.9, 23.7. HRMS (ESI) $C_{16}H_{12}F_4N_2O_3$ calcd. [M+Na]$^+$ 379.0676 observed 379.0698.

Figure 79:
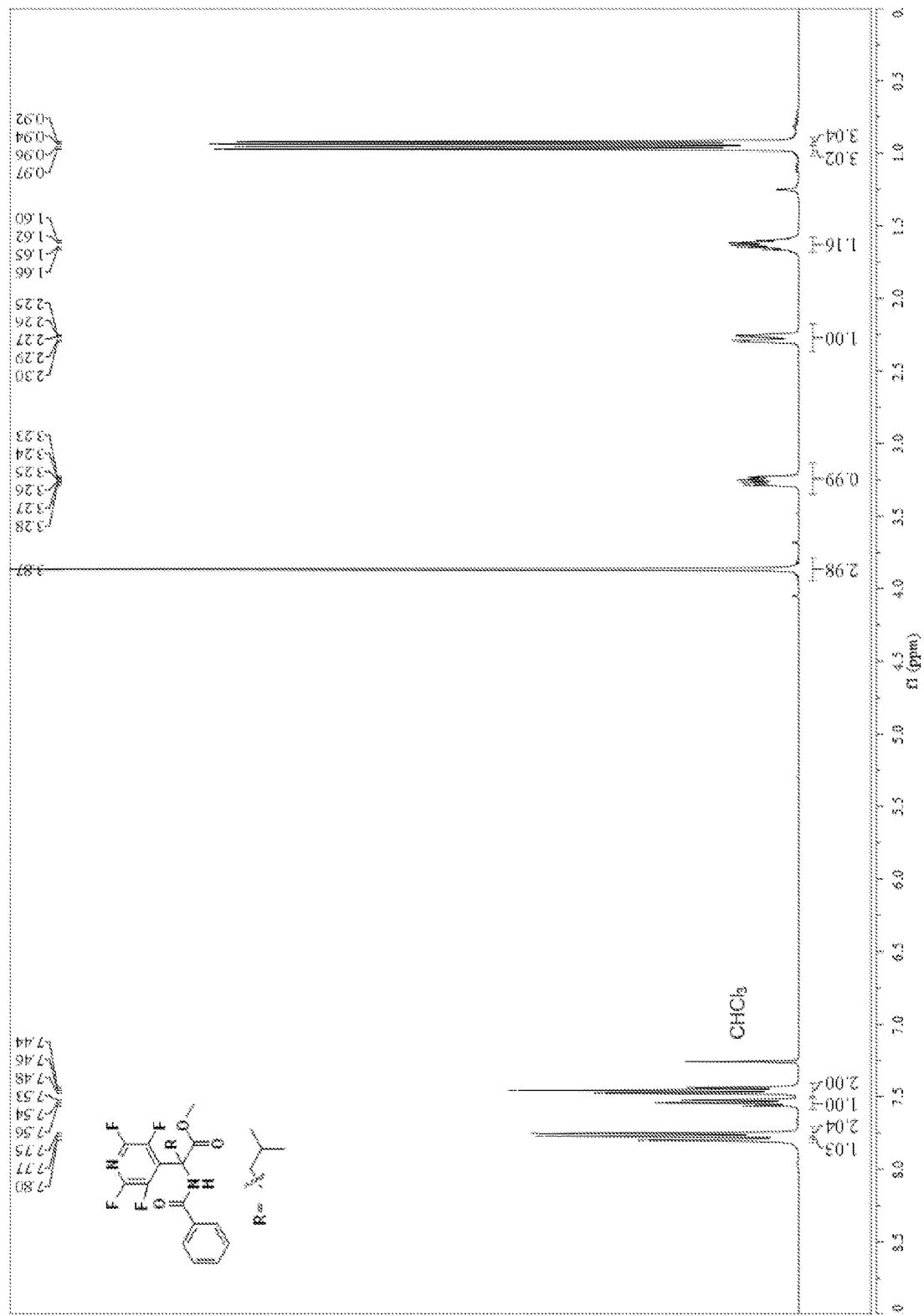
FIG. 79 contains a $^{1}$H NMR spectra (400 MHz), Chloroform-d) of species 6b.
Figure 80:
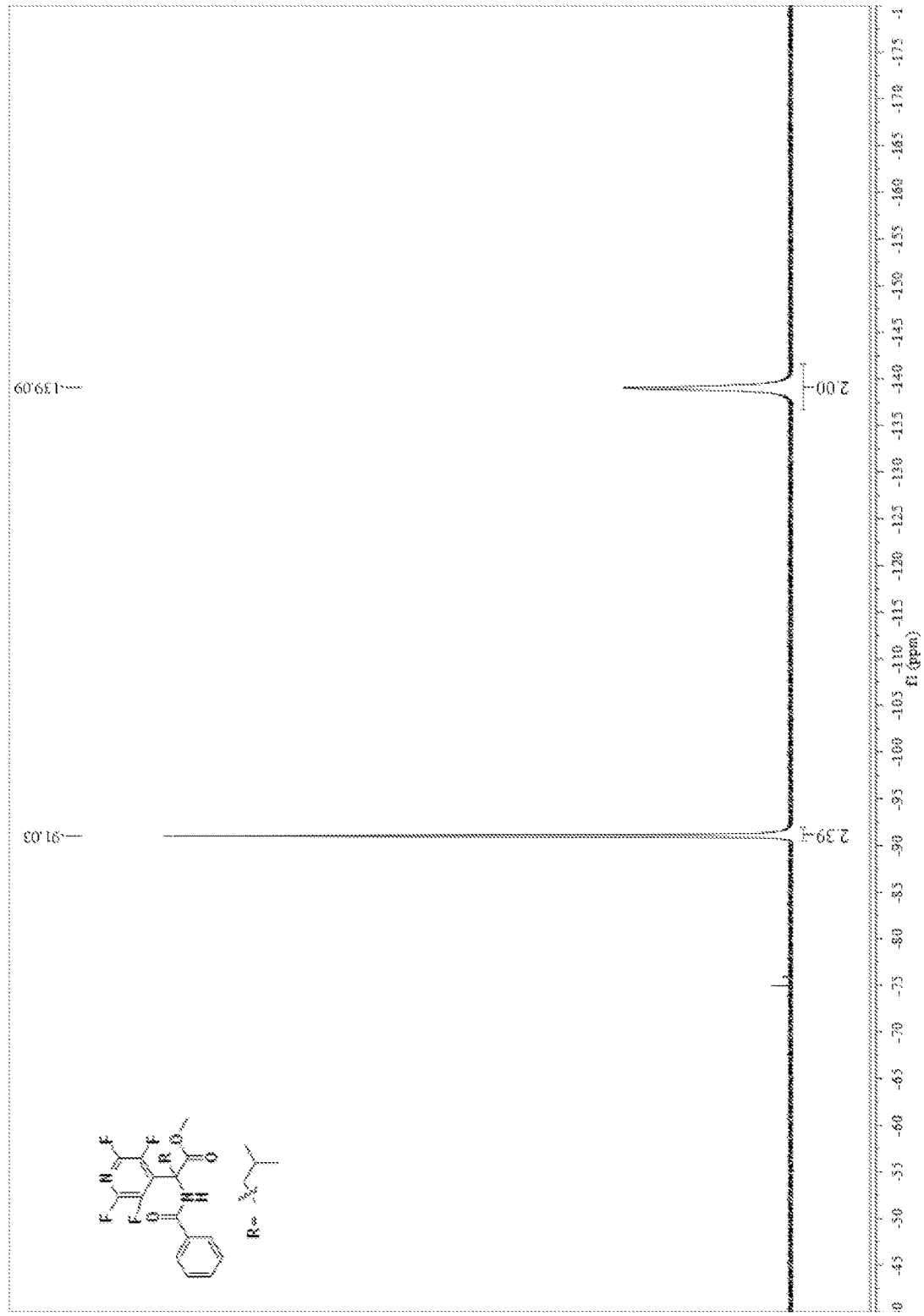
FIG. 80 contains a $^{19}$F NMR spectra (376 MHz), Chloroform-d) of species 6b.
Figure 81:
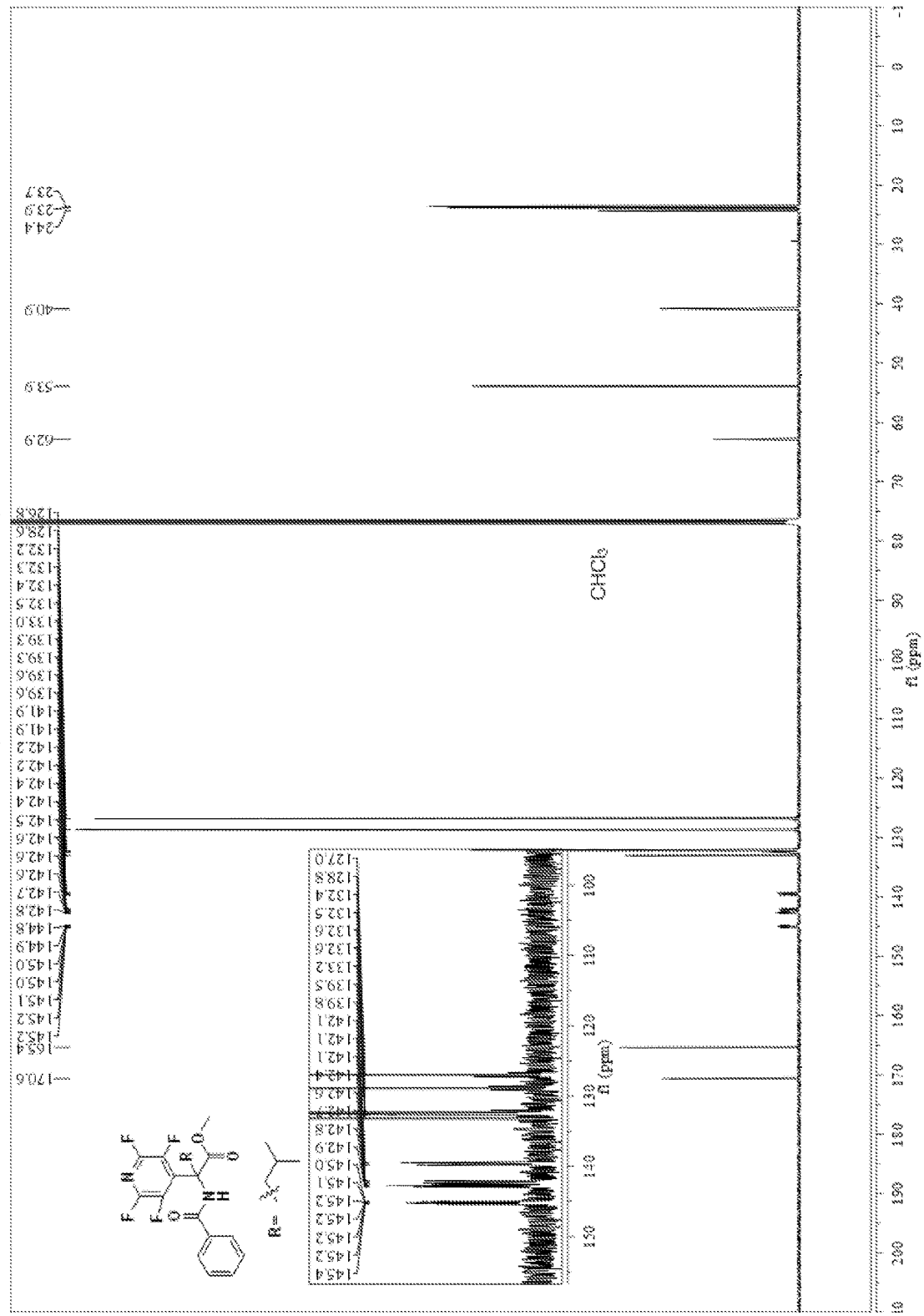
FIG. 81 contains a $^{13}$C NMR spectra (101 MHz), Chloroform-d) of species 6b.

6b methyl 2-benzamido-4-methyl-2-(perfluoropyridin-4-yl)pentanoate (FIGS. 6 and 79-81) was produced as a colorless oil with 74% yield (136 mg, 0.340 mmol). The general procedure F was followed using 4 4-isobutyl-2-phenyloxazol-5(4H)-one (100 mg, 0.460 mmol), pentafluoropyridine (79.7 mg, 0.472 mmol), N,N-diisopropylethylamine (595 mg, 4.6 mmol), trifluoroacetic acid (1040 mg, 9.2 mmol)/methanol (0.372 mL) and 0.460 mL of MeCN was used to afford 6b. FT-IR (neat) cm$^{-1}$ 2893, 1711, 1637, 1105. $^1$H NMR (400 MHz, Chloroform-d; FIG. 79) δ 7.80 (s, $^1$H), 7.76 (d, J=8.3 Hz, 2H), 7.54 (t, J=7.4 Hz, $^1$H), 7.46 (t, J=7.8 Hz, 2H), 3.87 (s, 2H), 3.40-2.14 (m, 2H), 1.74-1.50 (m, $^1$H), 0.96 (d, J=6.6 Hz, 2H), 0.93 (d, J=6.7 Hz, 2H). $^{19}$F NMR (376 MHz, Chloroform-d; FIG. 80) δ −90.47--−91.21 (m), −138.40--−140.05 (m). $^{13}$C NMR (101 MHz, Chloroform-d; FIG. 81) δ 170.6, 165.4, 145.4-142.3 (m), 140.6 (ddd, J=261.1, 27.0, 5.2 Hz), 132.9, 132.4 (t, J=10.4 Hz), 128.7, 126.8, 62.9, 53.9, 40.9, 24.4, 23.9, 23.7. HRMS (ESI) $C_{19}H_{18}F_4N_2O_3$ calcd. [M+H]$^+$ 399.1326 observed 399.1299.

Figure 82:
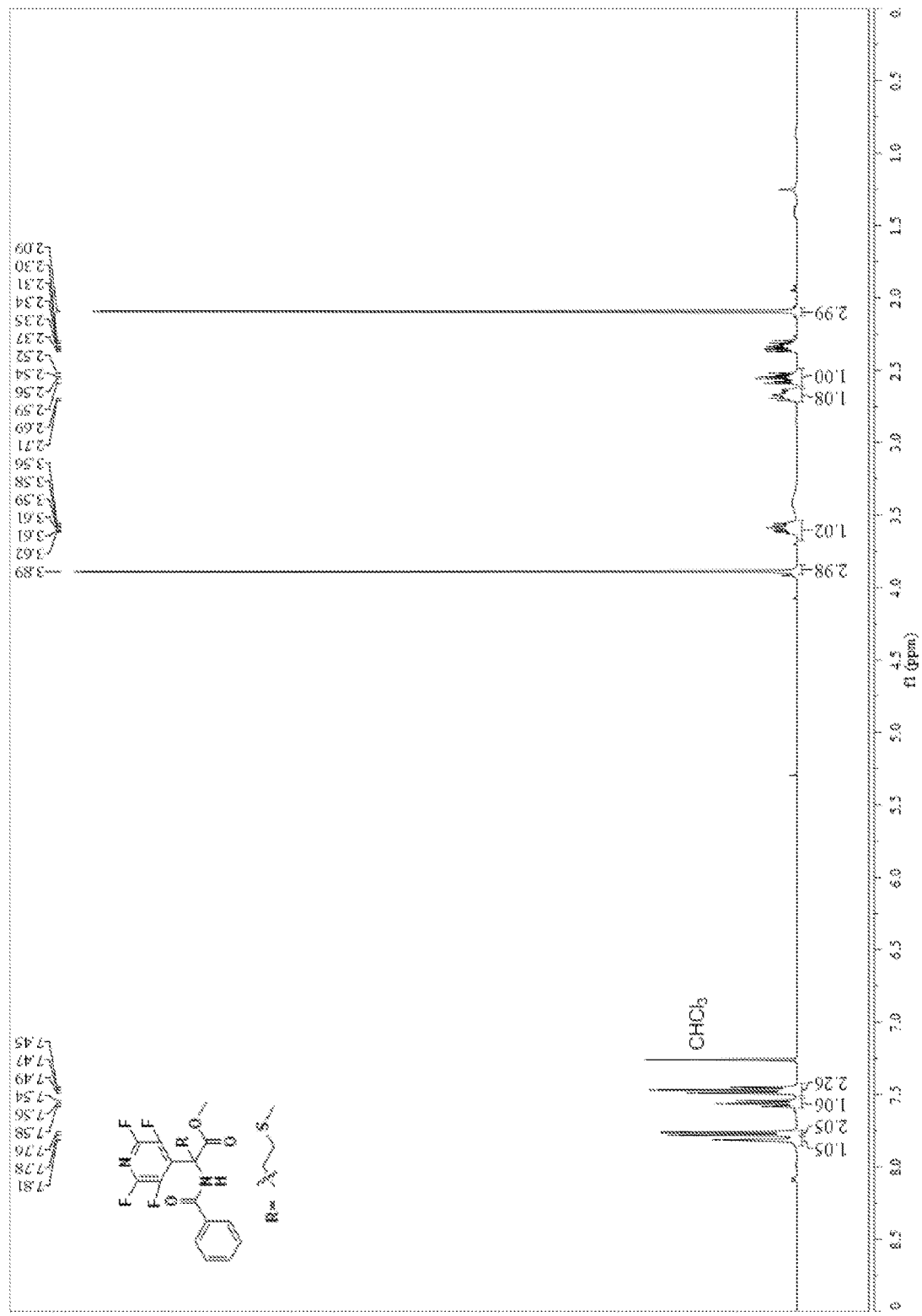
FIG. 82 contains a $^{1}$H NMR spectra (400 MHz), Chloroform-d) of species 6c.
Figure 83:
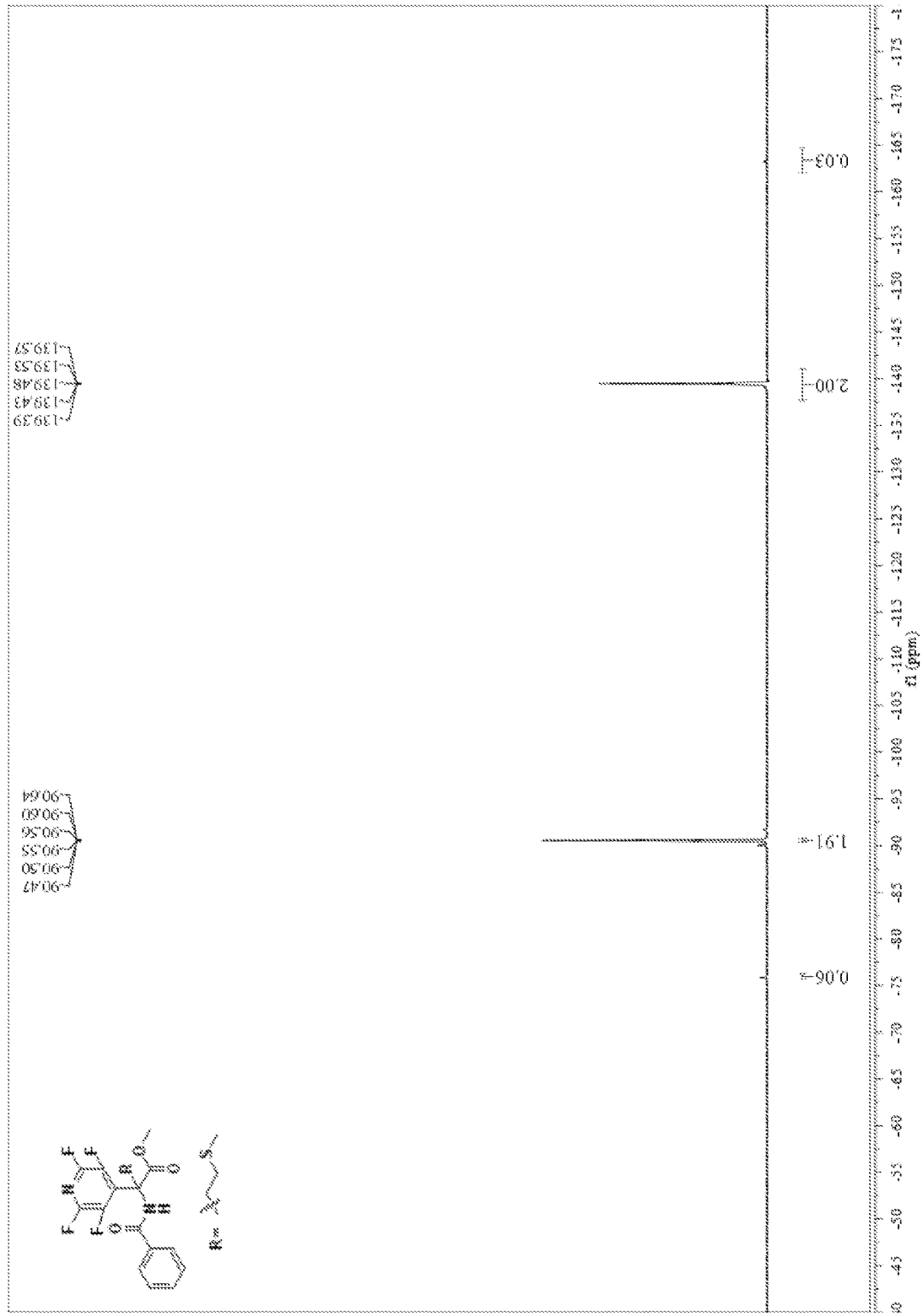
FIG. 83 contains a $^{19}$F NMR spectra (376 MHz), Chloroform-d) of species 6c.
Figure 84:
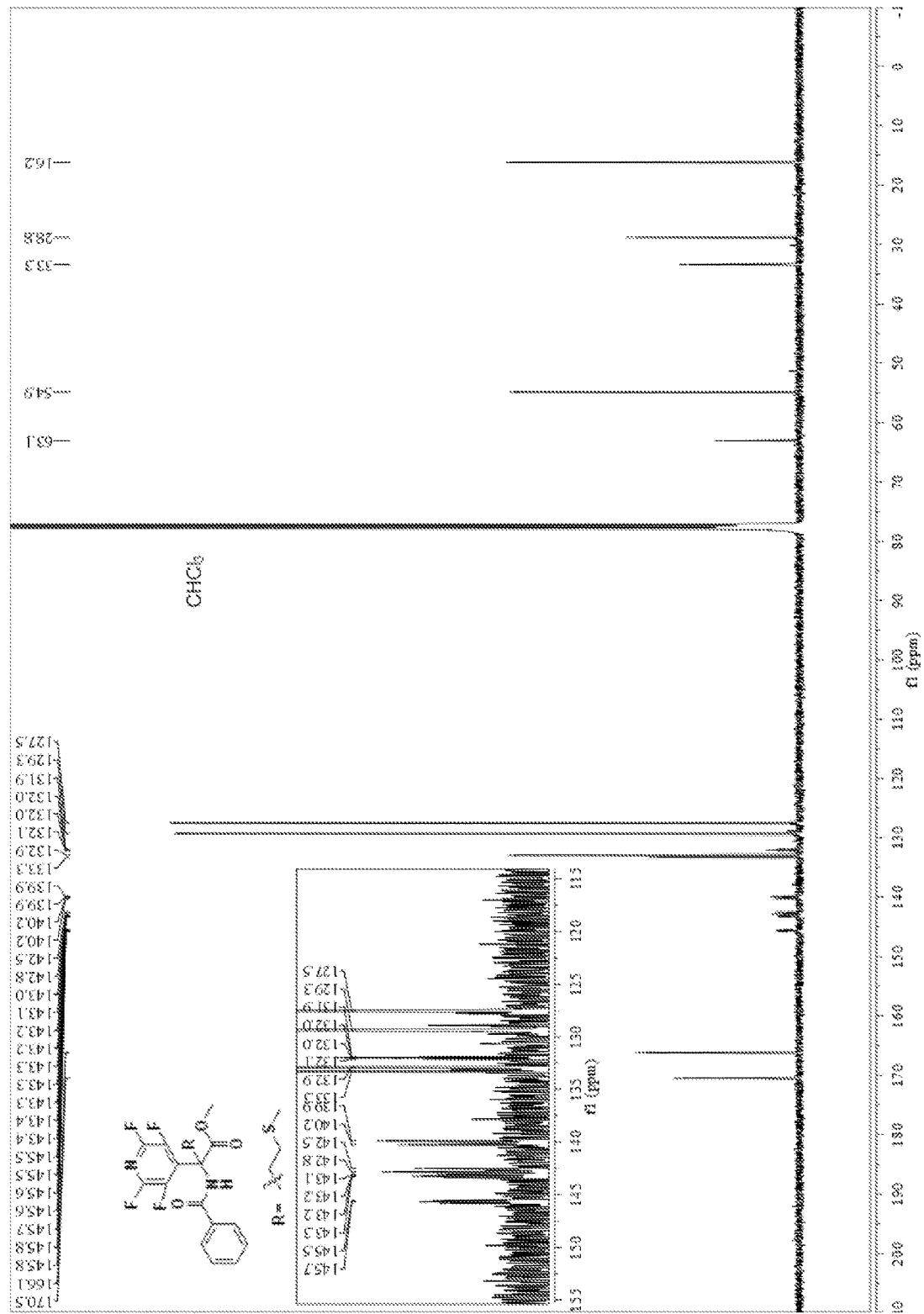
FIG. 84 contains a $^{13}$C NMR spectra (101 MHz), Chloroform-d) of species 6c.

6c methyl 2-benzamido-4-(methylthio)-2-(perfluoropyridin-4-yl)butanoate (FIGS. 6 and 82-84) was produced as a colorless oil, in 79% yield (69.7 mg, 0.167 mmol). The general procedure F was followed using 4-(2-(methylthio) ethyl)-2-phenyloxazol-5(4H)-one (50.0 mg, 0.212 mmol), pentafluoropyridine (36.8 mg, 0.218 mmol), N,N-diisopropylethylamine (274 mg, 2.12 mmol), trifluoroacetic acid (483 mg, 4.24 mmol)/methanol (0.171 mL) and 0.212 mL of MeCN was used to afford 6c. FT-IR (neat) cm$^{-1}$ 2799, 1739, 1655, 1005. $^1$H NMR (400 MHz, Chloroform-d; FIG. 82) δ 7.81 (s, $^1$H), 7.77 (d, J=8.5 Hz, 2H), 7.56 (t, J=7.4 Hz, $^1$H), 7.47 (t, J=7.6 Hz, 2H), 3.89 (s, 3H), 3.65-3.52 (m, $^1$H), 2.67 (dt, J=14.2, 5.8 Hz, $^1$H), 2.61-2.50 (m, $^1$H), 2.39-2.27 (m, $^1$H), 2.09 (s, 3H). $^{19}$F NMR (376 MHz, Chloroform-d; FIG. 83) δ −90.31--−90.85 (m), −139.48 (t, J=19.6 Hz). $^{13}$C NMR (101 MHz, Chloroform-d; FIG. 84) δ 170.5, 166.2, 145.9-142.9 (m), 141.4 (dd, J=261.5, 35.0 Hz), 133.3, 132.9, 132.0 (t, J=10.4 Hz), 129.3, 127.5, 63.1, 54.9, 33.4, 28.8, 16.2. HRMS (ESI) $C_{18}H_{16}F_4N_2O_3S$ calcd. [M+H]$^+$ 417.0891 observed 417.0862.

Figure 85:
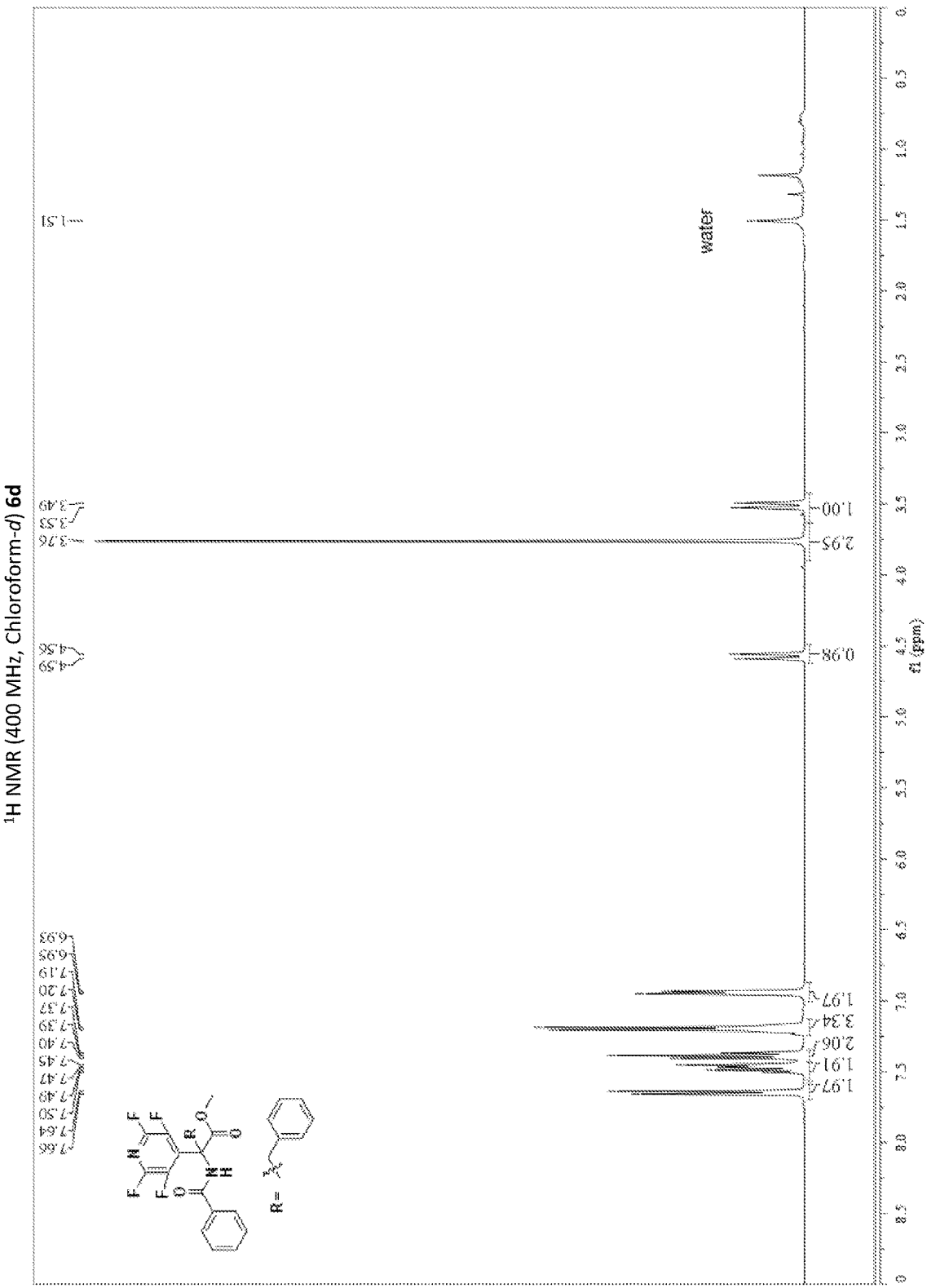
FIG. 85 contains a $^{1}$H NMR spectra (400 MHz), Chloroform-d) of species 6d.

6d methyl 7-benzamido-8,9,11-trifluoro-6,7-dihydro-114-1,5-(metheno)fluoronino[2,3-c]pyridine-7-carboxylate (FIGS. 6 and 85-87) was produced as a colorless oil with 71% yield (61.1 mg, 0.141 mmol). The general procedure F was followed using 4-benzyl-2-phenyloxazol-5(4H)-one (50.0 mg, 0.199 mmol), pentafluoropyridine (34.5 mg, 0.204 mmol), N,N-diisopropylethylamine (257 mg, 1.99 mmol), trifluoroacetic acid (453 mg, 3.98 mmol)/methanol (0.161 mL) and 0.199 mL of MeCN was used to afford 6d. FT-IR (neat) cm$^{-1}$ 3080, 1715, 1674, 1040. $^1$H NMR (400 MHz, Chloroform-d; FIG. 85) δ 7.65 (d, J=8.1 Hz, 2H), 7.48 (dd, J=13.9, 6.5 Hz, 2H), 7.39 (t, J=7.6 Hz, 2H), 7.20 (d, J=7.1

Figure 86:
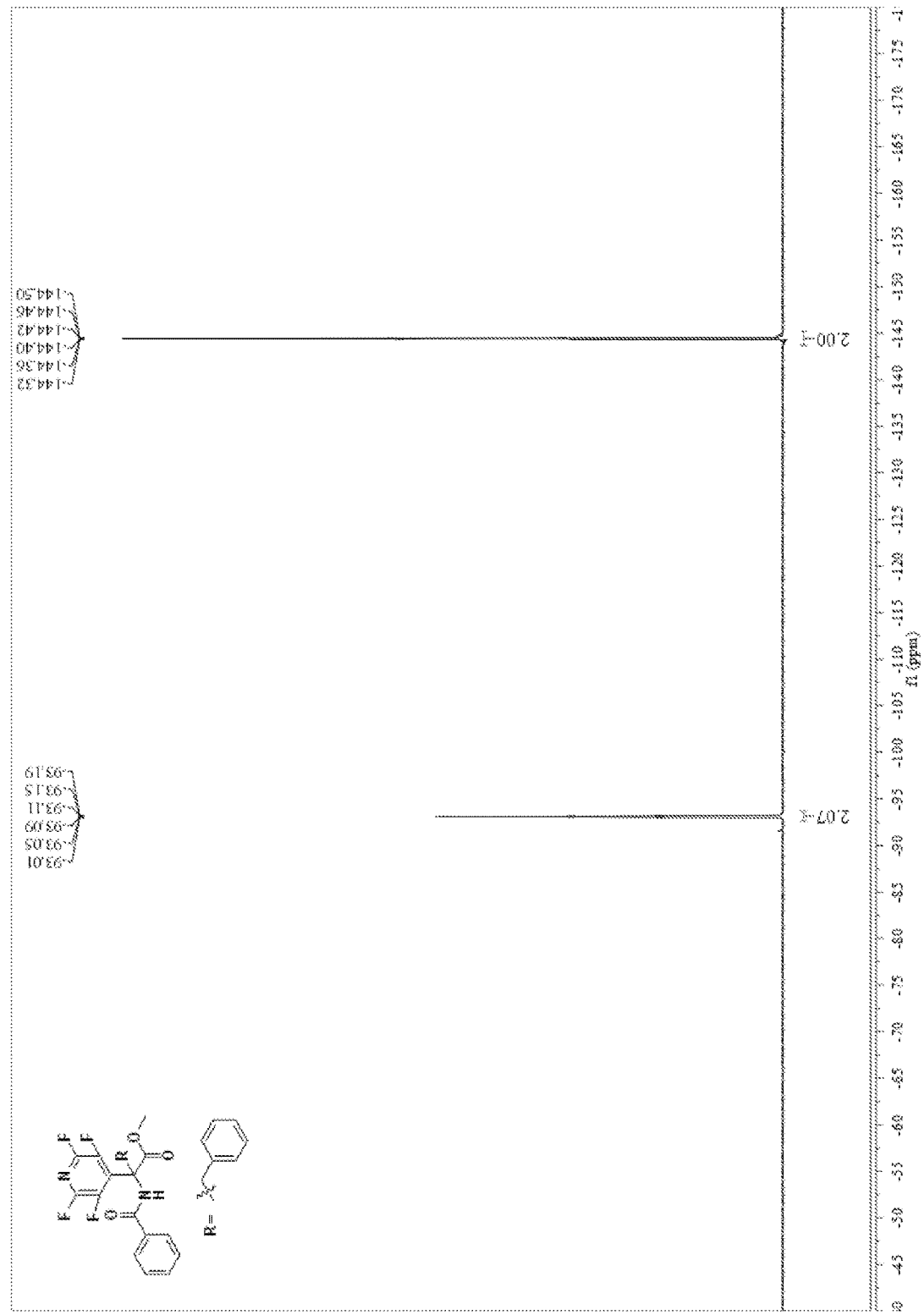
FIG. 86 contains a $^{19}$F NMR spectra (376 MHz), Chloroform-d) of species 6d.
Figure 87:
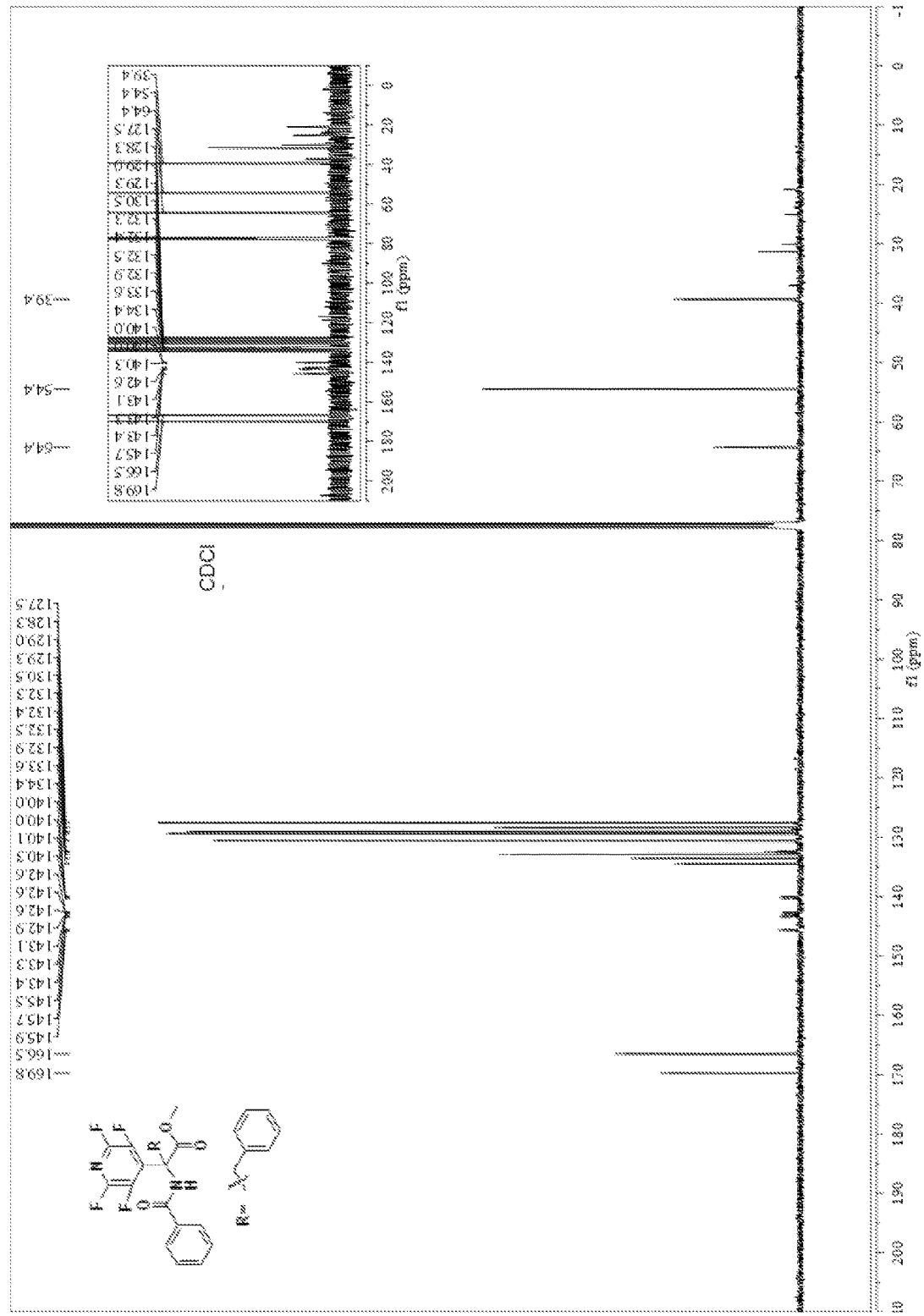
FIG. 87 contains a $^{13}$C NMR spectra (101 MHz), Chloroform-d) of species 6d.

Hz, 3H), 6.94 (d, J=7.5 Hz, 2H), 4.57 (d, J=13.5 Hz, 1H), 3.76 (s, 3H), 3.51 (d, J=13.5 Hz, 1H). $^{19}$F NMR (376 MHz, Chloroform-d; FIG. 86) δ −93.05 (ddd, J=23.2, 14.8, 7.7 Hz), −144.30--144.54 (m). $^{13}$C NMR (101 MHz, Chloroform-d; FIG. 87) δ 169.76, 166.49, 144.47 (dt, J=244.2, 17.1 Hz), 141.44 (dd, J=260.8, 23.6 Hz), 134.4, 133.6, 132.9, 132.4 (t, J=10.8 Hz), 130.5, 129.3, 129.0, 128.3, 127.5, 64.4, 54.5, 39.4. HRMS (ESI) $C_{22}H_{16}F_4NO_3$ calcd. [M+H]$^+$ 433.1170 observed 433.1140.

Figure 4:
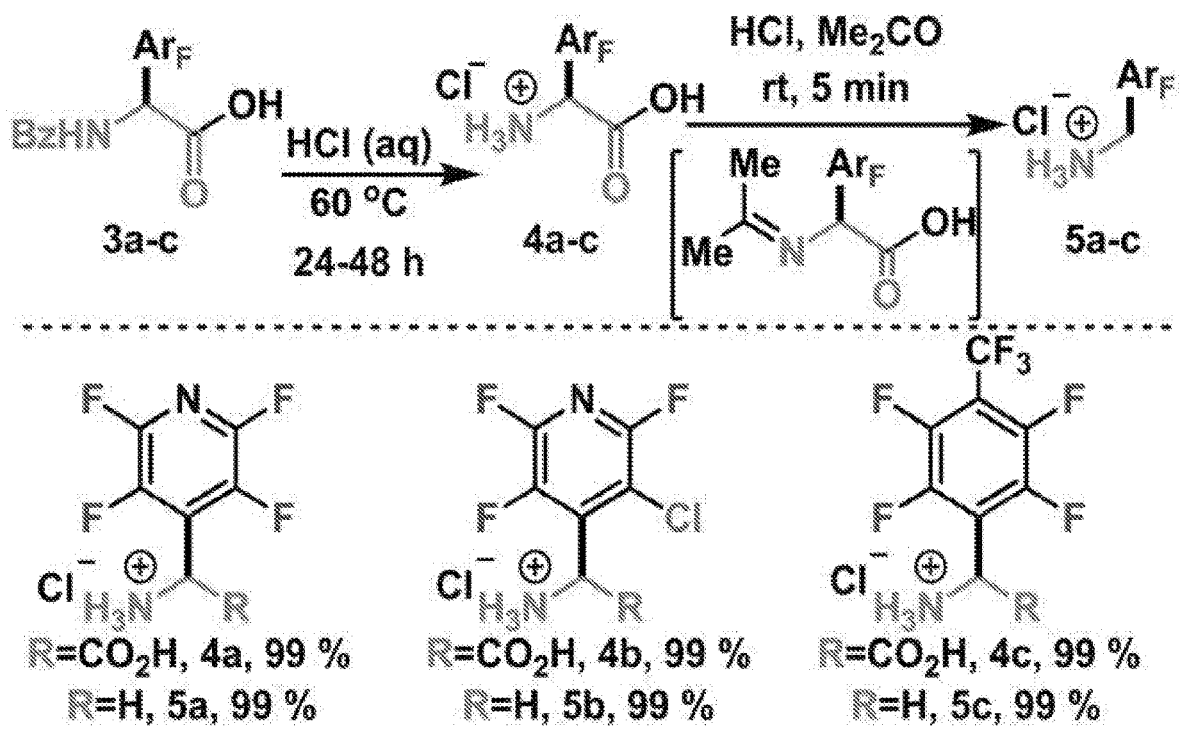
FIG. 4 illustrates debenzoylation of amino acids and Schiff Base mediated decarboxylation.
Figure 5:
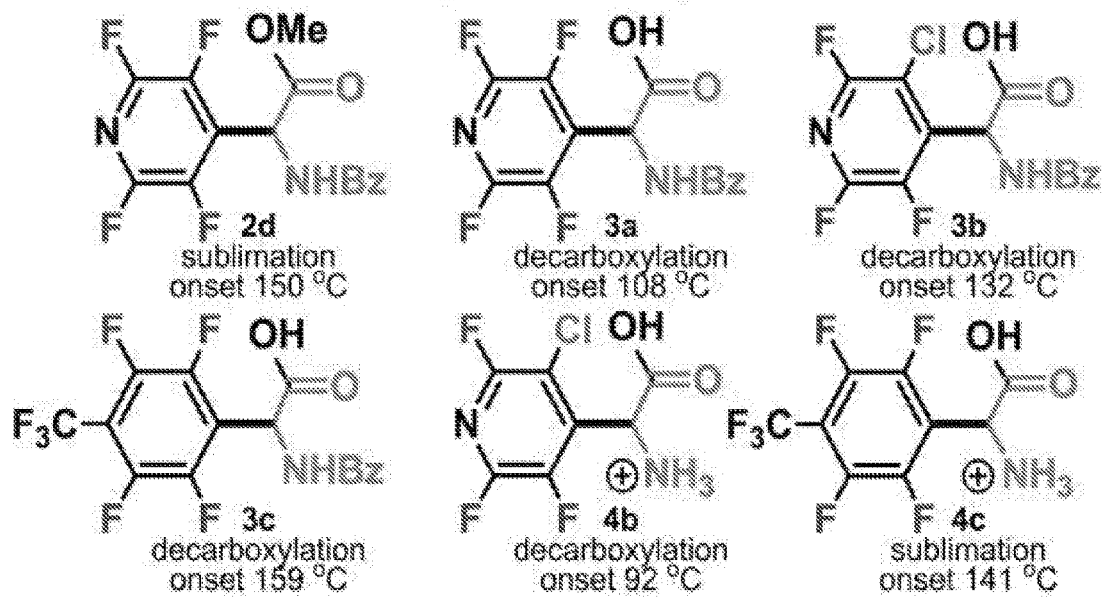
FIG. 5 illustrates thermal gravimetric analysis of α-multifluoroaryl amino acid derivatives.

General procedure G for the deprotection of perfluoroaryl-N-benzoyl amino acids (FIG. 4). The N-benzoyl amino acid (1.0 equiv) and 12 M HCl (0.01 M) was added to a round bottom flask and heated to 60° C. The reaction was monitored by $^{19}$F NMR, and after consumption of the starting material, the mixture was diluted with a half volume of H$_2$O and washed with equal volumes of toluene×3. The aqueous layer was concentrated in vacuo to give the product.

Figure 58:
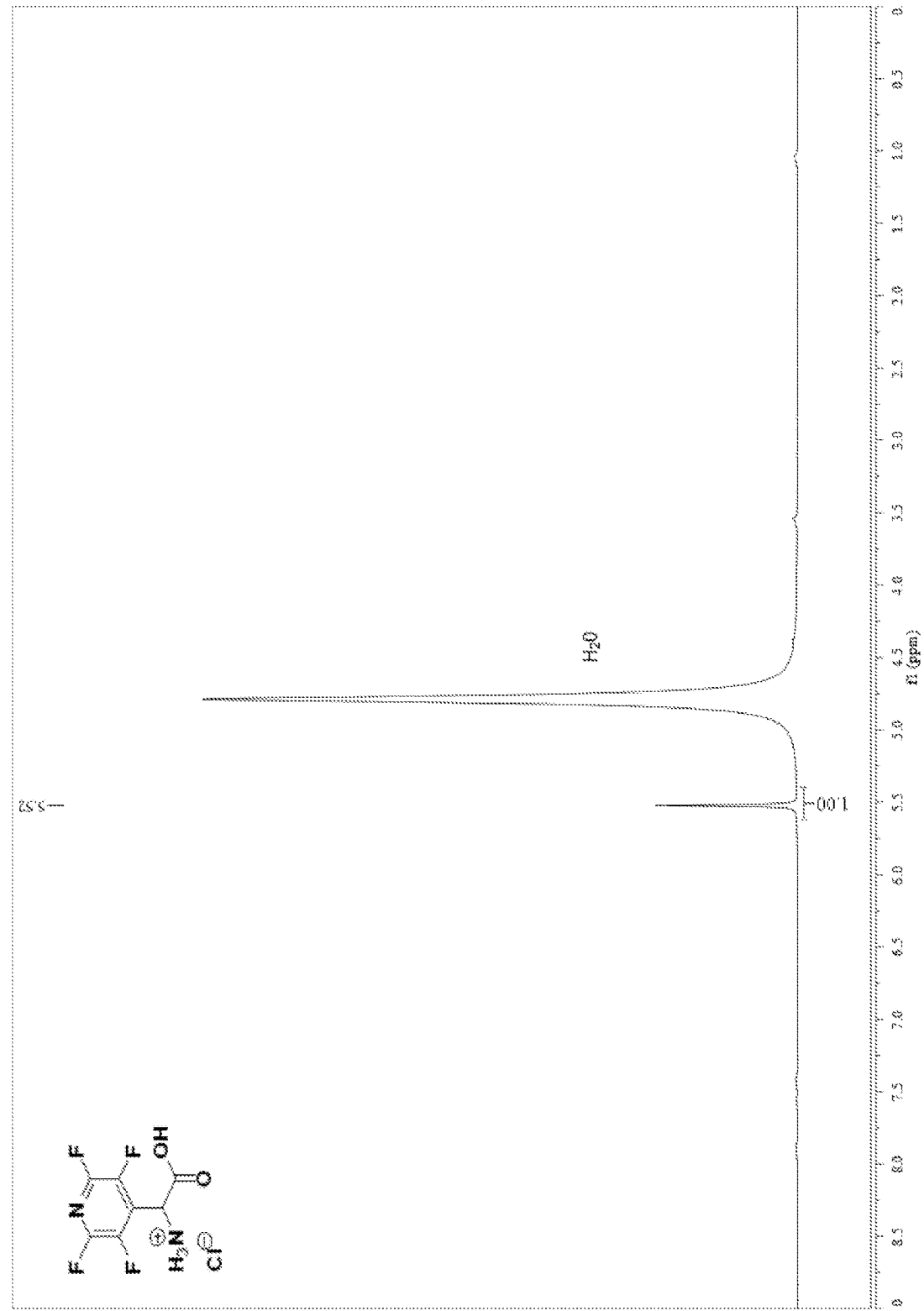
Figure 59:
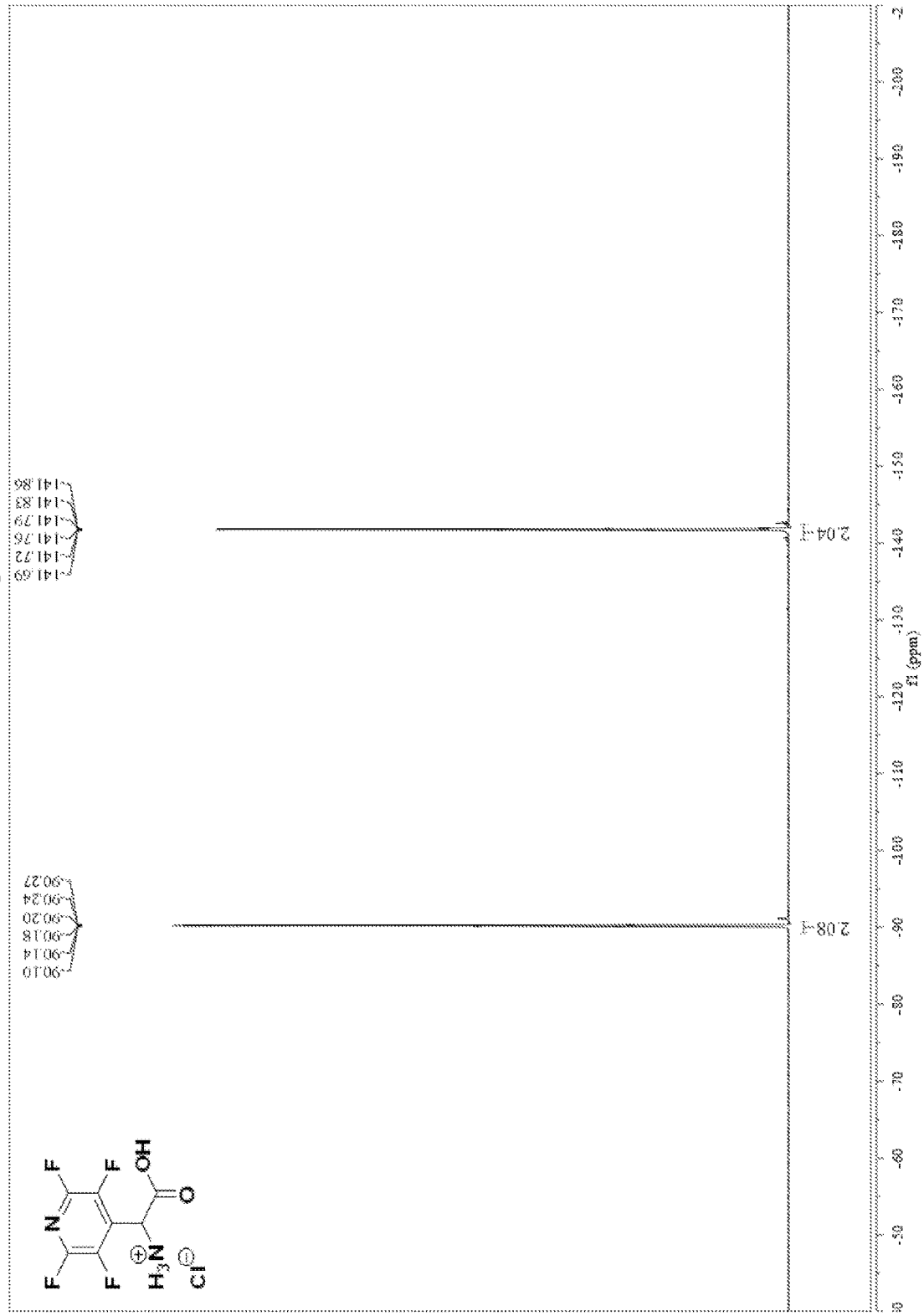
Figure 60:
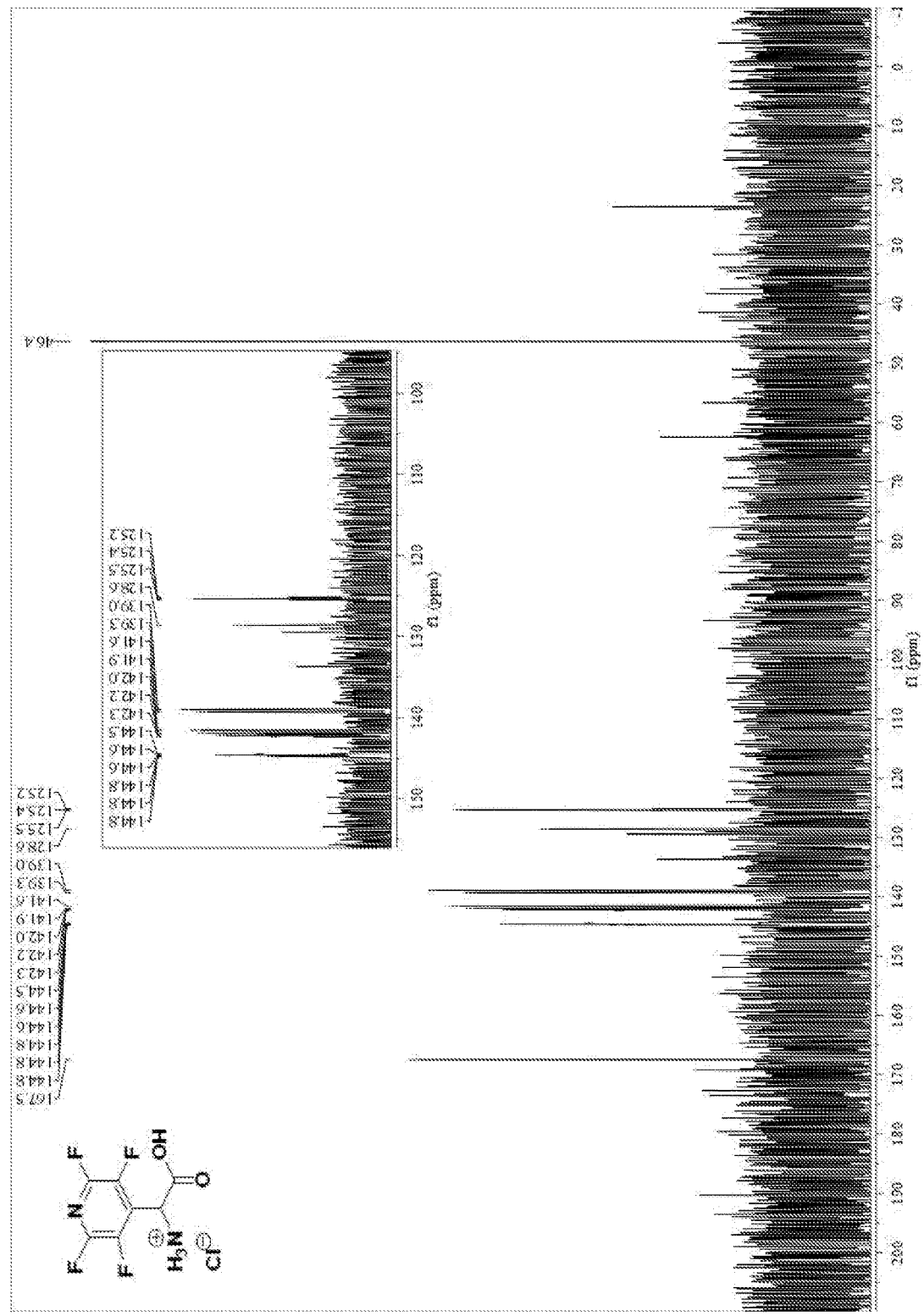

4a carboxy(perfluoropyridin-4-yl)methanaminium chloride (FIGS. 4 and 58-60) was produced as a white solid with 99% yield (59 mg, 0.228 mmol). The general procedure G was followed using 2-benzamido-2-(perfluoropyridin-4-yl) acetic acid (75 mg, 0.228 mmol) and 23.4 mL of 12 M HCl to afford 4a. FT-IR (neat) cm$^{-1}$ 3670, 3300, 1724, 1065. $^1$H NMR (400 MHz, Deuterium Oxide; FIG. 58) δ 5.52 (s, 1H). $^{19}$F NMR (376 MHz, Deuterium Oxide; FIG. 59) δ −89.95--90.40 (m), −141.50--142.06 (m). $^{13}$C NMR (101 MHz, Deuterium Oxide; FIG. 60) δ 167.55, 143.47 (dt, J=245.5, 16.5 Hz), 140.43 (dd, J=260.6, 35.0 Hz), 125.36 (t, J=16.6 Hz), 46.42. HRMS (ESI) $C_7H_5F_4N_2O_2Cl$ calcd. [M+]$^+$ 259.9976 observed 259.9964.

Figure 61:
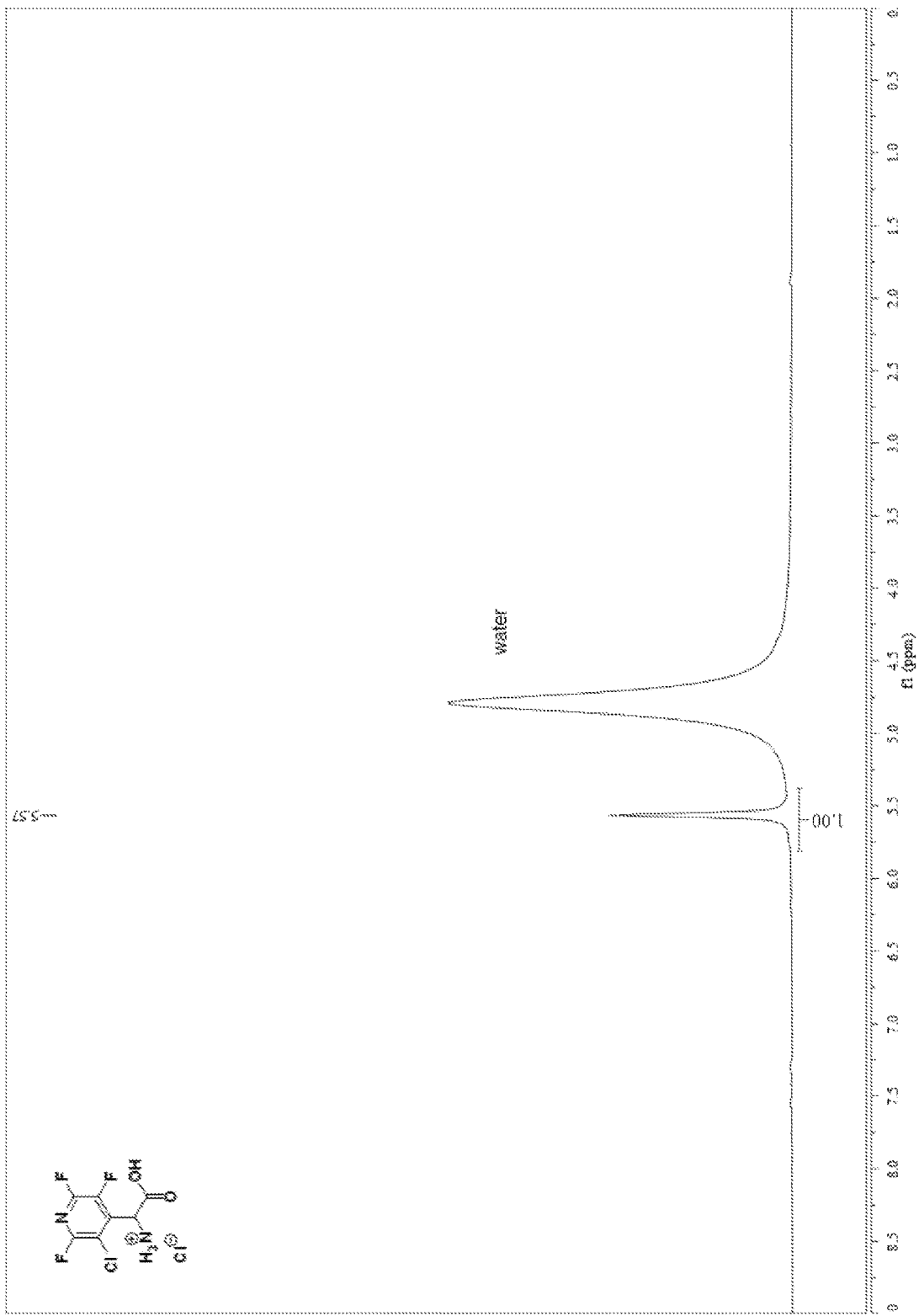
FIG. 61 contains a $^{1}$H NMR spectra (400 MHz), $D_2O$) of species 4b.
Figure 62:
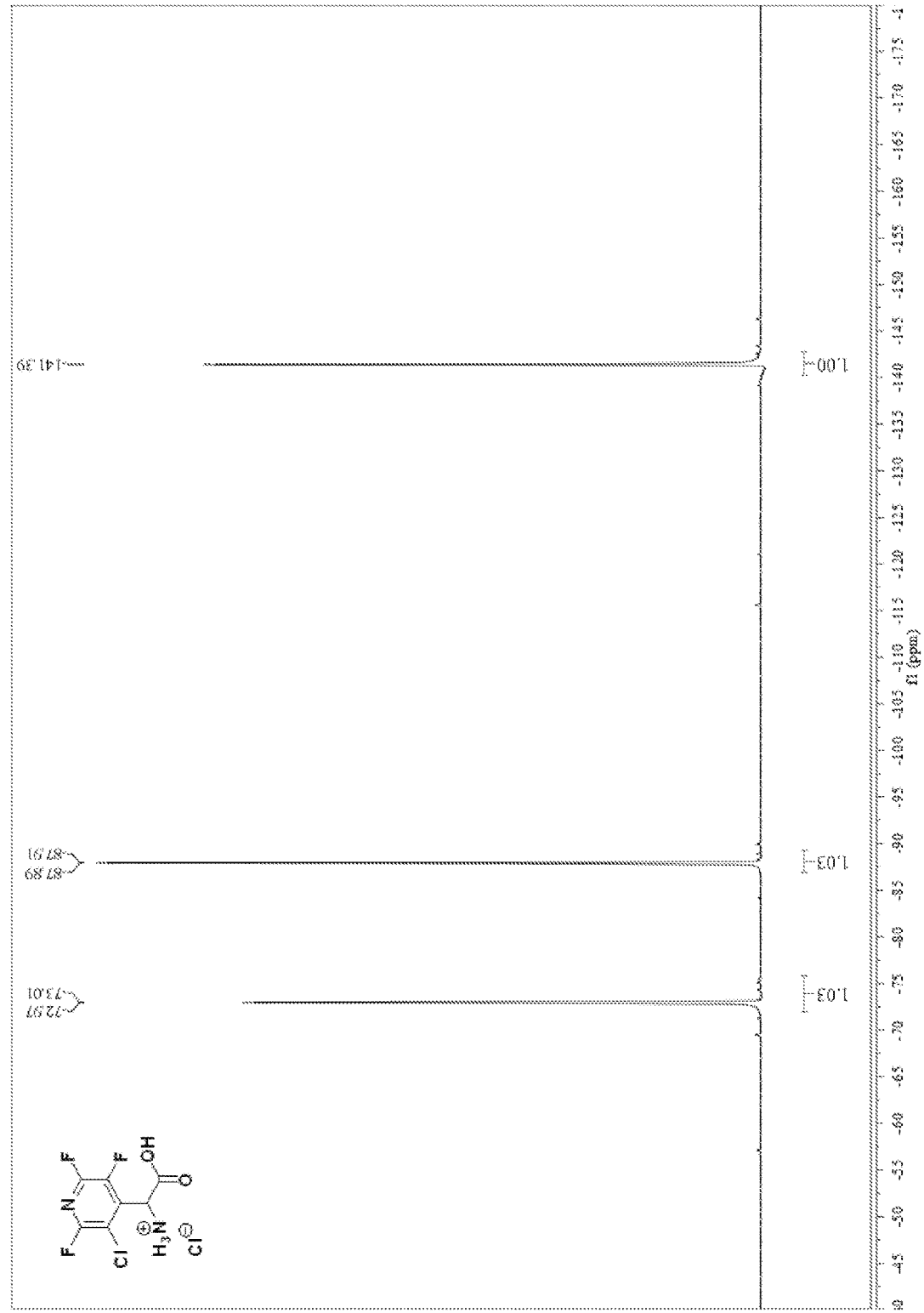
FIG. 62 contains a $^{19}$F NMR spectra (376 MHz), $D_2O$) of species 4b.
Figure 63:
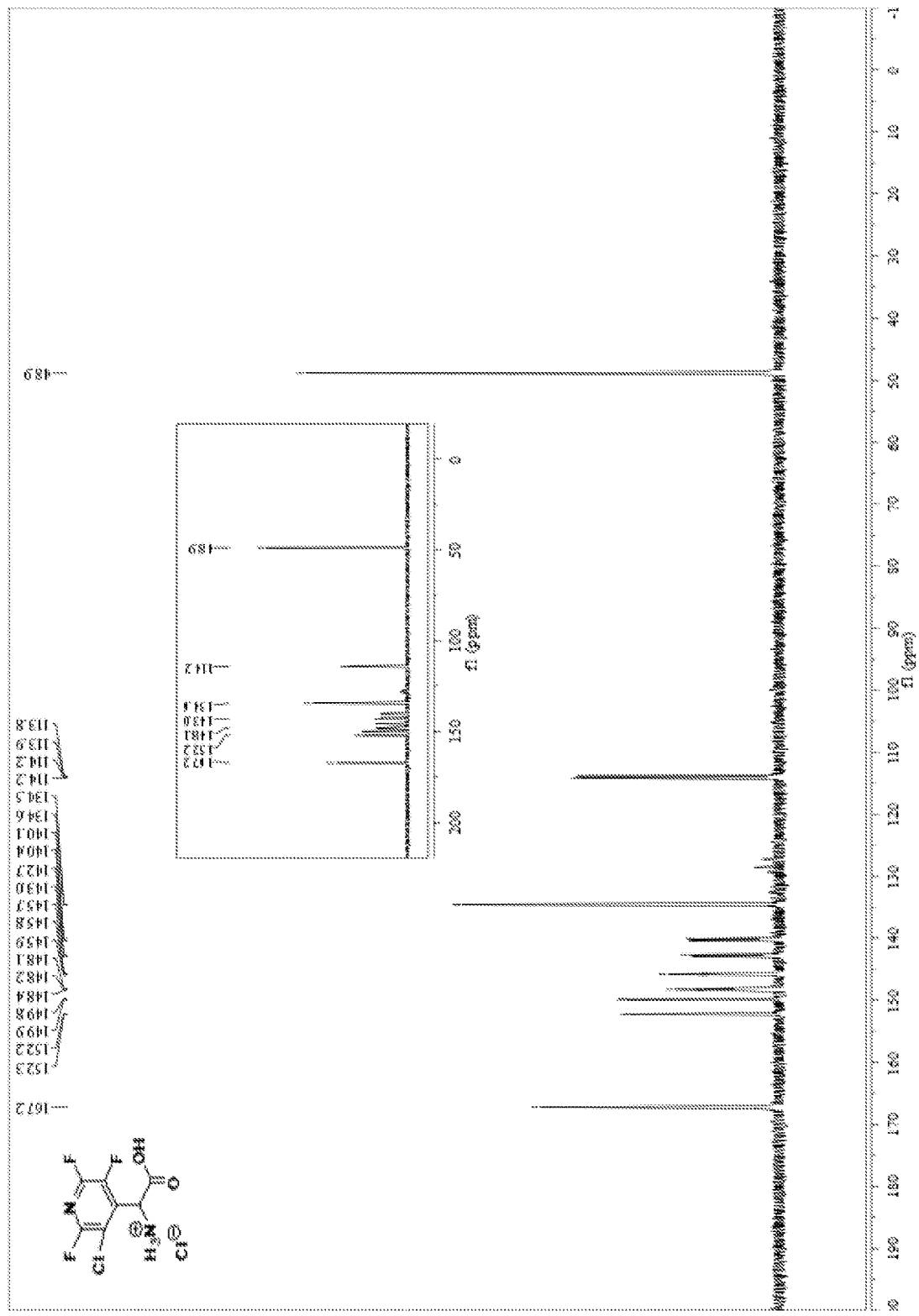
FIG. 63 contains a $^{13}$C NMR spectra (101 MHz), $D_2O$) of species 4b.

4b carboxy(3-chloro-2,5,6-trifluoropyridin-4-yl)methanaminium chloride (FIGS. 4 and 61-63) was produced as a white solid, in 99% yield (119 mg, 0.431 mmol). The general procedure G was followed using 2-benzamido-2-(3-chloro-2,5,6-trifluoropyridin-4-yl)acetic acid (150 mg, 0.435 mmol) and 43.5 mL of 12 M HCl to afford 4b. FT-IR (neat) cm$^{-1}$ 3683, 3300, 1715, 1034. $^1$H NMR (400 MHz, Deuterium Oxide; FIG. 61) δ 5.43 (s, 1H). $^{19}$F NMR (376 MHz, Deuterium Oxide; FIG. 62) δ −72.70--141.42 (m), −84.21--93.07 (m), −141.39. $^{13}$C NMR (101 MHz, Deuterium Oxide; FIG. 63) δ 167.2, 151.0 (dd, J=243.5, 10.3 Hz), 147.0 (dt, J=246.8, 14.6 Hz), 141.5 (dd, J=260.3, 31.8 Hz), 134.5 (d, J=12.7 Hz), 114.1 (dd, J=35.1, 4.9 Hz), 48.9. HRMS (ESI) $C_7H_5F_3N_2O_2Cl_2$ calcd. [M+]$^+$275.9680 observed 275.9672.

Figure 64:
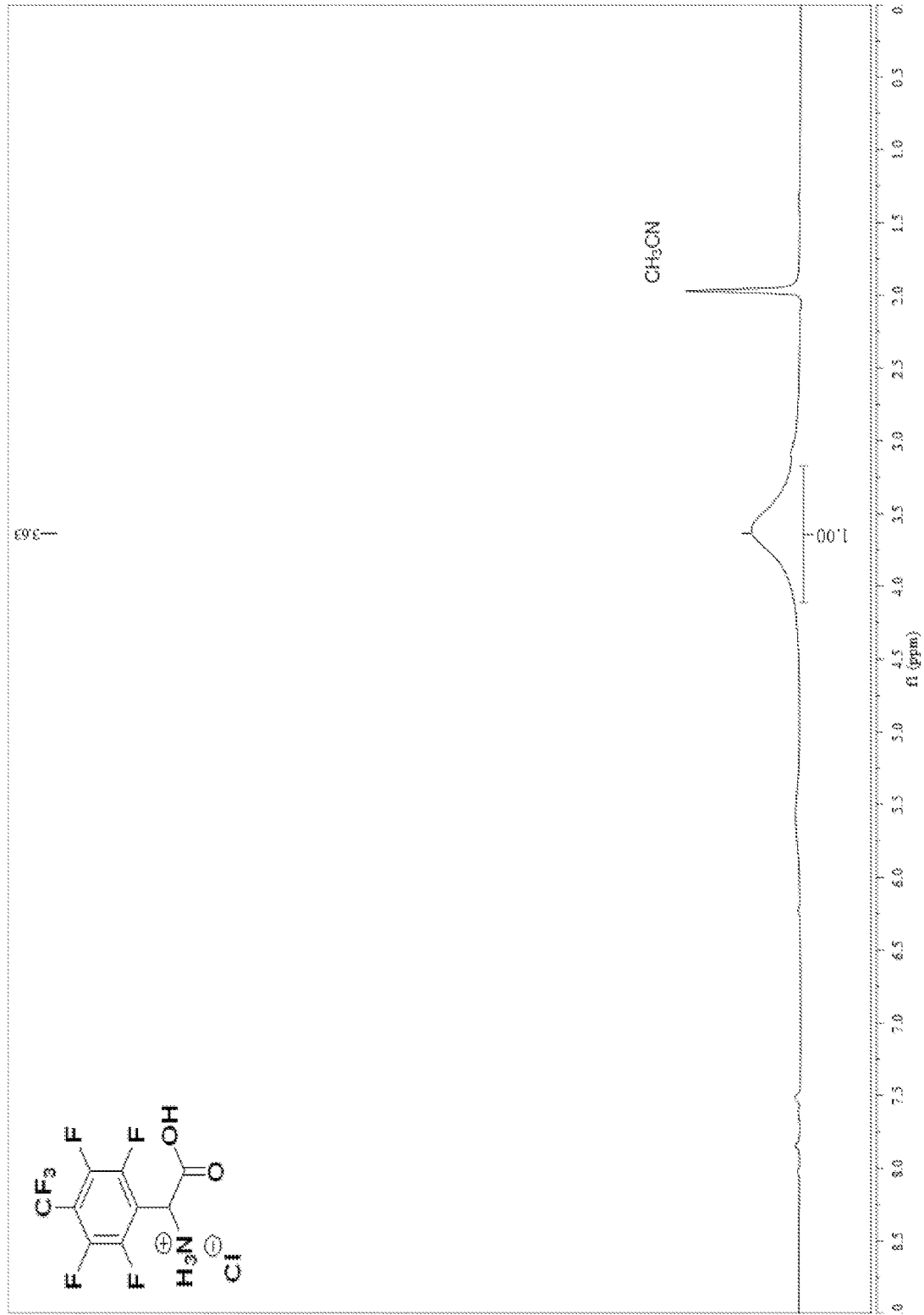
FIG. 64 contains a $^{1}$H NMR spectra (400 MHz), Acetonitrile-$d_3$) of species 4c.
Figure 65:
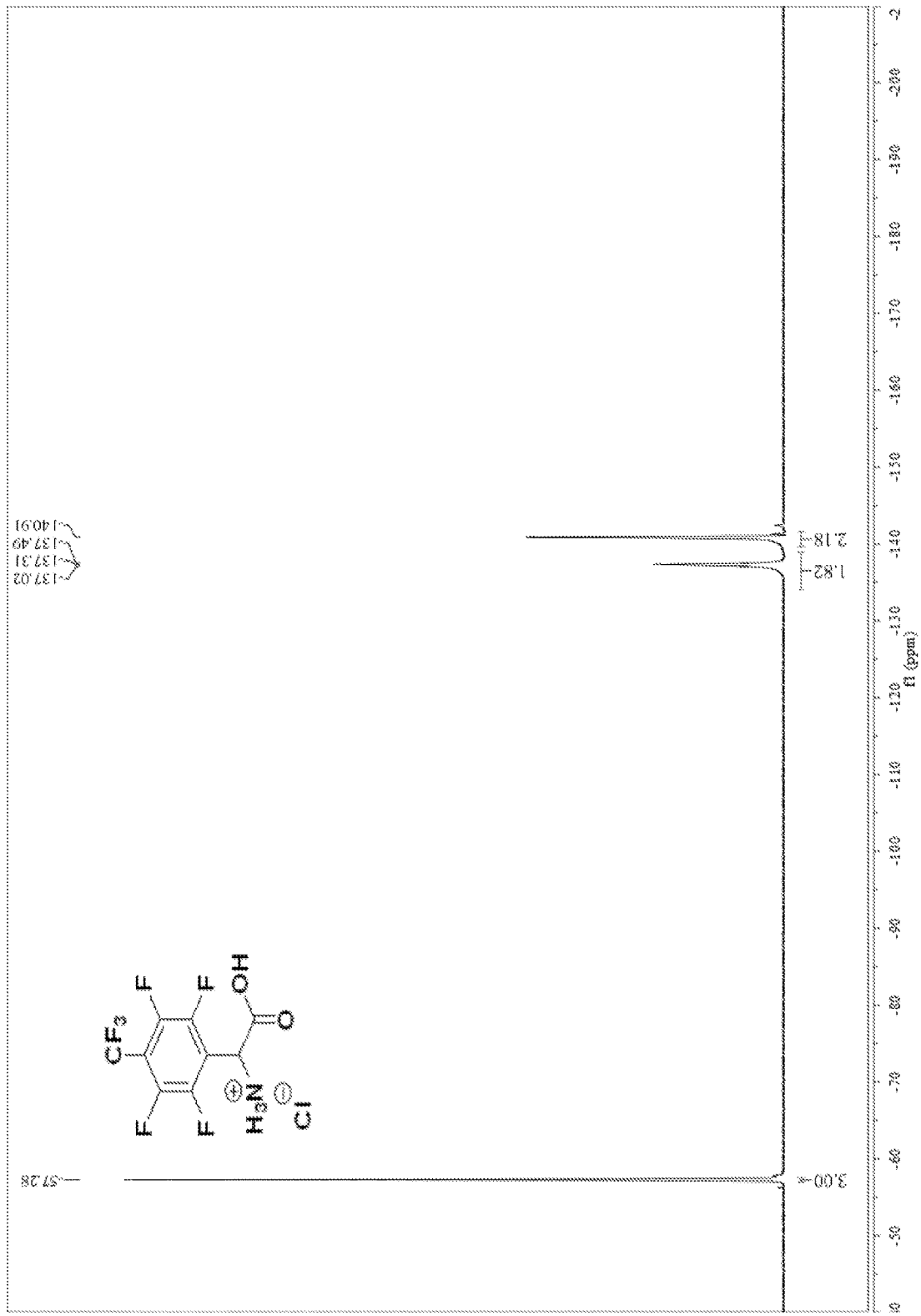
FIG. 65 contains a $^{19}$F NMR spectra (376 MHz), Acetonitrile-$d_3$) of species 4c.
Figure 66:
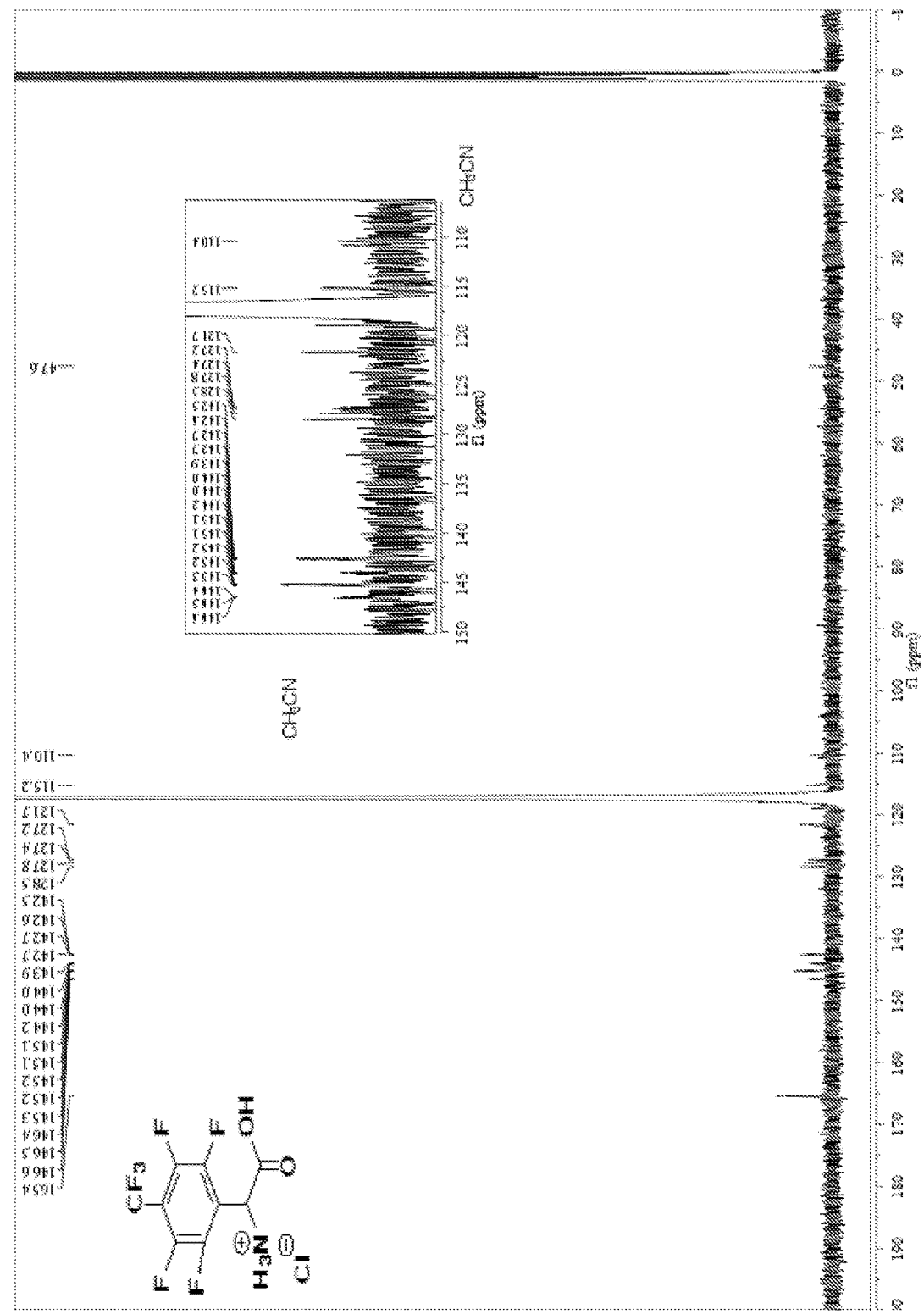
FIG. 66 contains a $^{13}$C NMR spectra (101 MHz), Acetonitrile-$d_3$) of species 4c.

4c carboxy(2,3,5,6-tetrafluoro-4-(trifluoromethyl)phenyl) methanaminium chloride (FIGS. 4 and 64-66) was produced as a white solid, in 99% yield (41.1 mg, 0.125 mmol). The general procedure G was followed using 2-benzamido-2-(2,3,5,6-tetrafluoro-4-(trifluoromethyl)phenyl)acetic acid (50 mg, 0.127 mmol) and 12.7 mL of 12 M HCl to afford 4c. FT-IR (neat) cm$^{-1}$ 3677, 3309, 1725, 1101. $^1$H NMR (400 MHz, Acetonitrile-d$_3$; FIG. 64) δ 3.63 (s, 1H). $^{19}$F NMR (376 MHz, Acetonitrile-d$_3$; FIG. 65) δ −57.28, −136.68--138.28 (m), −140.91. $^{13}$C NMR (101 MHz, Acetonitrile-d$_3$; FIG. 66) δ 165.4, 146.8-144.9 (m), 144.3-142.2 (m), 128.8-126.4 (m), 121.7, 115.5-114.6 (m), 47.6. HRMS (ESI) $C_9H_5F_7NO_2Cl$ calcd. [M+]$^+$326.9897 observed 326.9888.

General procedure H for the decarboxylation of perfluoroaryl amino acids (FIG. 4). The amino acid (1.0 equiv) and acetone 1 M were added to a round bottom flask with a magnetic stir bar and left to stir for 1 hour. The reaction was monitored by $^{19}$F NMR, and after consumption of the starting material, the mixture was concentrated in vacuo to give the product.

Figure 67:
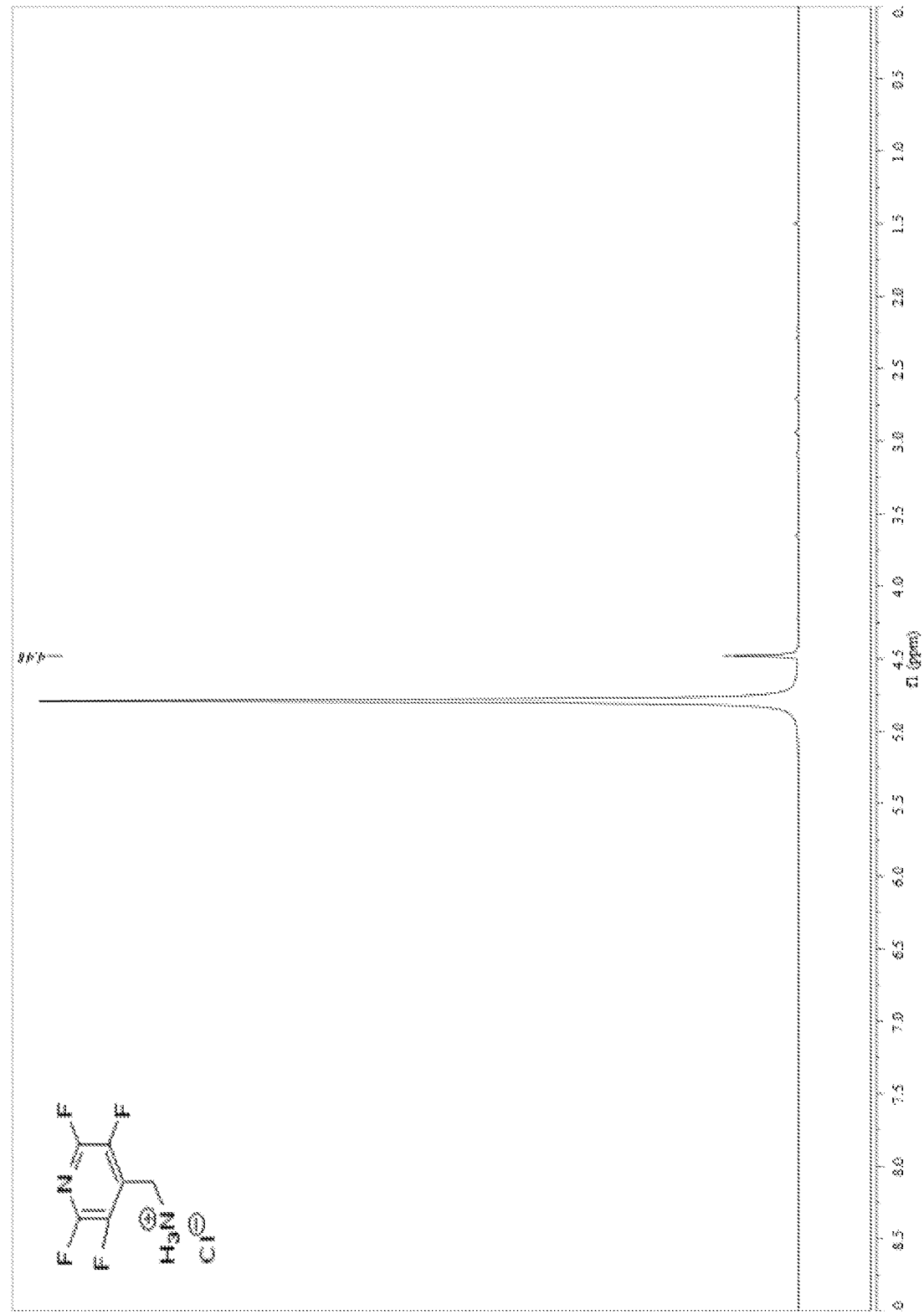
Figure 68:
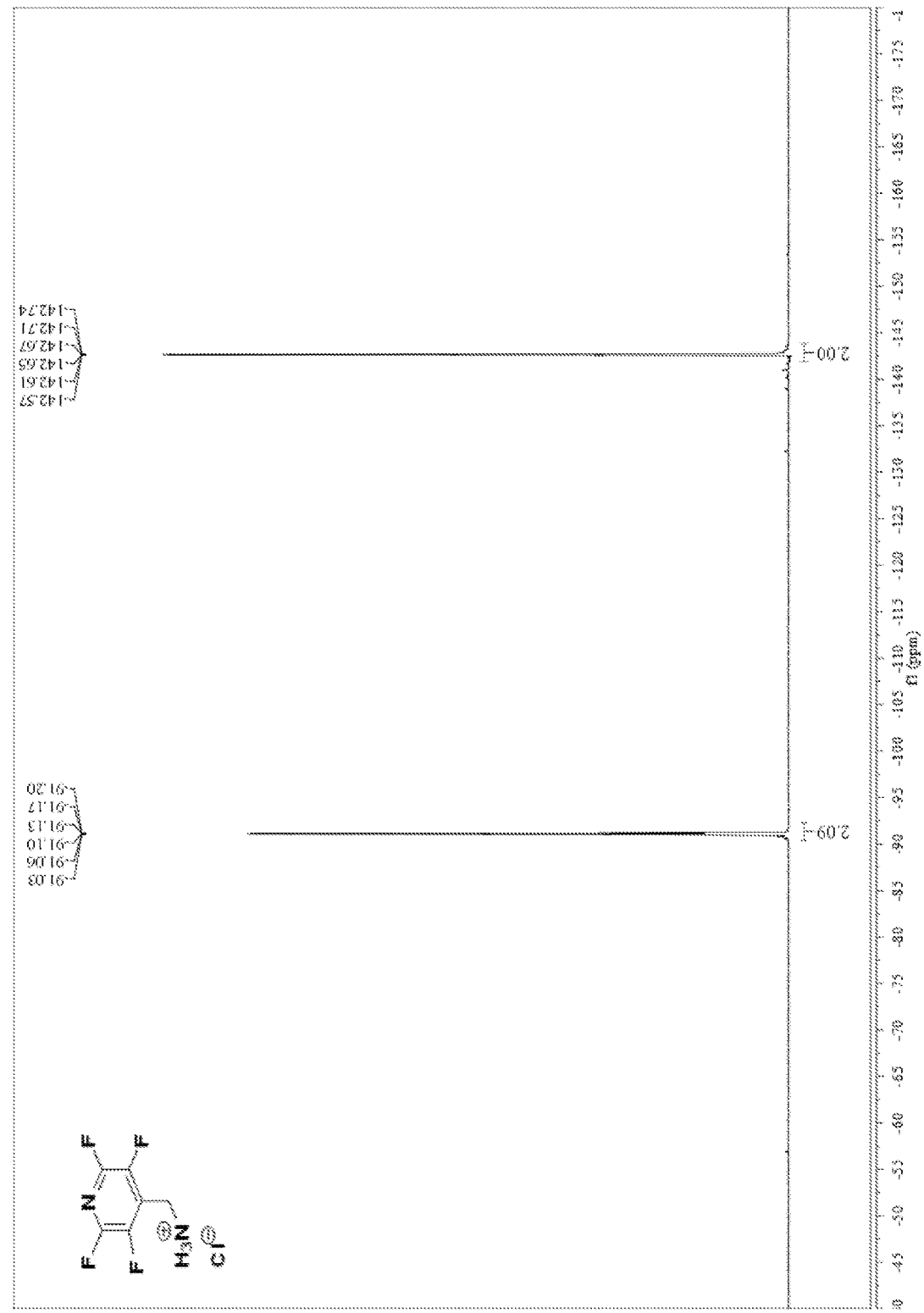
Figure 69:
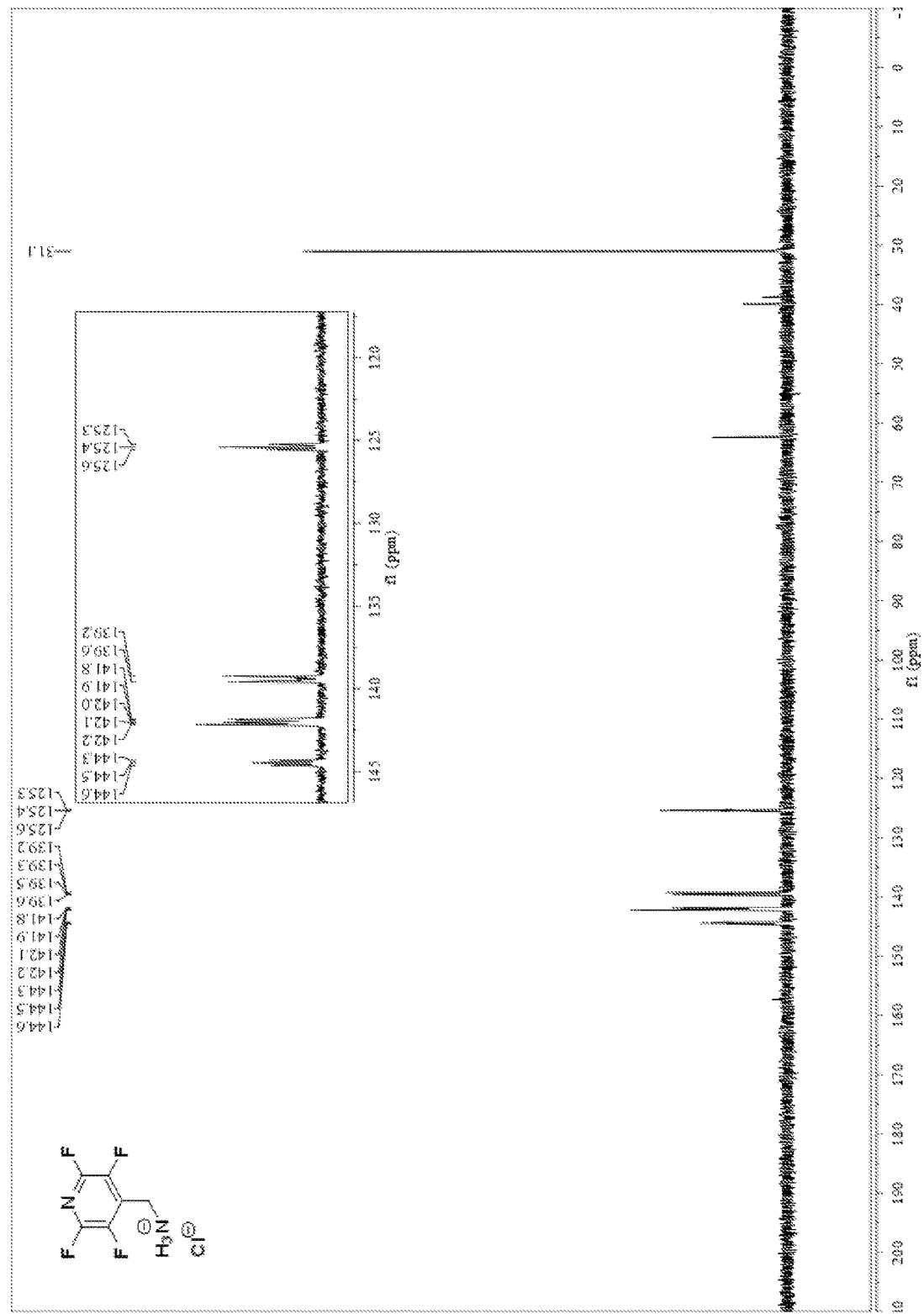

5a (perfluoropyridin-4-yl)methanaminium chloride (FIGS. 5 and 67-69) was produced as a white solid, in 99% yield (12.4 mg, 0.0572 mmol). The general procedure H was followed using carboxy(perfluoropyridin-4-yl)methanaminium chloride (15 mg, 0.0576 mmol) and 57.6 μL of acetone to afford 5a. FT-IR (neat) cm$^{-1}$ 3603, 3287, 3044, 1015. $^1$H NMR (400 MHz, Deuterium Oxide; FIG. 67) δ 4.36 (s, 1H). $^{19}$F NMR (376 MHz, Deuterium Oxide; FIG. 68) δ −91.12 (dq, J=28.3, 13.1 Hz), −142.50--142.83 (m). $^{13}$C NMR (101 MHz, Deuterium Oxide; FIG. 69) δ $^{13}$C NMR (101 MHz, Deuterium Oxide) δ 144.8-141.6 (m), 140.7 (dd, J=259.7, 34.7 Hz), 125.4 (t, J=15.9 Hz), 31.1. HRMS (ESI) $C_6H_5F_4N_2Cl$ calcd. [M+]$^+$216.0077 observed 216.0054.

Figure 70:
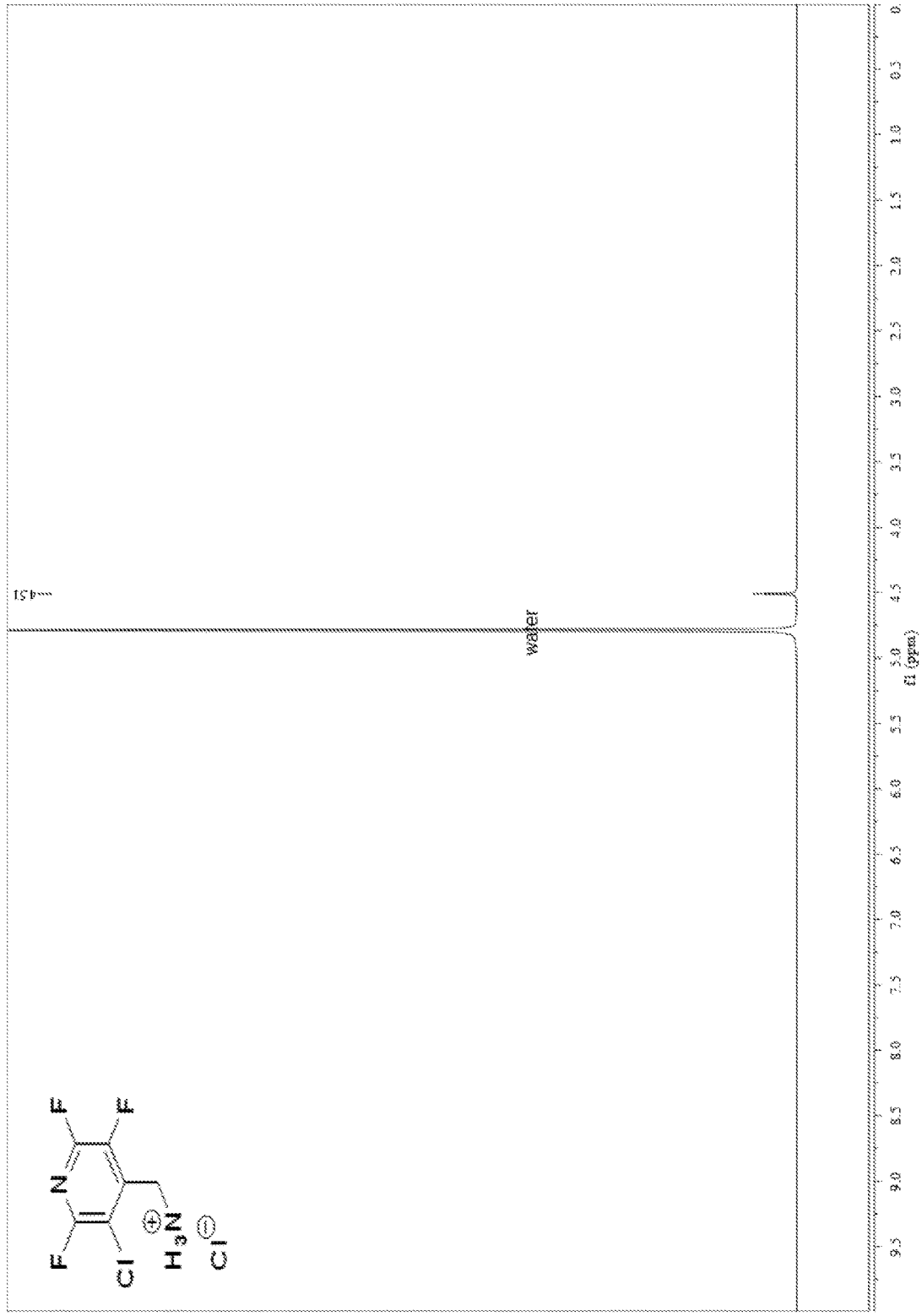
FIG. 70 contains a $^{1}$H NMR spectra (400 MHz), $D_2O$) of species 5b.
Figure 71:
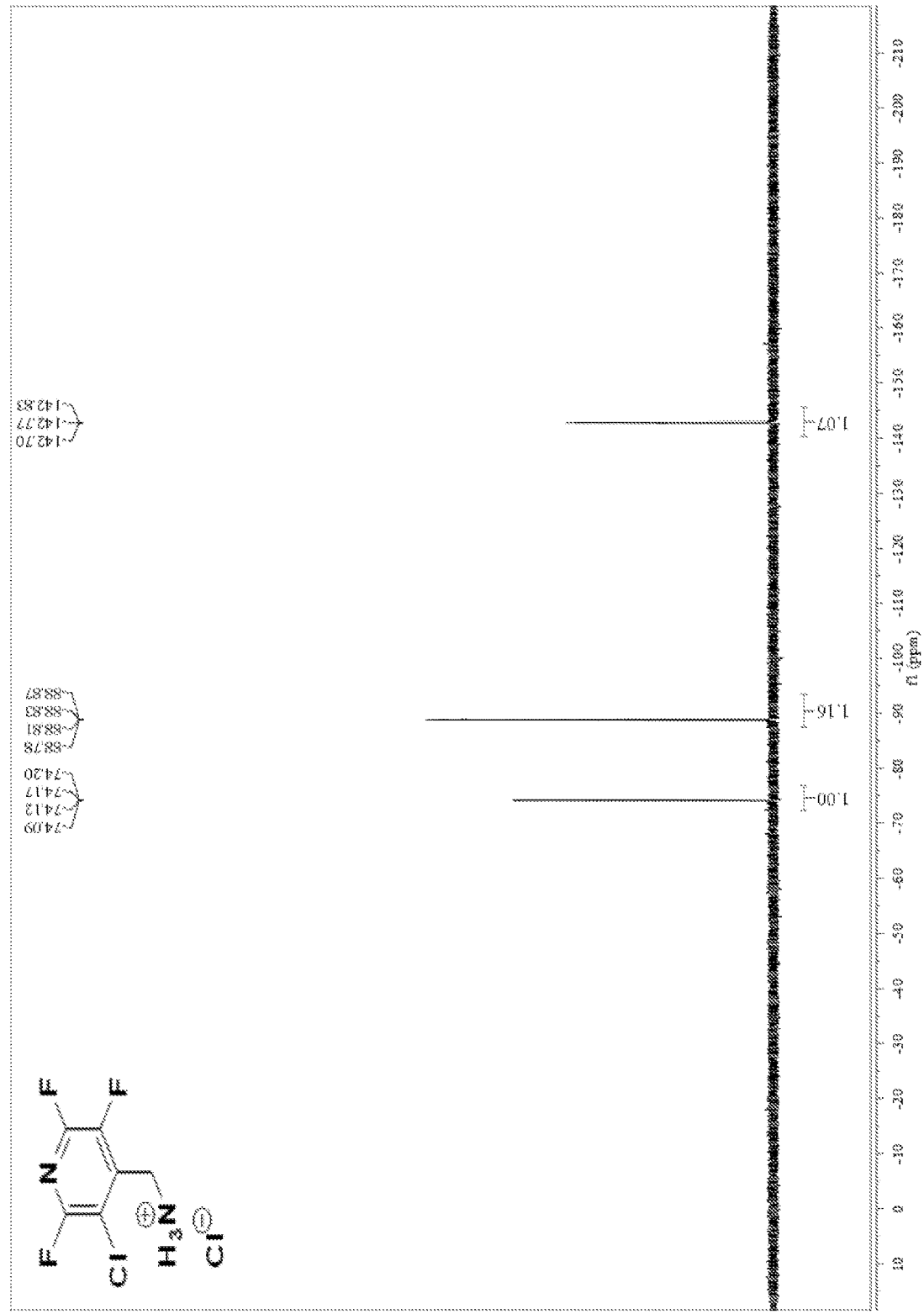
FIG. 71 contains a $^{19}$F NMR spectra (376 MHz), $D_2O$) of species 5b.
Figure 72:
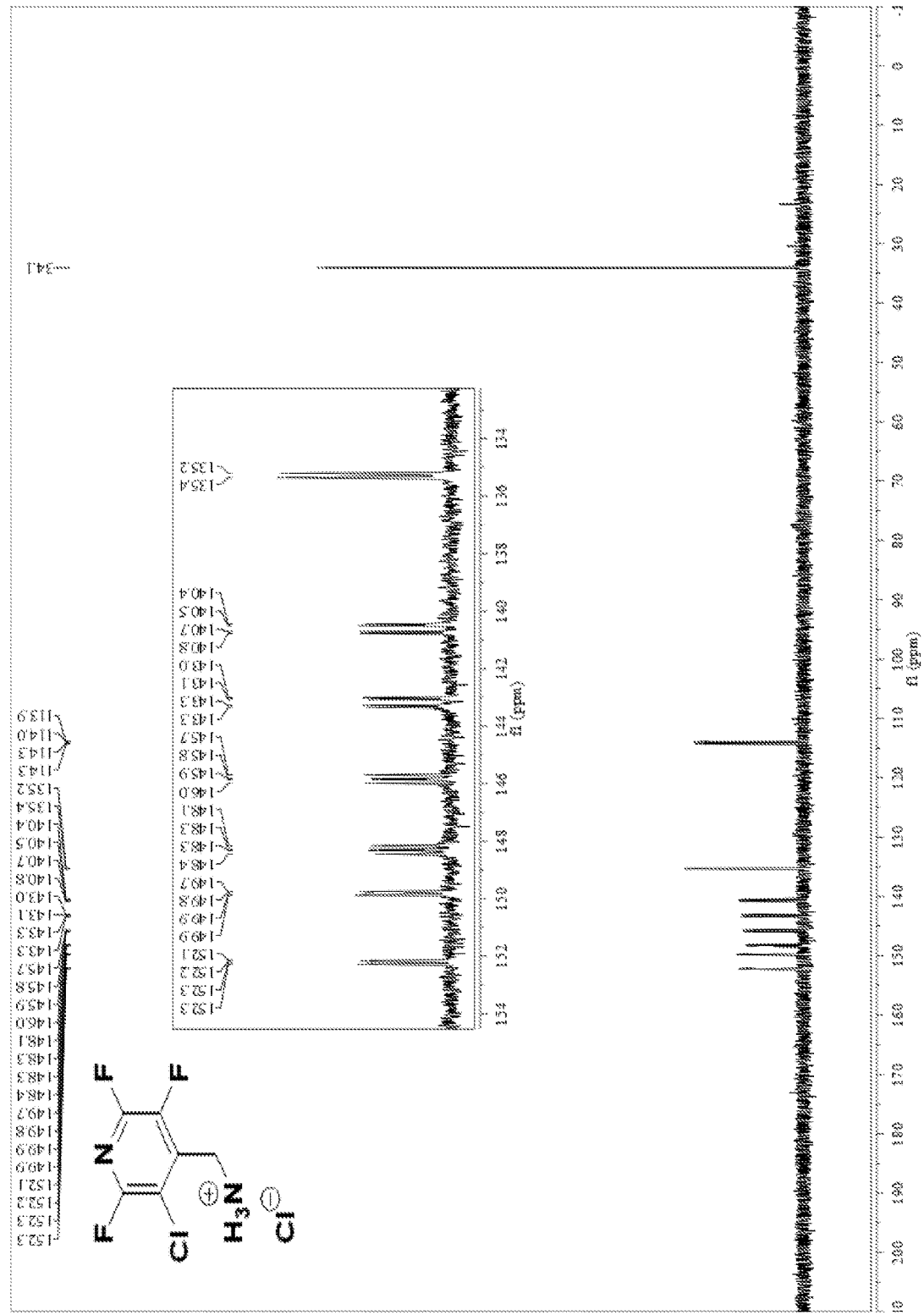
FIG. 72 contains a $^{13}$C NMR spectra (101 MHz), $D_2O$) of species 5b.

5b (3-chloro-2,5,6-trifluoropyridin-4-yl)methanaminium chloride (FIGS. 5 and 70-72) was produced as a white solid, in 99% yield (16.9 mg, 0.0725 mmol). The general procedure H was followed using carboxy(3-chloro-2,5,6-trifluoropyridin-4-yl)methanaminium chloride (25.0 mg, 0.0725 mmol) and 72.5 μL of acetone to afford 5b. FT-IR (neat) cm$^{-1}$ 3632, 3250, 3033, 1055. $^1$H NMR (400 MHz, Deuterium Oxide; FIG. 70) δ 4.51 (s, 1H). $^{19}$F NMR (376 MHz, Deuterium Oxide; FIG. 71) δ −74.14 (dd, J=27.7, 12.4 Hz), −88.82 (dd, J=21.4, 12.4 Hz), −140.28--147.60 (m). $^{13}$C NMR (101 MHz, Deuterium Oxide; FIG. 72) δ 151.0 (ddd, J=242.5, 11.9, 2.9 Hz), 147.1 (ddd, J=246.8, 17.6, 13.2 Hz), 141.9 (ddd, J=259.0, 27.0, 6.4 Hz), 135.3 (d, J=14.2 Hz), 114.1 (dd, J=34.7, 6.8 Hz), 34.1. HRMS (ESI) $C_6H_5ClF_3N_2Cl$ calcd. [M+]$^+$231.9782 observed 231.9799.

Figure 73:
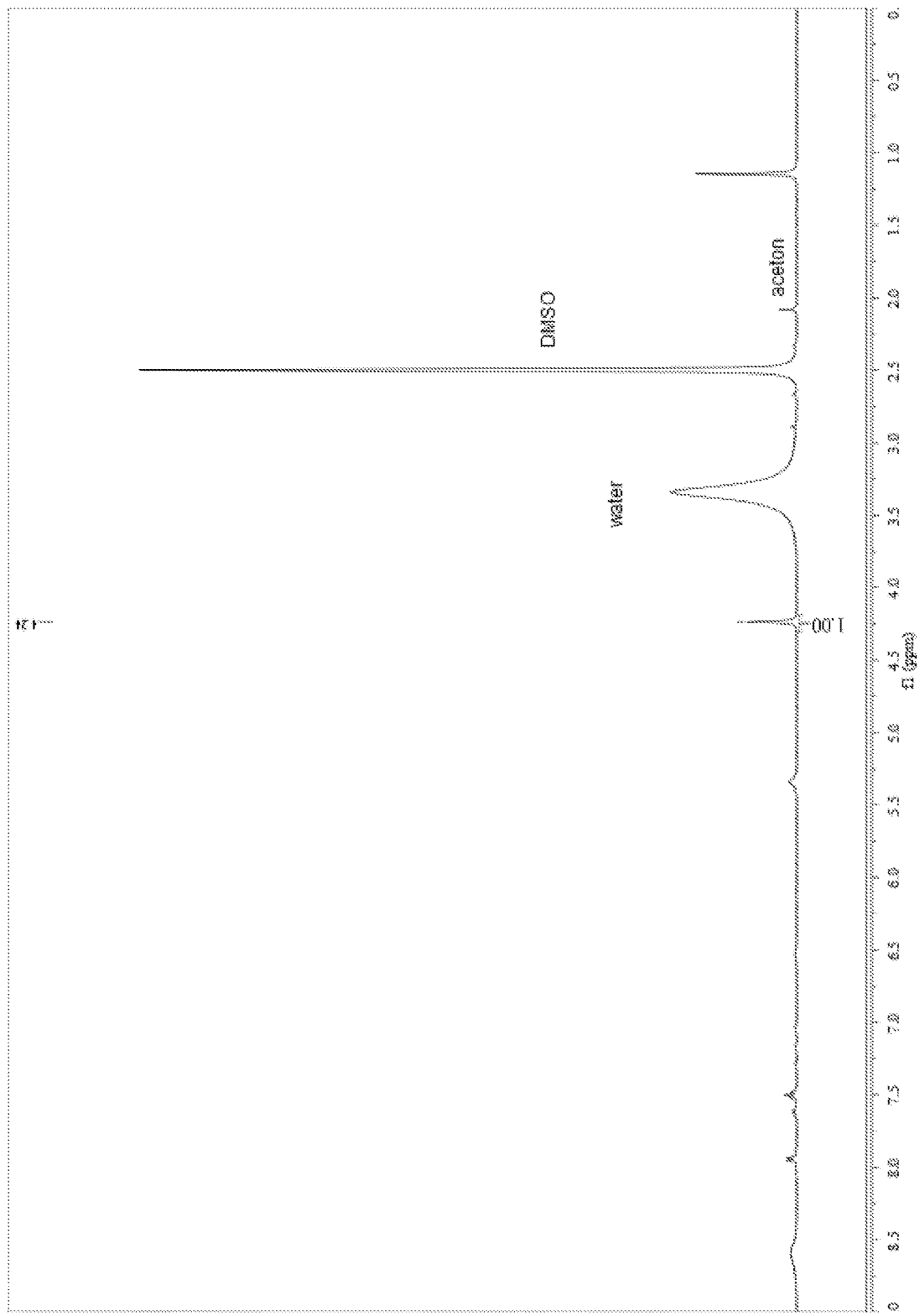
FIG. 73 contains a $^{1}$H NMR spectra (400 MHz), DMSO-$d_6$) of species 5c.
Figure 74:
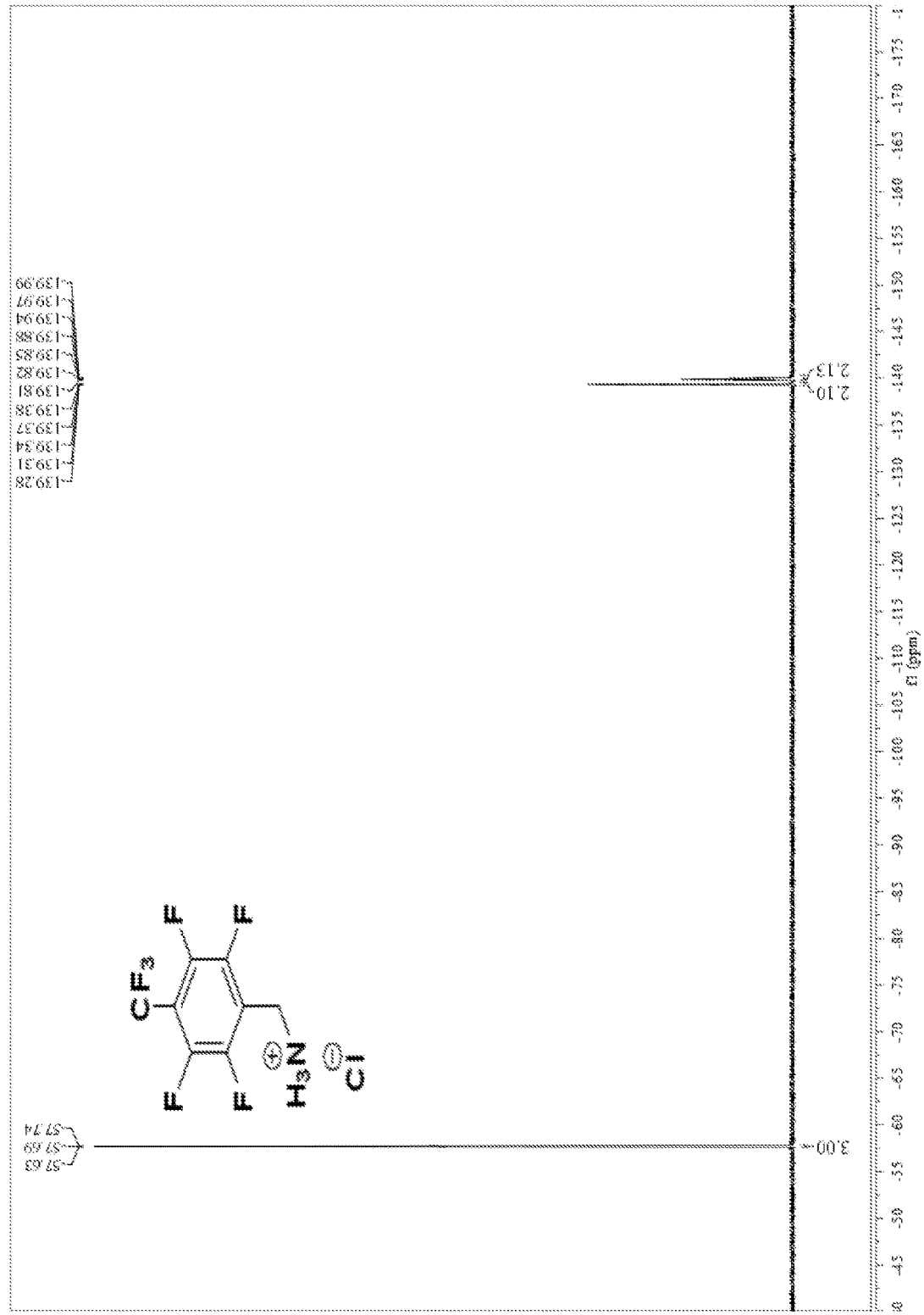
FIG. 74 contains a $^{19}$F NMR spectra (376 MHz), DMSO-$d_6$) of species 5c.
Figure 75:
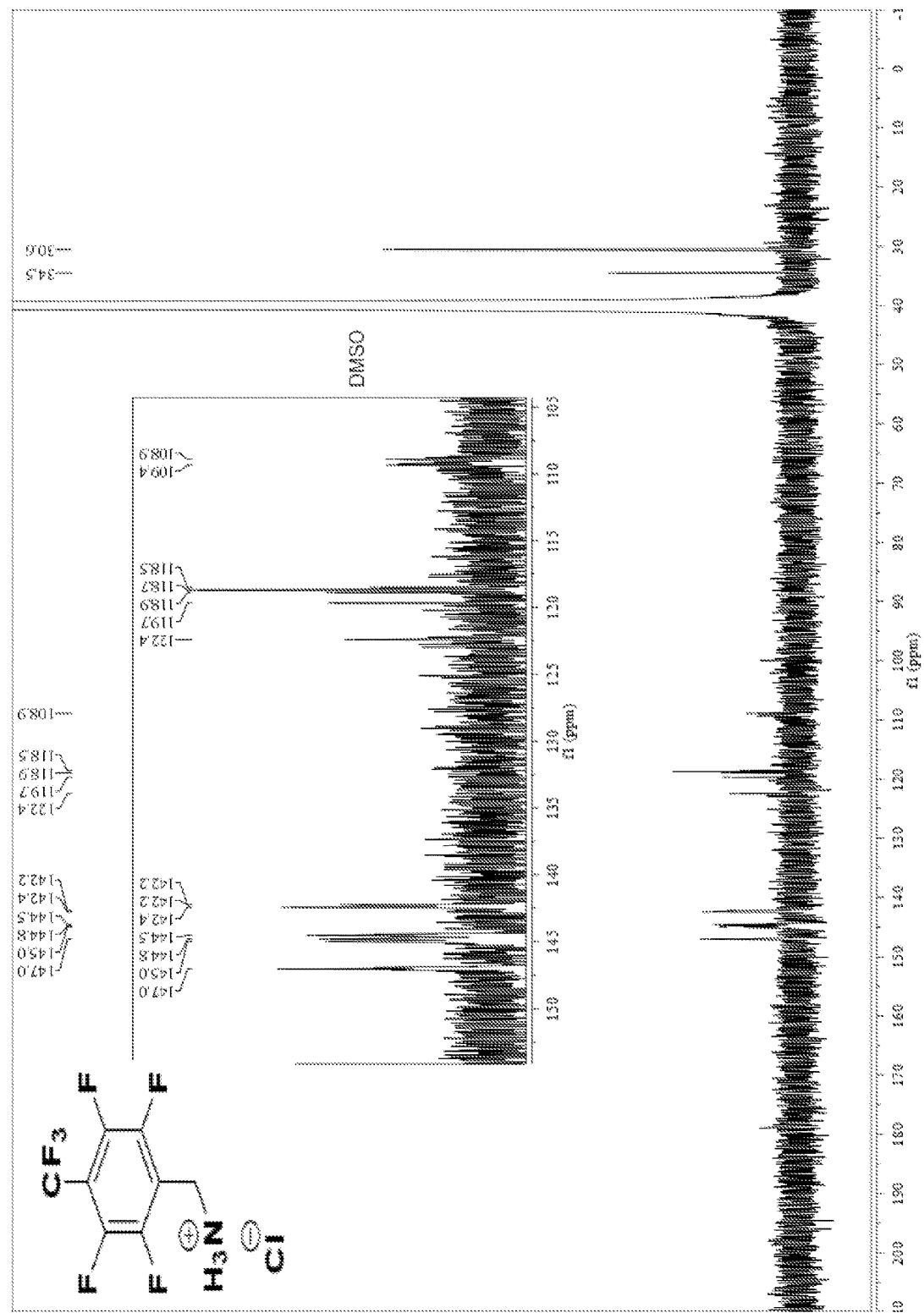
FIG. 75 contains a $^{13}$C NMR spectra (101 MHz), DMSO-$d_6$) of species 5c.

5c (2,3,5,6-tetrafluoro-4-(trifluoromethyl)phenyl)methanaminium chloride (FIGS. 5 and 73-75) was produced as a white solid, in 99% yield (10.7 mg, 0.027 mmol). The general procedure H was followed using carboxy(2,3,5,6-tetrafluoro-4-(trifluoromethyl)phenyl)methanaminium chloride (15 mg, 0.038 mmol) and 38 μL of acetone to afford 5c. FT-IR (neat) cm$^{-1}$ 3609, 3277, 3064, 1077. $^1$H NMR (400 MHz, DMSO-d$_6$; FIG. 73) δ 4.24 (s, 1H). $^{19}$F NMR (376 MHz, DMSO-d$_6$; FIG. 74) δ −57.69 (t, J=21.5 Hz), −139.33 (dt, J=17.2, 9.5 Hz), −139.69--140.09 (m). $^{13}$C NMR (101 MHz, DMSO-d$_6$; FIG. 75) δ 145.8 (d, J=251.7 Hz), 143.6 (dt, J=259.4, 18.4 Hz), 121.0 (d, J=276.2 Hz), 118.7 (d, J=35.9 Hz), 108.9, 30.6. HRMS (ESI) $C_8H_5F_7NCl$ calcd. [M+]$^+$282.9999 observed 283.0023.

Synthesis of 2-Aminohydantoins

Figure 7:
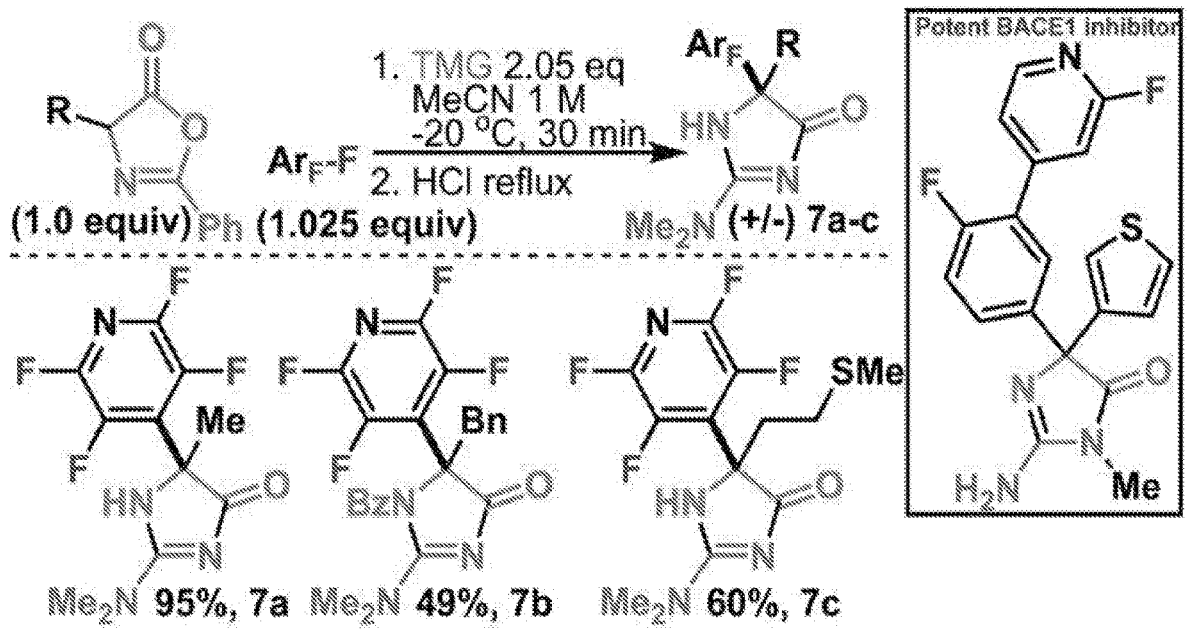
FIG. 7 illustrates one pot multicomponent synthesis of 2-aminohydantoins.

General Procedure I for Synthesis of 2-Aminohydantoins (FIG. 7):

Under an argon atmosphere, oxazolone (1 equiv), Ar$_F$—F (1.025 equiv), CH$_3$CN (1 M) were added to small test tube, which was fitted with a septum and cooled to −20° C. Then a steady stream of tetramethylguanidine (1.025 equiv.) was added to mixture down the side of the test tube glass, which facilitated cooling of the TMG solution. The reaction was left to react for 30 min, and then the cooling bath was removed. After, the reaction had warmed to room temperature, then a solution of 12 M aqueous hydrochloric acid (0.1 M) was added and refluxed for 24-48 h. The solution was diluted with a half volume of water and made neutral with NaHCO$_3$. The aqueous layer was extracted with EtOAc×3, and the organic layer was dried with MgSO$_4$ and concentrated, giving crude product. Purification of the crude product was purified by normal phase column chromatography.

Figure 88:
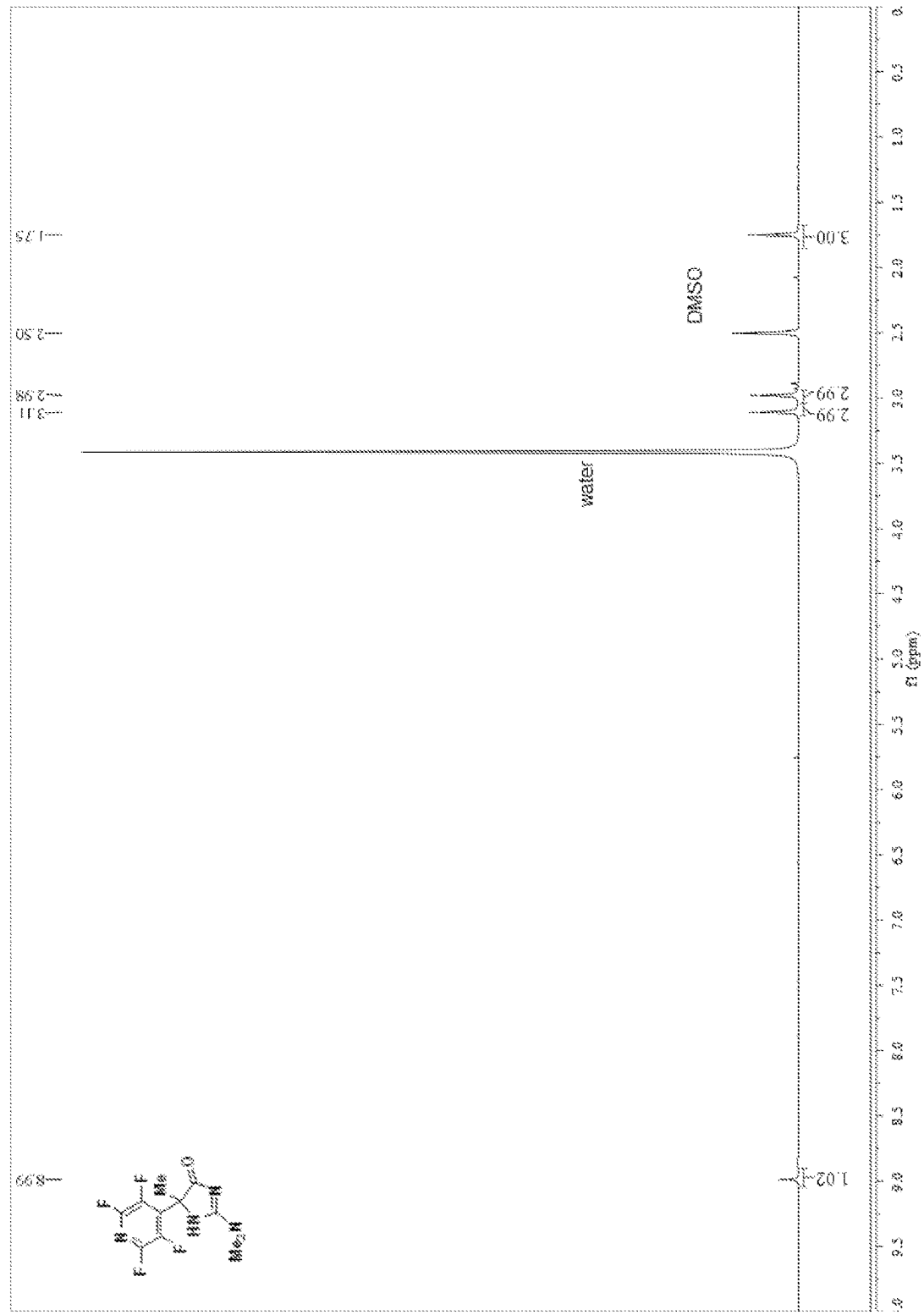
Figure 89:
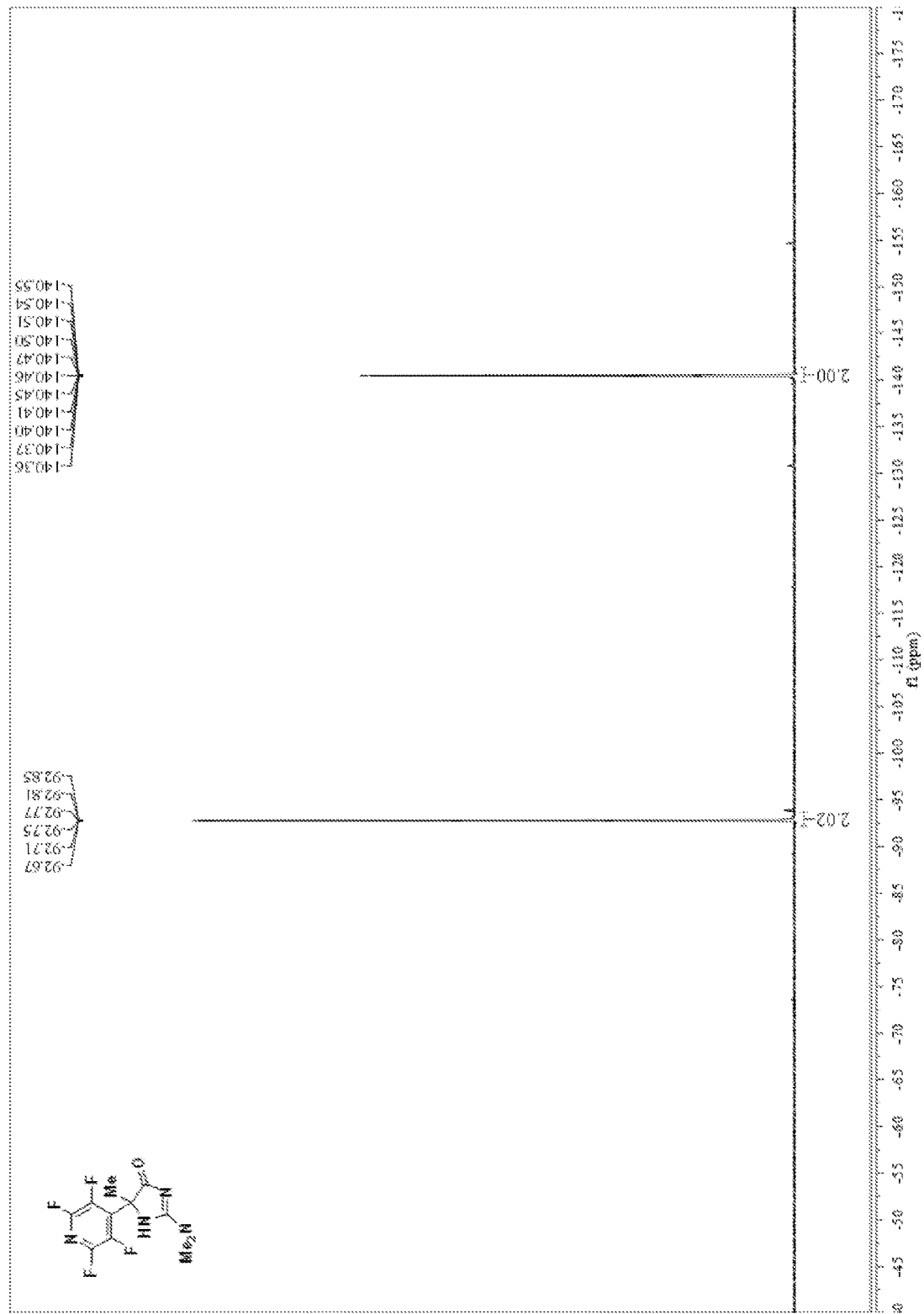
Figure 90:
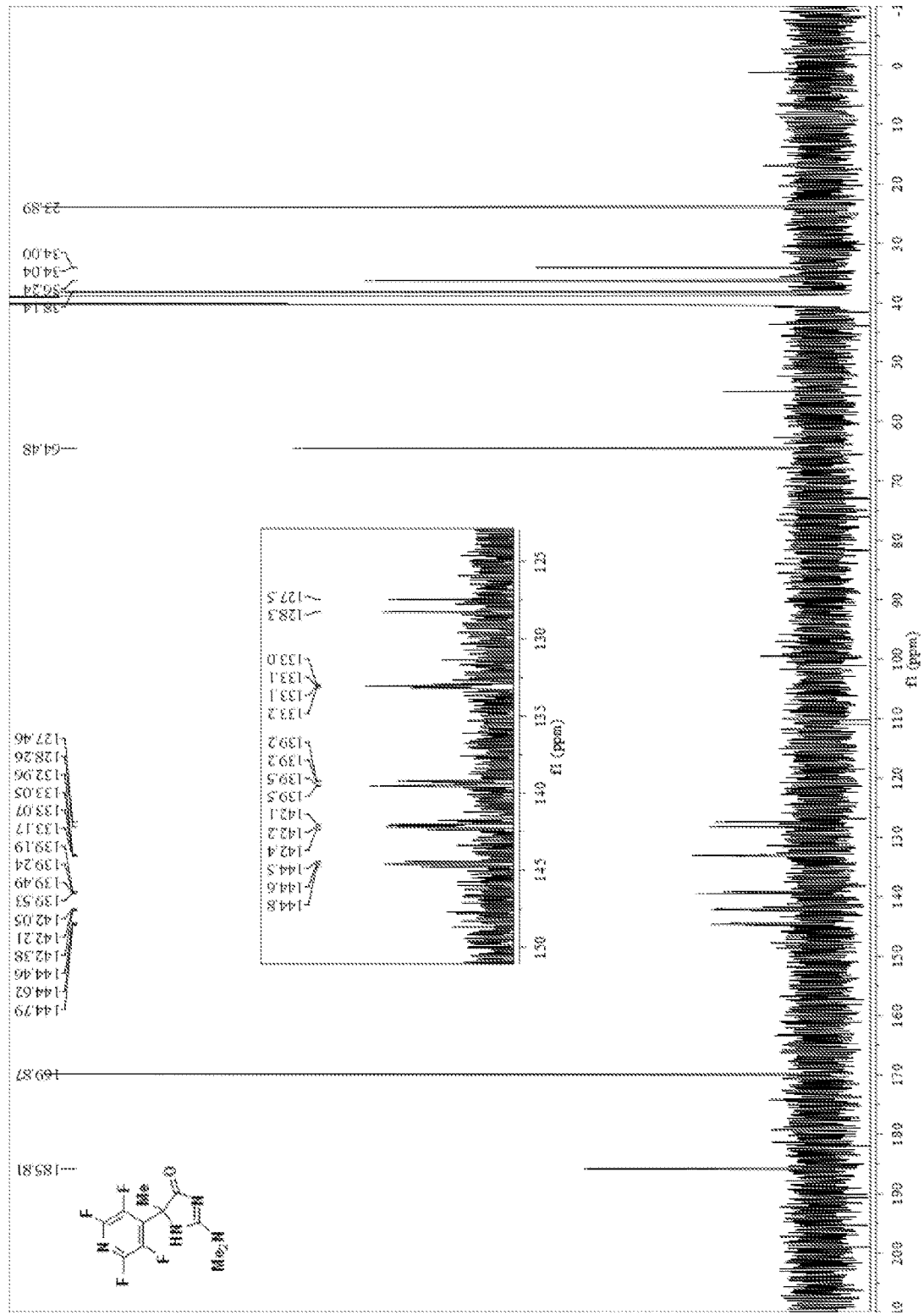

7a 2-(dimethylamino)-5-methyl-5-(perfluoropyridin-4-yl)-1,5-dihydro-4H-imidazol-4-one (FIGS. 7 and 88-90) was produced as a white solid, in 95% yield (314 mg, 1.08 mmol). The general procedure I was followed using 4-methyl-2-phenyloxazol-5(4H)-one (200 mg, 1.14 mmol), pentafluoropyridine (66.8 mg, 1.17 mmol), tetramethylguanidine (135 mg, 1.17 mmol), 11.4 mL HCl and 1.14 mL of MeCN was used to afford 7a. FT-IR (neat) cm$^{-1}$ 3203, 2967, 1730, 1035. $^1$H NMR (400 MHz, DMSO-d$_6$; FIG. 88)

δ 8.99 (s, $^1$H), 3.11 (s, 3H), 2.98 (s, 3H), 1.75 (s, 3H). $^{19}$F NMR (376 MHz, CD$_3$CN; not shown) δ −143.03, −143.64. $^{19}$F NMR (376 MHz, DMSO-d$_6$; FIG. 89) δ −92.57--93.01 (m), −140.20--140.83 (m). $^{13}$C NMR (101 MHz, DMSO-d$_6$; FIG. 90) δ 185.8, 169.9, 145.0-141.5 (m), 142.6-138.8 (m), 133.1 (t, J=10.6 Hz), 64.5, 38.1, 36.2, 23.9. HRMS (ESI) C11H$_{10}$F$_4$N$_4$O calcd. [M+K]$^+$329.0422 observed 329.0456.

Figure 91:
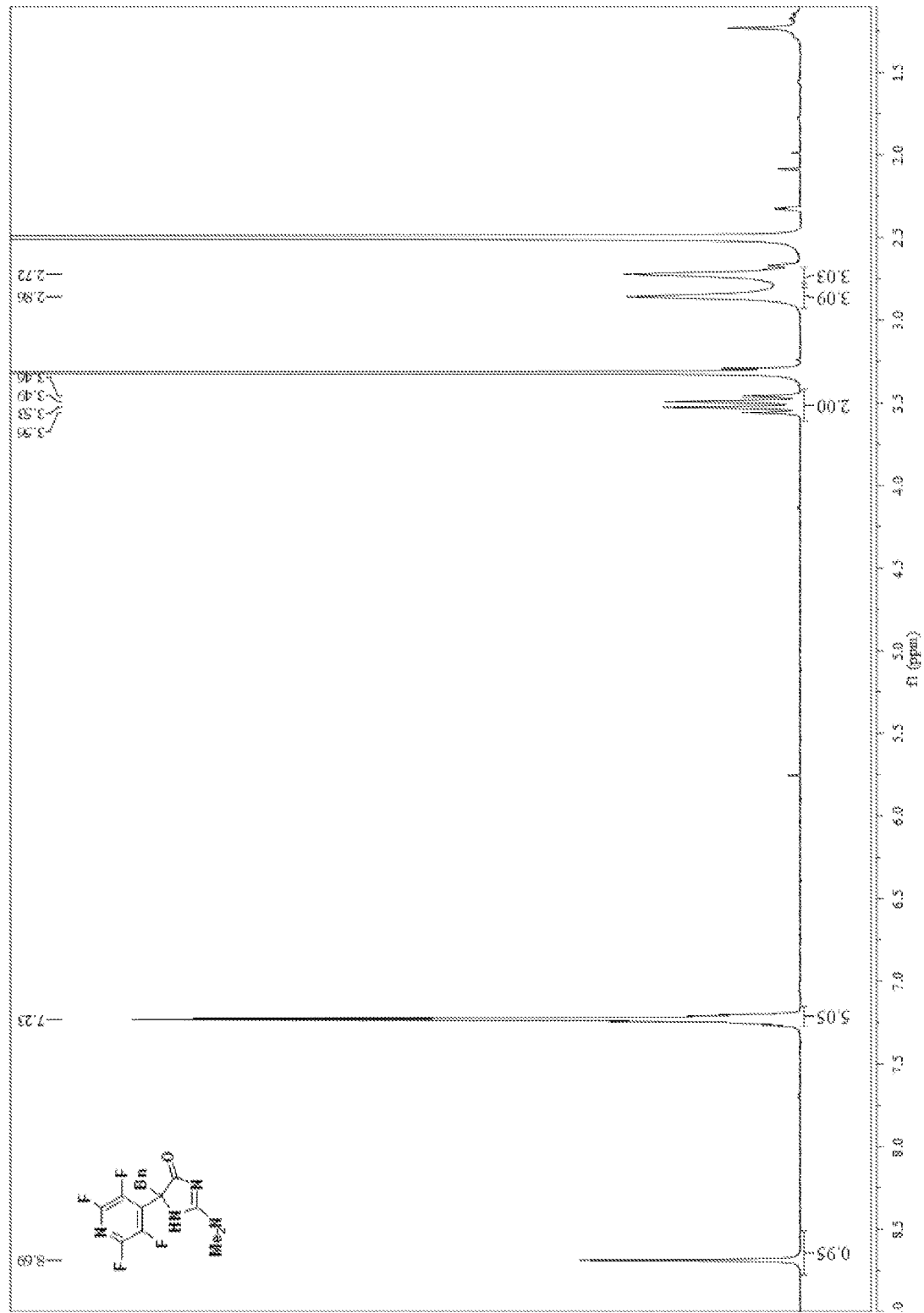
FIG. 91 contains a $^{1}$H NMR spectra (400 MHz), DMSO-$d_6$) of species 7b.
Figure 92:
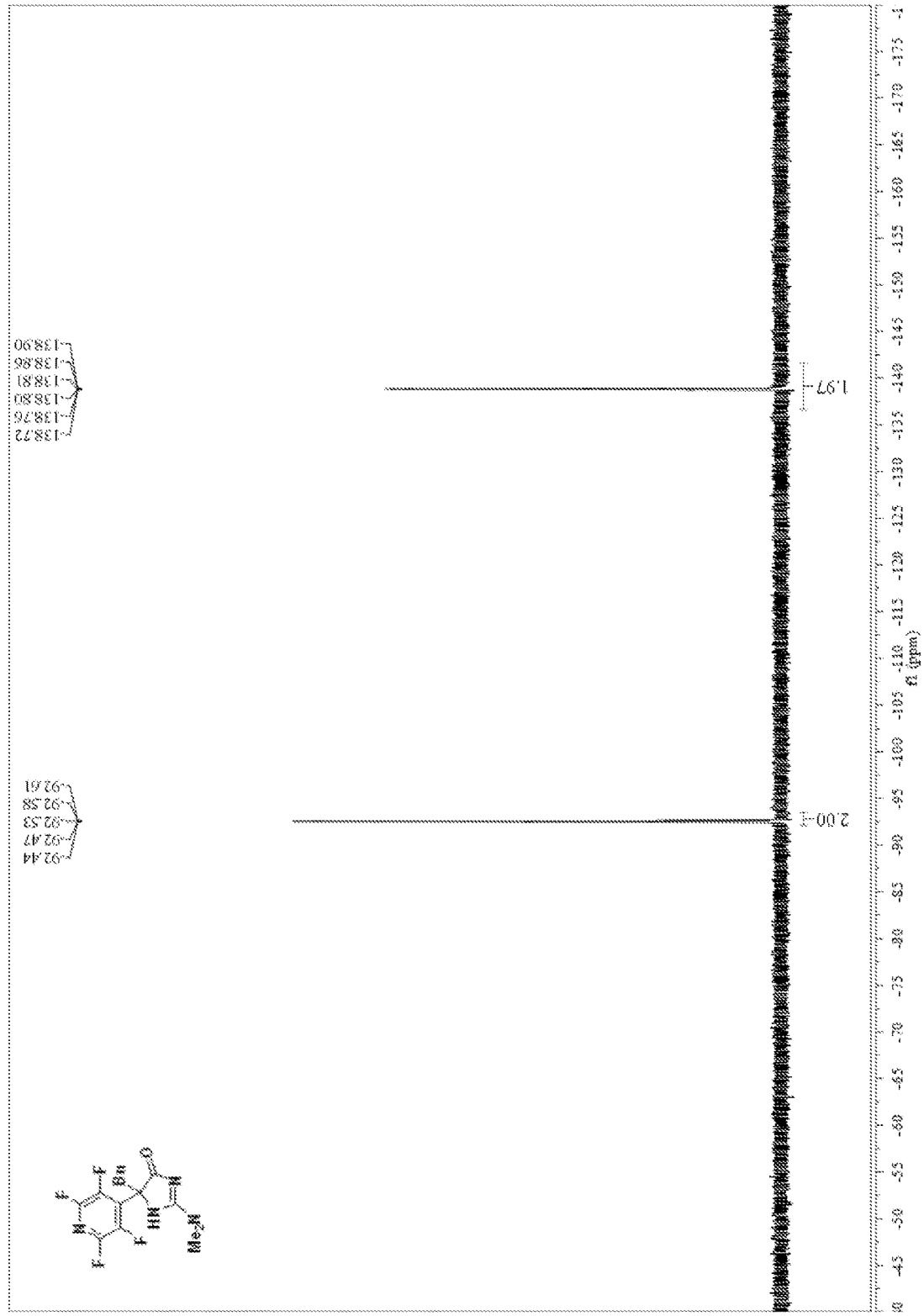
FIG. 92 contains a $^{19}$F NMR spectra (376 MHz), DMSO-$d_6$) of species 7b.
Figure 93:
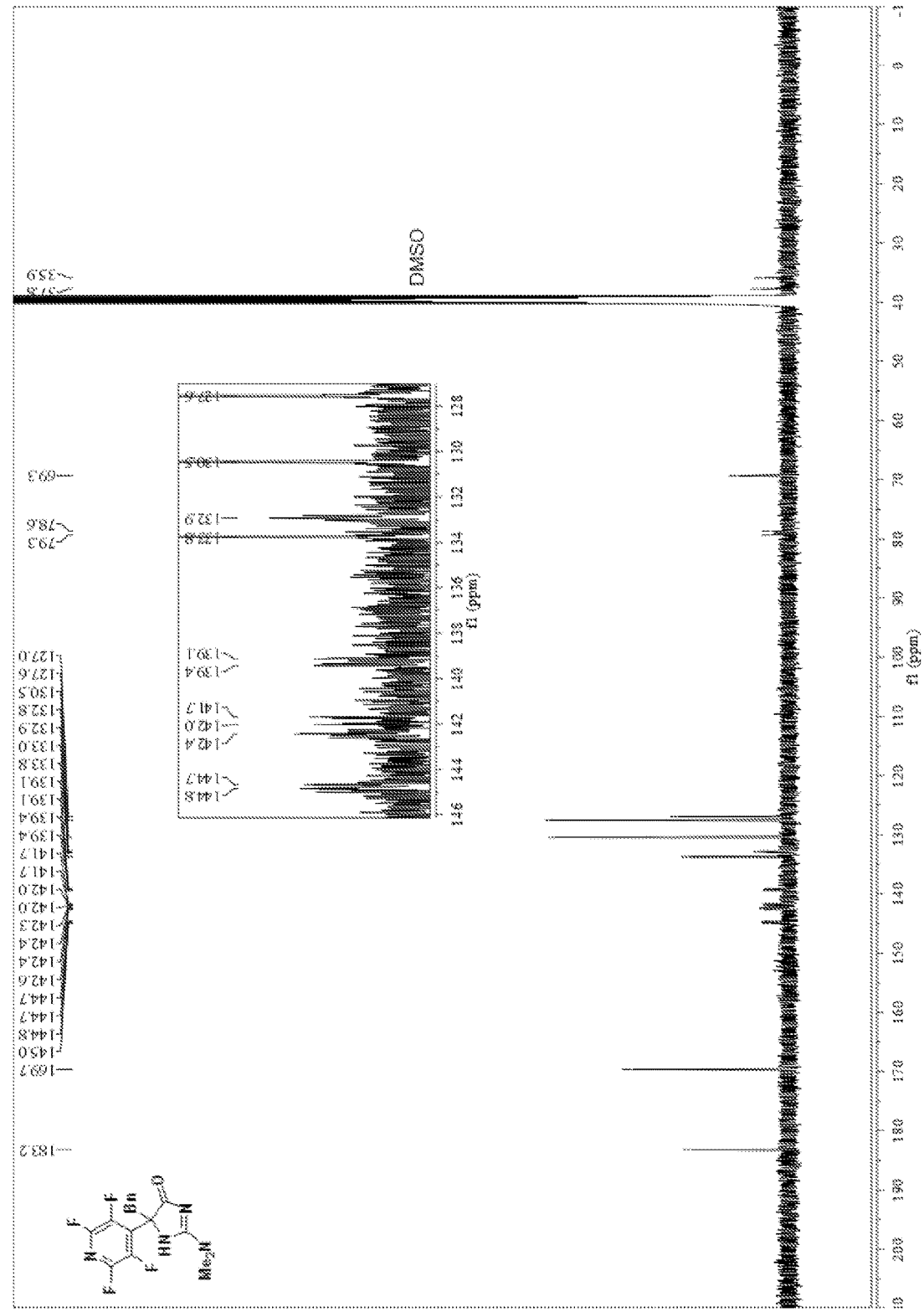
FIG. 93 contains a $^{13}$C NMR spectra (101 MHz), DMSO-$d_6$) of species 7b.

7b 5-benzoyl-2-(dimethylamino)-5-(perfluoropyridin-4-yl)-1,5-dihydro-4H-imidazol-4-one (FIGS. 7 and 91-93) was produced as a yellow oil, in 49% yield (37.1 mg, 0.0975 mmol). The general procedure I was followed using 4-benzyl-2-phenyloxazol-5(4H)-one (50 mg, 0.199 mmol), pentafluoropyridine (34.5 mg, 0.204 mmol), tetramethylguanidine (23.5 mg, 0.204 mmol), 1.99 mL HCl, and 0.199 mL of MeCN was used to afford 7b. FT-IR (neat) cm$^{−1}$ 3222, 2957, 1710, 1005. $^1$H NMR (400 MHz, DMSO-d$_6$; FIG. 91) δ 8.69 (s, $^1$H), 7.23 (s, 5H), 3.51 (q, J=13.0 Hz, 2H), 2.86 (s, 3H), 2.72 (s, 3H). $^{19}$F NMR (376 MHz, DMSO-d$_6$; FIG. 92) δ −92.27--92.81 (m), −138.65--138.98 (m). $^{13}$C NMR (101 MHz, DMSO-d$_6$; FIG. 93)) δ 183.2, 169.7, 145.23-142.16 (m), 142.13-138.90 (m), 133.76, 132.87 (t, J=10.9 Hz), 130.5, 127.6, 126.9, 78.6, 69.3, 37.7, 35.9. HRMS (ESI) C$_{17}$H$_{14}$F$_4$N$_4$O calcd. [M+H]$^+$ 367.1177 observed 367.1150.

Figure 94:
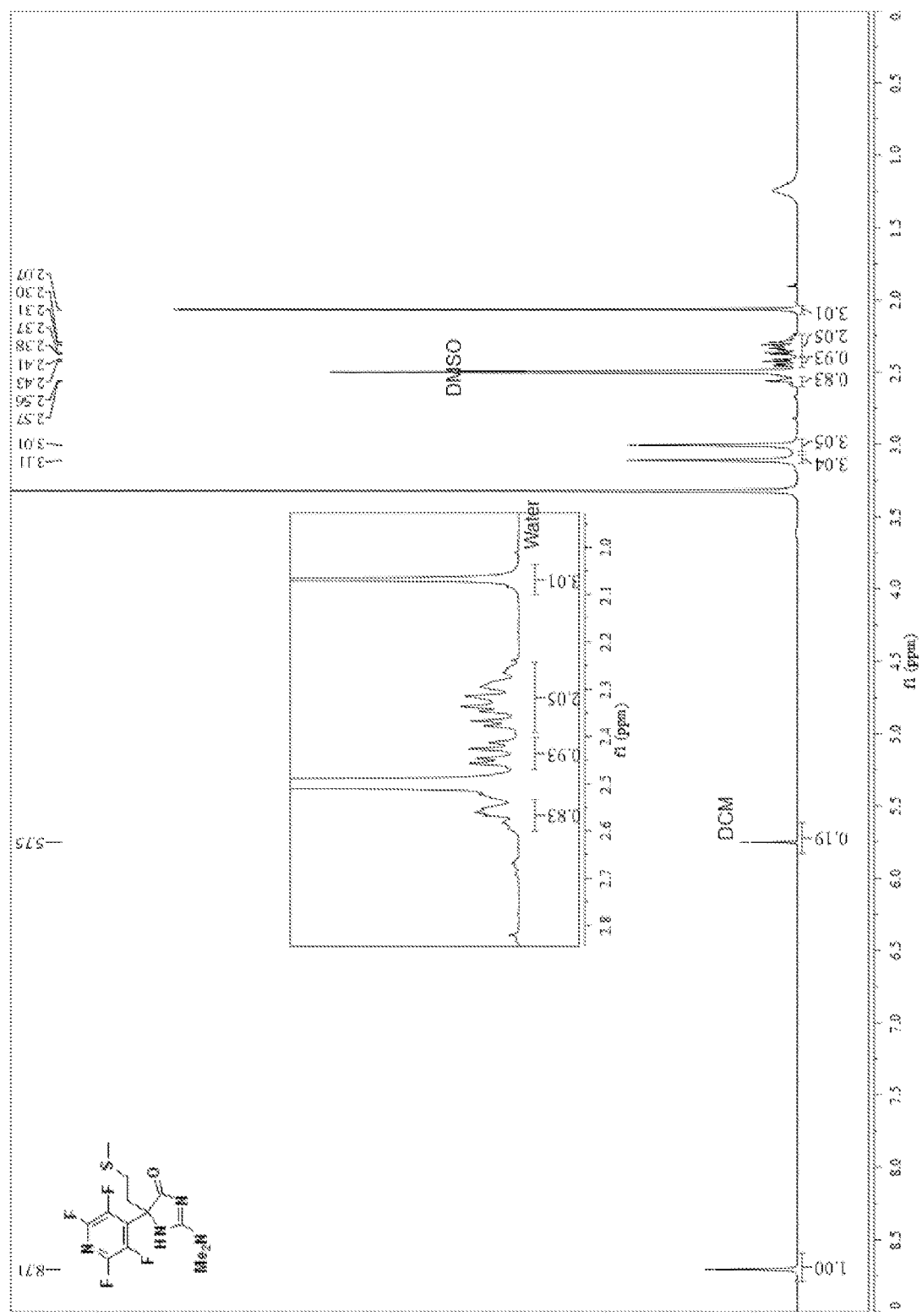
FIG. 94 contains a $^{1}$H NMR spectra (400 MHz), DMSO-$d_6$) of species 7c.
Figure 95:
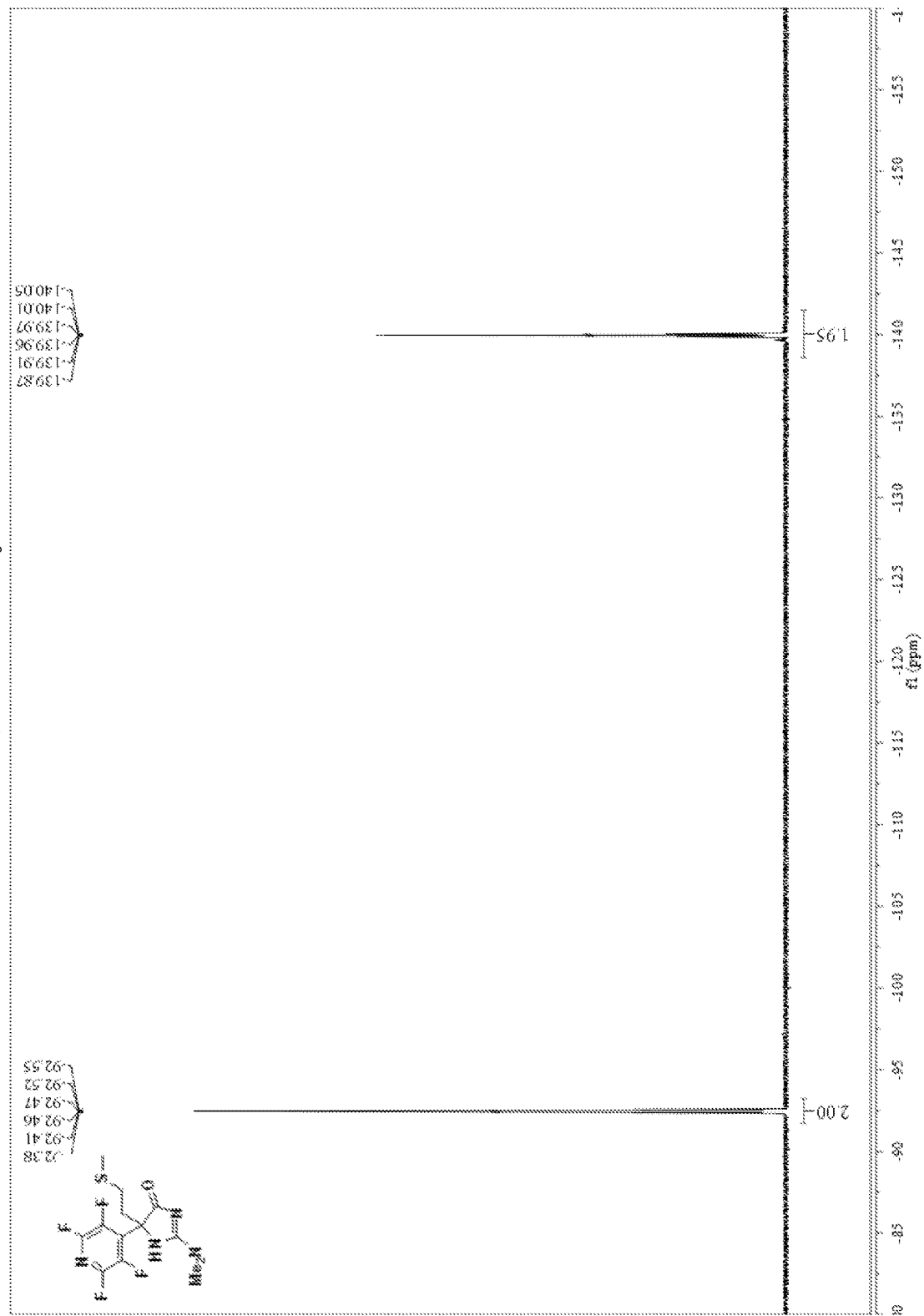
FIG. 95 contains a $^{19}$F NMR spectra (376 MHz), DMSO-$d_6$) of species 7c.
Figure 96:
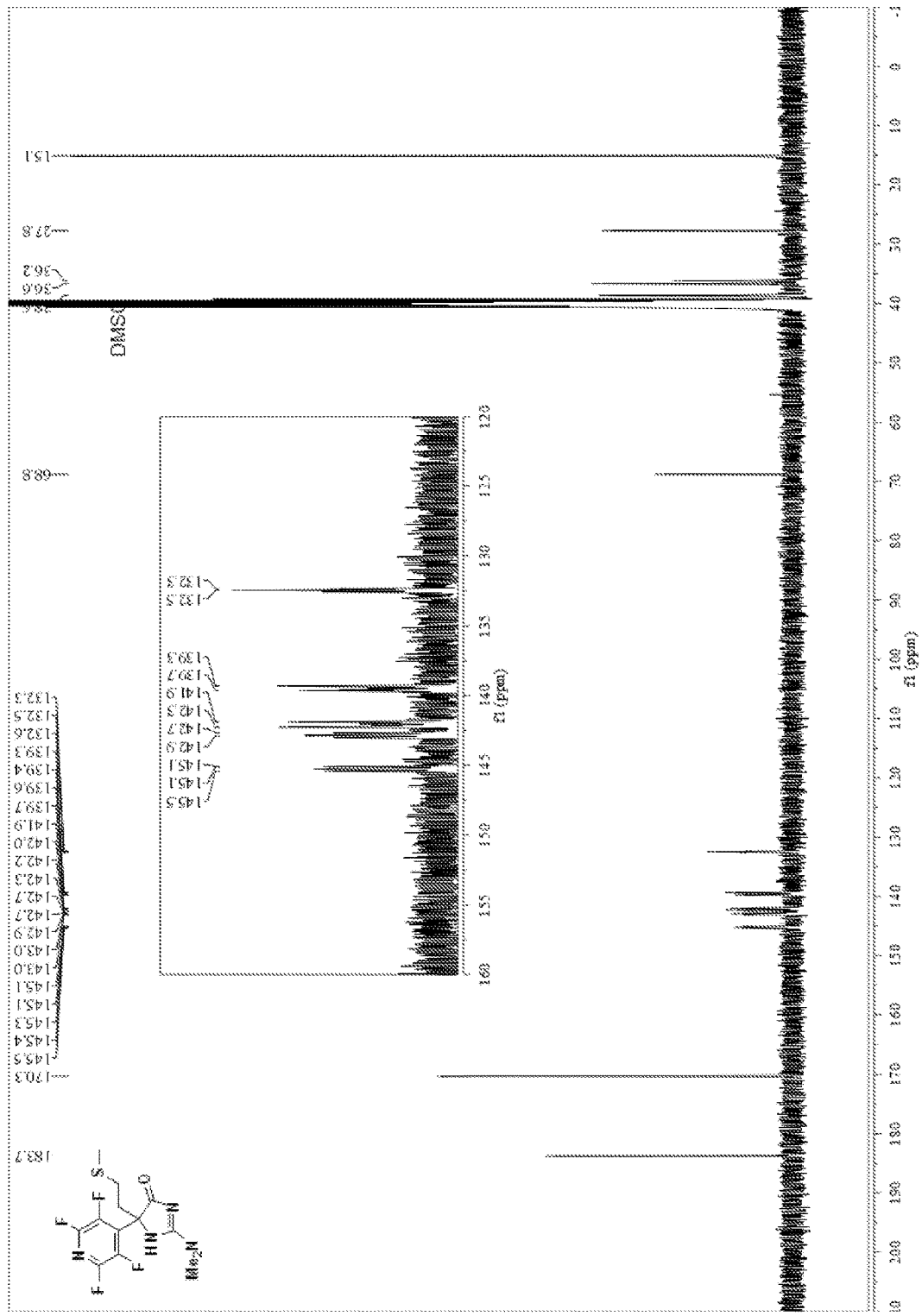
FIG. 96 contains a $^{13}$C NMR spectra (101 MHz), DMSO-$d_6$) of species 7c.

7c 2-(dimethylamino)-5-(2-(methylthio)ethyl)-5-(perfluoropyridin-4-yl)-1,5-dihydro-4H-imidazol-4-one (FIGS. 7 and 94-96) was produced as a yellow solid, in 60% yield (45.6 mg, 0.127 mmol). The general procedure I was followed using 4-(2-(methylthio)ethyl)-2-phenyloxazol-5(4H)-one (50 mg, 0.212 mmol), pentafluoropyridine (36.8 mg, 0.218 mmol), tetramethylguanidine (25.1 mg, 0.218 mmol), 2.12 mL HCl, and 0.212 mL of MeCN was used to afford 7c. FT-IR (neat) cm$^{−1}$ 2897, 2860, 1734, 1091. $^1$H NMR (400 MHz, DMSO-d$_6$; FIG. 94) δ 8.71 (s, $^1$H), 3.11 (s, 3H), 3.01 (s, 3H), 2.56 (d, J=2.7 Hz, $^1$H), 2.46-2.26 (m, 2H). $^{19}$F NMR (376 MHz, DMSO-d$_6$; FIG. 95) δ −92.35--92.61 (m), −139.85--140.08 (m). $^{13}$C NMR (101 MHz, DMSO-d$_6$; FIG. 96) δ 183.7, 170.3, 145.5-142.6 (m), 142.4-138.9 (m), 132.5 (t, J=11.0 Hz), 68.8, 38.6, 36.7, 36.2, 27.8, 15.1. HRMS (ESI) C$_{13}$H$_{14}$F$_4$N$_4$OS calcd. [M+H]$^+$ 351.0897 observed 351.0866.

Thus, in accordance with the present disclosure, there have been provided compositions, as well as methods of producing and using same, which fully satisfy the objectives and advantages set forth hereinabove. Although the present disclosure has been described in conjunction with the specific drawings, experimentation, results, and language set forth hereinabove, it is evident that many alternatives, modifications, and variations will be apparent to those skilled in the art. Accordingly, it is intended to embrace all such alternatives, modifications, and variations that fall within the spirit and broad scope of the present disclosure.

REFERENCES

The following references, to the extent that they provide exemplary procedural or other details supplementary to those set forth herein, are specifically incorporated herein by reference. In addition, the following is not intended to be an Information Disclosure Statement; rather, an Information Disclosure Statement in accordance with the provisions of 37 CFR § 1.97 will be submitted separately.

Ahrens et al. *Chem Rev*. (2015) 115:931-972.
Alemán et al. *Chem Eur J*. (2008) 14:10958-10966.
Al-Sayyab et al. *J Chem Soc C*. (1968) 406-410. doi: 10.1039/J39680000406.
Amii et al. *Chem Rev*. (2009) 109:2119-2183.
Badiola et al. *J Am Chem Soc*. (2014) 136:17869.
Chai et al. *Adv Synth Catal*. (2014) 356:2714-2718.
Cruz et al. *Med Chem*. (2014) 10:162-173.
D'Anello et al. *Chem Ber*. (1988) 121:67-73.
Fisk et al. *Chem Soc Rev*. (2007) 36:1432-1440.
Gung et al. *J Org Chem*. (2006) 71:9261-9270.
Hewlett et al. *Synthesis*. (2009) 2825-2839.
Johnson et al. *Org Lett*. (2016) 18:5364-5367.
Kiplinger et al. *Chem Rev*. (1994) 94:373-431.
Lentz et al. *Angew Chem Int Ed Engl*. (2013) 52:3328-3348.
Liu et al. *Org Lett*. (2003) 5:1915-1918.
Lu et al. *J Am Chem Soc*. (2016) 138:15805-15808.
Lv et al. *J Am Chem Soc*. (2012) 134:16216-16227.
Malamas et al. *Bioorg Med Chem Lett*. (2011) 21:5164-5170.
Margetic D. *Superbases for Organic Synthesis*. John Wiley & Sons, Ltd; 2009. pp. 9-48.
Melhado et al. *J Am Chem Soc*. (2007) 129:12638.
Mesaik et al. *Bioorganic & Medicinal Chemistry* (2004) 12:2049.
Pattison et al. *Tetrahedron* (2017) 73:437-454.
Petrov, V. *Fluorinated heterocyclic compounds: synthesis, chemistry, and applications*. (2009) Wiley, Hoboken, N.J.
Senaweera et al. *J Am Chem Soc*. (2014) 136:3002-3005.
Senaweera et al. *J Am Chem Soc*. (2016) 138:2520-2523.
Senaweera et al. *J Org Chem*. (2014) 79:10466-10476.
Singh et al. *Chem Sci*. (2015) 6:7206-7212.
Singh et al. *Chem Sci*. (2016) 7:6796-6802.
Tanaka et al. *Journal of Heterocyclic Chemistry* (2001) 38:131.
Wang et al. *J Am Chem Soc*. (2016) 138:265-271.
Weaver et al. *Tetrahedron*. (2014) 70:7413-7428.
Witkowska et al. *Journal of Peptide Science* (2001) 7:619.
Xie et al. *Angew Chem Int Ed Engl*. (2016) 55:9416-9421.

What is claimed is:

1. A method of synthesizing a polyfluorinated amino acid derivative, the method comprising the steps of:
   (a) deprotonating an oxazolone to yield an oxazolone enolate;
   (b) reacting the oxazolone enolate with a polyfluoroarene, resulting in nucleophilic aromatic substitution of the oxazolone with the polyfluoroarene to produce a polyfluoroarylated oxazolone intermediate; and
   (c) opening the oxazolone ring of the polyfluoroarylated oxazolone intermediate to form a polyfluoroaryl N-benzoyl protected amino acid derivative.

2. The method of claim 1, wherein the polyfluoroarene is a perfluoroarene, and the product of step (c) is a perfluoroaryl N-benzoyl protected amino acid derivative.

3. The method of claim 1, wherein the polyfluoroarene is a polyfluorinated heteroarene, and the product of step (c) is a polyfluoroheteroaryl N-benzoyl protected amino acid derivative.

4. The method of claim 1, further comprising the step of deprotecting the polyfluoroaryl N-benzoyl protected, amino acid derivative to produce a polyfluoroaryl amino acid derivative.

5. The method of claim 4, further comprising the step of decarboxylating the polyfluoroaryl amino acid derivative.

6. The method of claim 4, further comprising the step of isolating the polyfluoroaryl amino acid derivative.

7. The method of claim 1, wherein the amino acid is a derivative of alanine, glycine, methionine, phenylalanine, or valine.

8. The method of claim 1, wherein the amino acid is a derivative of arginine, asparagine, cysteine, glutamine, histidine, isoleucine, leucine, proline, serine, threonine, tryptophan, or tyrosine.

9. The method of claim 1, wherein step (c) is further defined as opening the oxazolone ring by exposing the polyfluoroarylated oxazolone intermediate to at least one of water, an alcohol, and a nucleophile.

10. The method of claim 9, wherein the nucleophile is NH$_3$ or tetramethyl guanidine (TMG).

11. The method of claim 1, further defined as a one pot synthesis method.

12. The method of claim 1, wherein the polyfluoroaryl N-benzoyl amino acid derivative is a polyfluoroaryl 2-aminohydantoin.

13. A one pot synthesis method for producing a polyfluorinated amino acid derivative, the method comprising the steps of:
combining, either simultaneously or wholly or partially sequentially:
(i) at least one oxazolone;
(ii) at least one polyfluoroarene;
(iii) at least one amine; and
(iv) at least one acid; and
wherein (i), (ii), (iii), and (iv) are reacted under one or more sets of reaction conditions to produce a polyfluoroaryl N-benzoyl protected amino acid derivative.

14. The method of claim 13, wherein (ii) is a perfluoroarene, and the product of the one pot synthesis method is a perfluoroaryl N-benzoyl protected amino acid derivative.

15. The method of claim 13, wherein (ii) is a polyfluorinated heteroarene, and the product of the one pot synthesis method is a polyfluoroheteroaryl N-benzoyl protected amino acid derivative.

16. The method of claim 13, wherein (iii) comprises at least one of diisopropylamine (DIPEA), tetramethyl guanidine (TMG), acetonitrile (ACN), and 1,8-diazabicyclo[5.4.0]undec-7-ene (DBU).

17. The method of claim 13, wherein (iv) comprises at least one of trifluoroacetic acid (TFA) and hydrochloric acid (HCl).

18. The method of claim 13, wherein (iv) is further defined as an acid/alcohol solution.

19. The method of claim 18, wherein the alcohol present in the acid/alcohol solution comprises at least one of methanol and ethanol.

20. The method of claim 13, wherein the product of the one pot synthesis method is a derivative of at least one of alanine, glycine, methionine, phenylalanine, or valine.

21. The method of claim 13, wherein the product of the one pot synthesis method is a derivative of arginine, asparagine, cysteine, glutamine, histidine, isoleucine, leucine, proline, serine, threonine, tryptophan, or tyrosine.

22. The method of claim 13, wherein the polyfluoroaryl N-benzoyl amino acid derivative is a polyfluoroaryl 2-aminohydantoin.

23. The method of claim 13, further defined as comprising at least two sets of reactions conditions, wherein:
(i), (ii), and (iii) are reacted at about −20° C. to provide a mixture; and
the mixture is allowed to warm to about room temperature prior to adding (iv).

24. The method of claim 23, wherein:
(iii) is a combination of ACN and TMG; and
(iv) is HCl or a TFA/alcohol solution.

25. The method of claim 13, wherein (i), (ii), and (iii) are mixed and reacted at room temperature prior to addition of (iv).

26. The method of claim 25, wherein:
(iii) comprises a combination of ACN and DBU or a combination of ACN and DIPEA; and
(iv) is a TFA/alcohol solution.

* * * * *